US012503682B2

(12) United States Patent
Roberts et al.

(10) Patent No.: US 12,503,682 B2
(45) Date of Patent: Dec. 23, 2025

(54) ARTHROSPIRA PLATENSIS NON-PARENTERAL THERAPEUTIC DELIVERY PLATFORM

(71) Applicant: LUMEN BIOSCIENCE, INC., Seattle, WA (US)

(72) Inventors: James Roberts, Seattle, WA (US); Michael Tasch, Seattle, WA (US); Mesfin Gewe, Bothell, WA (US); Benjamin Jester, Seattle, WA (US); Tracy Saveria, Seattle, WA (US)

(73) Assignee: Lumen Bioscience, Inc., Seattle, WA (US)

( * ) Notice: Subject to any disclaimer, the term of this patent is extended or adjusted under 35 U.S.C. 154(b) by 311 days.

(21) Appl. No.: 17/246,837

(22) Filed: May 3, 2021

(65) Prior Publication Data

US 2021/0338751 A1 Nov. 4, 2021

Related U.S. Application Data

(63) Continuation of application No. PCT/US2020/040794, filed on Jul. 2, 2020.

(Continued)

(51) Int. Cl.

*A61K 35/742* (2015.01)
*A61K 35/748* (2015.01)

(Continued)

(52) U.S. Cl.

CPC .............. *C12N 1/20* (2013.01); *A61K 35/742* (2013.01); *A61K 35/748* (2013.01);

(Continued)

(58) Field of Classification Search

CPC .. A61K 35/748; A61K 35/742; A61K 39/015; A61K 2039/505; A61K 2039/507;

(Continued)

(56) References Cited

U.S. PATENT DOCUMENTS

| | | | |
|---|---|---|---|
| 4,751,180 | A | 6/1988 | Cousens et al. |
| 4,873,192 | A | 10/1989 | Kunkel |

(Continued)

FOREIGN PATENT DOCUMENTS

| | | | |
|---|---|---|---|
| CN | 1177002 | A | 3/1998 |
| CN | 1528902 | A | 9/2004 |

(Continued)

OTHER PUBLICATIONS

Saerens, Dirk, et al. "Identification of a universal VHH framework to graft non-canonical antigen-binding loops of camel single-domain antibodies." Journal of molecular biology 352.3 (2005): 597-607. (Year: 2005).*

(Continued)

*Primary Examiner* — Louise W Humphrey
*Assistant Examiner* — Candice Lee Swift
(74) *Attorney, Agent, or Firm* — COOLEY LLP

(57) ABSTRACT

The present disclosure provides non-parenteral compositions comprising a recombinant *Spirulina* comprising at least one exogenous therapeutic. Compositions of the present disclosure can be used as vaccines and/or therapeutic drugs. The present disclosure also provides methods of making recombinant *Spirulina* comprising at least one exogenous therapeutic, and methods of treatment.

20 Claims, 119 Drawing Sheets

Specification includes a Sequence Listing.

Related U.S. Application Data

(60) Provisional application No. 62/943,075, filed on Dec. 3, 2019, provisional application No. 62/937,995, filed on Nov. 20, 2019, provisional application No. 62/870,478, filed on Jul. 3, 2019.

(51) Int. Cl.
*C07K 16/10* (2006.01)
*C12N 1/12* (2006.01)
*C12N 1/20* (2006.01)

(52) U.S. Cl.
CPC .......... *C07K 16/1003* (2023.08); *C12N 1/125* (2021.05); *C12N 1/205* (2021.05)

(58) Field of Classification Search
CPC ........ A61K 2039/517; A61K 2039/523; A61K 2039/543; A61K 2039/542; C12N 1/125; C12N 1/205; C12N 1/20; A61P 31/04; C07K 2317/22; C07K 2317/569; C07K 2317/62; C07K 2317/92; C07K 2317/94; C07K 16/10; C07K 16/121; C07K 16/1282; Y02A 50/30
See application file for complete search history.

(56) References Cited

U.S. PATENT DOCUMENTS

| | | | |
|---|---|---|---|
| 4,935,233 | A | 6/1990 | Bell et al. |
| 5,429,939 | A | 7/1995 | Misawa et al. |
| 5,589,581 | A | 12/1996 | Misawa et al. |
| 5,661,017 | A | 8/1997 | Dunahay et al. |
| 5,684,238 | A | 11/1997 | Ausich et al. |
| 5,811,273 | A | 9/1998 | Misawa et al. |
| 5,910,433 | A | 6/1999 | Kajiwara et al. |
| 5,972,690 | A | 10/1999 | Misawa et al. |
| 6,087,152 | A | 7/2000 | Hohmann et al. |
| 6,124,113 | A | 9/2000 | Hohmann et al. |
| 6,150,130 | A | 11/2000 | Misawa et al. |
| 6,207,409 | B1 | 3/2001 | Hohmann et al. |
| 6,214,575 | B1 | 4/2001 | Yano et al. |
| 6,291,204 | B1 | 9/2001 | Pasamontes et al. |
| 6,306,639 | B1 | 10/2001 | Woods et al. |
| 6,528,314 | B1 | 3/2003 | Le Mouellic et al. |
| 6,677,134 | B2 | 1/2004 | Pasamontes et al. |
| 6,929,928 | B2 | 8/2005 | Cheng et al. |
| 6,969,595 | B2 | 11/2005 | Brzostowicz et al. |
| 6,989,472 | B1 | 1/2006 | Carol et al. |
| 7,063,957 | B2 | 6/2006 | Chen |
| 7,064,196 | B2 | 6/2006 | Cheng et al. |
| 7,070,952 | B2 | 7/2006 | Cheng et al. |
| 7,074,604 | B1 | 7/2006 | Tang et al. |
| 7,091,031 | B2 | 8/2006 | Cheng et al. |
| 7,118,896 | B2 | 10/2006 | Kalscheuer et al. |
| 7,157,619 | B1 | 1/2007 | Lassner et al. |
| 7,176,000 | B2 | 2/2007 | Glazer et al. |
| 7,217,537 | B2 | 5/2007 | Miller, Jr. et al. |
| 7,223,909 | B2 | 5/2007 | Hauptmann et al. |
| 7,232,665 | B2 | 6/2007 | Cheng et al. |
| 7,232,666 | B2 | 6/2007 | Sharpe et al. |
| 7,252,964 | B2 | 8/2007 | Giraud et al. |
| 7,252,985 | B2 | 8/2007 | Cheng et al. |
| 7,288,387 | B2 | 10/2007 | Cheng et al. |
| 7,291,482 | B2 | 11/2007 | Cheng et al. |
| 7,385,123 | B2 | 6/2008 | Sauer et al. |
| 7,393,671 | B2 | 7/2008 | Cheng et al. |
| 7,422,873 | B2 | 9/2008 | Stead et al. |
| 7,425,625 | B2 | 9/2008 | Tang et al. |
| 7,427,593 | B1 | 9/2008 | Dahlqvist et al. |
| 7,498,026 | B2 | 3/2009 | Dahlqvist et al. |
| 7,504,236 | B2 | 3/2009 | Miller, Jr. et al. |
| 7,522,162 | B2 | 4/2009 | Cubicciotti |
| 7,695,931 | B2 | 4/2010 | Nishida et al. |
| 7,695,932 | B2 | 4/2010 | Stephanopoulos et al. |

| | | | |
|---|---|---|---|
| 7,741,070 | B2 | 6/2010 | Stephanopoulos et al. |
| 7,794,696 | B2 | 9/2010 | Van et al. |
| 7,794,969 | B1 | 9/2010 | Reppas et al. |
| 7,999,151 | B2 | 8/2011 | Choi et al. |
| 8,030,022 | B2 | 10/2011 | Tanaka et al. |
| 8,110,670 | B2 | 2/2012 | Hu et al. |
| 8,394,614 | B2 | 3/2013 | Roberts et al. |
| 8,394,621 | B2 | 3/2013 | Roberts et al. |
| 8,569,014 | B2 | 10/2013 | Tanaka et al. |
| 8,835,137 | B2 | 9/2014 | Roberts et al. |
| 9,029,120 | B2 | 5/2015 | Roberts et al. |
| 9,040,264 | B2 | 5/2015 | Kristof et al. |
| 9,523,096 | B2 | 12/2016 | Roberts et al. |
| 9,914,907 | B2 | 3/2018 | Roberts et al. |
| 10,336,982 | B2 | 7/2019 | Takeuchi et al. |
| 10,415,012 | B2 | 9/2019 | Takeuchi et al. |
| 10,415,013 | B2 | 9/2019 | Takeuchi et al. |
| 10,563,168 | B2 | 2/2020 | Roberts et al. |
| 10,654,901 | B2 | 5/2020 | Roberts et al. |
| 10,760,045 | B2 | 9/2020 | Roberts et al. |
| 10,787,488 | B2 | 9/2020 | Roberts et al. |
| 11,174,294 | B2 | 11/2021 | Roberts et al. |
| 11,279,912 | B2 | 3/2022 | Roberts et al. |
| 12,065,638 | B2 | 8/2024 | Takeuchi et al. |
| 2003/0003528 | A1 | 1/2003 | Brzostowicz et al. |
| 2003/0104379 | A1 | 6/2003 | Lagarias et al. |
| 2003/0148319 | A1 | 8/2003 | Brzostowicz et al. |
| 2003/0233675 | A1 | 12/2003 | Cao et al. |
| 2004/0077068 | A1 | 4/2004 | Brzostowicz et al. |
| 2004/0078846 | A1 | 4/2004 | Desouza et al. |
| 2004/0219629 | A1 | 11/2004 | Cheng et al. |
| 2004/0224383 | A1 | 11/2004 | Cheng et al. |
| 2005/0003474 | A1 | 1/2005 | Desouza et al. |
| 2005/0260699 | A1 | 11/2005 | Desouza et al. |
| 2005/0281839 | A1 | 12/2005 | Belay et al. |
| 2006/0053513 | A1 | 3/2006 | Steiger et al. |
| 2006/0059584 | A1 | 3/2006 | Klebsattel et al. |
| 2006/0088550 | A1 | 4/2006 | Bachmann et al. |
| 2006/0099670 | A1 | 5/2006 | Matuschek et al. |
| 2006/0099710 | A1 | 5/2006 | Donnelly et al. |
| 2006/0121468 | A1 | 6/2006 | Allnutt et al. |
| 2006/0121557 | A1 | 6/2006 | Hoshino et al. |
| 2006/0137043 | A1 | 6/2006 | Puzio et al. |
| 2006/0185038 | A1 | 8/2006 | De Block |
| 2006/0234333 | A1 | 10/2006 | Matuschek et al. |
| 2007/0059790 | A1 | 3/2007 | Miller, Jr. et al. |
| 2007/0065900 | A1 | 3/2007 | Dicosimo et al. |
| 2007/0065901 | A1 | 3/2007 | Dicosimo et al. |
| 2007/0065902 | A1 | 3/2007 | Dicosimo et al. |
| 2007/0065903 | A1 | 3/2007 | Dicosimo et al. |
| 2007/0269859 | A1 | 11/2007 | Lassner et al. |
| 2008/0107652 | A1 | 5/2008 | Durvasula et al. |
| 2008/0124755 | A1 | 5/2008 | Louie et al. |
| 2008/0160592 | A1 | 7/2008 | Dahlqvist et al. |
| 2008/0193970 | A1 | 8/2008 | Fardoux et al. |
| 2008/0301839 | A1 | 12/2008 | Ravanello |
| 2009/0035832 | A1 | 2/2009 | Koshland, Jr. |
| 2009/0142322 | A1 | 6/2009 | Ye |
| 2009/0155864 | A1 | 6/2009 | Bauer et al. |
| 2009/0175911 | A1 | 7/2009 | Cutting et al. |
| 2009/0197321 | A1 | 8/2009 | Chiou et al. |
| 2009/0203070 | A1 | 8/2009 | Devroe et al. |
| 2009/0215179 | A1 | 8/2009 | Gressel et al. |
| 2009/0220537 | A1 | 9/2009 | Tindle et al. |
| 2009/0226582 | A1 | 9/2009 | Ide et al. |
| 2009/0298143 | A1 | 12/2009 | Roessler et al. |
| 2010/0068776 | A1 | 3/2010 | Woods et al. |
| 2010/0081178 | A1 | 4/2010 | Roberts et al. |
| 2010/0184169 | A1 | 7/2010 | Roberts et al. |
| 2010/0251601 | A1 | 10/2010 | Hu et al. |
| 2010/0255551 | A1 | 10/2010 | Roberts et al. |
| 2011/0053216 | A1 | 3/2011 | Vermaas |
| 2011/0072714 | A1 | 3/2011 | Gaertner |
| 2011/0129474 | A1 | 6/2011 | Shoemaker et al. |
| 2011/0184152 | A1 | 7/2011 | Adams et al. |
| 2011/0244532 | A1 | 10/2011 | Hu et al. |
| 2011/0250659 | A1 | 10/2011 | Roberts et al. |
| 2011/0250663 | A1 | 10/2011 | Schirmer et al. |
| 2011/0252501 | A1 | 10/2011 | Abad et al. |

(56) References Cited

U.S. PATENT DOCUMENTS

| | | | |
|---|---|---|---|
| 2011/0277190 | A1 | 11/2011 | Abad |
| 2012/0115208 | A1 | 5/2012 | Ellison et al. |
| 2012/0142082 | A1 | 6/2012 | Sharpe et al. |
| 2012/0252080 | A1 | 10/2012 | Kristof et al. |
| 2013/0039889 | A1 | 2/2013 | McDonagh et al. |
| 2013/0058962 | A1* | 3/2013 | Shoemaker ...... A61K 39/39591 530/358 |
| 2013/0078686 | A1 | 3/2013 | Holtzapple et al. |
| 2013/0143284 | A1 | 6/2013 | Roberts et al. |
| 2013/0171677 | A1 | 7/2013 | Bryant et al. |
| 2013/0224811 | A1 | 8/2013 | Holtzapple et al. |
| 2013/0230537 | A1 | 9/2013 | Hussack et al. |
| 2013/0344549 | A1 | 12/2013 | Roberts et al. |
| 2014/0004580 | A1 | 1/2014 | Roberts et al. |
| 2014/0011264 | A1 | 1/2014 | Duhring et al. |
| 2014/0030785 | A1 | 1/2014 | Kallas et al. |
| 2014/0325710 | A1 | 10/2014 | Abad et al. |
| 2014/0356867 | A1 | 12/2014 | Peter et al. |
| 2015/0024442 | A1 | 1/2015 | Roberts et al. |
| 2015/0329868 | A1* | 11/2015 | Hickman .................. C12P 7/48 435/157 |
| 2016/0046902 | A1 | 2/2016 | Roberts et al. |
| 2017/0240872 | A1 | 8/2017 | Guo et al. |
| 2017/0240944 | A1 | 8/2017 | Heinnickel et al. |
| 2017/0298319 | A1 | 10/2017 | Takeuchi et al. |
| 2018/0051057 | A1 | 2/2018 | Roberts et al. |
| 2018/0134755 | A1 | 5/2018 | Roberts et al. |
| 2018/0222945 | A1 | 8/2018 | Roberts et al. |
| 2018/0305660 | A1 | 10/2018 | Takeuchi et al. |
| 2018/0312801 | A1 | 11/2018 | Takeuchi et al. |
| 2019/0002820 | A1 | 1/2019 | Takeuchi et al. |
| 2019/0062763 | A1 | 2/2019 | Roberts et al. |
| 2019/0093066 | A1 | 3/2019 | Roberts et al. |
| 2020/0017822 | A1 | 1/2020 | Takeuchi et al. |
| 2020/0172859 | A1 | 6/2020 | Roberts et al. |
| 2020/0392189 | A1 | 12/2020 | Roberts et al. |
| 2021/0047610 | A1 | 2/2021 | Roberts et al. |
| 2021/0213124 | A1 | 7/2021 | Roberts et al. |
| 2021/0338751 | A1 | 11/2021 | Roberts |
| 2022/0135627 | A1 | 5/2022 | Roberts et al. |
| 2024/0002481 | A1 | 1/2024 | Roberts |
| 2024/0150440 | A1 | 5/2024 | Roberts et al. |

FOREIGN PATENT DOCUMENTS

| | | | |
|---|---|---|---|
| CN | 1608132 | A | 4/2005 |
| CN | 1843150 | A | 10/2006 |
| CN | 101173214 | A | 5/2008 |
| CN | 103382482 | A | 11/2013 |
| CN | 103820459 | A | 5/2014 |
| CN | 104311649 | A | 1/2015 |
| CN | 104479010 | A | 4/2015 |
| CN | 104480133 | A | 4/2015 |
| CN | 108495685 | A | 9/2018 |
| CN | 112094342 | A | 12/2020 |
| EP | 0393690 | A1 | 10/1990 |
| EP | 0872554 | A2 | 10/1998 |
| EP | 1854889 | A1 | 11/2007 |
| JP | H06253863 | A | 9/1994 |
| JP | H1156360 | A | 3/1999 |
| JP | 200424232 | | 1/2004 |
| JP | 2006075097 | A | 3/2006 |
| JP | 2006191919 | A | 7/2006 |
| JP | 2006520254 | A | 9/2006 |
| JP | 3874897 | B2 | 1/2007 |
| JP | 2011512841 | A | 4/2011 |
| JP | 2015535224 | A | 12/2015 |
| JP | 2017526372 | A | 9/2017 |
| JP | 6253863 | B1 | 12/2017 |
| KR | 100788479 | B1 | 12/2007 |
| KR | 100845582 | B1 | 7/2008 |
| KR | 20090046376 | A | 5/2009 |
| KR | 20100051306 | A | 5/2010 |
| SG | 187250 | A1 | 3/2013 |
| TW | 200811098 | A | 3/2008 |
| WO | WO-9839457 | A1 | 9/1998 |
| WO | WO-9963055 | A1 | 12/1999 |
| WO | WO-0241833 | A2 | 5/2002 |
| WO | WO-02097137 | A1 | 12/2002 |
| WO | WO-2004003143 | A2 | 1/2004 |
| WO | WO-2004029234 | A1 | 4/2004 |
| WO | WO-2004087892 | A1 | 10/2004 |
| WO | WO-2006078050 | A2 | 7/2006 |
| WO | WO-2006096392 | A2 | 9/2006 |
| WO | WO-2007136762 | A2 | 11/2007 |
| WO | WO-2008119082 | A2 | 10/2008 |
| WO | WO-2008130437 | A2 | 10/2008 |
| WO | WO-2009009391 | A2 | 1/2009 |
| WO | WO-2009010826 | A2 | 1/2009 |
| WO | WO-2009036095 | A1 | 3/2009 |
| WO | WO-2009042950 | A1 | 4/2009 |
| WO | WO-2009062190 | A2 | 5/2009 |
| WO | WO-2009076559 | A1 | 6/2009 |
| WO | WO-2009089185 | A1 | 7/2009 |
| WO | WO-2009098089 | A2 | 8/2009 |
| WO | WO-2009111513 | A1 | 9/2009 |
| WO | WO-2009140696 | A2 | 11/2009 |
| WO | WO-2010006312 | A2 | 1/2010 |
| WO | WO-2010017245 | A1 | 2/2010 |
| WO | WO-2010019813 | A2 | 2/2010 |
| WO | WO-2010021711 | A1 | 2/2010 |
| WO | WO-2010022090 | A1 | 2/2010 |
| WO | WO-2010027516 | A2 | 3/2010 |
| WO | WO-2010033921 | A2 | 3/2010 |
| WO | WO-2010036951 | A2 | 4/2010 |
| WO | WO-2010042664 | A2 | 4/2010 |
| WO | WO-2010044960 | A1 | 4/2010 |
| WO | WO-2010048568 | A1 | 4/2010 |
| WO | WO-2010062480 | A2 | 6/2010 |
| WO | WO-2010062707 | A1 | 6/2010 |
| WO | WO-2010075440 | A1 | 7/2010 |
| WO | WO-2010075483 | A2 | 7/2010 |
| WO | WO-2010078584 | A1 | 7/2010 |
| WO | WO-2010104763 | A1 | 9/2010 |
| WO | WO-2010118410 | A1 | 10/2010 |
| WO | WO-2010126891 | A1 | 11/2010 |
| WO | WO-2010130725 | A1 | 11/2010 |
| WO | WO-2011008535 | A1 | 1/2011 |
| WO | WO-2011008565 | A1 | 1/2011 |
| WO | WO-2011011568 | A2 | 1/2011 |
| WO | WO-2011018116 | A1 | 2/2011 |
| WO | WO-2011029013 | A2 | 3/2011 |
| WO | WO-2011038132 | A1 | 3/2011 |
| WO | WO-2011038134 | A1 | 3/2011 |
| WO | WO-2011052003 | A1 | 5/2011 |
| WO | WO-2011059745 | A1 | 5/2011 |
| WO | WO-2011127069 | A1 | 10/2011 |
| WO | WO-2011127118 | A1 | 10/2011 |
| WO | WO-2012017199 | A1 | 2/2012 |
| WO | WO-2012033870 | A1 | 3/2012 |
| WO | WO-2012087963 | A1 | 6/2012 |
| WO | WO-2012087982 | A2 | 6/2012 |
| WO | WO-2013116517 | A2 | 8/2013 |
| WO | WO-2014013489 | A1 | 1/2014 |
| WO | WO-2014063253 | A1 | 5/2014 |
| WO | WO-2014164232 | A1 | 10/2014 |
| WO | WO-2014164566 | A2 | 10/2014 |
| WO | WO-2016040499 | A1 | 3/2016 |
| WO | WO-2016044336 | A1 | 3/2016 |
| WO | WO-2016073562 | A1 | 5/2016 |
| WO | WO-2016172438 | A1 | 10/2016 |
| WO | WO-2017011273 | A1 | 1/2017 |
| WO | WO-2017066468 | A1 | 4/2017 |
| WO | WO-2017139687 | A1 | 8/2017 |
| WO | WO-2019222711 | A1 | 11/2019 |
| WO | WO-2020018586 | A1 | 1/2020 |
| WO | WO-2022140696 | A1 | 6/2022 |

OTHER PUBLICATIONS

Barrera, Daniel J., et al. "Algal chloroplast produced camelid VHH antitoxins are capable of neutralizing botulinum neurotoxin." Plant biotechnology journal 13.1 (2015): 117-124. (Year: 2015).*

(56) References Cited

OTHER PUBLICATIONS

Wang, Qiong, et al. "Using a novel lysin to help control Clostridium difficile infections." Antimicrobial Agents and Chemotherapy 59.12 (2015): 7447-7457. (Year: 2015).*
Rosales-Mendoza, Sergio. Algae-based biopharmaceuticals. Cham: Springer, 2016. (Year: 2016).*
Alvin JW, Lacy DB. Clostridium difficile toxin glucosyltransferase domains in complex with a non-hydrolyzable UDP-glucose analogue. J Struct Biol. Jun. 2017; 198(3):203-209. doi: 10.1016/j.jsb.2017.04.006. Epub Apr. 19, 2017. PMID: 28433497; PMCID: PMC5534367. (Year: 2017).*
Chen, Peng, et al. "Structure of the full-length Clostridium difficile toxin B." Nature structural & molecular biology 26.8 (2019): 712-719. (Year: 2019).*
NCBI taxonomy; https://www.ncbi.nlm.nih.gov/Taxonomy/Browser/wwwtax.cgi?mode=Info&id=118562&lvl=3&lin=f&keep=1&srchmode=1 accessed Jul. 19, 2023 (Year: 2023).*
Dehghani, Jaber, et al. "Stable transformation of Spirulina (Arthrospira) platensis: a promising microalga for production of edible vaccines." Applied microbiology and biotechnology 102 (2018): 9267-9278. (Year: 2018).*
Bach, Horacio, et al. "*Escherichia coli* maltose-binding protein as a molecular chaperone for recombinant intracellular cytoplasmic single-chain antibodies." Journal of molecular biology 312.1 (2001): 79-93. (Year: 2001).*
Dixon, Chelsea, and Lisa R. Wilken. "Green microalgae biomolecule separations and recovery." Bioresources and Bioprocessing 5.1 (2018): 1-24. (Year: 2018).*
Kumar, Manoj, Jyoti Kulshreshtha, and Gajendra Pal Singh. "Growth and biopigment accumulation of cyanobacterium Spirulina platensis at different light intensities and temperature." Brazilian Journal of Microbiology 42 (2011): 1128-1135. (Year: 2011).*
Lin, L. P. (1985) "Microstructure of Spray-Dried and Freeze-Dried Microalgal Powders," Food Structure: vol. 4 : No. 2, Article 17 (Year: 1985).*
Business Wire, "Lumen Bioscience Announces Issuance of US Patent for Genetic Modification of Spirulina," Nov. 26, 2018, 3 pages.
Giallourou et al. A novel mouse model of Campylobacter jejuni enteropathy and diarrhea. PLoS Pathog. 14(3): e1007083, pp. 1-23 (2018).
International Search Report and Written Opinion issued by the International Searching Authority for Application No. PCT/US2020/040794, dated 15, pages.
Riazi et al. Pentavalent Single-Domain Antibodies Reduce Campylobacter jejuni Motility and Colonization in Chickens. PLoS One 8(12):e83928, pp. 1-12 (2013).
Extended European Search Report for European Application No. EP20834359 dated Jun. 30, 2023, 7 pages.
A935Y7—UniProtKB Database—2008, 2 pages.
Adir et al. "Structure of c-Phycocyanin from the Thermophilic Cyanobacterium Synechococcus vulcan us at 2.5 A: Structural Implications for Thermal Stability in Phycobilisome Assembly", 2001, vol. 313, p. 71-81.
Agarwal et al., "Gastrointestinal and Liver Manifestations of COVID-19," J Clin Exp Hepatol. May-Jun. 2020; 10(3): 263-265. Published online Apr. 1, 2020.
Akiyama, et al., "Nucleotide Sequence of Plasmid pAG1 of Marine *Cyanobacterium synechococcus* sp. PCC7002", DNA Res., 1998, vol. 5, pp. 127-129.
Altschul, S. F., et al., "Basic local alignment search tool", Journal of Molecular Biology (1990); 215(3): 403-410.
Alvarez et al., "Triacylglycerols in prokaryotic microorganisms," Appl. Microbial. Biotechnol. 60:367-376, 2002.
Alvey et al., "Attachment of noncognate chromophores to CpcA of *Synechocystis* sp. PCC 6803 and *Synechococcus* sp. PCC 7002 by heterologous expression in *Escherichia coli*.," Biochemistry 50(22):4890-4902 (2011).
Alvey et al., "Effects of Modified Phycobilin Biosynthesis in the *Cyanobacterium synechococcus* sp. Strain PCC 7002," Journal of Bacteriology, 193(7):1663-1671 (2011).
Ambati et al, "Astaxanthin: Sources, Extraction, Stability, Biological Activities and its Commercial Applications—a Review", Marine Drugs, Jan. 2014, vol. 12, 25 pgs.
Andersen K, et.al., "Neutralization of Clostridium difficile Toxin B Mediated by Engineered Lactobacilli That Produce Single-Domain Antibodies", Infection and Immunity, Nov. 2015, vol. 84 No. 2, pp. 395-406.
Angermayr, et al., "Engineering a cyanobacterial cell factory for production of lactic acid," (2012) Applied and Environmental Microbiology 78: 7098-7106 (2012).
Anonymous: UPI0000000F3D, Jul. 23, 2007 (Jul. 23, 2007), Retrieved from the Internet: URL:https://www.uniprot.org/uniparcUPI0000000F3D [retrieved on Nov. 8, 2018], 3 pages.
Anonymous: UPI0000000F3E, Jan. 23, 2007 (Jan. 23, 2007), Retrieved from the Internet: URL:https://www.uniprot.org/uniparc/UPI0000000F3E [retrieved on Nov. 8, 2018], 3 pages.
Anonymous: UPI00001BA0B6, Oct. 1, 2003 (Oct. 1, 2003), XP055522054, Retrieved from the Internet: URL:https://www.uniprot.org/uniparc/UPI00001BA0B6 [retrieved on Nov. 8, 2018], 2 pages.
Anonymous: UPI00001BA0C5, Oct. 1, 2003 (Oct. 1, 2003), Retrieved from the Internet: URL:https://www.uniprot.org/uniparc/UPI00001BA0C5[retrieved on Nov. 8, 2018], 2 pages.
Anonymous: UPI00001BA0CB, Oct. 1, 2003 (Oct. 1, 2003), Retrieved from the Internet: URL:https://www.uniprot.org/uniparc/UPI00001BA0CB[retrieved on Nov. 8, 2018], 2 pages.
Assiri et al., "Epidemiological, demographic, and clinical characteristics of 47 cases of Middle East respiratory syndrome coronavirus disease from Saudi Arabia: a descriptive study," Lancet Infect Dis Sep. 2013;13(9):752-61.
Bailey, et al., "Photoprotection in Cyanobacteria: Regulation of Light Harvesting", Photochemistry and Photobiology, vol. 84, No. 6, Nov. 1, 2008, pp. 1410-1420.
Ballicora et al., "ADP-Glucose Pyrophosphorylase, a Regulatory Enzyme for Bacterial Glycogen Synthesis", Microbiology and Molecular Biology Reviews, Jun. 2003, vol. 67, No. 2, 14 pgs.
Barzegari et al. "The Search for a Promising Cell Factory System for Production of Edible Vaccine," Human Vaccines & Immunotherapeutics 10(8):2497-2502 (2014).
Beckmann, et al., "Improvement of light to biomass conversion by de-regulation of light-harvesting protein translation in Chlamydomonas reinhardtii", Journal of Biotechnology, vol. 142, No. 1, Jun. 1, 2009, Elsevier Science Publishers, pp. 70-77.
Bhattacharya et al., "Evaluation of Three Spirulina Species Grown Under Similar Conditions for Their Growth and Biochemicals," Journal of the Science of Food and Agriculture, 2005, vol. 85, pp. 333-336.
Biswas, Avijit, "Identification and characterization of enzymes involved in the biosynthesis of different phycobiliproteins in cyanobacteria" ( 2011). University of New Orleans Theses and Dissertations. 446. Retrieved from the Internet Nov. 19, 2018: URL:https://scholarworks.uno.edu/cgi/viewcontent.cgi?referer=https://www.bing.com/&httpsredir=I&article=1244&context=td, 211 pages.
Blot et al., "Phycourobilin in Trichromatic Phycocyanin from Oceanic Cyanobacteria Is Formed Post-translationally by a Phycoerythrobilin Lyase-Isomerase," J. Biol. Chem., 284(14):9290-8 (2009).
Bouvier-Nave, et al., "Expression in yeast and tobacco of plant cDNAs encoding acyl CoA: diacylglycerol acyltransferase", Eur. J. Biochem, 2000, vol. 267, pp. 85-96.
Buikema et al., "Expression of the Anabaena hetR gene from a copper-regulated promoter leads to heterocyst differentiation under repressing conditions," Proc. Natl. Acad. Sci. USA, 98:2729-2734 (2001).
Burgers et al., "Structure of smAKAP and its regulation by PKA-mediated phosphorylation," FEBS J. 283(11):2132-2148 (2016).
Buschiazzo et al., "Crystal structure of Glycogen Synthase: Homologous Enzymes Catalyze Glycogen Synthesis and Degradation", The EMBO Journal, Jul. 2004, vol. 23, No. 16, 10 pgs.

(56) References Cited

OTHER PUBLICATIONS

Cai Y.A., et al., "Recombinant Phycobiliproteins: Recombinant C-Phycocyanins Equipped with Affinity Tags, Oligomerization, and Biospecific Recognition Domains," Analytical Biochemistry, Mar. 2001, vol. 290(2), pp. 186-204.
Cao Breeding and characterization of amino acid-analogue-resistant mutants of Arthrospira platensis. World Journal of Microbiology and Biotechnology, Rapid Communications of Oxford 30. 423-428 (2013).
Chen et al., "Well-tolerated Spirulina extract inhibits influenza virus replication and reduces virus-induced mortality," Scientific Reports 6(1), pp. 1-11 (2016). Retrieved from the Internet: URL:https://www.nature.com/articles/srep24 253.pdf.
Christensen et al., "Lipid domains of mycobacteria studied with fluorescent molecular probes," Molecular Microbiolof!V 31(5):1561-1572, 1999.
Christie, "Coenzyme A and Acyl Carrier Protein: Structure, Occurrence, Biology and Analysis", retrieved on Sep. 14, 2012, at lipidlibrary.aocs.org, Scottish Crop Research Institute, Feb. 24, 2011, pp. 1-4.
Chung et al., "Insertional inactivation studies of the csmA and csmC genes of the green sulfur bacterium Chlorobium vibrioforme 8327: the chlorosome protein CsmA is required for viability but CsmC is dispensable," FEMS Microbiol. Lett., 1998; 164: 353-361.
Chungjatupornchai et al., "Isolation and Characterization of Synechococcus PCC7942 Promoters: tRNApro Gene Functions as a Promoter" Current Microbiology 38: 210-216, 1999.
Coates et al, "Characterization of Cyanobacterial Hydrocarbon Composition and Distribution of Biosynthetic Pathways", PLOS one, vol. 9, Jan. 2014, pp. 1-12.
Cohen et al., "Construction of biologically functional bacterial plasmids in vitro," Proc. Natl. Acad Sci. US.A. 70:3240-3244 (Nov. 1973).
Coleman et al., "Physiological and Nutritional Regulation of Enzymes of TriacylglycerolSynthesis," Annu. Rev. Nutr. 20:77-103, Jan. 1, 2000.
Cooper, et al., "Evolution of Thermal Dependence of Growth Rate of *Escherichia coli* Populations during 20,000 Generations in a Constant Environment", Evolution, vol. 55, No. 5, 2001, pp. 889-896.
Courchesne, et al., "Enhancement of lipid production using biochemical, genetic and transcription factor engineering approaches", Journal of Biotechnology, Elsevier Science Publishers, Amsterdam, NL, vol. 141, No. 1-2, Apr. 20, 2009, pp. 31-41.
Crawford et al., "Protocol and Reagents for Pseudotyping Lentiviral Particles with SARS-CoV-2 Spike Protein for Neutralization Assays," Viruses. May 6, 2020;12(5):513, 15 pages.
Dahlqvist, et al., "Phospholipid:diacylglycerol acyltransferase: An enzyme that catalyzes the acyl-CoA-independent formation of triacylglycerol in yeast and plants." Proc Natl Acad Sci USA (2000); 97 (12): 6487-6492.
Daniel et al., "Induction of a Novel Class of Diacylglycerol Acyltransferases and Triacylglycerol Accumulation in *Mycobacterium tuberculosis* as It Goes into a Dormancy-Like State in Culture" Journal of Bacteriology 186(15): 5017-5030, Aug. 2004.
Database Uniprot entry P00308. C-phycocyanin-1 alpha chain. [online]. Oct. 24, 2015 [retrieved Nov. 17, 2016). Available on the internet: , 2 pages.
Database Uniprot entry P00312. C-phycocyanin-1 beta chain. [online]. Jun. 24, 2015, 6 pages retrieved Nov. 17, 2016). Available on the internet: , 3 pages.
Daum et al., "Biochemistry, Cell Biology and Molecular Biology of Lipids of *Saccharomyces cerevisiae*," Yeast 14:1471-1510, 1998.
Dauvillee David et al., "Engineering the Chloroplast Targeted Malarial Vaccine Antigens in Chlamydomonas Starch Granules," PloS One 2010, vol. 5, issue 12, e15424, 8 pages.
David et al. "High-Resolution Crystal Structures of Trimeric and Rod Phycocyanin," Journal of Molecular Biology 405(1):201-213 (2010).
Davis et al., "Overproduction of Acetyl-CoA Carboxylase Activity Increases the Rate of Fatty Acid Biosynthesis in *Escherichia coli*," The Journal of Biological Chemistry 275(37):28593-28598, Sep. 15. 2000.
De Philippis et al., "Exocellular polysaccharides from cyanobacteriaand their possible applications," FEMS Microbiol. Reviews, 1998; 22:151-175.
Dehghani J, et.al., "Stable transformation of Spirulina (Arthrospira) platensis: a promising microalga for production of edible vaccines", Applied Microbiology and Biotechnology, Nov. 2018, vol. 102 No. 21, pp. 9267-9278.
Devereux et al. "A comprehensive set of sequence analysis programs for the VAX" Nucleic Acids Research 12(1):387-395 (Jan. 11, 1984).
Dobrikova AG et al, "Effect of partial or complete elimination of light-harvesting complexes on the surface electric properties and the functions of cyanobacterial photosynthetic membranes", Physiologia Plantarum, 2013, 147(2):248-260 Epub Jun. 22, 2012.
Dong et al, "Four Different Methods Comparison for Extraction of Astaxanthin from Green Alga Haematococcus Dluvialis", The Scientific World Journal, vol. 2014, Jan. 2014, Article ID 694305, 6 pgs.
Dorne et al., "Do thylakoids really contain phosphatidylcholine?" Proc. Natl. Acad. Sci. USA, vol. 87, Jan. 1990, pp. 71-74.
Ducat et al. "Engineering Cyanobacteria to Generate High Value Products", Review, Special Issue—Applied Microbiology, Trends in Biotechnology, Feb. 2011, vol. 29, No. 2, 9 pgs.
Duran et al., "The efficient functioning of photosynthesis and respiration in *Synechocystis* sp. PCC 6803 strictly requires the presence of either cytochrome c6 or plastocyanin," J. of Biol. Chem., 2004; 279:7229-7233.
Durdakova et al., Microalgae/cyanobacteria: the potential green future of vitamin B12 production. Critical Reviews in Food Science and Nutrition (2022) https://doi.org/10.1080/10408398.2022.2130156 (Year: 2022).
Espinosa et al., "Cross-talk And Regulatory Interactions Between The Essential Response Regulator Rpab And Cyanobacterial Circadian Clock Output," Proceedings of the National Academy of Sciences, 12(7):2198-2203 (2015).
Extended European Search Report for Application No. EP21194272.7, mailed on Dec. 13, 2021, 12 pages.
Extended European Search Report issued by the European Patent Office for Application No. 19802590.0, dated Feb. 3, 2022, 6 pages.
Fang et al., "Rapid mutation of Spirulina platensis by a new mutagenesis system of atmospheric and room temperature plasmas (ARTP) and generation of a mutant library with diverse phenotypes," PLoS ONE 8, e77046, pp. 1-12 (Oct. 2013).
Fass, D., "Disulfide bonding in protein biophysics." Annu Rev Biophys (2012); 41: 63-79. Epub Dec. 20, 2011.
Fen Wang, "Construction and Transformation of Spirulina platensis Expression Vector" (Chinese Language), Chinese Master's Theses Full-text Database—Basic Sciences, Issue 9, 56 pages including English translation (2009).
Fu et al., "Mass-Spectral Identffication and Purffication of Phycoerythrobilin and Phycocyanobilin," J. Biochem. 179:1-6 (1979).
Fujisawa et al, "Genomic Structure of an Economically Important Cyanobacterium, Arthrospira (Spirulina) Platensis NIES-39", DNA Research 17, Advance Access Publication Mar. 2010, pp. 85-103.
Fukui et al. "Relationship between color development and protein conformation in the phycocyanin molecule", 2004, Dyes and Pigments, vol. 63, p. 89-94.
Gao, et al., "A Novel Cyanophage with a Cyanobacterial Nonbleaching Protein A Gene in the Genome", Journal of Virology, Jan. 2012, vol. 86, No. 1, pp. 236-245.
GenBank, Accession No. BX569694.1, Feb. 2015, www.ncbi.nlm.nih.gov.
GenBank Accession No. CP000100. Synechococcus elongatus PCC 7942, complete genome (Dec. 2007), 3 pages.
Gibson, et al., "Enzymatic assembly of DNA molecules up to several hundred kilobases." Nature Methods (Apr. 12, 2009); 6(5): 343-345.
Glazer et al. "Fluorescent tandem phycobiliprotein conjugates", Sep. 1983, Biophysical Journal, vol. 43, p. 383-386.

(56) References Cited

OTHER PUBLICATIONS

Gormley et al., "Pathogen cross-transmission via building sanitary plumbing systems in a full scale pilot test-rig," PLOS ONE Feb. 10, 2017, 13 pages.
Gribskov and Burgess, "Sigma factors from *E. coli*, B. subtilis, phage SP01, and phage T4 are homologous proteins", Nucleic Acids Res. Aug. 26, 1986; 14(16): 6745-63.
Gu et al., "COVID-19: Gastrointestinal Manifestations and Potential Fecal-Oral Transmission," Gastroenterology. May 2020; 158(6):1518-1519. Epub Mar. 3, 2020.
Hallmann et al., "Gene replacement by homologous recombination in the multicellular green alga Volvox carteri," Proc. Natl. Acad. USA, 1997; 94:7469-7474.
Han et al., "Digestive Symptoms in COVID-19 Patients With Mild Disease Severity: Clinical Presentation, Stool Viral RNA Testing, and Outcomes," Am J Gastroenterol. Jun. 2020;115(6):916-923.
Han et al., "The Cellular Functions of the Yeast Lipin Homolog Pahlp are Dependent on Its Phosphatidate Phosphatase Activity" The Journal of Biological Chemistry 282(51): 37026-37035, Dec. 21, 2007.
Han et al., "The *Saccharomyces cerevisiae* Lipin Homolog Is a Mg2+-dependent Phosphatidate Phosphatase Enzyme" The Journal of Biological Chemistry 281(14): 9210-9218, Apr. 7, 2006.
Harker et al., "Biosynthesis of Ketocarotenoids in Transgenic Cyanobacteria Expressing the Algal Gene for B-C-4-Oxygenase, crtO", FEBS Letters 404, Jan. 1997, 6 pgs.
Harwood, "Recent advances in the biosynthesis of plant fatty acids", Biochimica et Biophysica Acta (BBA)—Lipids and Lipid Metabolism, vol. 1301, No. 1-2, May 1, 1996, pp. 7-56.
Hasunuma et al. "Overexpression of flv3 improves photosynthesis in the cyanobacterium *Synechocystis* sp. PCC6803 by enhancement of alternative electron flow," Biotechnology for Biofuels (Dec. 2014) 7:493, pp. 1-10.
He et al., "The high light-inducible polypeptides in Synechocystis PCC6803. Expression and function in high light," J. Biol. Chem., 2001; 276:306-314.
Herranen et al., "Regulation of photosystem I reaction center genes in *Synechocystis* sp. strain PCC 6803 during Light acclimation," Plant Cell Physiol., 2005; 46:1484-1493.
Hickman et al, "Glycogen Synthesis is a Required Component of the Nitrogen Stress Response in Synechococcus Elongatus PCC 7942", Algal Research, Feb. 2013, pp. 98-106.
Hiroaki Kato et al: "Interactions Between Histidine Kinase NbIS and the Response Regulators RpaB and SrrA are Involved in the Bleaching Process of the Cyanobacterium Synechococcus elongatus PCC 7942", Plant and Cell Physiology 52(12):2115-2122 (2011).
Hobbs, et al., "Cloning of a cDNA encoding diacylglycerol acyltransferase from *Arabidopsis thaliana* and its functional expression." FEBS Lett (1999); 452 (3): 145-149.
Hofvander et al., "A prokaryotic acyl-CoA reductase performing reduction of fatty acyl-CoA to fatty alcohol", Elsevier B. B., FEBS Letters, Federation of European Biochemical Societies, 2011, 585, 6 pages.
Hu et al., "Microalgal triacylglycerols as feedstocks for biofuel production: perspectives and advances", The Plant Journal, vol. 54, 2008, pp. 621-639.
Imamura et al., "Growth Phase-dependent Activation of Nitrogen-relatedGenes by a Control Network of Group 1 and Group 2 Factors in a Cyanobacterium*," J. Biol. Chem., 281:2668-2675 (2006).
Imashimizu et al, "Thymine at-5 Is Crucial for cpc Promoter Activity of *Synechocystis* sp. Strain PCC 6714", Journal of Bacteriology, Nov. 2013, vol. 185, No. 21, 4 pgs.
International Search Report and Written Opinion issued by the International Searching Authority for Application No. PCT/US2022/013529, mailed May 6, 2022, 9 pages.
Ip et al. "pH-induced conformational changes of AcrA, the membrane fusion protein of *Escherichia coli* multidrug efflux system," Journal of Biological Chemistry 278(50):50474-50482 (2003).
Iwai et al., "Improved genetic transformation of the thermophilic cyanobacterium, Thermosynechococcus elongatus BP-1," Plant Cell Physiol., 2004; 45:171-175.
Jako, et al., "Seed-Specific Over-Expression of an *Arabidopsis* cDNA Encoding a Diacylglycerol Acyltransferase Enhances Seed Oil Content and Seed Weight." Plant Physiol (2001); 126 (2): 861-874.
Jakobiak et al., "The bacterial paromomycin resistance gene, aphH, as a dominant selectable marker in Volvox carteri," Protist, 2004 155:381-393.
Jantaro et al, "Suppression of the Lethality of High Light to a Quadruple HLI Mutant by the Inactivation of the Regulatory Protein PfsR in Synechocystis PCC 6803", Journal of Biological Chemistry, vol. 281, No. 41, Oct. 2006, 10 pgs.
Jeamton et al., Overcoming Intrinsic Restriction Enzyme Barriers Enhances Transformation Efficiency in Arthrospira platensis CI. Plant and Cell Physiology 58, 822-830 (2017).
Jiang et al., "Inhibition of Fatty Acid Synthesis in *Escherichia coli* in the Absence of Phospholipid Synthesis and Release of Inhibition by Thioesterase Action," Journal of Bacteriology 176(10):2814-2821, 1994.
Jin et al, "Crystal Structure of Potato Tuber ADP-Glucose Pyrophosphorylase", The EMBO Journal, Feb. 2005, vol. 24, No. 4, 11 pgs.
Joet et al., "Involvement of a plastid terminal oxidase in plastoquinone oxidation as evidenced by expression of the *Arabidopsis thaliana* enzyme in tobacco," J Biol Chem. (2002) 277:31623-31630.
Jung et al., "Candidate Genes for the Phycoerythrocyanin Subunit Lyase. Biochemical Analysis of pecE and pecF Interposon Mutants," J. Biol. Chem., 270, 12877-12884 (1995).
Kaczmarzyk et al., "Fatty Acid Activation in Cyanobacteria Mediated by Acyl-Acyl Carrier Protein Synthetase Enables Fatty Acid Recycling," Plant Physiology, vol. 152, Mar. 2010, pp. 1598-1610.
Kahn et al., "rpbA controls transcription of the constitutive phycocyanin gene set in Fremyella diplosiphon," J. Bacterial. 179(24): 7695-7704 (1997).
Kaiser et al., "Fatty Aldehydes in Cyanobacteria Are a Metabolically Flexible Precursor for a Diversity of Biofuel Products", PLOS ONE, vol. 8, No. 3, Mar. 11, 2013, 11 pages.
Kalscheuer and Steinbchel, "A Novel Bifunctional Wax Ester Synthase/Acyl-CoA: Diacylglycerol Acyltransferase Mediates Wax Ester and Triacylglycerol Biosynthesis in Acinetobacter calcoaceticus ADP1." The Journal of Biological Chemistry (2002); 278 (10): 8075-8082.
Kalscheuer, et al., "Analysis of Storage Lipid Accumulation in Alcanivorax borkumensis: Evidence for Alternative Triacylglycerol Biosynthesis Routes in Bacteria", Journal of Bacteriology, vol. 189, No. 3, Feb. 2007, pp. 918-928.
Kalscheuer et al., "Microdiesel: *Escherichia coli* engineered for fuel production," Microbiology 152:2529-2536, 2006.
Kalscheuer et al., "Neutral Lipid Biosynthesis in Engineered *Escherichia coli*: Jojoba Oil-Like Wax Esters and Fatty Acid Butyl Esters," Applied and Environmental Microbiology 72(2):1373-1379, 2006.
Karradt, et. al., "NbIA, a Key Protein of Phycobilisome Degradation, Interacts with ClpC, a HSP100 Chaperone Partner Jf a Cyanobaceterial Clp Protease", The Journal of Biological Chemistry vol. 283, No. 47, Nov. 21, 2008, 18 pages.
Kawata et al., "Transformation of Spirulina platensis strain Cl (*Arthrospira* sp. PCC9438) with Tn5 transposase-transposon DNA-cation liposome complex," Marine Biotechnology. 6, 355-363 (2004).
Khan Z, et.al., "Nutritional and therapeutic potential of Spirulina", Current Pharmaceutical Biotechnology, Oct. 2005, vol. 6 No. 5, pp. 373-379.
Khozin-Goldberg, et al., "Unraveling algal lipid metabolism: Recent advances in gene identification", Biochimie, Masson, Paris, FR, vol. 93, No. 1, Jan. 1, 2011, pp. 91-100.
Kim et al., "Infection and Rapid Transmission of SARS-CoV-2 in Ferrets," Kim et al., 2020, Cell Host & Microbe 27, 704-709. May 13, 2020.
Kindle et al., Stable nuclear transformation of Chlamydomonas using the Chlamydomonas gene for nitrate reductase, J. Cell Biol., 1989; 109:2589-2601, retrieved from jcb.rupress.org on Nov. 6, 2018.

(56) References Cited

OTHER PUBLICATIONS

Kirst et al., "Maximizing photosynthetic efficiency and culture productivity in cyanobacteria upon minimizing the phycobilisome light-harvesting antenna size," Biochim Biophys Acta 1837(10):1653-1654 (2014).
Klanchui et al., Systems Biology and Metabolic Engineering of Arthrospira Cell Factories. Computational and Structural Biotechnology Journal 3(4):e201210015-8, pp. 1-8 (Oct. 2012).
Koksharova et al., "Genetic tools for cyanobacteria," Appl. Micrbiol. Biotechnol. 58:123-137, 2002.
Kurreck, Antisense Technologies, Eur. J. Biochem 2003 270_1628-1644.
Kwon, et al., "Reduced light-harvesting antenna: Consequences on cyanobacterial metabolism and photosynthetic productivity", Algal Research, vol. 2, No. 3, May 24, 2013, pp. 188-195.
Larter, "The Navy is locking down staff at boot camp for up to 90 days," Navy Times, 4 pages, Mar. 25, 2020.
Lawson et al., "Proposal to restrict the genus *Clostridium prazmowski* to *Clostridium butyricum* and related species," International Journal of Systematic and Evolutionary Microbiology 66:1009-1016 (2016).
Lazar, E. et al., "Transforming Growth Factor $\alpha$: Mutation of Aspartic Acid 47 and Leucine 48 Results in Different Biological Activities," Molecular and Cellular Biology, 8(3):1247-1252 (1988).
Lea-Smith, et al., "Phycobilisome-Deficient Strains of *Synechocystis* sp. PCC 6803 Have Reduced Size and Require Carbon-Limiting Conditions to Exhibit Enhanced Productivity," Plant Physiology, vol. 165(2), Jun. 2014, pp. 705-714.
Lenski, et al., "Evolutionary Response of *Escherichia coli* to Thermal Stress", The American Naturalist, vol. 142, Supplement: Evolutionary Responses to Environmental Stress, 1993, pp. S47-S64.
Leung et al., "Enteric involvement of severe acute respiratory syndrome-associated coronavirus infection," Gastroenterology. Oct. 2003;125(4):1011-1017.
Li et al., "Characterization of *Synechocystis* sp. Strain PCC 6803 and Deltanbl Mutants under Nitrogen-Deficient Conditions", Arch Microbial Jun. 29, 2002, vol. 178, No. 4, pp. 256-266.
Li et al., "Role of air distribution in SARS transmission during the largest nosocomial outbreak in Hong Kong," IIndoor Air. Apr. 2005;15(2):83-95. doi: 10.1111/j.1600-0668.2004.00317.x.
Li et al., "Substantial undocumented infection facilitates the rapid dissemination of novel coronavirus (SARS-CoV-2)," Science 2020, 6 pages.
Liang et al, "Carotenoid Biosynthesis in Cyanobacteria: Structural and Evolutionary Scenarios Based on Comparative Genomics", Intl Journal of Biological Sciences, Aug. 2006, 2(4), pp. 197-207.
Liu et al., "CO2-limitation-inducible Green Recovery of fatty acids from cyanobacterial biomass," PNAS Early Edition, www.pnas.org/cgi/doi/10.1073/pnas.1103016108, 2011. (4 pages). es.
Liu et al., "Fatty acid production in genetically modified cyanobacteria," PNAS Early Edition, www.pnas.org/cgi/doi/10.1073/pnas.1103014108, 2011. (6 pages).
Liu et al., "Production and secretion of fatty acids in genetically engineered cyanobacteria," Proc Natl Acad Sci U S A . Jul. 2, 2010, 6 pages.
Lu et al, "Molecular Cloning and Characterization of the pgm Gene Encoding Phosphoglucomutase of *Escherichia coli*", Journal of Bacteriology, Sep. 1994, vol. 176, No. 18, 6 pgs.
Ludwig et al., "Transformation and gene replacement in the facultatively chemoheterotrophic, unicellular cyanobacterium *Synechocystis* sp. PCC6714 by electroporation.," Appl. Microbiol. Biotechnol., 2008; 78:729-735.
Luque et al., "Convergence of two global transcriptional regulators o nitrogen induction of the stress acclimation gene nblA i the cyanobacterium *Synechococcus* sp. PCC 7942," (Molecular Microbiology (2001), 41(4), 937-947).
Maccoll, "Allophycocyanin and energy transfer," Biochima et Biophys Acta. 1657:73-81 (2004).
Macete E., et al., "Safety and Immunogenicity of the RTS,S/AS02A Candidate Malaria Vaccine in Children Aged 1-4 in Mozambique," Tropical Medicine and International Health 2007, vol. 12, No. 1, pp. 37-46.
Macintyre, et al., "Photoacclimation of Photosynthesis Irradiance Response Curves and Photosynthetic Pigments in Microalgae and Cyanobacteria", Journal of Phycology, vol. 38, No. 1, Feb. 1, 2002, pp. 17-38.
Maddox et al, "Elevated Serum Levels in Human Pregnancy of a Molecule Immunochemically Similar to Eosinophil Granule Major Basic Protein", Journal Exp. Med, vol. 158, Oct. 1983, 16 pgs.
Maeda et al., "cis-acting sequences required for NtcB-dependent, nitrite-responsive positive regulation of the nitrate assimilation operon in the cyanobacterium *Synechococcus* sp. strain PCC 7942," J. Bacterial.; 180:4080-4088 (1998).
Makino et al, "Characterization of Cyanobacterial Carotenoid Ketolase CrtW anad Hydroxylase CrtR by Complementation Analysis in *Escherichia coli*", Pant Cell Physiology, Oct. 2008, vol. 49, No. 12, 12 pgs.
Mali et al., "RNA-guided human genome engineering via Cas9", Science. Feb. 15, 2013; 339(6121): 823-6. Epub Jan. 3, 2013.
Marin et al., J. Bacteriol., "Salt-Dependent Expression of Glucosylglycerol-Phosphate Synthase, Involved in Osmolyte Synthesis in the Cyanobacterium*Synechocystis* sp. Strain PCC 6803," 2002; 184:2870-2877.
Marin et al., "Osmotic stress in *Synechocystis* sp. PCC 6803: low tolerance towards nonionic osmotic stress results from lacking activation of glucosylglycerol accumulation," Microbiology, 152, p. 2023-2030, Mar. 13, 2006.
Marin et al., Plant Physiol., "Gene Expression Profiling Reflects PhysiologicalProcesses in Salt Acclimation of *Synechocystis*sp. Strain PCC 6803," 2004; 136:3290-3300.
Martelli et al. "Thermal stability improvement of blue colorant C-Phycocyanin from Spirulina platensis for food industry applications," Process Biochemistry 49(1):154-159 (2014).
Mary et al., "Effects of high light on transcripts of stress-associated genes for the cyanobacteria *Synechocystis* sp. PCC 6803 and Prochlorococcus MED4 and MIT9313," Microbiol., 2004; 150:1271-1281.
Matsui et al., "Microbial Interactions Affecting the Natural Transformation of Bacillus Subtilis in a Model Aquatic Ecosystem," FEMS Microbiology Ecology 45(3):211-218 (2003).
Mcdonald et al., "Flexibility In Photosynthetic Electron Transport: The Physiological Role of Plastoquinol Terminal Oxidase (PTOX)," Biochimica et Biophysica Acta (BBA)—Bioenergetics 1807(8):pp. 954-967 (2011).
Mell et al., Natural Competence and the Evolution of DNA Uptake Specificity. Journal of Bacteriology 196:1471-1483 (2014).
Mendez-Alvarez et al., "Transformation of Chlorobium limicola by a plasmid that confers the ability to utilize thiosufate," J. Bacterial., 176:7395-7397 (1994).
Mermet-Bouvier et al., "A Conditional Expression Vector for the Cyanobacteria *Synechocystis* sp. Strains PCC6803 and PCC6714 or *Synechococcus* sp. Strains PCC7942 and PCC6301" Current Microbiology 28: 145-148, 1994.
Mermet-Bouvier et al., "Transfer and Replication ofRSFI0IO-Derived Plasmids in Several Cyanobacteria of the Genera Synechocystis and Synechococcus," Current Microbiology 27:323-327, 1993.
Miao, et al., "Changes in Photosynthesis and Pigmentation in an agp Deletion Mutant of the Cyanobacterium *Synechocystis* sp.", Biotechnology Letters, Mar. 2003, vol. 25, No. 5, pp. 391-396.
Mongold et al., "Evolutionary Adaptation to Temperature. IV. Adaptation of *Escherichia coli* at a Niche Boundary," Evolution, vol. 50, No. 1, 1996, pp. 35-43.
Moran, "Synechococcus vulcan us J.J.Copeland 1936" page from Algae Base, last updated Apr. 6, 2021. G.M. Guiry in Guiry, M.D. & Guiry, G.M. AlgaeBase. World-wide electronic publication, National University of Ireland, Galway. www.algaebase.org; searched on Oct. 11, 2023. p. 1-2.
Morgan-Kiss et al., "The *Escherichia coli*fadK (ydiD) Gene Encodes an Anerobically Regulated Short Chain Acyl-CoA Synthetase," The Journal of Biological Chemistry 279(36):37324-37333, 2004.

(56) References Cited

OTHER PUBLICATIONS

Moronta-Barrios, et al., "In vivo features of signal transduction by the essential response regulator RpaB from Synechococcus elongatus PCC 7942", Microbiology, vol. 158, No. 5, 2012, pp. 1229-1237.
Muramatsu et al., "Characterization of high-light-responsive promoters of the psaAB genes in *Synechocystis* sp. PCC 6803," Plant Cell Physiol., 47:878-890 (2006).
Nakajima et al., "Improvement of microalgal photosynthetic productivity by reducing the content of light harvesting pigment", Journal of Applied Phycology, Kluwer Academic Publishers, Apr. 1, 1999, pp. 195-201.
Nakajima, et al., "Improvement of photosynthesis in dense microalgal suspension by reduction of light harvesting pigments", Journal of Applied Phycology, vol. 9, Dec. 1, 1997, pp. 503-510.
Nakajima, et al., "Reduced photoinhibition of a phycocyanin-deficient mutant of Synechocystis PCC 6714", Journal of Applied Phycology, vol. 10, No. 5, Jan. 1, 1998, pp. 447-452.
Nakamura et al., "Plastidic Phosphatidic Acid Phosphatases Identified in a Distinct Subfamily of Lipid Phosphate Phosphatases with Prokaryotic Origin," The Journal of Biological Chemistry 282(39):29013-29021, 2007.
NCBI Gene ID 951909 "glgc glucose-1-phosphate adenylyltransferase [*Synechocystis* sp. PCC 6803]" Aug. 2003 downloaded from http://www.ncbi.nlm.nih.gov/gene on Jun. 2, 2011, 2 pages.
NCBI Reference Sequence NC_016640.1, dated Jun. 11, 2013, 1 page.
Nedbal et al., "A photobioreactor system for precision cultivation of photoautotrophic microorganisms and for high-content analysis of suspension dynamics," Biotechnol. Bioeng., 2008; 100:902-910.
Niederholtmeyer, et al., "Engineering cyanobacteria to synthesize and export hydrophilic products," (2010) Applied and Environmental Microbiology 76: 3462-3466.
Nishizuka, "Intracellular Signaling by Hydrolysis of Phospholipids and Activation of Protein Kinase C" Science 258: 607-614, Oct. 23, 1992.
Page et al., "Appln. Environ. Microbiol.," American Society for Microbiology, Jun. 15, 2012, 14 pages.
Page, et al., "Reduction of Photoautotrophic Productivity in the Cyanobacterium *Synechocystis* sp. Strain PCC 6803 bl Phycobilisome Antenna Truncation", Applied and Environmental Microbiology, vol. 78, No. 17, Sep. 1, 2012, pp. 5349-6351.
Perrineau, et al., "Evolution of Salt Tolerance in a Laboratory Reared Population of Chlamydomonas Reinhardtii", Environmental Microbiology, vol. 16, No. 6, 2014, pp. 1755-1766.
Perrone et al., "The Chlamydomonas IDA7 Locus Encodes a 140-kDaDynein Intermediate Chain Required to Assemble the I1 Inner Arm Complex," Molecular Biology of the Cell vol. 9, 3351-3365 (1998).
Qi et al., "Application of the Synechococcus nirA Promoter to Establlish an Inducible Expression System for Engineering the Synechocystis Tocopherol Pathway", Applied and Environmental Microbiology, Oct. 2005, vol. 71, No. 10, 7 pgs.
Qiu et al., "Metabolic engineering of Aeromonas hydrophila for the enhanced production of poly(3-hydroxybutyrate-co-3-hydroxyhexanoate)," Appl. Mircobiol. Biotechnol. 69:537-542, 2006.
Quintana, et al., "Renewable energy from Cyanobacteria: energy production optimization by metabolic pathway engineering," Appl Microbiol Biotechnol 91:471-490 (2011).
Radakovits et al., "Genetic Engineering of Algae for Enhanced Biofuel Production", Eukaryotic Cel, vol. 9, No. 4, Apr. 2010, pp. 486-501.
Ramey et al., Genome Engineering in Cyanobacteria: Where We Are and Where We Need To Go, ACS Synthetic Biol. 4:1186-96 (2015).
Rastogi et al. "Physico-chemical factors affecting the in vitro stability of phycobiliproteins from Phormidium rubidum A09DM", Apr. 29, 2015, Bioresource Technology, vol. 190, p. 219-226.
Robertson, et al., "The absolute configurations and pharmacological activities of the optical isomers of fluoxetine, a selective serotonin-uptake inhibitor", Journal of Medicinal Chemistry (1988); 31(7): 1412-1417.
Ronen-Tarazi et al, "The Genomic Region of rbcLS in *Synechococcus* sp. PCC 7942 Contains Genes Involved in the Ability to Grow Under Low CO2 Concentration and in Chlorophyll Biosynthesis", Plant Physiol., vol. 108, Aug. 1995, 9 pgs.
Rothan and Byrareddy "The epidemiology and pathogenesis of coronavirus disease (COVID-19) outbreak," J Autoimmun. May 2020;109:102433 5 pages. Epub Feb. 26, 2020.
Ruffing, "Engineered cyanobacteria Teaching an old bug new tricks", Bioengineered Bugs, vol. 2, No. 3, May 1, 2011, Sandia National Laboratories, pp. 136-149.
Ruffing, et al., "Physiological Effects of Free Fatty Acid Production in Genetically Engineered Synechococcus elongatus PCC 7942", Biotechnology and Bioengineering, vol. 109, No. 9, Sep. 9, 2012, pp. 2190-2199.
Saha et al., "Cytosolic Triacylglycerol Biosynthetic Pathway in Oilseeds. Molecular Cloning and Expression of Peanut Cytosolic Diacylglycerol Acyltransferase" Plant Physiology 141: 1533-1543, Aug. 2006.
Samartzidou et al., "Transcriptional and posttranscriptional control of mRNA from IrtA, a light-repressed transcript in *Synechococcus* sp. PCC 7002," Plant Physiol., 1998; 117:225-234.
Sato, et al., "sll1961 is a novel regulator of phycobilisome degradation during nitrogen starvation in the yanobacterium *Synechocystis* sp PCC 6803", FEBS Letters 582, 2008, 4 pages.
Schirmer et al., "Microbial Biosynthesis of Alkanes," Science, vol. 329, Jul. 30, 2010, pp. 559-562.
Sendersky, et. al., "NbIC, a novel component required for pigment degradation during starvation in Synechococcus DCC 7942", Molecular Microbiology 58(3), Sep. 22, 2005, 11 pages.
SEQ ID: WP_178888959.1, dated Jun. 7, 2022, 1 page.
Sharp and Li, "The codon Adaptation Index—a measure of directional synonymous codon usage bias, and its potential applications." Nucleic Acids Res (1987); 15(3): 1281-1295.
Singh et al., "Bioactive Compounds from Cyanobacteria and Microalgae: An Overview," Critical Reviews in Biotechnology 25:73-95, 2005.
Skruglewicz, et al., Edible Algae System—(Growing Spirulina in space). Steps to Growing Spirulina Algae. Blog post (online). Element 14. Oct. 17, 2020 [retrieved on Apr. 1, 2022]. Retrieved from the Internet: https://community.element14.com/challenges-projects/design-challenges/1-meter-of-pi/b/blog/posts/blog-1-eas---steps-to-growing-spirulina-algae], 11 pages.
Smith et al. "Comparison of biosequences", Advances in Applied Mathematics, (1981); 2(4):482-489.
Song, et al., "Exploitation of Oil-bearing Microalgae for Biodiesel," Chinese Journal of Biotechnology, vol. 24, No. 1, Mar. 1, 2008, pp. 341-348, retrieved on Mar. 1, 2008.
Soni, R.A., et al., "Spirulina—From growth to nutritional product: A review," Trends in Food Science & Technology, vol. 69, Part A, Nov. 2017, pp. 157-171.
Sorger et al., "Triacylglycerol biosynthesis in yeast," Appl Microbiol Biotechnol, vol. 61, 2003, pp. 289-299.
Specht, E.A., et al., "Algae-based oral recombinant vaccines," Front Microbial, Published on Feb. 17, 2014, vol. 5—2014, URL: https://doi.org/10.3389/fmicb.2014.00060, 7 pages.
Steinbrenner et al., "Transformation of the Green Alga Haematococcus pluvialis with a Phytoene Desaturase for Accelerated Astaxanthin Biosynthesis," Appl Environ. Microbiol., 2006; 72:7477-7484.
Stoveken, et al., "Bacterial Acyltransferases as an Alternative for Lipase-Catalyzed Acylation for the Production of Oleochemicals and Fuels," Angew. Chem Int. Ed. 47: 3688-3694 (2008).
Stoveken, et al., "The Wax Ester Synthase/Acyl Coenzyme A:Diacylglycerol Acyltransferase from *Acinetobacter* sp. Strain ADP1: Characterization of a Novel Type of Acyltransferase." J Bacteriol (2005); 187 (4): 1369-1376.
Su et al. Structural insights into the cold adaptation of the photosynthetic pigment-protein C—phycocyanin from an Arctic cyanobacterium. Biochimica et Biophysica Acta 1858:325-335 (2017).

(56) References Cited

OTHER PUBLICATIONS

Sun et al., "Functional complementation of a nitrate reductase defective mutant of a green alga Dunaliella viridis by introducing the nitrate reductase gene," (2006) Gene, 377: 140-149 (2006).
Suzuki, et al., "Carbohydrate Metabolism in Mutants of the Cyanobacterium Synechococcus elongatus PCC 7942 Defective in Glycogen Synthesis", Applied and Environmental Microbiology, vol. 76, No. 10, May 15, 2010, pp. 3153-3159.
Swanson, et al., "Characterization of Phycocyanin Produced by cpcE and cpcF Mutants and Identification of an Identification of an Intergenic Suppressor of the Defect in Bilin Attachment", The Journal of Biological Chemistry, vol. 267, No. 23, The American Society for Biochemistry and Molecular Biology, Inc., 1992, pp. 16146-16154.
Tan et al., "Establishment of a Micro-Particle Bombardment Transformation Systemfor Dunaliella salina," J. Microbiol., 2005; 43:361-365.
Taton et al. The circadian clock and darkness control natural competence incyanobacteria. Nature Communications 11(1688) pp. 1-11 (Apr. 2020).
Tilzer et al., "Light-Dependence of Photosynthesis and Growth in Cyanobacteria: Implications for their Dominance in Eutropic Lakes," N. England J. Marine and Freshwater Research. 1987. 21: 401-412).
Toyomizu et al., "Effective transformation of the cyanobacterium Spirulina platensis using electroporation," J Applied Phycology. 13, 209-214 (2001).
Uniprot, Accession No. 054715, 2015, www.uniprot.org., 3 pages.
UniProt Accession No. A0A0D2CT51 (A0A0D2CT51_9EURO), Apr. 29, 2015 [online]. [Retrieved on Apr. 6, 2022], 8 pages, Retrieved from the InternetURL:https://www.uniprot.org/uniprot/AOAOD2CT51.
UniProt Accession No. A0A510UPM1 (A0A510UPM1_9CELL), Oct. 16, 2019 [online]. 8 pages, [Retrieved on Apr. 6, 2022]. Retrieved from the Internet URL:https://www.uniprot.org/uniprot/AOA510UPM1.
Uniprot, Accession No. Q7U4P2, 2015, www.uniprot.org., 1 page.
Van Heeke et al., "The N-terminal Cysteine of Human Asparagine Synthetase is Essential for Glutamine-dependent Activity" The Journal of Biological Chemistry 264(33): 19475-19477, Nov. 25, 1989.
Voelker et al., "Alteration of the Specificity and Regulation of Fatty Acid Synthesis of *Escherichia coli* by Expression of a Plant Medium-Chain Acyl-Acyl Carrier Protein Thioesterase," Journal of Bacteriology 176(23):7320-7327, 1994.
Wada et al., "Temperature-Induced Changes in the Fatty Acid Composition of the Cyanobacterium, Synechocystis PCC6803", Plant Physiology, American Society of Plant Physiologists, Rockville, MD, US, vol. 92, Jan. 1, 1990, pp. 1062-1069.
Waditee et al., "Overexpression of a Na+/H+ antiporter confers salt tolerance on a freshwater cyanobacterium, making it capable of growth in sea water," PNAS 99 (6):4109-4114 (2002).
Waltermann et al., "Key enzymes for biosynthesis of neutral lipid storage comounds in prokaryotes: Propoerties, function and occurrence of wax ester synthases/acyl-CoA:diacylglycerol acyltransferases", Biochimie 89, 2007, pp. 230-242.
Waltermann et al., "Mechanism of lipid-body formation in prokaryotes: how bacteria fatten up," Molecular Microbiology 55(3):750-763, 2005.
Waltermann et al., "Neutral Lipid Bodies in Prokaryotes: Recent Insights into Structure, Formation, and Relationship to Eukaryotic Lipid Depots," Journal of Bacteriology 187(11):3607-3619, 2005.
Wang, "Conditional Investigation on the Electroporation to Transformation for Spirulina platensis" (Chinese Language), High-tech Communication, Issue 10, 13 pages including English translation (2002).
Welch et al., "Design Parameters to Control Synthetic Gene Expression in *Escherichia coli*," PLoS One, Sep. 2009, vol. 4, Issue 9, e7002, 10 pages.
Welch et al., "You're one in a googol: optimizing genes for protein expression," J. of the Royal Society, Interface 6 (Suppl 4):S467-S476 (2009).
WHO, WHO issues consensus document on the epidemiology of SARS, Wkly Epidemiol Rec (WER) 78 (43), 2003: 373-375.
Wikipedia, Spirulina (dietary supplement), dated Feb. 28, 2024, pp. 1-2.
Wirth et al., "Transformation of various species of gram-negative bacteria belonging to 11 different genera bv electroporation," Mal. Gen. Genet. 216:175-177, 1989.
Wrapp et al., "Cryo-EM Structure of the 2019-nCoV Spike in the Prefusion Conformation," bioRxiv, 30 pages. Feb. 15, 2020.
Wu, et al., "Modification of carbon partitioning to enhance PHB production in *Synechocystis* sp. PCC6803", Enzyme Microb. Technol., 2002, vol. 30, pp. 710-715.
Xiao et al., "Evidence for Gastrointestinal Infection of SARS-CoV-2," Gastroenterol May 2020;158(6):1831-1833, and Supplementary Material pp. E1-E3. Epub Mar. 3, 2020.
Xiaohuan Zheng, "Expression of Human Epidermal Growth Factor hEGF in Spirulina" (Chinese Language), Chinese Master's Theses Full-text Database—Basic Sciences, vol. 12, 9 pages including English translation (2009).
Xu et al., "Characteristics of pediatric SARS-CoV-2 infection and potential evidence for persistent fecal viral shedding," Nat Med, Mar. 13, 2020, 9 pages.
Xu, "Guidelines for Experiments on Marine Organisms" (Chinese), Ocean Press, Jun. 2004, 5 pages (Non-English). Publication No. xxx was cited in an Office Action issued in Chinese patent application No. Appln No. 201580048316.0. The reference is a Chinese Master's thesis entitled, "Study of Expression of Human Epidermal Growth Factor (hEGF) in Spirulina Platensis.".
Xue et al., "A New Strategy for Lipid Production by Mix Cultivation of Spirulina Platensis and Rhodotorula Glutinis," Applied Biochemistry and Biotechnology 160(2):498-500 (2010).
Yan et al., "The Potential for Microalgae as Bioreactors to Produce Pharmaceuticals," International Journal of Molecular Sciences 17(6), pp. 1-24 (2016).
Yen et al., "DGAT enzymes and triacylglycerol biosynthesis," Journal of Lipid Research, 49: 2283-2301 (2008).
Yeo et al., "Enteric involvement of coronaviruses: is faecal-oral transmission of SARS-CoV-2 possible?," Lancet Gastroenterol Hepatol. Apr. 2020;5(4):335-337.
Yiwei Zhu, "Construction of luxAB Expression Vector of Spirulina platensis and Electroporation Transformation" (Chinese Language), Chinese Master's Theses Full-text Database—Basic Sciences, Issue S2, 28 pages including English translation (2011).
Yoskikawa, et al., "Single-Laboratory Validation of a Method for the Determination of C-Phycocyanin and Allophycocyanin in Spirulina (Arthrospira) Supplements and Raw Materials by Spectrophotometry", J_ AOAC Int., 2008 vol. 91 (3), pp. 524-529.
Yu et al., "Production of Eicosapentaenoic Acid by a Recombinant Marine Cyanobacterium, *Synechococcus* sp." Lipids 35(10): 1061-1064, 2000.
Zhang et al., "Crystal Structure of the Carboxyltransferase Domain of Acetyl-Coenzyme a Carboxylase" Science 299: 2064-2067, Mar. 28, 2003.
Zhang et al., "Molecular and serological investigation of 2019-nCoV infected patients: implication of multiple shedding routes," Emerg Microbes Infect. Feb. 17, 2020;9(1):386-389.
Zhang et al., "Molecular effect of FadD on the regulation and metabolism of fatty acid in *Escherichia coli*," FEMS Microbiol. Lett. 259:249-253, 2006.
Zhang et al., "Optimum Conditions for Transformation of *Synechocystis* sp. PCC 6803," J. Microbiol., 2007; 45(5):241-245.
Zhang et al., "Preliminary Studies on the Genetic Transformation of Spirulina Platensis," College of Marine Life Sciences. Ocean University of Qingdao, Qingdao, F. Chen and Y. Jiang (eds.), Algae and their Biotechnological Potential, 263-269 (2001), Jul. 3-6, 2000 in Hong Kong.
Zhang et al., "Study on the Expression of Transthymosin Gene Spirulina and Its Immune-Enhancing Activity" (Chinese), Fujian Journal of Agriculture, vol. 20, Issue 4, pp. 228-232, published on Dec. 31, 2005).

(56) References Cited

OTHER PUBLICATIONS

Zhao et al., "Novel activity of a phycobiliprotein lyase: both the attachment ofphycocyanobilin and the isomerization to phycoviolobilin are catalyzedby the proteins PecE and PecF encoded by the phycoerythrocyaninoperon," FEBS Lett., 469:9-13 (2000).
Zhenlian KE, "Establishment of Transformation and Expression System of Spirulina platensis" (Chinese Language), Chinese Doctor's and Master's Theses Full-text Database (Master's)—Basic Sciences, Issue 1, 41 pages including English translation (2002).
Zhou et al., "The cpcE and cpcF Genes of *Synechococcus* sp. PCC 7002," J. Biol. Chem., 267:16138-16145 (1992).
Algal Resources, vol. 11 No. 1, 2, 2018, p. 58(S02), 8 pages including English machine pages.
Georgianna and Mayfield, "Exploiting diversity and synthetic biology for the production of algal biofuels," Nature 488(7411):329-35 (Aug. 16, 2012).
Jester et al., "Expression and manufacturing of protein therapeutics in spirulina," bioRxiv, 25 pages (Jan. 27, 2021).
Lykidis et al., "Genomic prospecting for microbial biodiesel production," U.S. Department of Energy Office of Science, Biological and Environmental Research Program and The University of California, Lawrence Berkeley National Laboratory, 2008. 39 pages.
Mohd et al., "Agrobacterium: a potent human pathogen," Reviews in Medical Microbiology. 24(4):94-97 (Oct. 2013).
Pourseif et al., "A domain-based vaccine construct against SARS-CoV-2, the causative agent of COVID-19 pandemic: development of self-amplifying mRNA and peptide vaccines," Bioimpacts. 11(1):65-84. (2021). Epub Dec. 10, 2020.
Proceedings of General Meeting of the Japanese Society for Immunology, vol. 31, 2001, p. 240 (3-B-W17-45-O/P), 8 pages including English machine translation.
Zhang et al., Transformation of Cyanobacteria *Synechococcus* sp. PCC7942 and the expression of thymosin $\alpha 1$ using homologous recombination plasmid pUTK, Marine Science, vol. 25, Issue 6, 8 pages including English machine translation (Jun. 30, 2001).
Alterman et al., Inhibition of Rumen Methanogens by a Novel Archaeal Lytic Enzyme Displayed on Tailored Bionanoparticles, Frontiers in Microbiology 9:9:2378, pp. 1-14 (Oct. 9, 2018).
Jester B.W., et al., "Development of Spirulina for the Manufacture and Oral Delivery of Protein Therapeutics," Nature Biotechnology, 2022, vol. 40, pp. 956-964.
Kawata Y et al., "Development of Host Vector Systems for Microalgae III, Transformation of Spirulina Platensis," Bulletin of the Osaka National Research Institute AIST, 1994, vol. 45 No. 2, p. 35-40, (16 pages including English Machine Translation).
Maccoll, "Cyanobacterial Phycobilisomes," Journal of Structural Biology, vol. 124, 311-334 pages 1998.
Muyldermans "Nanobodies: Natural Single-Domain Antibodies" Annual Review of Biochemistry, 2013;82(1) 775-797.
Ryan M.P., et al., "*Brevundimonas* spp: Emerging global opportunistic pathogens," Virulence, 2018, vol. 9(1), pp. 480-493.
Solomon, Katie, The host immune response to Clostridium difficile infection, Therapeutic Advances in Infectious Disease 1(1) 19-35 (2013).
Uniprot, A0A2A2HE75_9EURY, Accession: A0A2AHE75, 2 pages, Feb. 22, 2023 [retrieved Nov. 21, 2024]. Retrieved from the Internet URL: rest.uniprot.org/unisave/A0A2A2HE75?format=txt&versions=14.

* cited by examiner

Oral Spirulina-VHH provides complete protection against campylobacter
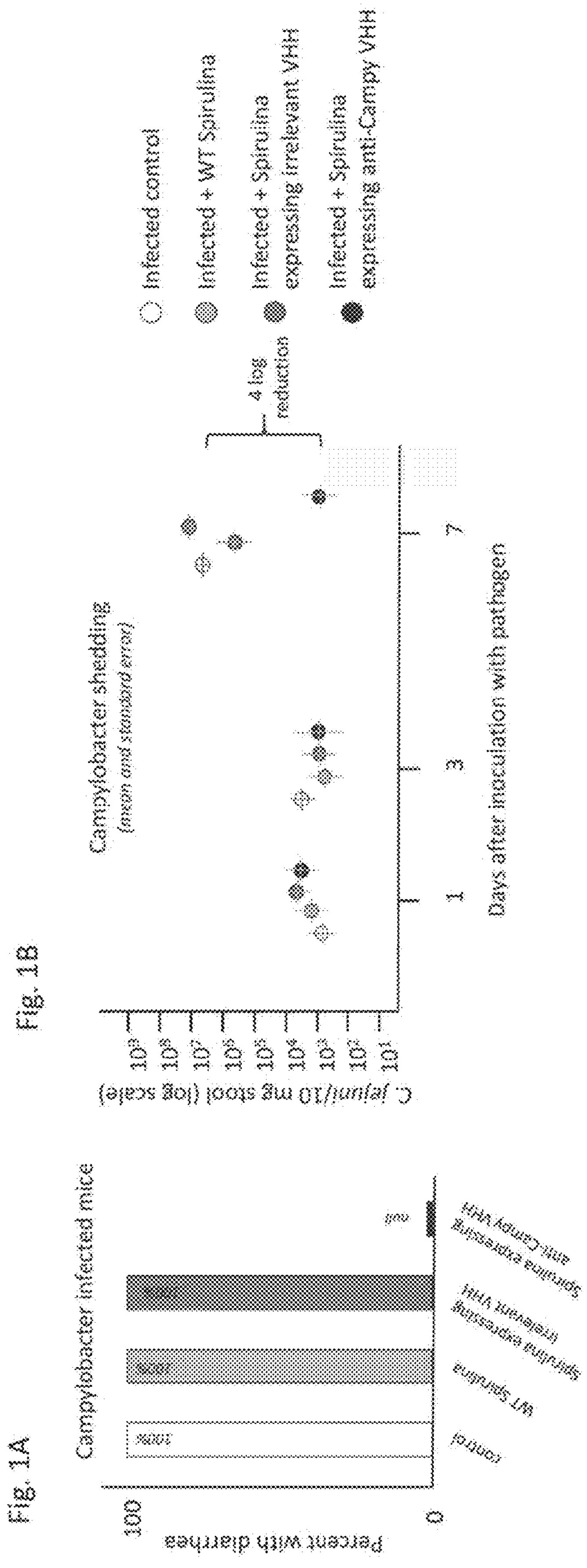

Oral Spirulina-VHH is anti-inflammatory during campylobacter infection 24 h
72 h
body weight variation (g)
CFU/g feces
C. jejuni infected
+ SP526, 1.33 mg
+ SP526, 0.399 mg
+ SP526, 0.133 mg
+ SP806, 1.33 mg
+ SP806, 0.399 mg
+ SP806, 0.133 mg
+ SP651, 1.33 mg
+ SP651, 0.399 mg
+ SP651, 0.133 mg

Encapsulation by Spirulina protects VHH antibodies in the stomach

Simulated stomach environment (pH= 3; pepsin= 2,000 U/ml)

Microscope images of Spirulina/VHH incubated in the simulated stomach environment Long-term stability of anti-Campy VHH in dried biomass Reduction of inflammatory biomarkers Weight Changes in mice pretreated with Spirulina Weight changes and pathogen shedding in mice pretreated with Spirulina body weight variation (g)
Not infected
Only infected
SP651, 1.2 mg
SP257, 1.2 mg 24 h
72 h
CFU/g feces
not infected
only infected
SP651, 1.2 mg
SP257, 1.2 mg
% PMNs (Gr1+CD11b+)
ns LCN2 (ng/g feces)

Weight changes and pathogen shedding in mice pretreated with a protease-resistant variant in Spirulina inflammatory markers and lamina propria leukocyte infiltration in mice pretreated with spirulina LCN2 (ng/g feces)
% PMNs (Gr1+CD11b+)
not infected
C.jejuni infected
+ SP526, 1.2 mg
+ SP526, 0.36 mg
+ SP526, 0.12 mg
+ SP806, 1.2 mg
+ SP806, 0.36 mg
+ SP806, 0.12 mg
+ SP651, 1.2 mg
+ SP651, 0.36 mg
+ SP651, 0.12 mg # chick body weight following inoculation with C. jejuni quantitative Campylobacter colonization in infected birds Anti-PigETEC VHH designed for Protein Expression in Spirulina
Fig. 22A
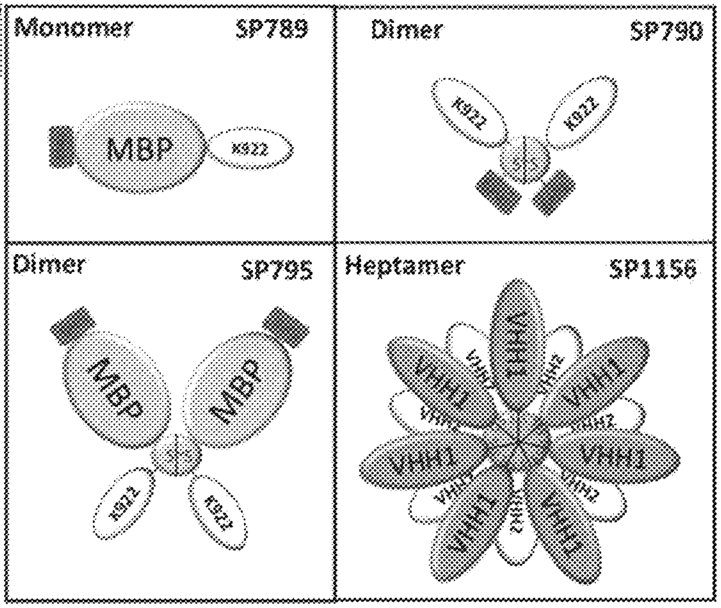
Fig. 22B
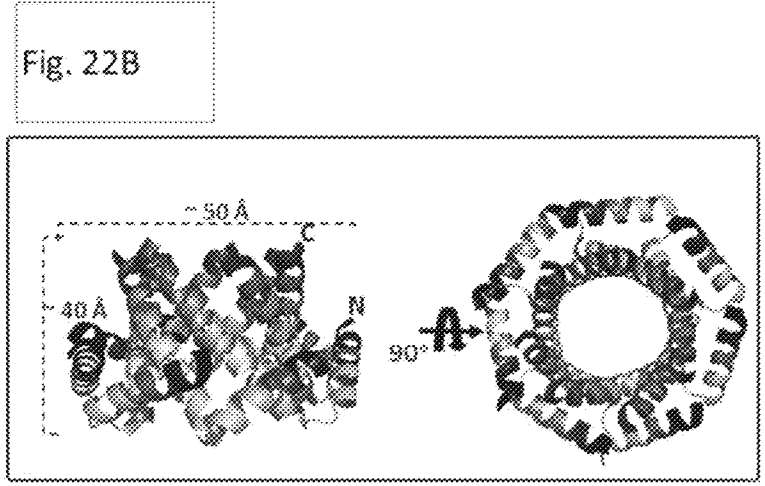
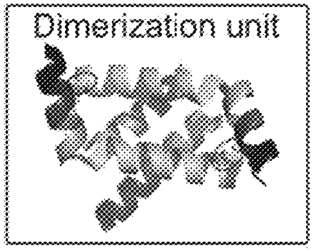
Fig. 22C Anti-Pig ETEC VHH designed for Protein Expression in Spirulina Anti-Pig ETEC VHH designed for Protein Expression in Spirulina Protein expression in Spirulina - Anti-Norovirus P protein VHHs Protein expression in Spirulina - Anti-Norovirus P protein VHHs Protein expression in Spirulina - Anti-Norovirus P protein VHHs Anti-HuNoV VHHs target the most prevalent HuNoV Genotypes

Anti-HuNoV VHHs target the most prevalent HuNoV Genotypes

HBGA blocking assay (surrogate neutralization)

A

HBGA blocking assay (surrogate neutralization)

B

```
Nano-85   QVQLQESGGGLVQPGGSLRLSCAASGSIFSIYAMGWYRQAPGKQRELVASISSGGGTNY
N85_K922  QVQLQESGGGLVQPGGSLRLSCAVS----------WFRQAPGKEREFVAT-------YY
          ***********************.*----------* ****** ** **        *

Nano-85   ADSVKGRFTISGDNAKNTVYLQMNSLKPEDTAVYYCKREDYSAYAPPSGSRGRGTQVTVSS
N85_K922  ADSVKGRFTISRDNAKNTVYLQMNSLKPEDTAVYYCAA------------WGQGTQVTVSS
          *********** ************************               * ********
```

| | SP833_lyo | SP833 | SP834_lyo | SP834 | SP1241_lyo | SP1241 |
|---|---|---|---|---|---|---|
| EC50 (M) | 1.25E-9 | 1.04E-9 | 2.29E-9 | 2.75E-9 | 2.51E-7 | 3.53E-7 |

| | SP835_lyo | SP835 | SP864_lyo | SP864_B1 | SP864_B2 |
|---|---|---|---|---|---|
| EC50 (M) | 3.67E-8 | 2.73E-8 | 2.59E-8 | 2.12E-8 | 1.71E-8 |

Protein expression in Spirulina - Anti-Tumor Necrosis Factor VHH

Protein expression in Spirulina - Anti-Tumor Necrosis Factor VHH

Protein expression in Spirulina - Anti-Tumor Necrosis Factor VHH

| Strain | SP865 | SP1030 |
| --- | --- | --- |
| EC50 | 2.171 | 5.445 |

Anti-TcdB VHH expression in spirulina: Gen 2 5D and E3 multimers

Percent of total protein represented by transgene product

Tri_VHH: ~27 kD

Trx_Tri_VHH: ~39 kD

Trx_Pent_VHH: ~46 kD

Trx_VHH: ~25 kD

Tested against Spirulina lysates at (Hi): 125ug/ml (25nM)
(Lo): 12.5ug/ml (2.5nM)

Fig. 39B Cell Rounding Assay results ("+" is no rounding, "-" is all round, "+/-" is mixed)

| SP968 | | SP981 (5D) | | SP989 (5D) | | SP1090 | | SP1096 | | SP745 | |
|---|---|---|---|---|---|---|---|---|---|---|---|
| Hi/.01 | + | Hi/.01 | + | Hi/.01 | + | Hi/.01 | + | Hi/.01 | + | Hi/.01 | + |
| Hi/.1 | + | Hi/.1 | + | Hi/.1 | + | Hi/.1 | + | Hi/.1 | + | Hi/.1 | + |
| Hi/1. | +/- | Hi/1. | + | Hi/1. | + | Hi/1. | +/- | Hi/1. | +/- | Hi/1. | +/- |
| Lo/.01 | + | Lo/.01 | + | Lo/.01 | + | Lo/.01 | + | Lo/.01 | + | Lo/.01 | + |
| Lo/.1 | + | Lo/.1 | + | Lo/.1 | + | Lo/.1 | + | Lo/.1 | + | Lo/.1 | +/- |
| Lo/1. | +/- | Lo/1. | +/- | Lo/1. | +/- | Lo/1. | - | Lo/1. | - | Lo/1. | - |

| SP974 | | SP982 | | SP990 | | SP1091 (5D) | | SP1097 | | SP746 | |
|---|---|---|---|---|---|---|---|---|---|---|---|
| Hi/.01 | + | Hi/.01 | + | Hi/.01 | + | Hi/.01 | + | Hi/.01 | + | Hi/.01 | + |
| Hi/.1 | + | Hi/.1 | + | Hi/.1 | + | Hi/.1 | + | Hi/.1 | + | Hi/.1 | + |
| Hi/1. | - | Hi/1. | - | Hi/1. | - | Hi/1. | + | Hi/1. | +/- | Hi/1. | + |
| Lo/.01 | + | Lo/.01 | + | Lo/.01 | + | Lo/.01 | + | Lo/.01 | + | Lo/.01 | + |
| Lo/.1 | + | Lo/.1 | + | Lo/.1 | +/- | Lo/.1 | + | Lo/.1 | + | Lo/.1 | + |
| Lo/1. | - | Lo/1. | - | Lo/1. | - | Lo/1. | +/- | Lo/1. | +/- | Lo/1. | +/- |

| SP977 (5D) | | SP985 (5D) | | SP1086 (E3) | | SP1094 | | SP1102 | | SP747 | |
|---|---|---|---|---|---|---|---|---|---|---|---|
| Hi/.01 | + | Hi/.01 | + | Hi/.01 | + | Hi/.01 | + | Hi/.01 | + | Hi/.01 | + |
| Hi/.1 | + | Hi/.1 | + | Hi/.1 | + | Hi/.1 | + | Hi/.1 | + | Hi/.1 | + |
| Hi/1. | + | Hi/1. | + | Hi/1. | + | Hi/1. | +/- | Hi/1. | - | Hi/1. | - |
| Lo/.01 | + | Lo/.01 | + | Lo/.01 | + | Lo/.01 | + | Lo/.01 | + | Lo/.01 | + |
| Lo/.1 | + | Lo/.1 | + | Lo/.1 | + | Lo/.1 | +/- | Lo/.1 | + | Lo/.1 | + |
| Lo/1. | +/- | Lo/1. | +/- | Lo/1. | +/- | Lo/1. | - | Lo/1. | - | Lo/1. | - |

| SP978 | | SP986 | | SP1087 (5D) | | SP1095 (E3/5D) | | SP744 (5D) | | SP994 | |
|---|---|---|---|---|---|---|---|---|---|---|---|
| Hi/.01 | + | Hi/.01 | + | Hi/.01 | + | Hi/.01 | + | Hi/.01 | + | Hi/.01 | +/- |
| Hi/.1 | +/- | Hi/.1 | + | Hi/.1 | + | Hi/.1 | + | Hi/.1 | + | Hi/.1 | - |
| Hi/1. | - | Hi/1. | - | Hi/1. | + | Hi/1. | + | Hi/1. | + | Hi/1. | - |
| Lo/.01 | + | Lo/.01 | + | Lo/.01 | + | Lo/.01 | + | Lo/.01 | + | Lo/.01 | +/- |
| Lo/.1 | +/- | Lo/.1 | +/- | Lo/.1 | + | Lo/.1 | + | Lo/.1 | + | Lo/.1 | - |
| Lo/1. | - | Lo/1. | - | Lo/1. | + | Lo/1. | + | Lo/1. | + | Lo/1. | - |

$2^{nd}$ Vero cell tcdB assay: morphology + cytotoxicity: More refined morphology criteria 5 = All adherent, normal
4 = Perceptible increase in rounded cells, mostly adherent though
3 = Many rounded cells, clear decrease in adherent cells
2 = Mostly rounded, rare adherent cells
1 = No adherent cells, all rounded, often evidence of fragmented cells SP977
5D_dMS2

SP981
5D_dQ$_\beta$

SP985
5D_dPP7

SP1086
Trx_TRI_E3

SP1087
Trx_TRI_5D

SP1091
Trx_PENT_SD

SP1095
E3_Trx_TRI_5D

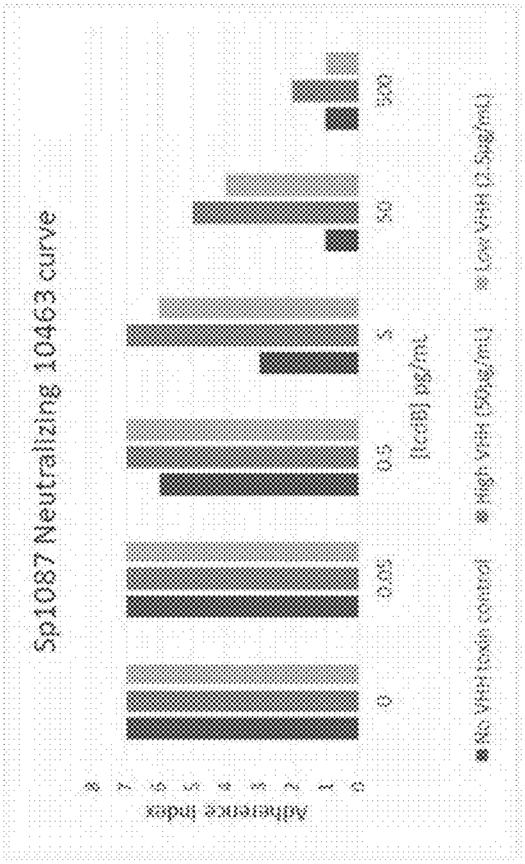
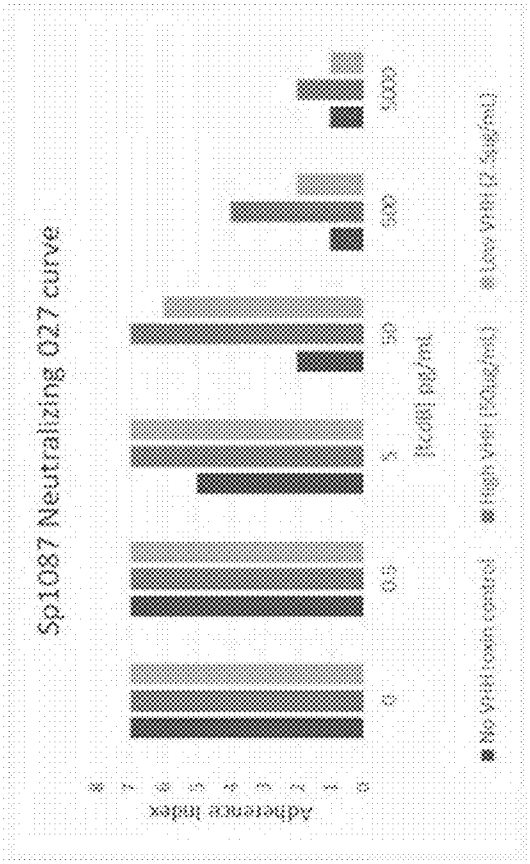
Fig. 41K

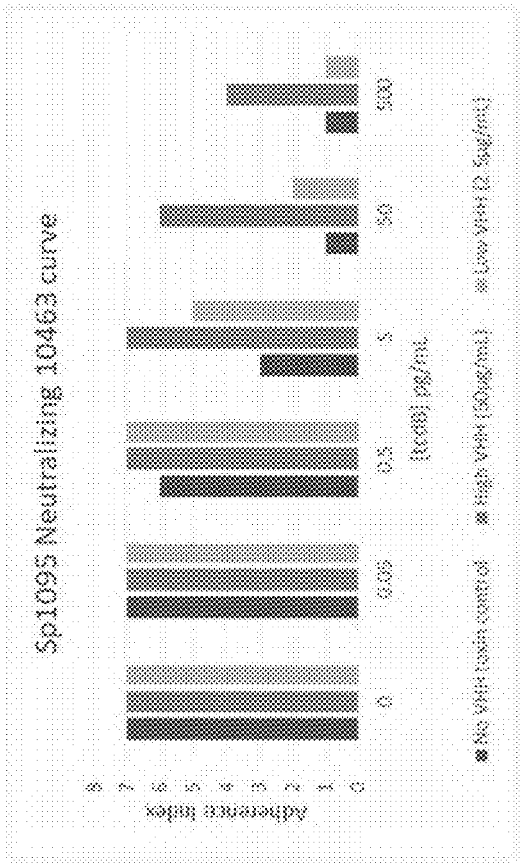
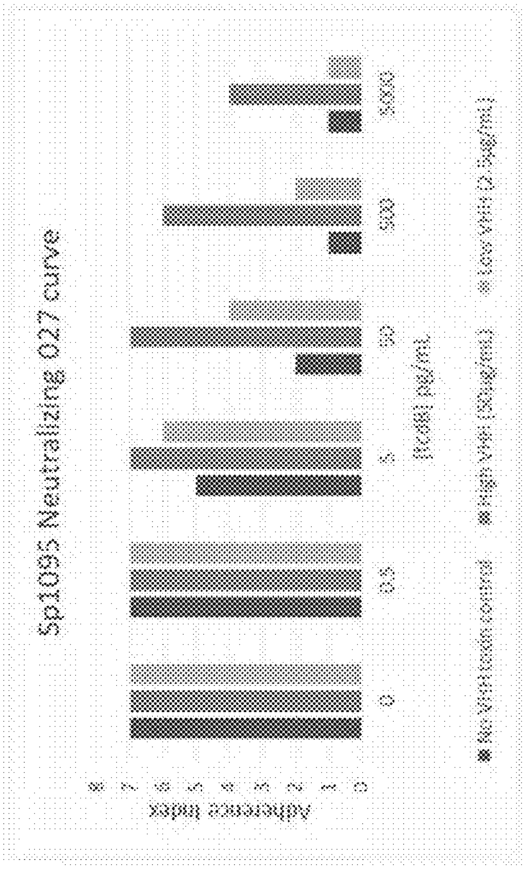
Fig. 41M

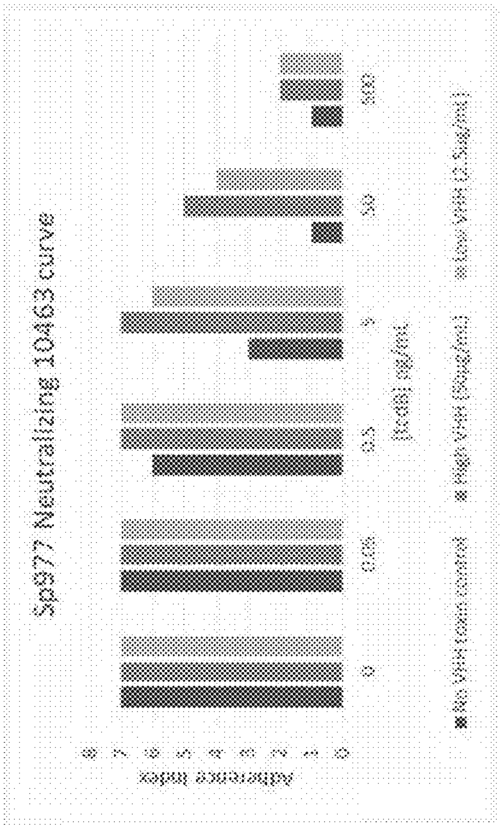
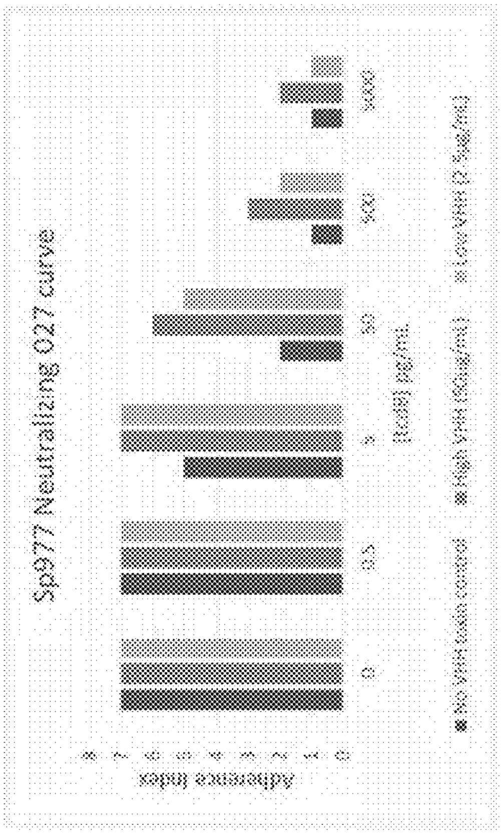
Fig. 41N

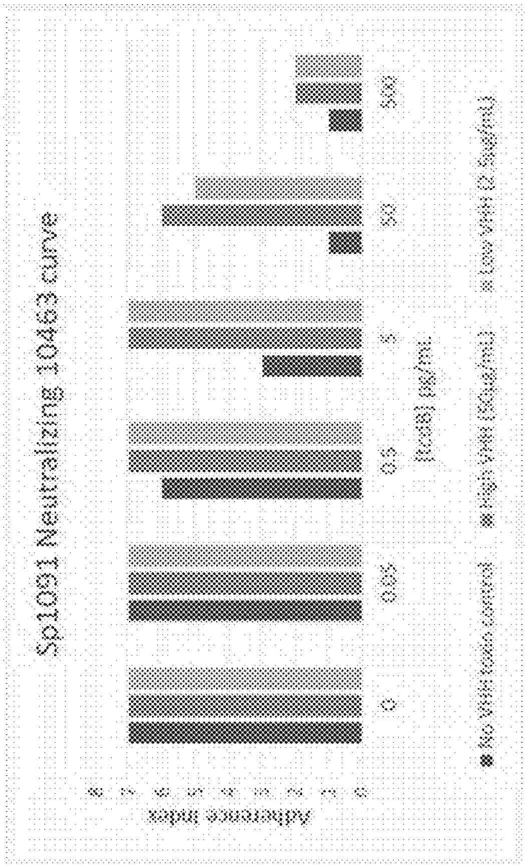
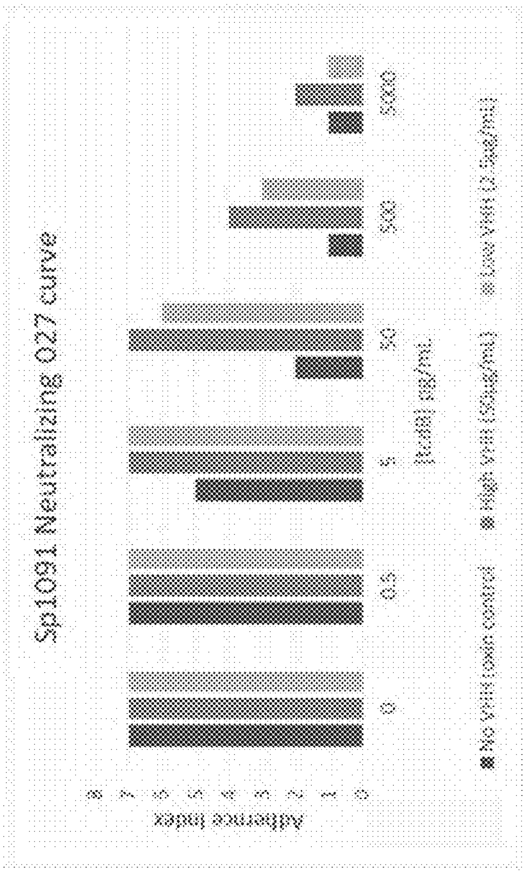
Fig. 41O

| TcdB ng/ml | No VHH | VHH, 100 ng/ml (2 nM) 5D | E3 | 7F | 2D | 5E |
|---|---|---|---|---|---|---|
| 0.00001 | 7 | 7 | 7 | 7 | 7 | 7 |
| 0.0001 | 7 | 7 | 7 | 7 | 7 | 7 |
| 0.001 | 6 | 7 | 7 | 7 | 7 | 7 |
| 0.01 | 5 | 7 | 7 | 6 | 7 | 6 |
| 0.1 | 2 | 6 | 6 | 3 | 3 | 2 |
| 1 | 1 | 3 | 2 | 1 | 1 | 1 |
| 10 | 1 | 1 | 1 | 1 | 1 | 1 |

| | |
|---|---|
| 5D | 0.65nM |
| E3 | 0.03nM |
| 7F | 8.8nM |
| 5E | 0.03nM |
| B12 | 0.07nM |

VHH, 100 ng/ml total

| TcdB ng/ml | none | 5D+E3+7F | 5D+E3+2D | 5D+E3+5E | E3+7F+2D | 5D+7F+5E |
|---|---|---|---|---|---|---|
| 0.00001 | 7 | 7 | 7 | 7 | 7 | 7 |
| 0.0001 | 7 | 7 | 7 | 7 | 7 | 7 |
| 0.001 | 6 | 7 | 7 | 7 | 7 | 7 |
| 0.01 | 5 | 7 | 7 | 7 | 7 | 7 |
| 0.1 | 2 | 7 | 7 | 7 | 6 | 7 |
| 1 | 1 | 7 | 6.1 | 6 | 4 | 4 |
| 10 | 1 | 3 | 2.1 | 2 | 1 | 1 |

VHH, 100 ng/ml total

| TcdB ng/ml | none | SD | E3 | 7F | SD+E3+7F |
|---|---|---|---|---|---|
| 0.00001 | 7 | 7 | 7 | 7 | 7 |
| 0.0001 | 7 | 7 | 7 | 7 | 7 |
| 0.001 | 6 | 7 | 7 | 7 | 7 |
| 0.01 | 5 | 7 | 7 | 6 | 7 |
| 0.1 | 2 | 6 | 6 | 3 | 7 |
| 1 | 1 | 3 | 2 | 1 | 7 |
| 10 | 1 | 1 | 1 | 1 | 3 |

Note: All VHH conditions 100 mg/ml Spirulina lysate

Fig. 45A

TcdB — VHH, 50 ng/ml total (1 nM)

| pM | ng/ml | none | 5D | E3 | 7F | 5D+E3+7F |
|---|---|---|---|---|---|---|
| 1.5 | 0.5 | 1 | 5 | 3 | 1.1 | 7 |
| 15 | 5 | 1 | 2 | 1 | 1.1 | 6 |
| 150 | 50 | 1 | 1 | 1 | 1.1 | 1 |

TcdB — VHH, 500 ng/ml total (10 nM)

| pM | ng/ml | none | 5D | E3 | 7F | 5D+E3+7F |
|---|---|---|---|---|---|---|
| 1.5 | 0.5 | 1 | 6 | 4 | 2 | 7 |
| 15 | 5 | 1 | 2 | 1 | 1.1 | 7 |
| 150 | 50 | 1 | 1 | 1 | 1.1 | 6 |

TcdB — VHH, 5000 ng/ml total (100 nM)

| pM | ng/ml | none | 5D | E3 | 7F | 5D+E3+7F |
|---|---|---|---|---|---|---|
| 1.5 | 0.5 | 1 | 6 | 4 | 2 | 7 |
| 15 | 5 | 1 | 3 | 1 | 1.1 | 7 |
| 150 | 50 | 1 | 1 | 1 | 1.1 | 7 |

Fig. 47A

| | PP7-5D | E3 | 2D | 5E | 7F | B12 | C6 |
|---|---|---|---|---|---|---|---|
| PP7-5D | 100ng/ml | 50 + 50 | → | → | → | → | → |
| E3 | | 100ng/ml | 50 + 50 | → | → | → | → |
| 2D | | | 100ng/ml | 50 + 50 | → | → | → |
| 5E | | | | 100ng/ml | 50 + 50 | → | → |
| 7F | | | | | 100ng/ml | 50 + 50 | → |
| B12 | | | | | | 100ng/ml | 50 + 50 |
| C6 | | | | | | | 100ng/ml |

[TcdB]
300 pg/ml
100 pg/ml
10 pg/ml
0

Fig. 47B

| | PP7-5D | E3 | 2D | 5E | 7F | B12 | C6 |
|---|---|---|---|---|---|---|---|
| PP7-5D | 1<br>2<br>5 | 2<br>5<br>7 | | | | | |
| E3 | | 2<br>4<br>7 | 4<br>6<br>7 | 3<br>5<br>7 | 4<br>5<br>7 | | |
| 2D | | | 1<br>3<br>6 | | 2<br>5<br>7 | 2<br>4<br>7 | |
| 5E | | | | 1<br>1<br>5 | 2<br>3<br>6 | | |
| 7F | | | | | 1<br>1<br>5 | | |
| B12 | | | | | | 1<br>1<br>5 | |
| C6 | | | | | | | 1<br>1<br>2 |

| [TcdB] | No VHH |
|---|---|
| 300 pg/ml | 1 |
| 100 pg/ml | 1 |
| 10 pg/ml | 2 |
| 0 | 7 |

VHH 5D

1. Alpha-helix [GA(EAAAK)$_n$AG], where n= 0, 1, 2, 3
2. Proline-rich helix [G(PA)$_n$G, where n= 0, 5, 10, 15

1. VHH_linker_dPP7.VLP_6xH and/or

2. MBP_Heptamer_linker_VHH_6xH 8 or 16 Constructs/Strains

VHH E3 co-crystalized with TcdB

Clostridium toxin B (TcdB),
co-crystalized with 3 neutralizing VHHs

Fig. 54
5D Constructs, 10 μg/ml lysate
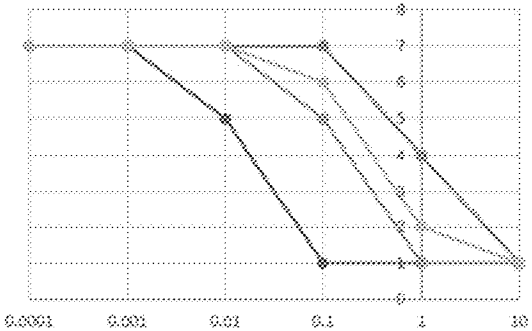
| TcdB (ng/ml) | No VHH | MBP-5D 1306 | MBP-5HVZ-5D 1311 | 5D-AnkC1 1314 |
|---|---|---|---|---|
| 10 | 1 | 1 | 1 | 1 |
| 1 | 1 | 4 | 1 | 2 |
| 0.1 | 1 | 7 | 5 | 6 |
| 0.01 | 5 | 7 | 7 | 7 |
| 0.001 | 7 | 7 | 7 | 7 |
| 0.0001 | 7 | 7 | 7 | 7 |
| 0.0000 1 | 7 | 7 | 7 | 7 |
E3 Constructs , 10 μg/ml lysate
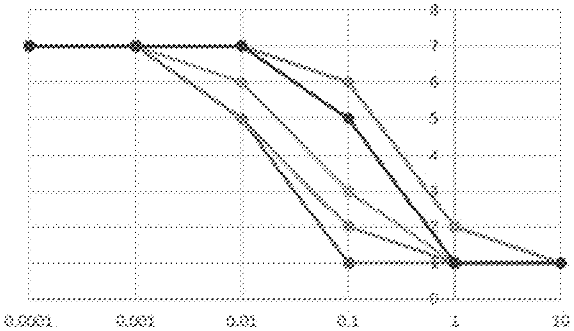
| TcdB (ng/ml) | No VHH | MBP-E3 1307 | MBP-4BoF-E3 1309 | MBP-5HVZ-E3 1312 | E3-AnkC1 1315 | Trx-E35 745 | E3-AP20 968 |
|---|---|---|---|---|---|---|---|
| 10 | 1 | 1 | 1 | 1 | 1 | 1 | 1 |
| 1 | 1 | 2 | 1 | 2 | 1 | 2 | 1 |
| 0.1 | 1 | 6 | 3 | 6 | 2 | 6 | 5 |
| 0.01 | 5 | 7 | 6 | 7 | 5 | 7 | 7 |
| 0.001 | 7 | 7 | 7 | 7 | 7 | 7 | 7 |
| 0.000 1 | 7 | 7 | 7 | 7 | 7 | 7 | 7 |
7F Constructs , 10 μg/ml lysate
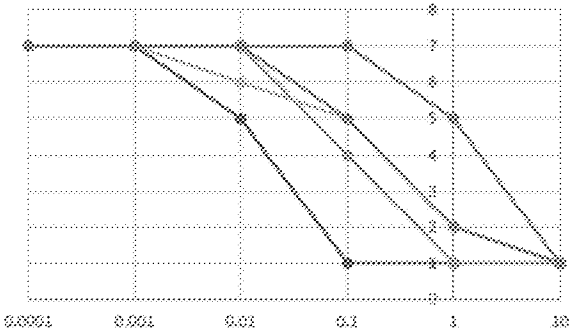
| TcdB (ng/ml) | No VHH | MBP-7F 1308 | MBP-4BoF-7F 1310 | MBP-5HVZ-7F 1313 | 7F-AnkC1 1316 |
|---|---|---|---|---|---|
| 10 | 1 | 1 | 1 | 1 | 1 |
| 1 | 1 | 5 | 1 | 2 | 2 |
| 0.1 | 1 | 7 | 4 | 5 | 5 |
| 0.01 | 5 | 7 | 7 | 6 | 7 |
| 0.001 | 7 | 7 | 7 | 7 | 7 |
| 0.0001 | 7 | 7 | 7 | 7 | 7 |
| 0.0000 1 | 7 | 7 | 7 | 7 | 7 |

Mix 6: 5D+E3+7F, 33.3 μg/ml lysate *each*

| TcdB (ng/ml) | no VHH | Mix 6 | 5D | E3 | 7F |
|---|---|---|---|---|---|
| 25 | 1 | 7 | 1 | 1 | 1 |
| 5 | 1 | 7 | 2 | 1 | 1 |
| 0.5 | 1 | 7 | 5 | 3 | 2 |
| 0.05 | 1 | 7 | 6 | 6 | 6 |

Note: Mix and individual VHHs at 100 μg/ml total

Note: mixture of 3 Spirulina-expressed VHHs substantially more potent than individual constituents Note: Adhesion index is score by visual inspection of proportion of cells of normal morphology, adherent to tissue culture wells.
1=none adherent; 4=50:50 adherent:round/dissociated; 7=normal, all adherent
2=rare adherent; 3=mostly non-adherent; 5=mostly adherent; 6=rare non-adherent

Fig. 57

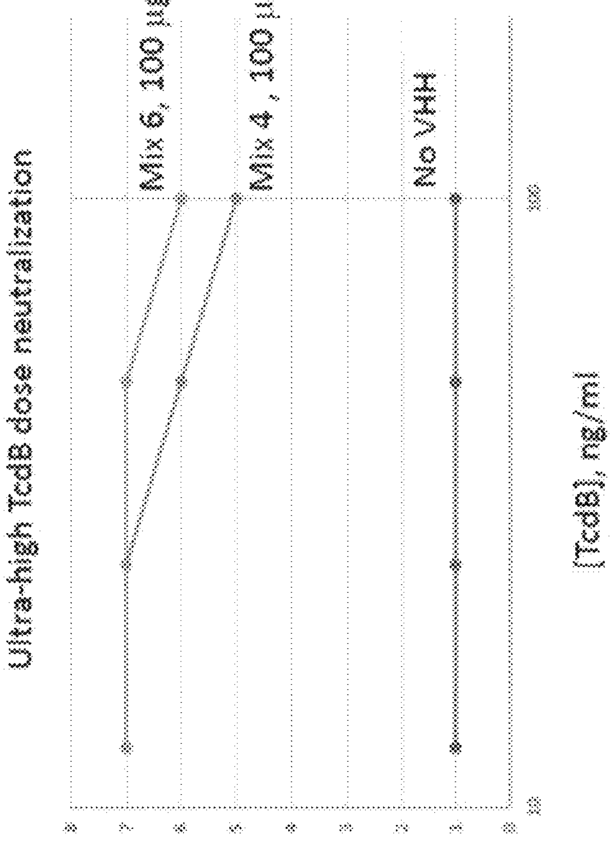

Note: Based on concentration of [TcdB] in human fecal samples from infected patients (mean=4 ng/ml), and likely concentration following 1g ingestion of spirulina containing 1% VHH (~10µg/ml), neutralization properties of spirulina lysates were evaluated.

Data shows that suboptimal VHH concentration (2 µg/ml) can effectively neutralize 25x high-range clinical concentration of TcdB.

| C. jejuni strain: | % identity to 81-176: | ~IC50 | Relevance: |
|---|---|---|---|
| 81-176 | 100% | 30 nM | Highly virulent strain found in humans. |
| 11168 | 78% | 60 nM | Human isolate; complete genome. |
| CG8421 | 77% | 30 nM | Human isolate used in clinical trials. |
| RM1221 | 75% | 60 nM | Chicken isolate; complete genome. |

Fig. 62

A double-blind, placebo-controlled study to evaluate the safety and prophylactic activity of LMN-101 against *C. jejuni* CG8421 (human challenge strain)

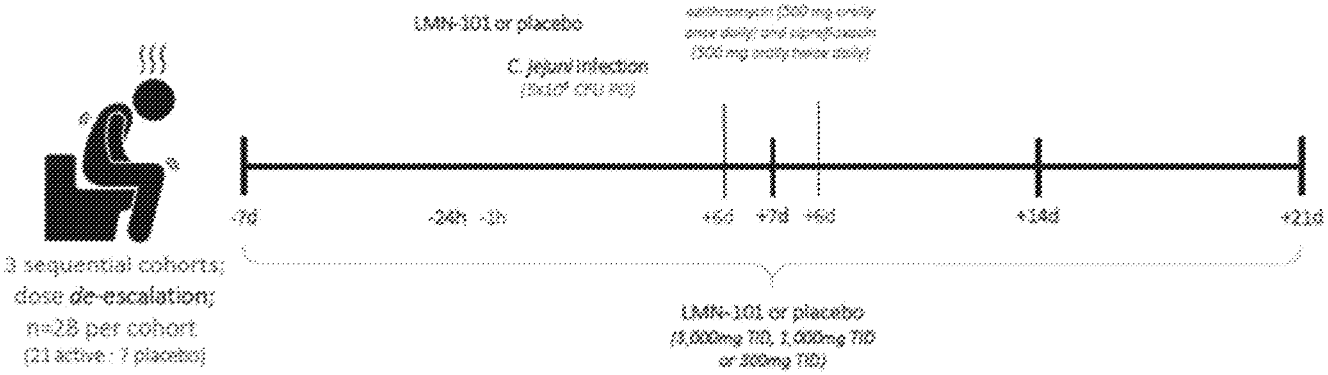

Endpoints:

- Safety and tolerability of LMN-101
- Incidence of campylobacteriosis in high-dose, mid-dose, low-dose and all LMN-101 subjects versus placebo subjects
- Dose-response relationship between LMN-101 and symptoms, including campylobacteriosis incidence
- Duration and severity of campylobacteriosis symptoms in LMN-101 subjects versus placebo subjects
- Rates of recrudescence of campylobacter stool shedding and campylobacteriosis clinical symptoms.
- Biomarkers of inflammation in LMN-101 subjects versus placebo subjects
- Serum pharmacokinetics of LMN-101
- Serum anti-drug antibodies

Fig. 64

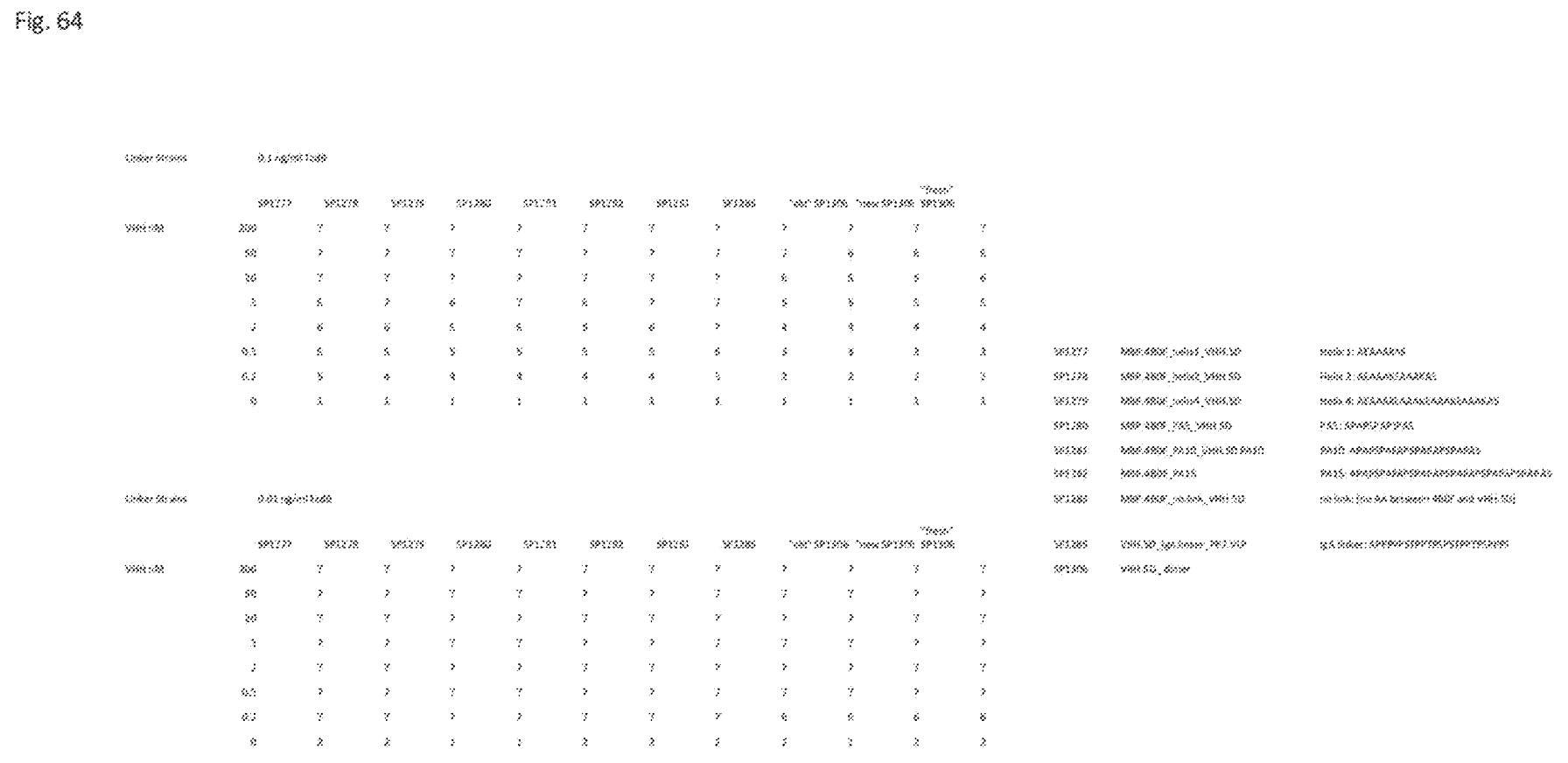

Under Stress [illegible] ug/ml [illegible]

| | | SP1277 | SP1278 | SP1279 | SP1280 | SP1281 | SP1282 | SP1283 | SP1285 | "old" SP1306 | "new" SP1306 | "fresh" SP1306 |
|---|---|---|---|---|---|---|---|---|---|---|---|---|
| [illegible] | 200 | 7 | 7 | 7 | 7 | 7 | 7 | 7 | 7 | 7 | 7 | 7 |
| | 50 | 7 | 7 | 7 | 7 | 7 | 7 | 7 | 7 | 6 | 6 | 6 |
| | 20 | 7 | 7 | 7 | 7 | 7 | 7 | 7 | 6 | 5 | 5 | 6 |
| | 5 | 5 | 7 | 6 | 7 | 6 | 7 | 7 | 5 | 5 | 5 | 5 |
| | 2 | 6 | 6 | 5 | 5 | 5 | 6 | 7 | 4 | 5 | 4 | 4 |
| | 0.5 | 5 | 5 | 5 | 5 | 5 | 5 | 6 | 5 | 5 | 3 | 3 |
| | 0.2 | 5 | 4 | 4 | 4 | 4 | 4 | 5 | 2 | 2 | 2 | 3 |
| | 0 | 1 | 1 | 1 | 1 | 1 | 1 | 1 | 1 | 1 | 1 | 1 |

Under Stress [illegible] ug/ml [illegible]

| | | SP1277 | SP1278 | SP1279 | SP1280 | SP1281 | SP1282 | SP1283 | SP1285 | "old" SP1306 | "new" SP1306 | "fresh" SP1306 |
|---|---|---|---|---|---|---|---|---|---|---|---|---|
| [illegible] | 200 | 7 | 7 | 7 | 7 | 7 | 7 | 7 | 7 | 7 | 7 | 7 |
| | 50 | 7 | 7 | 7 | 7 | 7 | 7 | 7 | 7 | 7 | 7 | 7 |
| | 20 | 7 | 7 | 7 | 7 | 7 | 7 | 7 | 7 | 7 | 7 | 7 |
| | 5 | 7 | 7 | 7 | 7 | 7 | 7 | 7 | 7 | 7 | 7 | 7 |
| | 2 | 7 | 7 | 7 | 7 | 7 | 7 | 7 | 7 | 7 | 7 | 7 |
| | 0.5 | 7 | 7 | 7 | 7 | 7 | 7 | 7 | 7 | 7 | 7 | 7 |
| | 0.2 | 7 | 7 | 7 | 7 | 7 | 7 | 7 | 6 | 6 | 6 | 6 |
| | 0 | 2 | 2 | 2 | 2 | 2 | 2 | 2 | 2 | 2 | 2 | 2 |

| | | |
|---|---|---|
| SP1277 | [illegible] | [illegible] |
| SP1278 | [illegible] | [illegible] |
| SP1279 | [illegible] | [illegible] |
| SP1280 | [illegible] | [illegible] |
| SP1281 | [illegible] | [illegible] |
| SP1282 | [illegible] | [illegible] |
| SP1283 | [illegible] | [illegible] |
| SP1285 | [illegible] | [illegible] |
| SP1306 | [illegible] | |

ARTHROSPIRA PLATENSIS NON-PARENTERAL THERAPEUTIC DELIVERY PLATFORM

CROSS REFERENCE TO RELATED APPLICATIONS

This Application is a continuation of International Patent Application No. PCT/US2020/040794 filed Jul. 2, 2020 which claims priority to U.S. Provisional Patent Application No. 62/870,478 filed Jul. 3, 2019, U.S. Provisional Patent Application No. 62/937,995 filed Nov. 20, 2019, and U.S. Provisional Patent Application No. 62/943,075 filed Dec. 3, 2019, the entire contents of each which are incorporated by reference herein.

INCORPORATION BY REFERENCE OF THE SEQUENCE LISTING

The contents of the text file submitted electronically herewith are incorporated herein by reference in their entirety: A computer readable format copy of the Sequence Listing (filename: LUBI-029_03US_Corr_SeqList.ST25txt, date recorded: Apr. 30, 2021, file size≈100 kilobytes).

FIELD

The disclosure is directed to non-parenteral therapeutic compositions. In particular, the disclosure provides oral, nasal, and respiratory (inhalation) compositions comprising recombinant *Spirulina*, wherein the recombinant *Spirulina* comprises one or more exogenous therapeutics.

BACKGROUND

Non-parenteral administration of therapeutics is a convenient, portable, and inexpensive mode of administration. Nasal and oral administration of therapeutics is commonly practices, however, oral therapeutics are exposed to harsh conditions in the digestive tract and may be degraded before they can exert their effect. Further, these therapeutics are expensive to make and require purification of the therapeutic along with the development of compositions that will protect the oral therapeutics from the digestive enzymes and low pH the therapeutic is subjected to after administration. More cost-effective and stable compositions are required for non-parenteral administration.

SUMMARY OF THE INVENTION

The present application solves the problem of cost and exposure of the therapeutic to degradation in the digestive, nasal and respiratory tract by administering the therapeutic to the subject in *Spirulina*. *Spirulina* is a cyanobacterium that can last in the digestive, nasal and respiratory tract, thus protecting the encapsulated therapeutic until the *Spirulina* reaches its destination (e.g. in the gastrointestinal tract). Moreover, *Spirulina* are easily cultivated and harvested, grows rapidly, can be dried to avoid spoilage, and can be consumed raw. Indeed, *Spirulina* is approved for human consumption and is commonly consumed as a supplement.

Provided herein are non-parenteral compositions comprising a recombinant *Spirulina*, wherein the recombinant *Spirulina* comprises at least one exogenous therapeutic, prophylactic molecule or combinations of two or more exogenous therapeutics or prophylactic molecules. The exogenous therapeutic may be a compound produced by microorganisms or plants. In particular, the exogenous therapeutic may be anti-microbial compound or a polypeptide. In some embodiments, the exogenous therapeutic or prophylactic molecule is a VHH and/or a lysin.

In some embodiments, the present disclosure provides non-parenterally delivered compositions comprising a recombinant *Spirulina*, wherein the recombinant *Spirulina* comprises at least one therapeutic or prophylactic molecule, or a combination of two or more therapeutics or prophylactic molecules. In some embodiments, the therapeutic or prophylactic molecule is delivered to the gastrointestinal tract. In some embodiments, the therapeutic or prophylactic molecule is delivered nasally. In some embodiments, the therapeutic or prophylactic molecule is delivered by respiration (inhalation). In some embodiments, the therapeutic or prophylactic molecule is delivered systemically. In some embodiments, the therapeutic or prophylactic molecule is delivered locally.

In some embodiments, the therapeutic or prophylactic molecule is or combination of two or more therapeutics or prophylactic molecules are endogenous *Spirulina* molecule. In some embodiments, the endogenous *Spirulina* molecule is found in higher concentrations than found in naturally-occurring *Spirulina*.

In some embodiments, the therapeutic or prophylactic molecule or combination of two or more therapeutics or prophylactic molecules are exogenous to *Spirulina*. In some embodiments, the exogenous molecule is produced by a different bacteria, parasite, protozoa, virus, phage, algae, animal, or plant.

In some embodiments, the combination contains two or more therapeutic or prophylactic molecules that are endogenous to *Spirulina*. In some embodiments, the combination contains two or more therapeutic or prophylactic molecules that are exogenous to *Spirulina*. In some embodiments, the combination contains two or more therapeutic or prophylactic molecules that are a mixture of endogenous and exogenous to *Spirulina*. In some embodiments, the combination contains two or more therapeutic or prophylactic molecules, where at least one of the therapeutic or prophylactic molecules is present in greater copy numbers (e.g. two times, three times, four times, five times, or more) than another therapeutic or prophylactic molecule present in the combination.

In some embodiments, the exogenous molecule is a polypeptide or a fragment thereof. In some embodiments, the exogenous polypeptide is an antibody or fragment thereof. In some embodiments, the antibody or fragment thereof is selected from the group consisting: of full length antibody, a monospecific antibody, a bispecific antibody, a trispecific antibody, an antigen-binding region, heavy chain, light chain, VHH, VH, VL, a CDR, a variable domain, scFv, Fc, Fv, Fab, $F(ab)_2$, reduced IgG (rIgG), monospecific $Fab_2$, bispecific $Fab_2$, trispecific $Fab_3$, diabody, bispecific diabody, trispecific triabody, minibody, nanobody, IgNAR, V-NAR, HcIgG, or a combination thereof.

In some embodiments, the exogenous polypeptide is selected from the group consisting of: insulin, C-peptide, amylin, interferon, a hormone, a receptor, a receptor agonist, a receptor antagonist, an incretin, GLP-1, glucose-dependent insulinotropic peptide (GIP), an immunomodulatory, an immunosuppressor, a peptide chemotherapeutic, an anti-microbial peptide, magainin, NRc-3, NRC-7, buforin IIb, BR2, p16, Tat, TNFalpha, and chlorotoxin.

In some embodiments, the exogenous polypeptide is an antigen or epitope. In some embodiments, the antigen or epitope is derived from an infectious microorganism, a tumor antigen or a self-antigen associated with an autoimmune disease.

In some embodiments, the exogenous polypeptide is a catalytic enzyme or fragment thereof, such as a lysin, that cleaves the cell wall.

In some embodiments, the recombinant *Spirulina* contains a combination of one or more different antibodies or antibody fragments. In some embodiments, the recombinant *Spirulina* contains a combination of one or more different VHHs. In some embodiments, the recombinant *Spirulina* contains a combination of one or more different antibodies or antibody fragments and one or more polypeptides. In some embodiments, the recombinant *Spirulina* contains a combination of one or more different VHHs and one or more polypeptides. In some embodiments, the recombinant *Spirulina* contains a combination of one or more different VHHs and one or more lysin polypeptides.

In some embodiments, administration of the recombinant *Spirulina* to a subject prevents, treats or ameliorates a disease or disorder. In some embodiments, the disease or disorder is selected from the group consisting of: Celiac Disease, Type 1 diabetes, Type 2 diabetes, cancer, an inflammatory disorder, a gastrointestinal disease, an autoimmune disease or disorder, an endocrine disorder, gastroesophageal reflux disease (GERD), ulcers, high cholesterol, inflammatory bowel disorder, irritable bowel syndrome, crohn's disease, ulcerative colitis, constipation, vitamin deficiency, iron deficiency, and diarrhea.

In some embodiments, administration of the recombinant *Spirulina* to a subject treats, prevents, or ameliorates an infection. In some embodiments, the infection results in disorders such as acute respiratory distress syndrome (ARDS), pneumonia, pericarditis, stroke, and COVID-19.

In some embodiments, the infection is bacterial, viral, fungal, or parasitical. In some embodiments, the bacteria causing the infection is selected from the group consisting of: *E. coli*, Enterotoxigenic *E. coli* (ETEC), *Shigella, Mycobacterium, Streptococcus, Staphylococcus, Shigella, Campylobacter, Salmonella, Clostridium, Corynebacterium, Pseudomonas, Neisseria, Listeria, Vibrio, Bordetella, Helicobacter, Anthrax, Enterohemmorrhagic E. coli* (EHEC), *Enteroaggregative E. coli* (EAEC), and *Legionella.*

In some embodiments, the virus causing the infection is selected from the group consisting of: bacteriophage, RNA bacteriophage (e.g. MS2, AP205, PP7 and Qβ), Coronavirus, Infectious Haematopoietic Necrosis Virus, Parvovirus, Herpes Simplex Virus, Hepatitis A virus, Hepatitis B virus, Hepatitis C virus, Measles virus, Mumps virus, Rubella virus, HIV, Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, White Spot Syndrome Virus, a coronavirus, MERS, SARS, and SARS-CoV-2.

In some embodiments, the fungus causing the infection is selected from the group consisting of: *Aspergillus, Candida, Blastomyces, Coccidioides, Cryptococcus*, and *Histoplasma.*

In some embodiments, the parasite causing the infection is selected from the group consisting of: *Plasmodium, P. falciparum, P. malariae, P. ovale, P. vivax, Trypanosoma, Toxoplasma, Giardia, Leishmania Cryptosporidium*, helminthic parasites: *Trichuris* spp., *Enterobius* spp., *Ascaris* spp., *Ancylostoma* spp. and *Necatro* spp., *Strongyloides* spp., *Dracunculus* spp., *Onchocerca* spp. and *Wuchereria* spp., *Taenia* spp., *Echinococcus* spp., and *Diphyllobothrium* spp., *Fasciola* spp., and *Schistosoma* spp.

In some embodiments, the exogenous polypeptide or a fragment thereof is in a fusion protein.

In some embodiments, the recombinant *Spirulina* comprises a nucleic acid encoding the exogenous polypeptide or fragment thereof. In some embodiments, at least 2, at least 3, at least 4, or at least 5 copies of a nucleic acid sequence encoding the at least one exogenous polypeptide or fragment thereof are present in the recombinant *Spirulina*. In some embodiments, 2, 3, 4, 5, 6, 8, 10, 15, 20, 25, 30, 40, or 50 copies of a nucleic acid sequence encoding the at least one exogenous polypeptide or fragment thereof are present in the recombinant *Spirulina*. In some embodiments, at least 2, at least 3, at least 4, or at least 5 copies of the at least one exogenous polypeptide or fragment thereof are present in a single molecule of the exogenous polypeptide expressed in the recombinant *Spirulina.*

In some embodiments, 2, 3, 4, 5, 6, 8, 10, 15, 20, 25, 30, 40, or 50 copies of the at least one exogenous polypeptide or fragment thereof are present in a single molecule of the exogenous polypeptide expressed in the recombinant *Spirulina.*

In some embodiments, within the molecule of the exogenous polypeptide or fragment thereof, the copies of the exogenous polypeptide are linked in tandem.

In some embodiments, within the molecule of exogenous polypeptide or fragment thereof, the copies of the exogenous polypeptide or fragment thereof are separated by a spacer sequence.

In some embodiments, within the molecule of exogenous polypeptide or fragment thereof, some of the copies of the exogenous polypeptide or fragment thereof are linked in tandem and the remaining copies of the exogenous polypeptide or fragment thereof are separated by a spacer sequence. In some embodiments, the spacer sequence is between about 1 and 50 amino acids long. In some embodiments, more than one spacer sequence is present within the molecule of the exogenous polypeptide or fragment thereof. In some embodiments, the recombinant *Spirulina* comprises at least 2, at least 3, at least 4, or at least 5 different exogenous polypeptides or fragments thereof.

In some embodiments, the fusion protein comprises a carrier or a chaperone protein. In some embodiments, the carrier protein is selected from the group consisting of: maltose binding protein, hedgehog hepatitis virus-like particle, thioredoxin, and phycocyanin. In some embodiments, the fusion protein comprises a scaffold protein.

In some embodiments, the at least one exogenous polypeptide is linked to a scaffold protein at the N-terminus or the C-terminus, or in the body of the scaffold protein. In some embodiments, the scaffold protein is selected from the oligomerization domain of C4b-binding protein (C4BP), cholera toxin b subunit, or oligomerization domains of extracellular matrix proteins. In some embodiments, the at least one exogenous polypeptide and the scaffold protein are separated by about 1 to about 50 amino acids.

In some embodiments, the fusion protein comprises multiple copies of the at least one exogenous polypeptide or fragment thereof, wherein the at least one exogenous polypeptide or fragment thereof and the scaffold protein are arranged in any one of the following patterns: (E)n-(SP), (SP)-(E)n, (SP)-(E)n-(SP), (E)n1-(SP)-(E)n2, (SP)-(E)n1-(SP)-(E)n2, and (SP)-(E)n1-(SP)-(E)n2-(SP), wherein E is the at least one exogenous polypeptide or fragment thereof, SP is the scaffold protein, n, n1, and n2 represent the number of copies of the at least one exogenous polypeptide or fragment thereof.

In some embodiments, the recombinant *Spirulina* comprises an anti-*Campylobacter* VHH. In some embodiments, the *campylobacter* is a *C. jejuni*. In some embodiments, the VHH binds to a *campylobacter* component. In some embodiments, the VHH binds flagellin. In some embodiments, administration increases *Campylobacter* shedding. In some embodiments, administration reduces the levels of biomarkers. In some embodiments, the biomarker is an inflammation biomarker.

In some embodiments, the recombinant *Spirulina* comprises a VHH that binds to an anti-*Clostridium* toxin. In some embodiments, the *Clostridium* is *C. difficile*. In some embodiments, the VHH binds to a *Clostridium* component, toxin A, or toxin B or both. In some embodiments, the VHH comprises the amino acid sequence of any of SEQ ID NO:s 5-17 or fragment thereof.

In some embodiments, the recombinant *Spirulina* comprises a VHH that binds to a norovirus P domain. In some embodiments, the VHH comprises the amino acid sequence of any of SEQ ID NOs: 40-79 or a fragment thereof.

In some embodiments, the recombinant *Spirulina* comprises a VHH that binds to a malaria polypeptide. In some embodiments, the recombinant *Spirulina* comprises a malaria antigen. In some embodiments, the malaria antigen is Circumsporozoite protein (CSP). In some embodiments, the malaria antigen comprises at least one NANP repeat. In some embodiments, the recombinant *Spirulina* comprises a nucleotide sequence encoding a malaria antigen. In some embodiments, the recombinant *Spirulina* comprises an amino acid sequence comprising a malaria antigen. In some embodiments, the recombinant *Spirulina* comprises the molecules of any of SEQ ID NOs: 26-31. In some embodiments, the recombinant *Spirulina* comprising a malaria antigen or VHH is administered intranasally. In some embodiments, the extract of a recombinant *Spirulina* comprising a malaria antigen or VHH is administered intranasally.

In some embodiments, the therapeutic or prophylactic molecule is monomeric.

In some embodiments, the therapeutic or prophylactic molecule is multimeric.

In some embodiments, the therapeutic or prophylactic molecule is trimeric. In some embodiments, the therapeutic or prophylactic molecule is pentameric. In some embodiments, the therapeutic or prophylactic molecule is heptameric. In some embodiments, the multimer is heteromeric. In some embodiments, the multimer is homomeric. In some embodiments, the multimer is arranged in a nanoparticle. In some embodiments, the multimer binds to a target or target molecule at a high affinity. In some embodiments, the multimer binding affinity is greater than that of a monomer or a dimer.

In some embodiments, the multimer has an $EC_{50}$ of over 5 μg/mL. In some embodiments, the multimer has an $EC_{50}$ of over 10 μg/mL. In some embodiments, the multimer has an $EC_{50}$ of about 5 μg/mL to about 40 μg/mL. In some embodiments, the multimer has an $EC_{50}$ of between about 0.10 to about 100 nM. In some embodiments, the multimer has an $EC_{50}$ of between about 0.2 nM to about 55 nM. In some embodiments, the multimer binding affinity is greater than that of a multimer comprising fewer copies of the exogenous therapeutic or fewer copies of combinations of exogenous therapeutics. In some embodiments, administration of *Spirulina* comprising multimeric exogenous therapeutics results in a smaller dose of *Spirulina* for efficacy than administration of a *Spirulina* comprising a monomer of the same exogenous therapeutic.

In some embodiments, the recombinant *Spirulina* is selected from the group consisting of: *A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri Stizenberger, A. jenneri* f. *purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata f. acutissima, A. neapolitana, A. nordstedtii, A. oceanica, A. okensis, A. pellucida, A. platensis, A. platensis* var. non-constricta, *A. platensis* f. *granulate, A. platensis* f. *minor, A. platensis* var. *tenuis, A. santannae, A. setchellii, A. skujae, A. spirulinoides* f. *tenuis, A. spirulinoides, A. subsalsa, A. subtilissima, A. tenuis, A. tenuissima*, and *A. versicolor*. In some embodiments, the recombinant *Spirulina* is non-living. In some embodiments, the recombinant *Spirulina* is dried, spray dried, freeze-dried, or lyophilized.

In some embodiments, the non-parenteral compositions comprise a pharmaceutically acceptable excipient.

In some embodiments, the composition survives in the gastrointestinal tract or a simulated stomach environment. In some embodiments, the composition survives in the gastrointestinal tract or a simulated stomach environment for at least 5 minutes. In some embodiments, the composition survives in the gastrointestinal tract or a simulated stomach environment overnight.

In some embodiments, the composition survives in the nasal cavity. In some embodiments, the composition survives in the upper respiratory tract. In some embodiments, the composition survives in the airway. In some embodiments, the composition survives in the nasal cavity, upper respiratory tract and/or the airway for at least 5 minutes. In some embodiments, the composition survives in the nasal cavity, upper respiratory tract and/or the airway overnight.

In some embodiments, the present disclosure provides method of treating or preventing a disease or disorder in a subject in need thereof, comprising administering to the subject the non-parenterally delivered composition of the disclosure.

In some embodiments, administration of the non-parenterally delivered composition decreases or prevents development of *campylobacter* symptoms.

In some embodiments, administration of the delivered composition decreases or prevents the development of inflammation in the subject.

In some embodiments, the present disclosure provides methods of treating or preventing a *C. difficile* infection comprising administering to a subject the non-parenterally delivered composition of the instant disclosure. In some embodiments, administration of the non-parenterally delivered composition decreases or prevents development of *C. difficile* symptoms. In some embodiments, the present disclosure provides methods of treating or preventing a malaria infection comprising administering the compositions of the instant disclosure via inhalation or intranasally. In some embodiments, inhaled or instranasal administration of the composition decreases or prevents development of malaria symptoms.

In some embodiments, the present disclosure provides methods of treating or preventing a coronavirus infection comprising administering the compositions of the instant disclosure via inhalation or intranasally. In some embodiments, inhaled or instranasal administration of the composition decreases or prevents development of coronavirus symptoms.

In some embodiments, the present disclosure provides methods of treating or preventing a malaria infection comprising administering to a subject the non-parenterally delivered composition of the instant disclosure. In some embodiments, administration of the non-parenterally delivered composition decreases or prevents development of malaria symptoms.

In some embodiments, the present disclosure provides methods of treating or preventing a coronavirus (e.g. SARS, SARS-CoV-2) infection comprising administering to a subject the non-parenterally delivered composition of the instant disclosure. In some embodiments, administration of the non-parenterally delivered composition decreases or prevents development of coronavirus infection symptoms (e.g. ARDS, inflammation).

In some embodiments, provided herein are methods of making the non-parenteral compositions described herein, the method comprising introducing at least one exogenous therapeutic into a *Spirulina*.

In some embodiments, provided herein are methods of making the non-parenteral compositions described herein, the method comprising introducing a nucleic acid sequence encoding the at least one exogenous therapeutic into a *Spirulina*.

In some embodiments, provided herein are non-parenteral antigenic compositions comprising a recombinant *Spirulina*, wherein the recombinant *Spirulina* comprises at least one exogenous antigenic epitope, wherein a nucleic acid sequence encoding the at least one exogenous antigenic epitope is integrated into the *Spirulina* via homologous recombination.

In some embodiments, provided herein are non-parenteral antigenic compositions prepared by a method comprising: introducing a nucleic acid sequence encoding at least one exogenous antigenic epitope into a *Spirulina* and integrating the nucleic acid sequence into the *Spirulina* via homologous recombination.

BRIEF DESCRIPTION OF THE DRAWINGS

FIG. 1A-B shows oral *Spirulina* monomeric anti-*campylobacter* VHH provides complete protection against *campylobacter* infection in mice. Administration of an oral gavage containing 10% *Spirulina* biomass (425 μg of the monomeric VHH per dose) daily for five days stops incidence of diarrhea in *Campylobacter*-infected mice (Panel A) and decreases *Campylobacter* shedding (Panel B) compared to controls.

FIG. 3 A. Mice were infected with $10^8$ CFU *C. jejuni* at time 0, and treated with PBS (infected), *Spirulina* strain SP651 (anti-*C. jejuni*), or SP257 (irrelevant VHH). Body weight variation represents weight change 72 hours post-infection. FIG. 3 B. Caeca from animals were examined and scored for histopathology at 72 hours post-infection.

FIG. 4A. body weight variation at 72 hours post-infection. FIG. 4B. pathogen shedding at 24 and 72 hours post infection. C. stool lipocalin-2 (LCN2) levels and percentage of myeloid cells infiltrating the lamina propria (% PMNs) at 72 hours post-infection. LCN2 was measured by ELISA. Gr1+, CD11b+ myeloid cells infiltrating lamina propria were identified by FACS.

FIG. 5A. body weight changes at 72 hours post-infection. FIG. 5B. pathogen shedding at 24 and 72 hours post infection. White circles represent uninfected control mice. Mice treated with SP526 and SP806 were treated concurrently and therefore used the same uninfected and infected control groups.

VHH in *Spirulina* can still be detected after overnight exposure (Panel A), and the *Spirulina* cells themselves remain intact (Panel B).

Figure 12:
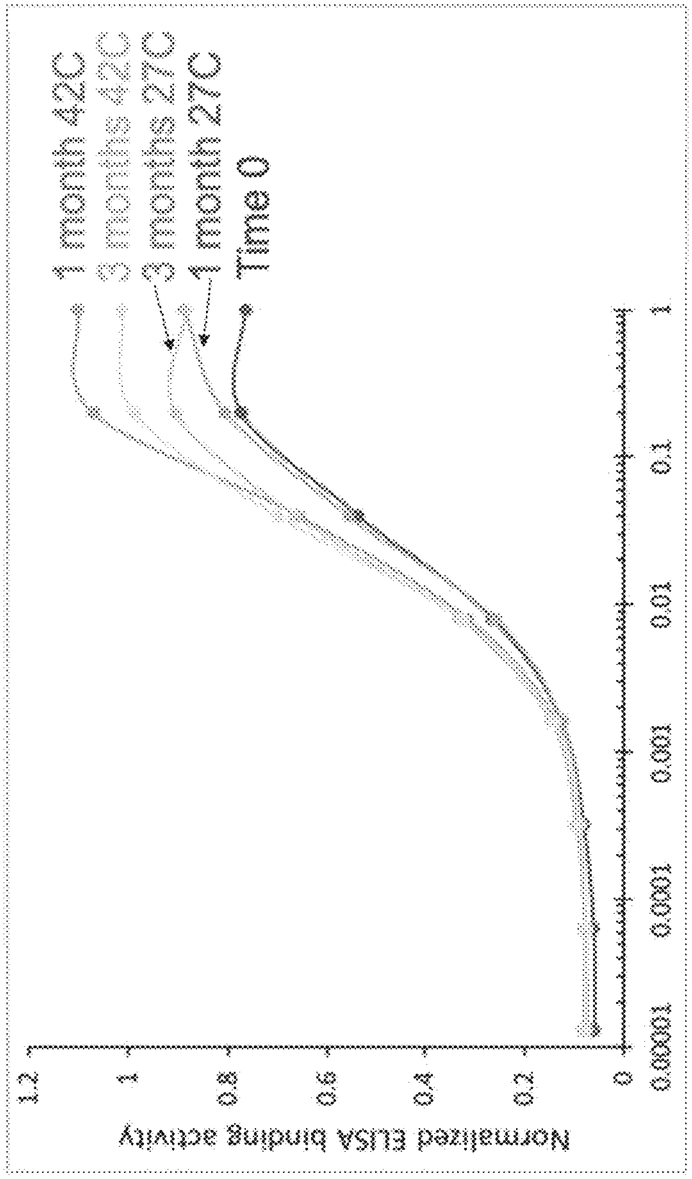

FIG. 12 demonstrates that anti-*campylobacter* expressed in *Spirulina* are stable long-term at elevated temperatures in dried biomass. Each curve represents serial 1:5 dilutions of biomass resuspended in PBS, incubated in ELISA plate wells coated with flagellin antigen, and detected with an anti-His-tag antibody. Results were normalized to the binding activity of the purified VHH assayed at the same.

Figure 13:
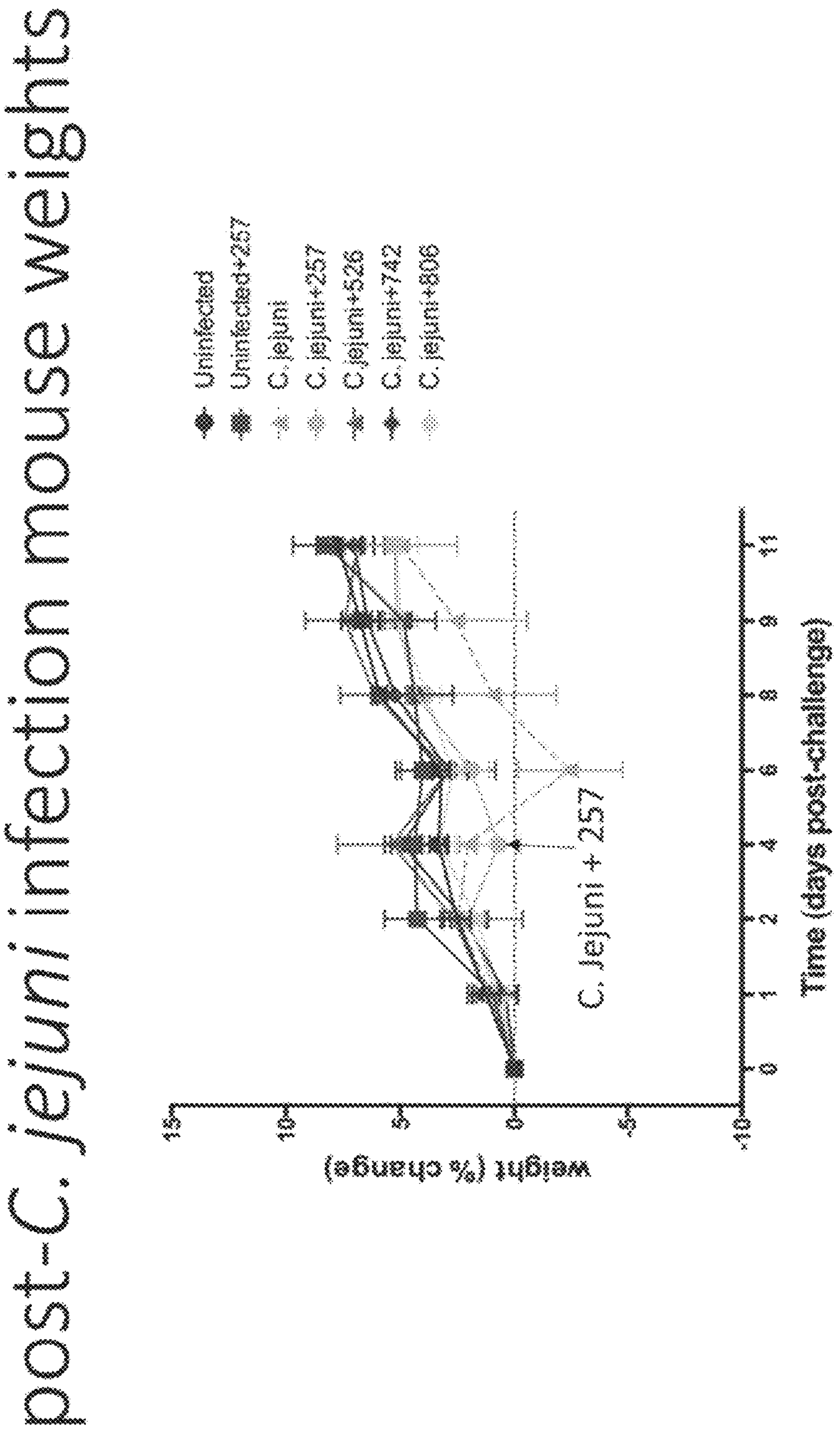

FIG. 13 demonstrates post-*C. jejuni* infection mouse weights. On day 0, mice were weighed, infected with *C. jejuni*, and treated with the indicated *Spirulina* strain (SP257, SP526, SP742, or SP806). Mice were then weighed every 2 days post-infection, and % weight change was calculated based on initial weight.

Figure 14:
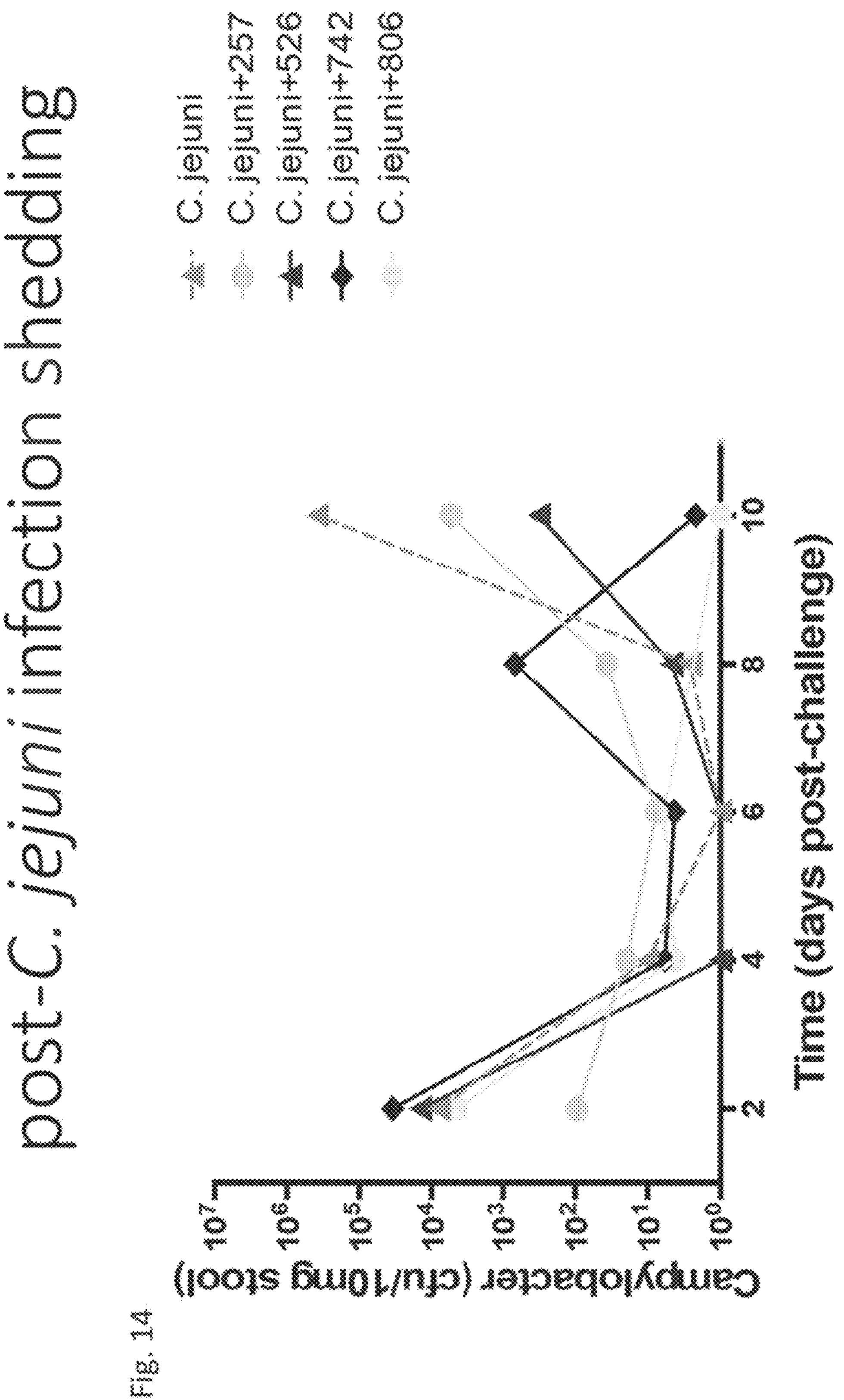

FIG. 14 demonstrates *C. jejuni* shedding. Groups of mice were challenged with *C. jejuni* on day 0 and treated with the indicated *Spirulina* strain (SP257, SP526, SP742, SP806). Every 2 days post-infection, stool samples were collected from each mouse, and the mean *C. jejuni* colony counts (cfu) per 10 mg stool for was measured.

Figure 15:
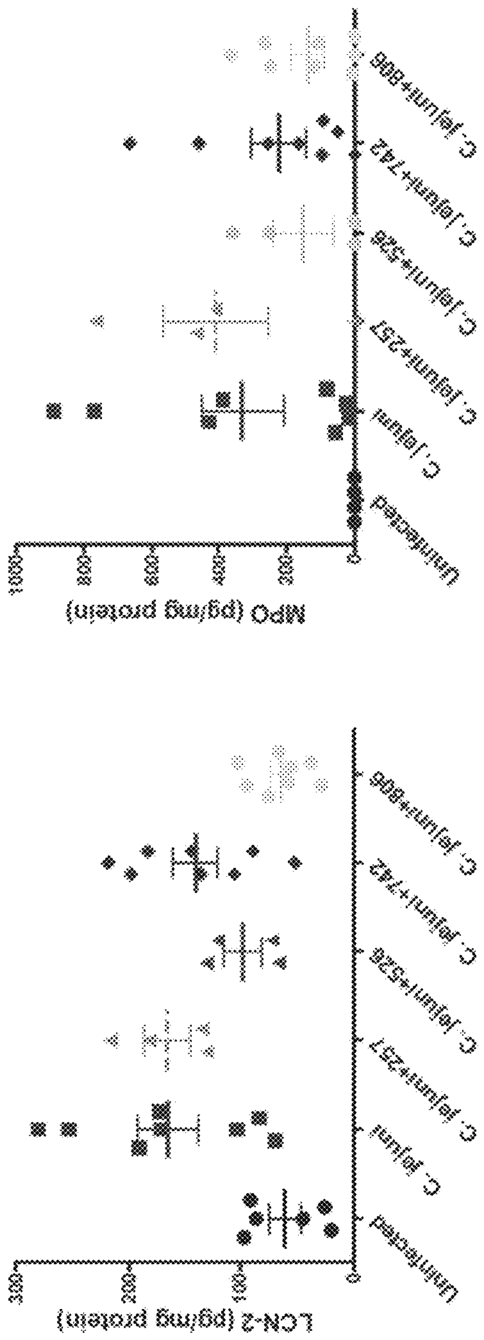

FIG. 15 demonstrates Inflammatory biomarkers in *C. jejuni*-infected mice treated with *Spirulina*. On day 11 post-infection and treatment with the indicated *Spirulina* strain (SP257, SP526, SP742, or SP806), the levels of two inflammatory biomarkers, lipocalin-2 (LCN2) (left) and myeloperoxidase (MPO) (right), were measured in stool samples. Group numbers refer to *Spirulina* strains used for treatment.

Figure 16:
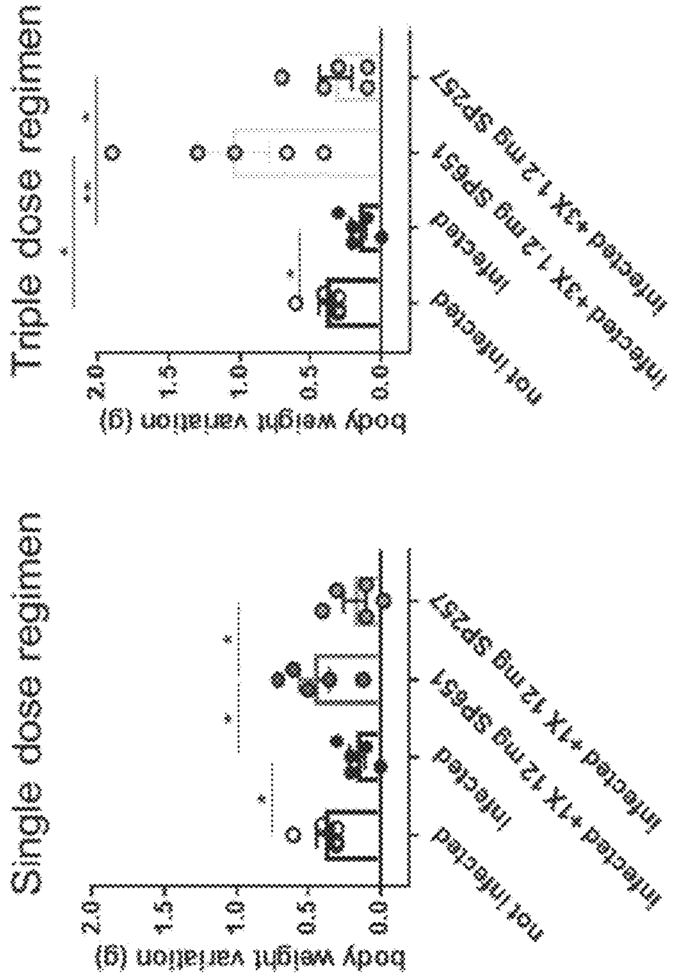

FIG. 16 demonstrates weight changes in mice pretreated with *Spirulina* and infected with *C. jejuni*. Mice were pretreated with one dose (left) or three doses (right) of *Spirulina*. Mice were infected with $10^8$ CFU *C. jejuni* at time 0, and treated with PBS (infected), *Spirulina* strain SP651 (anti-*C. jejuni*), or SP257 (irrelevant VHH). Body weight variation represents weight change 72 hours post-infection.

Figures 17A, 17B, 17C:
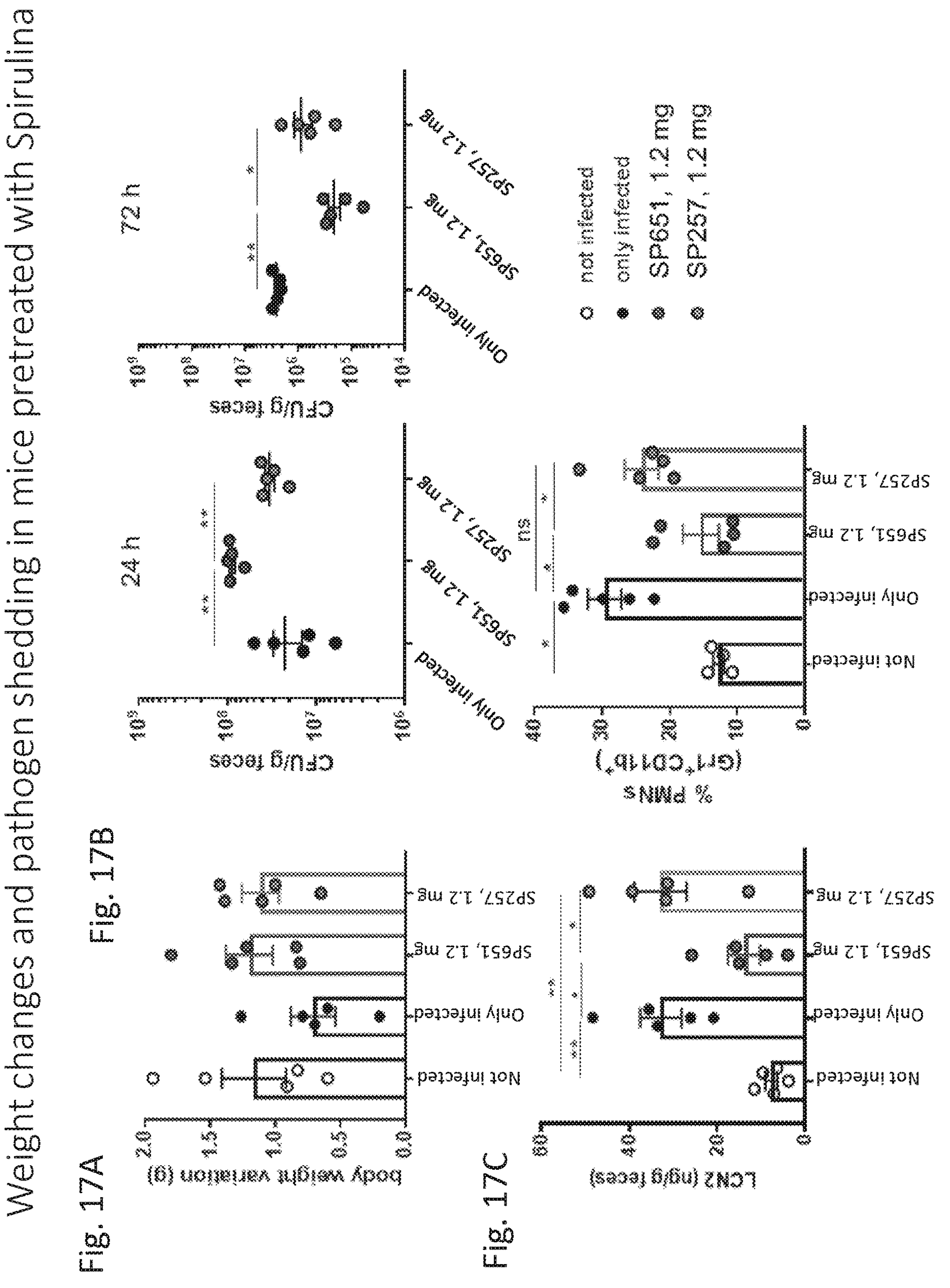

FIG. 17A-C demonstrates weight changes and pathogen shedding in mice pretreated with a single dose of *Spirulina* and infected with *C. jejuni*. Mice were pretreated with 1.2 mg of *Spirulina*, inoculated with 108 CFU *C. jejuni* at time 0, and treated with PBS (infected), *Spirulina* SP651 (anti-*C. jejuni* VHH), or SP257 (irrelevant VHH). A, body weight variation at 72 hours post-infection. B, pathogen shedding at 24 and 72 hours post infection. C, stool lipocalin-2 (LCN2) levels at 72 hours post-infection. D, Gr1+, CD11b+ myeloid cells infiltrating lamina propria were identified by FACS.

Figures 18A, 18B:
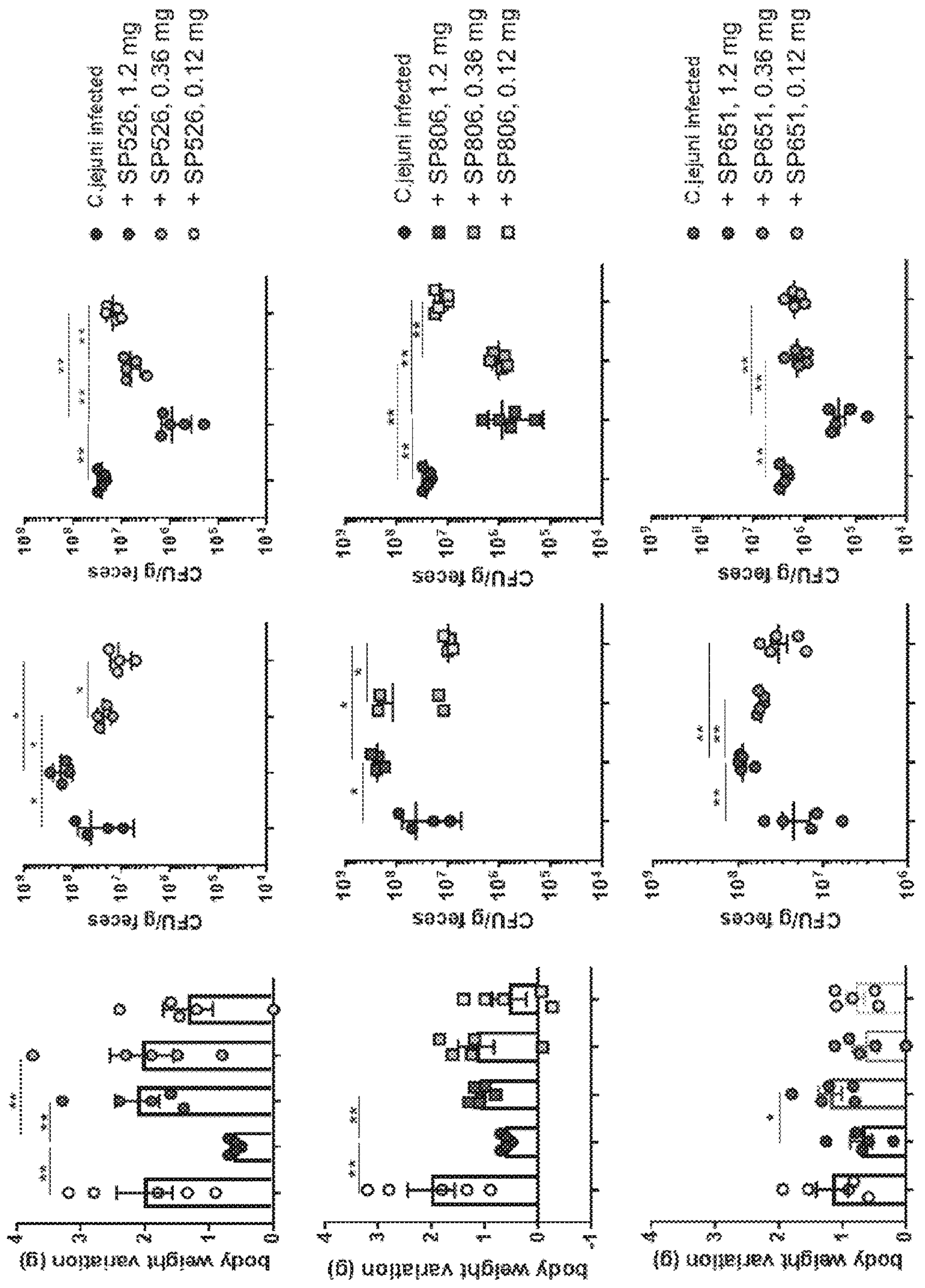

FIG. 18A-B demonstrates weight changes and pathogen shedding in mice pretreated with a protease-resistant VHH variant in *Spirulina* and infected with *C. jejuni*. Mice were pretreated with a single dose of varying concentration of *Spirulina*-VHH, and infected with $10^8$ CFU of *C. jejuni*. Each row of data represents a different treatment strain (SP526, SP806, or SP651). A, body weight changes at 72 hours post-infection. B) pathogen shedding at 24 and 72 hours post infection. White circles represent uninfected control mice. Mice treated with SP526 and SP806 were treated concurrently and therefore used the same uninfected and infected control groups.

Figures 19A, 19B:
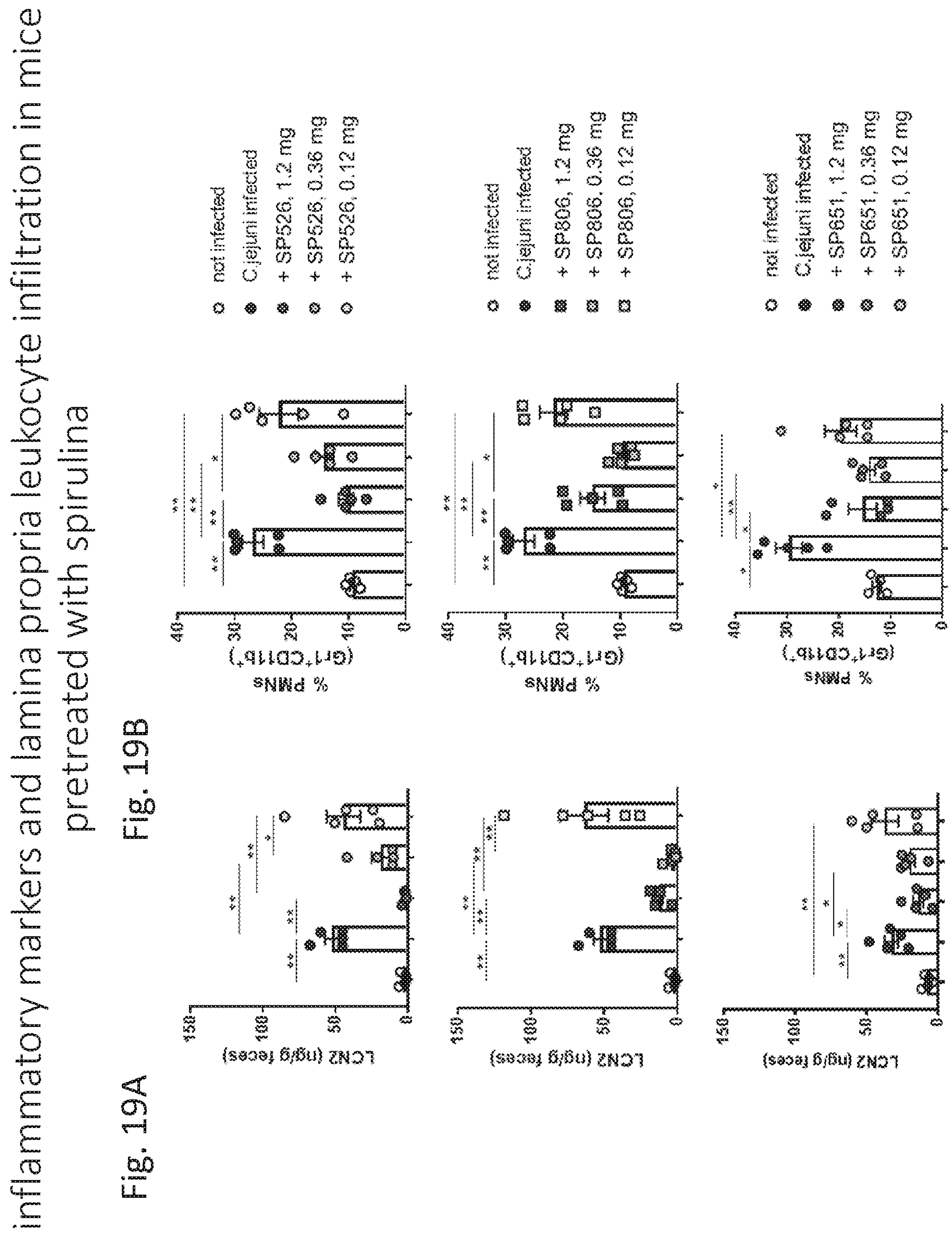

FIG. 19A-B demonstrates inflammatory markers and lamina propria leukocyte infiltration in mice pretreated with *Spirulina* and infected with *C. jejuni*. Mice were pretreated with a single dose of varying concentrations of *Spirulina*-VHH and infected with $10^8$ CFU of *C. jejuni*. Each row of data represents a different treatment strain (SP526, SP806, or SP651). A, stool lipocalin-2 (LCN2) levels 72 hours post-infection. B, Gr1+, CD11b+ myeloid cells infiltrating lamina propria were identified by FACS. White circles represent uninfected control mice. Mice treated with SP526 and SP806 were treated concurrently and therefore used the same uninfected and infected control groups FIG. 20 demonstrates chick body weight following inoculation with *C. jejuni*. Birds were treated with therapeutic (SP526, SP651), irrelevant (SP257), or no *Spirulina* (Campy) prior to inoculation with *C. jejuni* 81-176, and weights measured at intervals.

Figure 21:
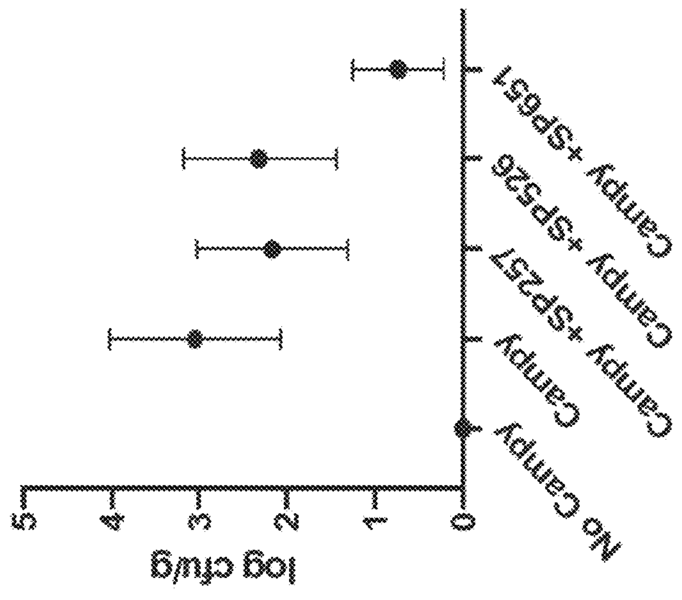

FIG. 21 demonstrates quantitative *Campylobacter* colonization moderated by *Spirulina*-expressed VHH. Birds were treated as in FIG. 12. At 72 hours post inoculation with $10^8$ CFU *Campylobacter* birds were euthanized and cecal contents were collected for quantitative bacterial load determination.

FIG. 22A-C shows *Spirulina* Expression Constructs. A) Expression constructs designed for *Spirulina* expression. VHH orientation, chaperone fusion partner used and oligomeric state of the final product indicated. Selected *Spirulina* strains expressing the anti-CfaE VHHs reported with a number preceded by the designation "SP." B) The complement binding protein C4B heptamerization domain molecular structure (PDB ID 4B0F). Intermolecular disulfide bonds link monomers to form heptamer. C) The dimerization domain of cAMP-dependent protein kinase type I-alpha regulatory subunit used to express homo dimeric VHHs. Intermolecular disulfide bonds link monomers to form dimer.

Figures 23A, 23B, 23C:
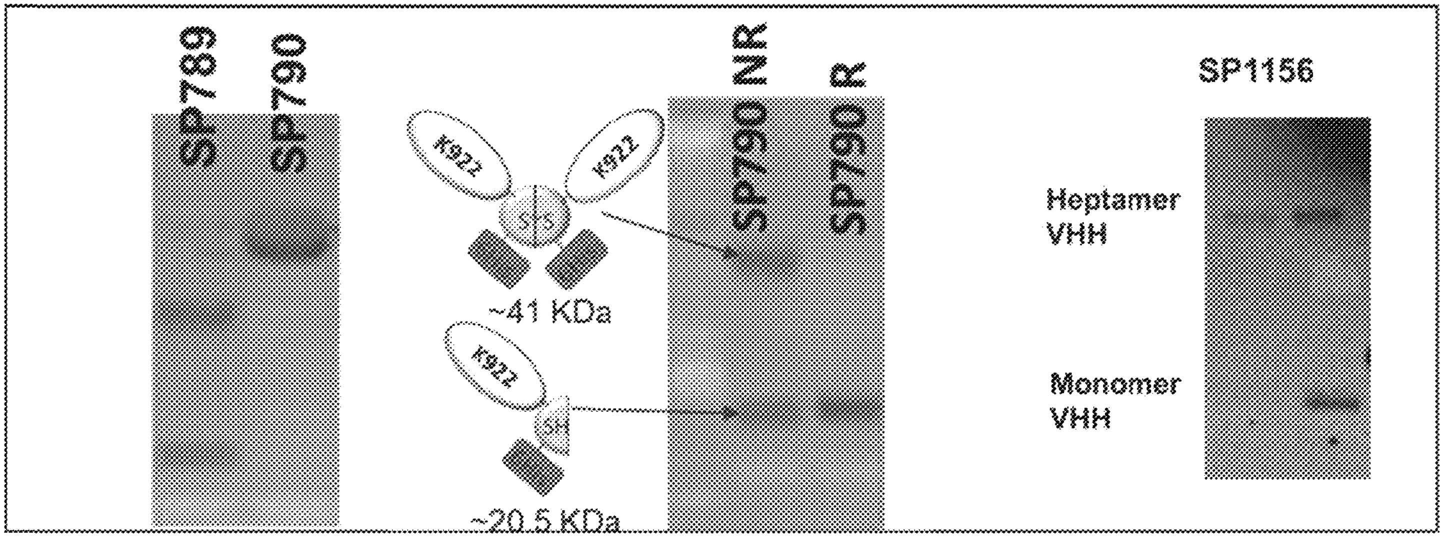

FIG. 23A-C shows VHH Expression in *Spirulina*. A) Example *Spirulina* expression of monomeric and dimeric VHHs as analyzed by Western Blotting. B) Intermolecular disulfide bond formation in the dimerization domain is confirmed by SDS-PAGE gel under reducing (R) and non-reducing (NR) conditions. Corresponding fragments and molecular sizes are indicated. C) Expression of a hetero-heptameric VHH that target the adhesion domains on F4+ and F18+ pig ETEC.

Figure 24A:
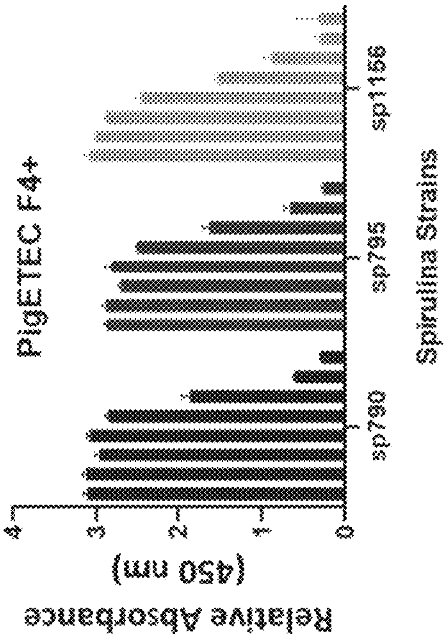
Figure 24B:
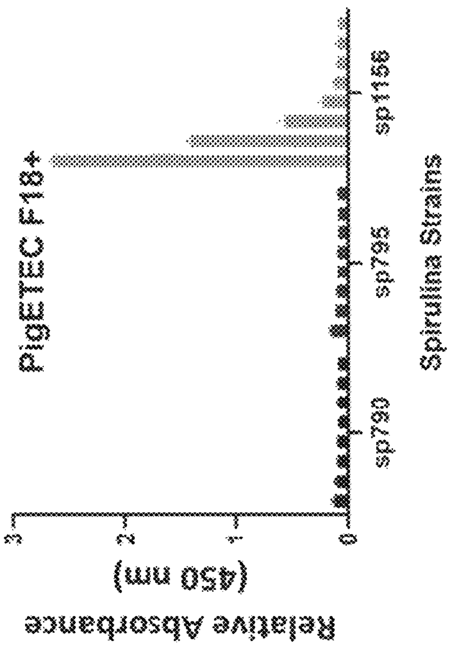

FIG. 24A-B shows A) ELISA based VHH activity of *Spirulina* strains binding to the F4+ adhesin tip domain, FaeG. Antibody titration was measured as a dilutions of total protein extracts from starting concentration of 1000 μg/ml. The homo-dimeric and hetero-heptameric constructs bind antigen well. B) ELISA based VHH activity of *Spirulina* strains binding to the F18+ adhesin tip domain, FedF. Antibody titration was measured as a dilutions of total protein extracts from starting concentration of 1000 μg/ml. The hetero-heptameric constructs bind antigen the antigen well while VHHs that are raised against F4+ adhesin show no binding to F18+ adhesin.

Figure 25B:
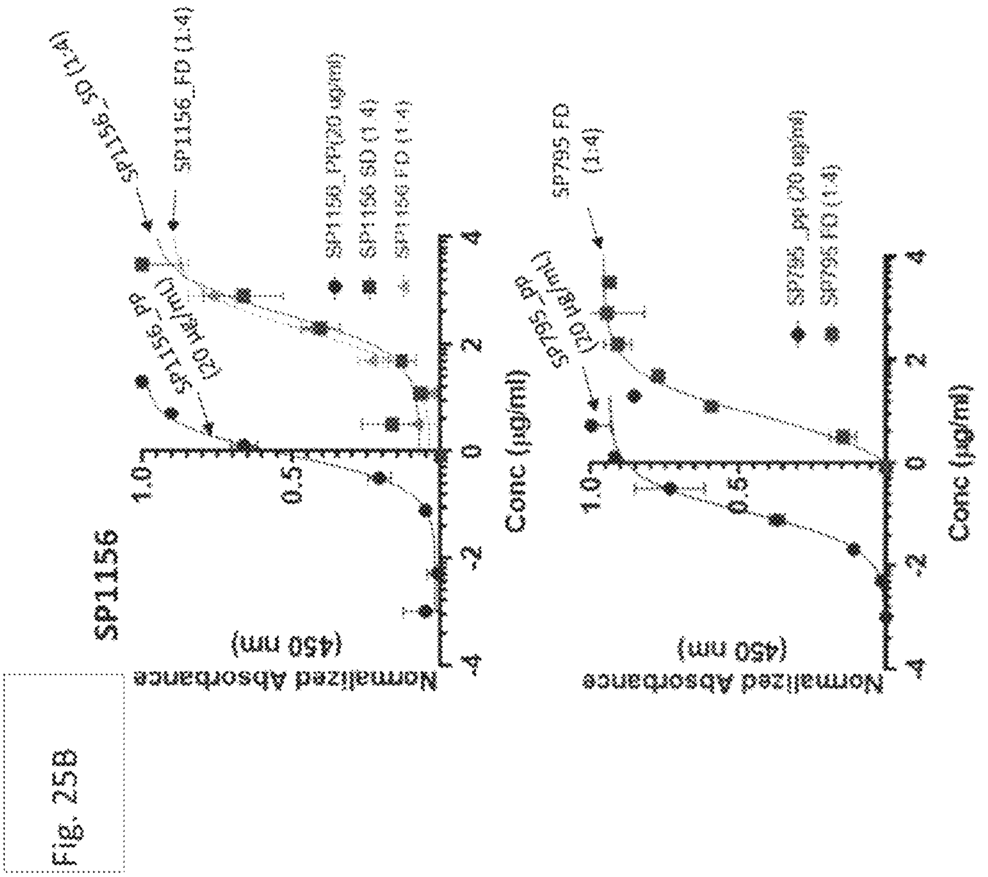
Figure 25A:
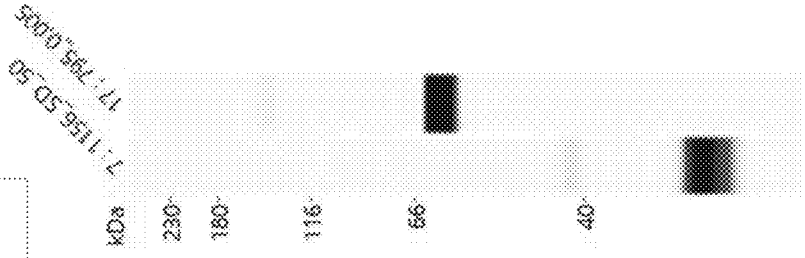
Figure 25C:
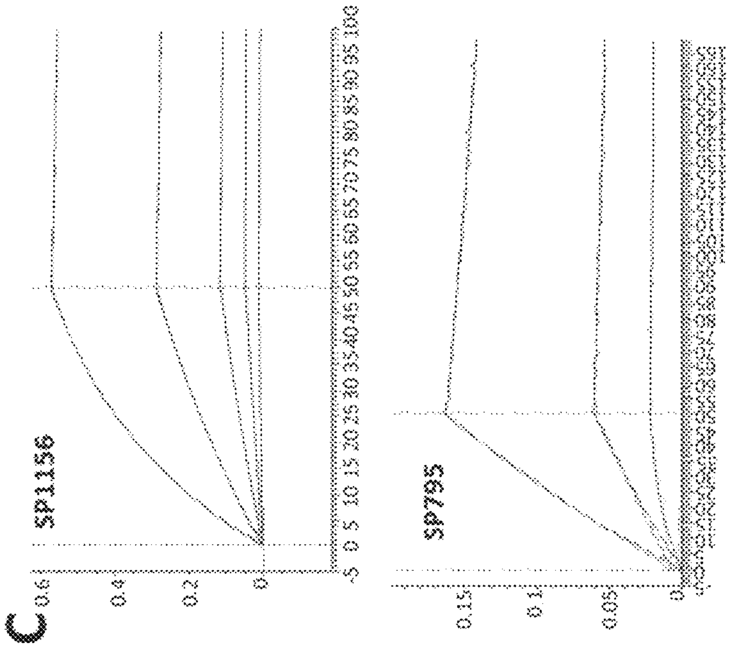

FIG. 25A-C: A) shows Western Blot demonstrating the protein expresseion in dried *Spirulina* biomass. B) shows that VHH in a *Spirulina* slurry from spray-dried (SD) and freeze-dried (FD) powder show comparable ELISA based binding. C) shows the antigen binding efficiency of *Spirulina* expressing VHHs assessed using BLI-based kinetics measurement; biotin-tagged FaeG was loaded on Strptavidin biosensors, and binding to *Spirulina* extract was measured.

Figure 26A:
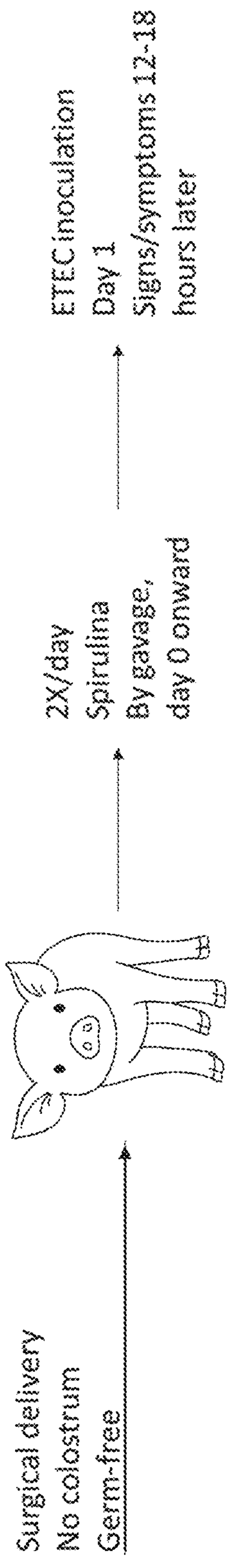
Figure 26B:
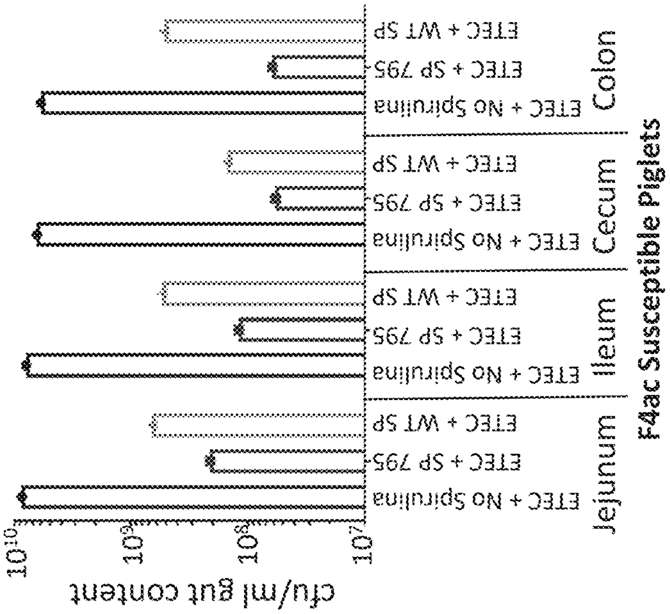
Figure 26C:
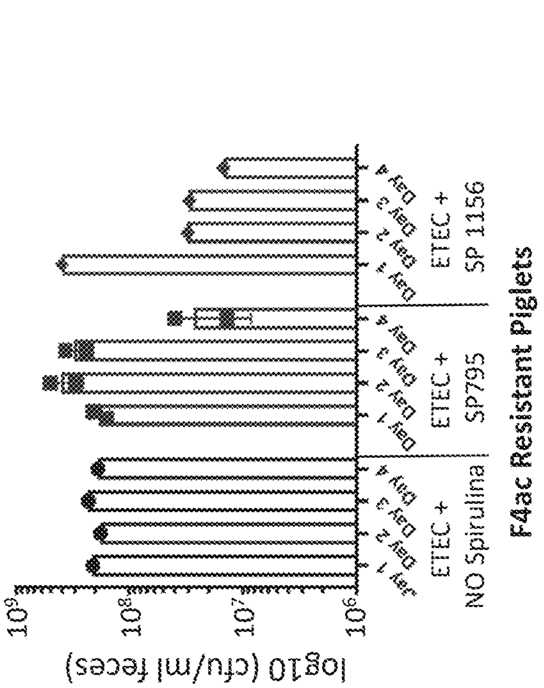

FIG. 26A-C. Gnobiotic bacterial challenge study. A0 shows an overview of oral gavage protocol using the gnobiotic piglet model. B) shows the effect of administration of SP795 on gut bacterial load. C) shows the effect of SP795 and SP-1156 on bacterial shedding in K88-resistant piglets.

Figure 27A:
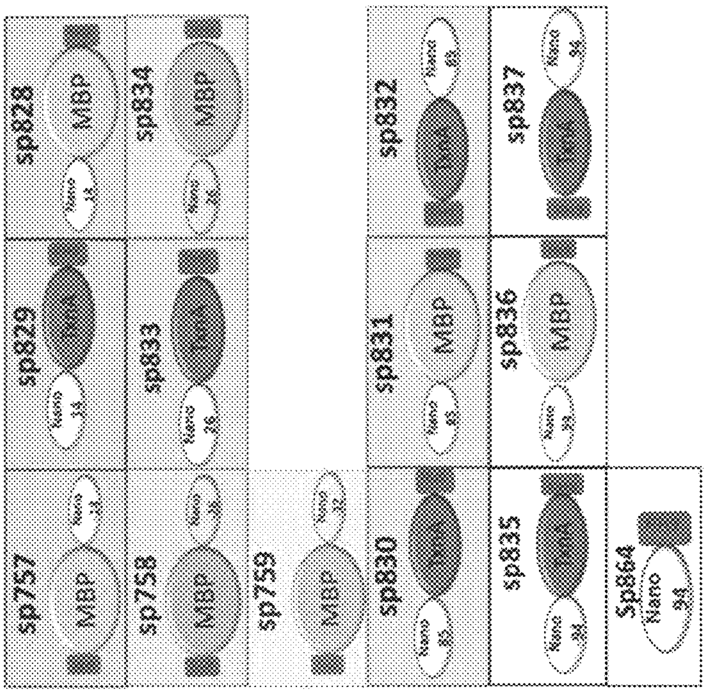
Figure 27B:
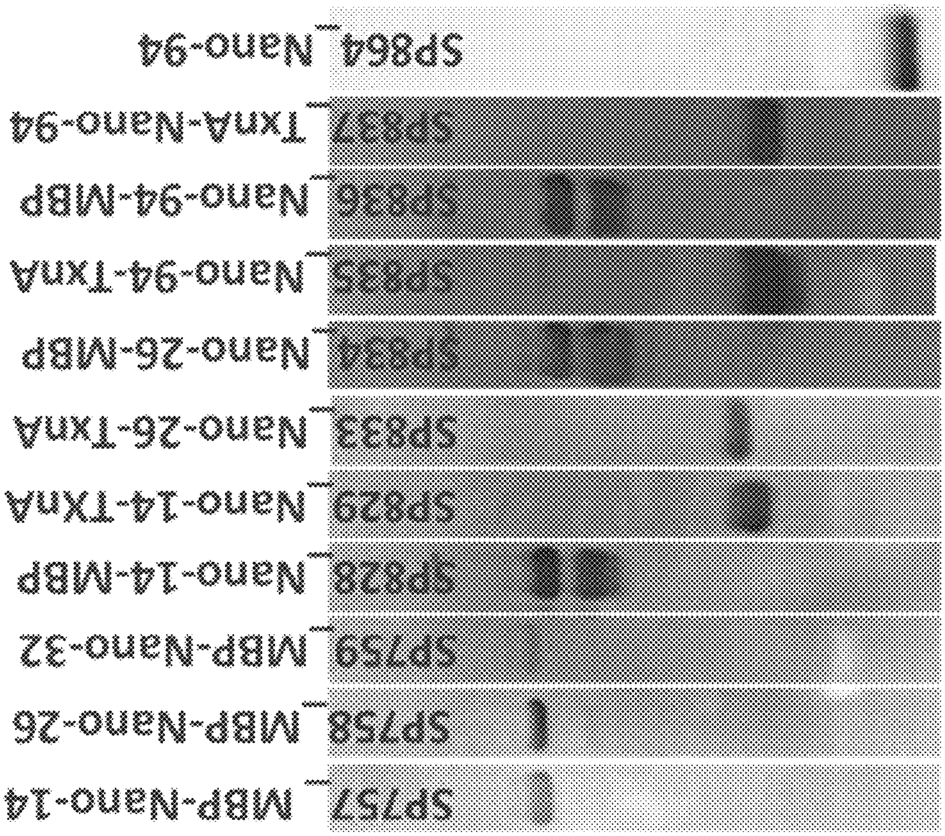
Figure 27C:
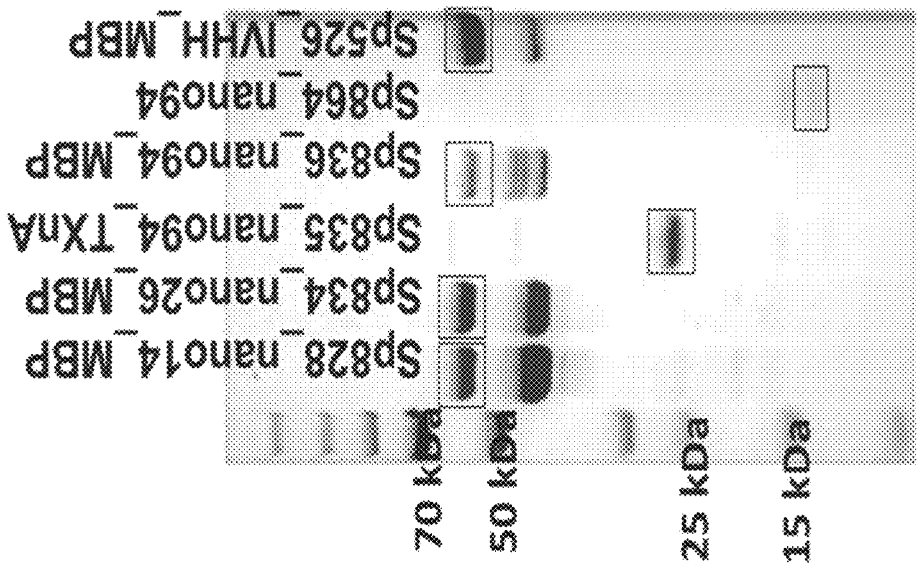

FIG. 27A-C shows anti-Norovirus *Spirulina* Expression Constructs. A) Expression constructs designed for *Spirulina* expression. VHH orientation, and chaperone fusion partner used with selected *Spirulina* strains expressing the anti-CfaE VHHs reported with a number preceded by the designation "SP."B) Protein expression in *Spirulina* strains is assessed by Western Blotting. C) NI-NTA purified protein from strains expressing VHHs are assayed by SDS-PAGE gel and Coomassie staining. Expected full length fragments are indicated with red boxes.

Figure 28A:
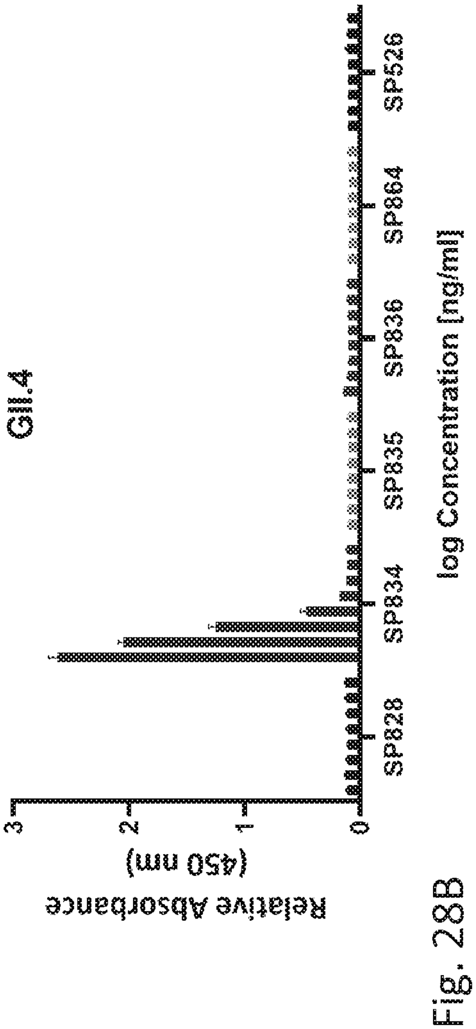
Figure 28B:
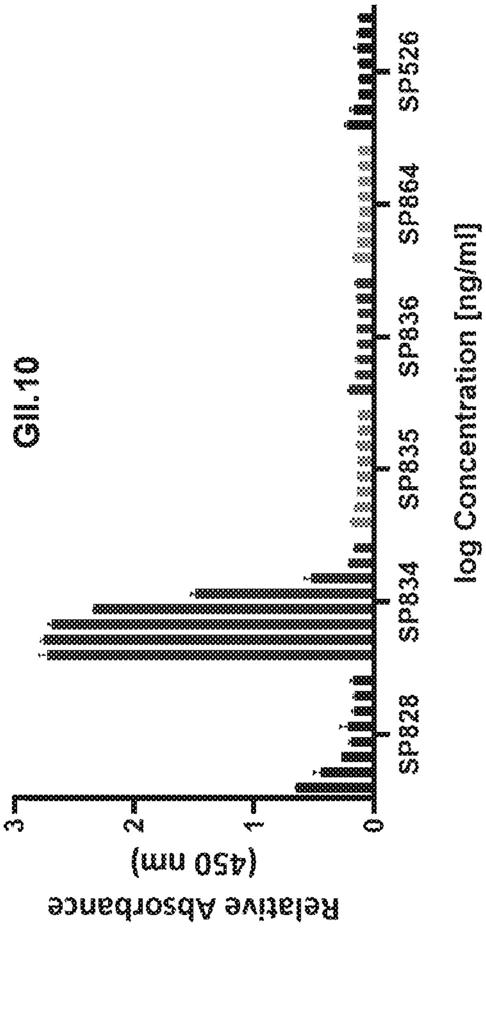
Figure 28C:
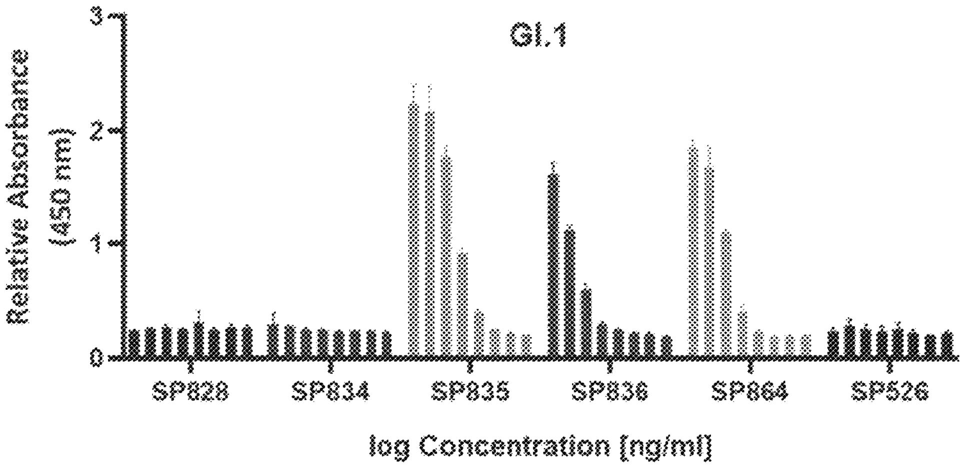

FIG. 28A-C shows anti-Norovirus VHH Binding Activity. A) ELISA based VHH activity of *Spirulina* strains binding to GII.4 HuNoV genotype capsid protrusion protein (P1). *Spirulina* expressed, Ni-NTA purified VHHs were tittered in dilution series from starting concentration of 20 μg/m. SP834 (Nano-26-MBP) show good binding to the GII.4 P1 domain. B) ELISA based VHH activity of *Spirulina* strains binding to GII.10 HuNoV genotype capsid protrusion protein (P1). *Spirulina* expressed, Ni-NTA purified VHHs were tittered in dilution series from starting concentration of 20 μg/m. SP834 (Nano-26-MBP) show good binding to the GII.10 P1 domain. C) ELISA based VHH activity of *Spirulina* strains binding to GI.1 HuNoV genotype capsid protrusion protein (P1). *Spirulina* expressed, Ni-NTA purified VHHs were tittered in dilution series from starting concentration of 20 μg/m. SP835 (Nano-94-TxnA), SP836 (Nano-94-MBP), SP864 (Nano-94) show good binding to the GI.1 P1 domain.

Figure 29A:
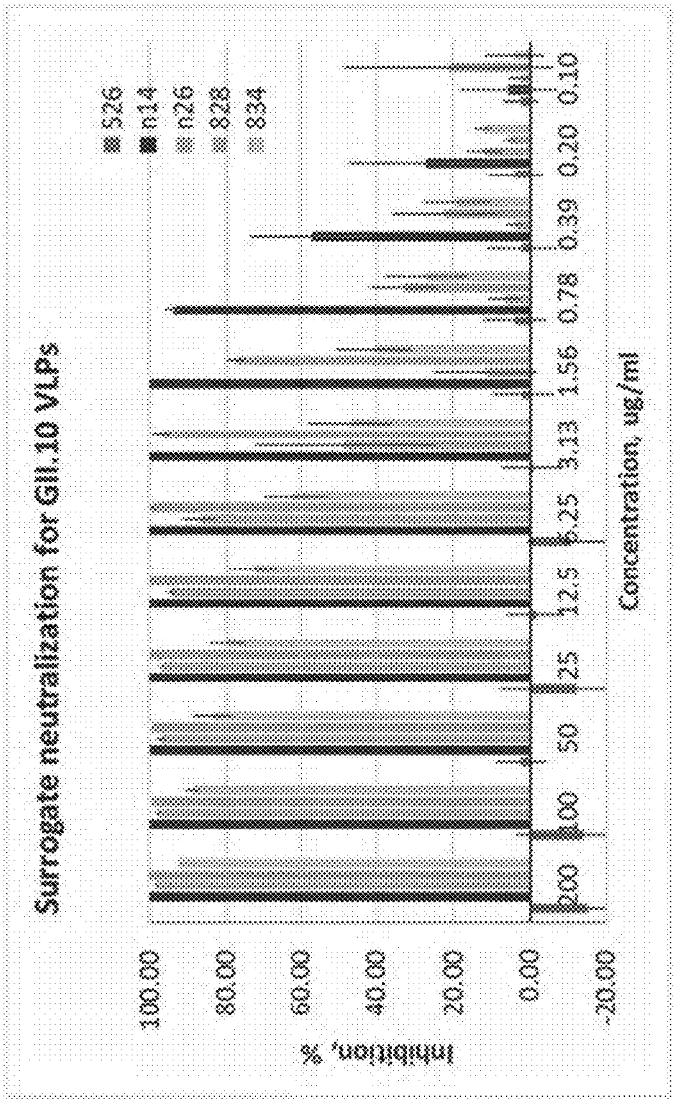
Figure 29B:
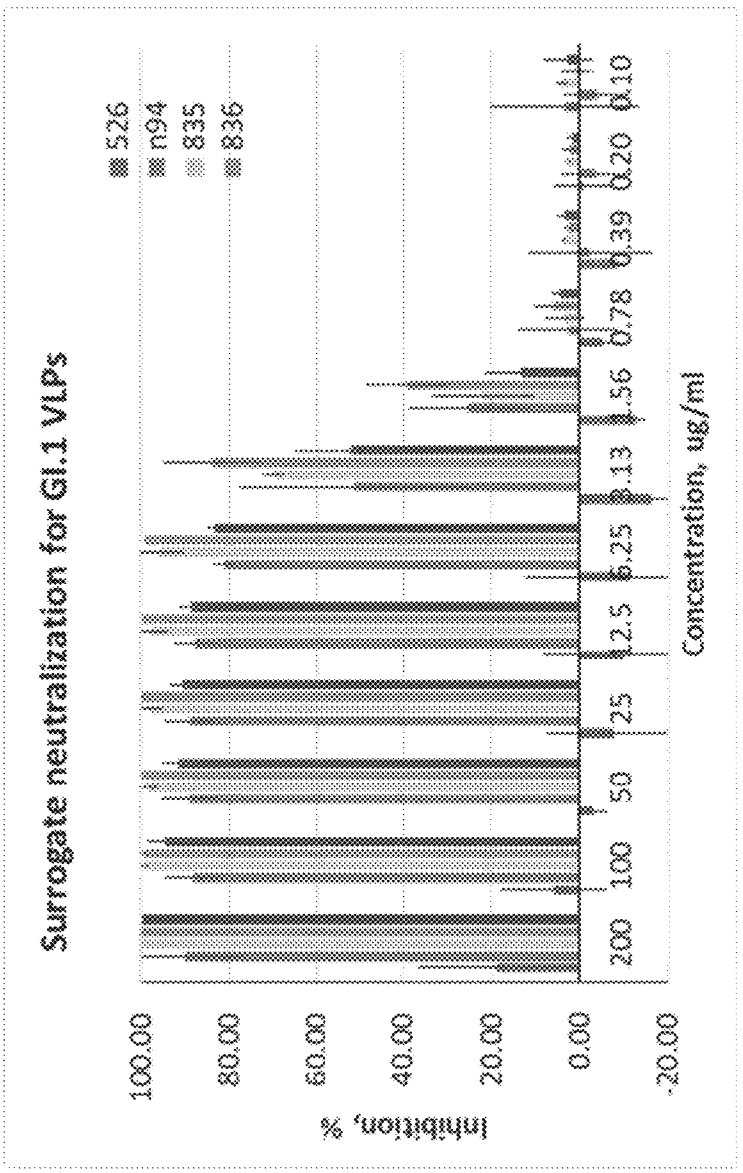

FIG. 29A-B shows a Surrogate Neutralization Assay. Plates were coated with Pig Gastric Mucin (PGM) and blocked with skim milk. GII.10 (2 ug/ml) or GI.1 VLPs (1 ug/ml) were pre-incubated with serially diluted samples for 1 h at RT and added to the plates. Bound VLPs were detected with GI.1 specific biotinylated nanobody NB60 or GII.10 polyclonal sera. Antibodies were detected with corresponding secondary antibodies (strep-HRP or anti-rabbit-HRP). (A) *Spirulina* expressed and Ni-NTA purified VHHs show HBGA blocking properties a similar range to the controls. (B) *Spirulina* expressed Ni-NTA purified VHHs show comparable HBGA blocking properties with controls.

Figures 30A, 30B:
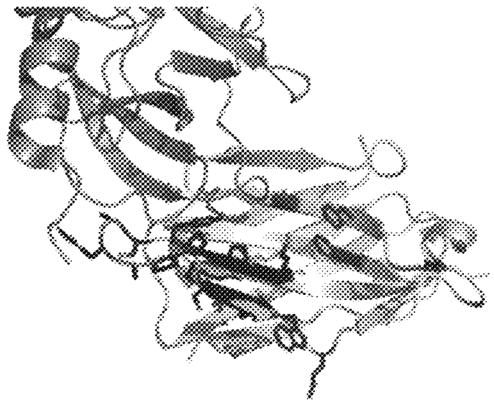

FIG. 30A-B: Sequence alignment of Nano85 and K922, anti-human norovirus (HuNoV) protrusion (P) domain antibody. Antibody CDRs are highlighted in blue. Amino acid positions that affect antigen binding are boxed. B) shows structural analysis of framework region amino acid differences between Nano85 and K922 based on the HuNoV GII.10 P domain bound Nano85 structure (PDB ID 4X7E). The boxed amino acid sidechains indicate mutations incorporated in loop grafted Nano85. Nano85 CDR3 that dominate interactions in antigen binding are circled.

Figure 31B:
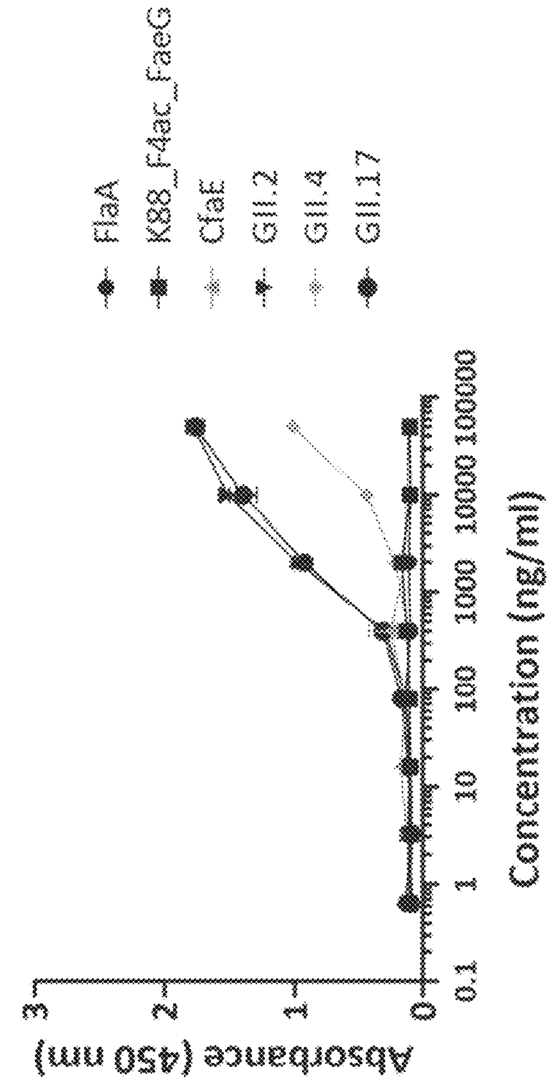
Figure 31A:
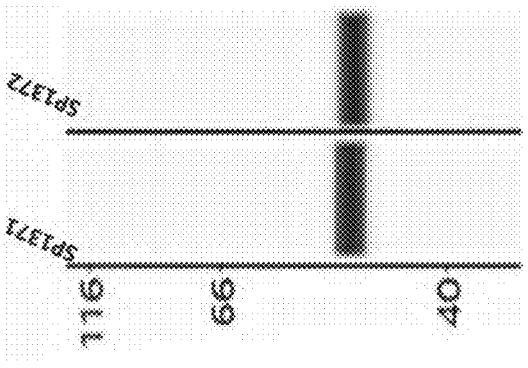
Figure 31C:
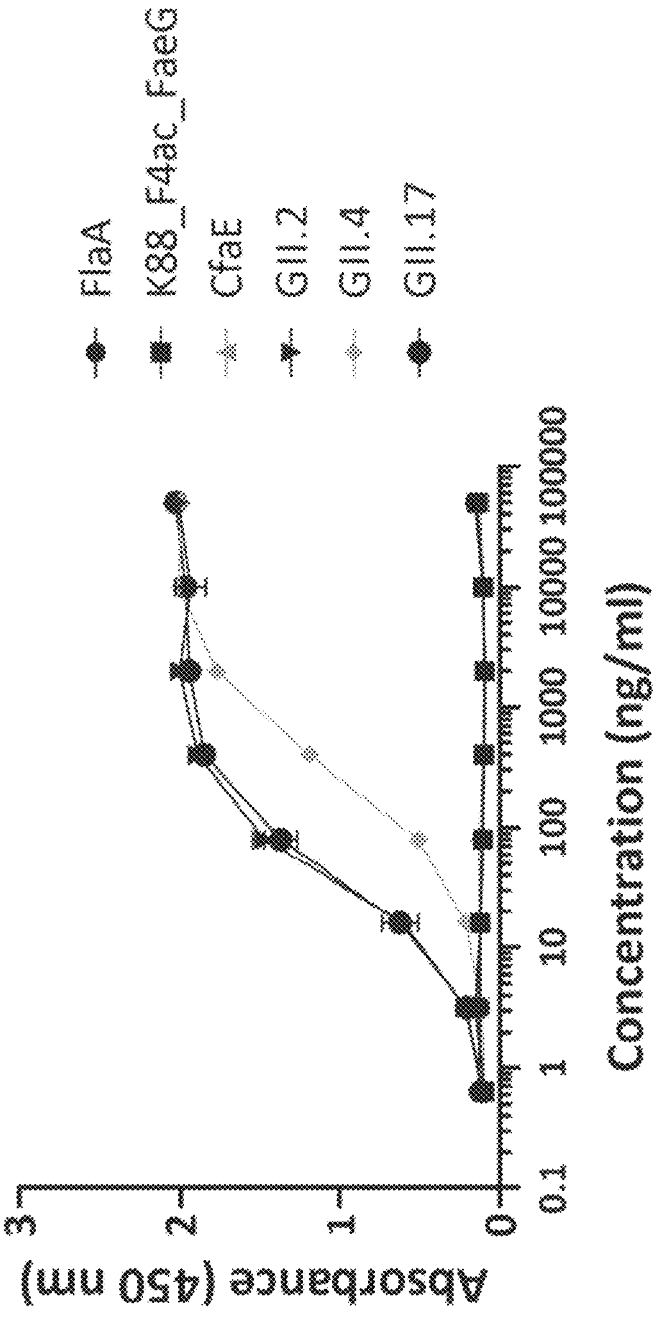

FIG. 31A-C: A) shows Western Blot analysis of *Spirulina* strains transformed with C-terminal MBP fused original Nano 85 (SP1371) and loop grafted nano85 (SP1372) show protein expression. B & C) show bacterial expressed original Nano85 (B), and loop grafted Nano85 (C) show binding to recombinant P domains derived from various HuNoV Gii strains (GII.2, GII.4, and GII.17).

Figure 32A:
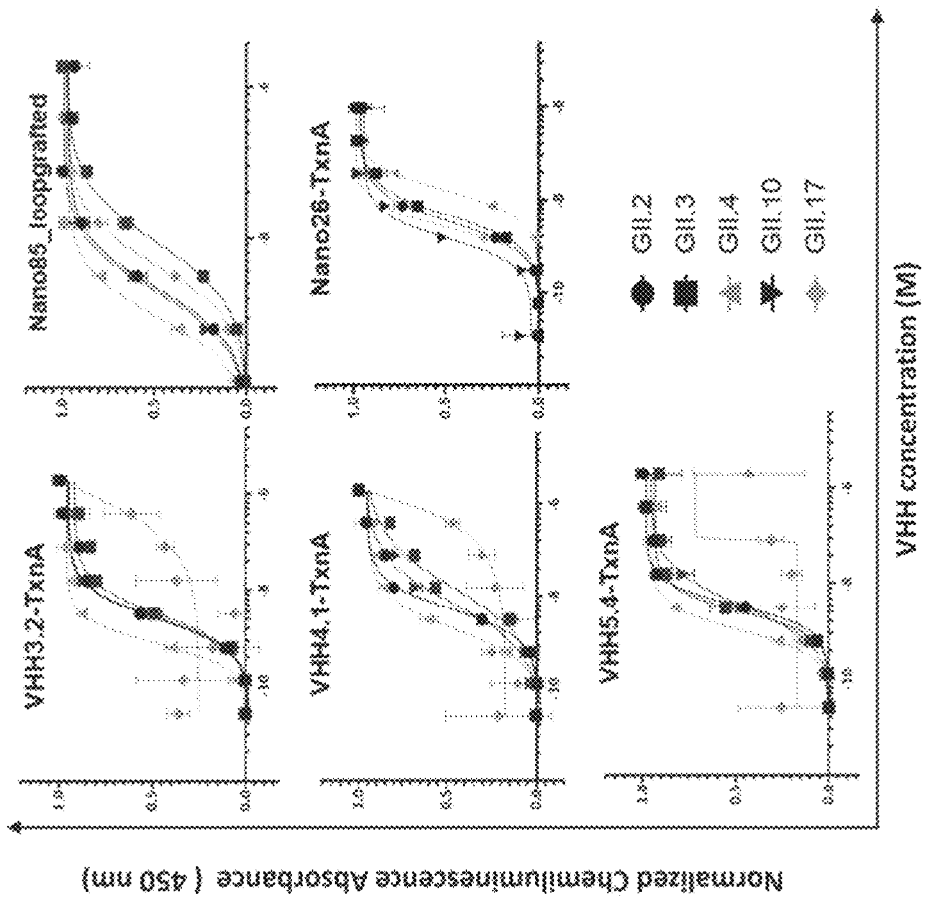
Figure 32B:
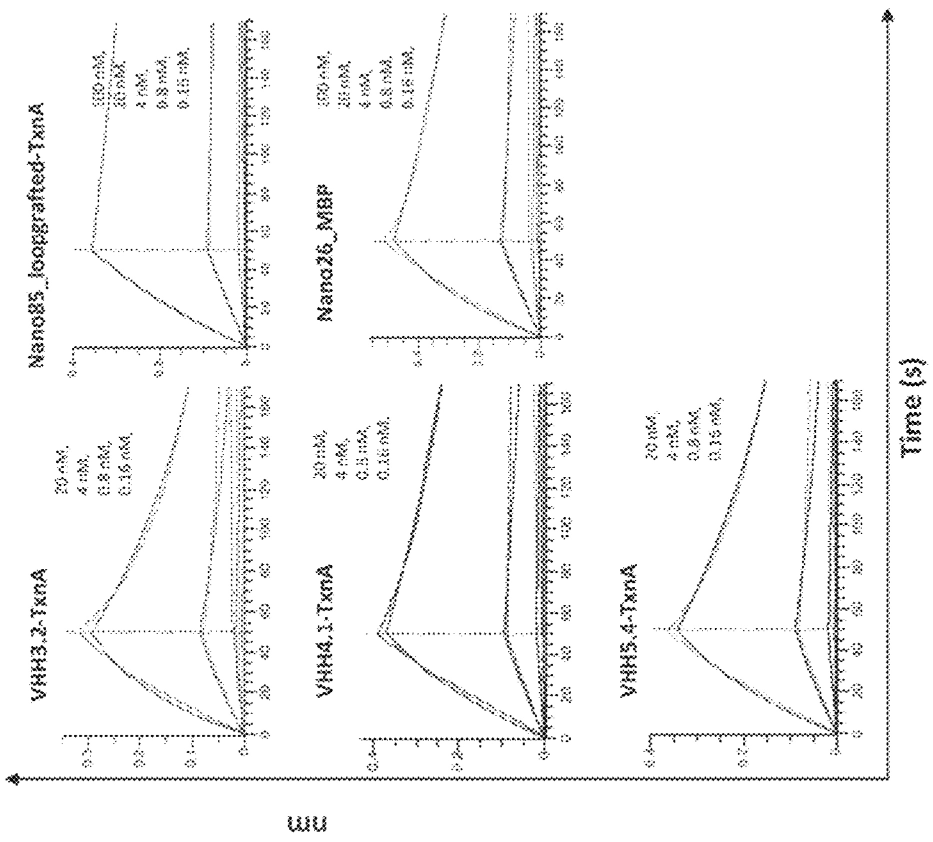

FIG. 32A-B: Binding kinetics and cross-reactivity of bacterial expressed recombinant anti-Human Norovirus (HuNoV) P domain targeting VHHs. A shows ELISA based binding and cross-reactivity of various VHHs raised against HuNoV Genotype GII.10 Protrusion (P) domain (Nano85 loop grafted and Nano26) or GII.4 P domain (VHH3.2, VHH4.1, and VHH5.4) expressed recombinantly in a bacterial expression system. Nano26 and Nano85 show broad cross-reactivity while VHH3.2, VHH4.1, and VHH5.4 show no binding against the recombinant GII.17 P domain. B shows BLI based binding kinetics of various VHHs raised against HuNoV Genotype GII.10 P domain (Nano85 loop grafted and Nano26) or GII.4 P domain (VHH3.2, VHH4.1, and VHH5.4). Biotin tagged recombinant GII.2 P domain at 100 nM was used as an antigen. VHH concentrations used to generate binding kinetics are indicated for each VHH.

Figure 33A:
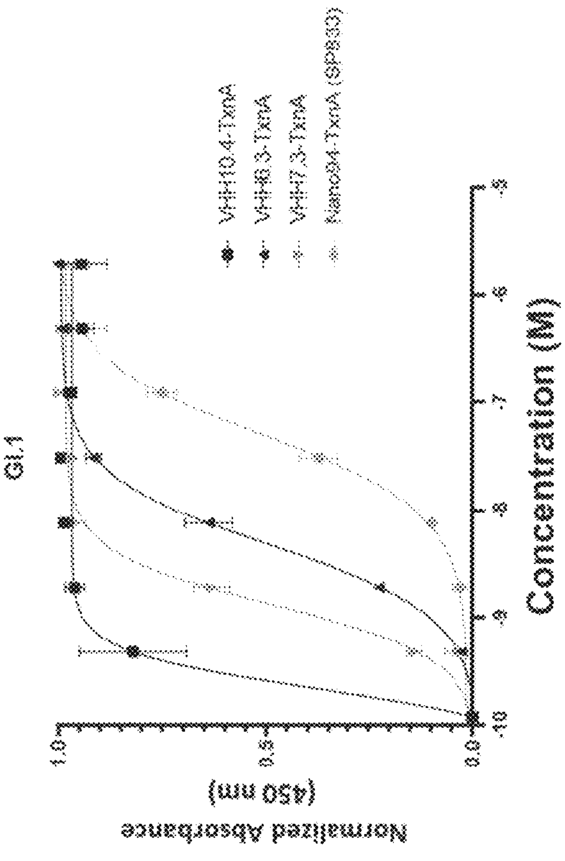
Figure 33B:
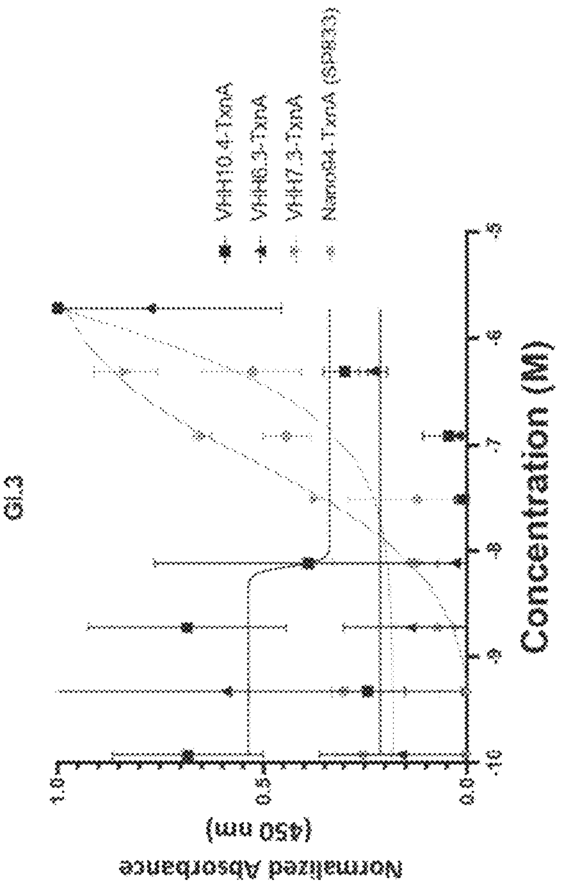

FIG. 33A-B: ELISA based binding and cross-reactivity of anti-Human Norovirus (HuNoV) P domain targeting VHHs. A) shows ELISA based binding of VHHs raised against HuNoV Genotype GI.1 Protrusion (P) domain, Nano94, VHH10.4, VHH6.3, VHH7.3. The VHHs tested exhibit binding EC50 ranging from 0.21 nM to 50.07 nM, where *Spirulina* expressed recombinant nano94-TxnA shows the weakest binding. B) shows cross-reactivity of VHHs against the recombinant HuNoV GI.3 P domain. The VHH7.3 was cross-reactive binding against the GI.3 P domain.

Figure 34A:
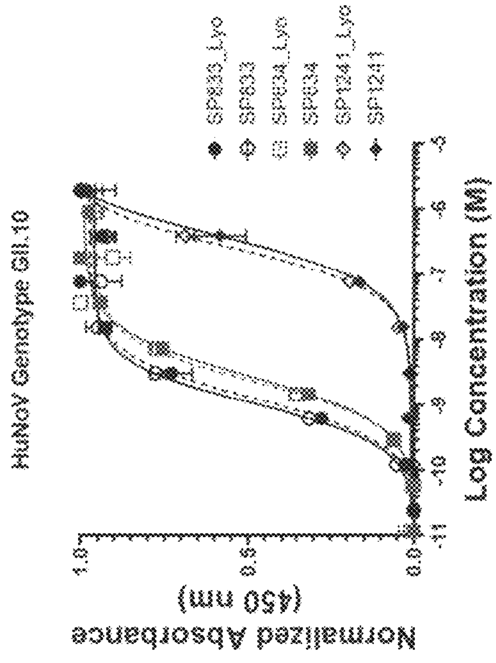
Figure 34B:
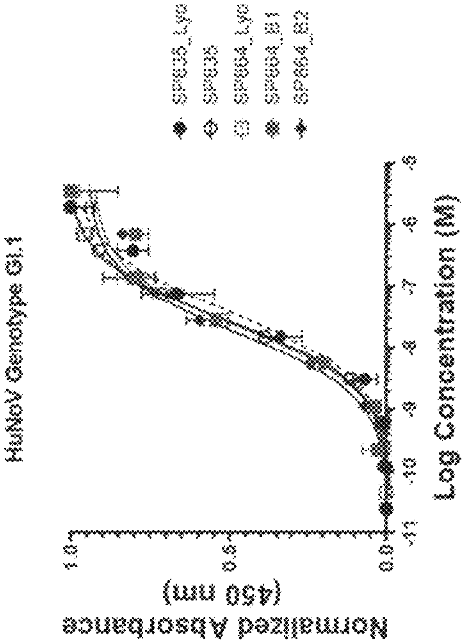

FIG. 34A-B: *Spirulina* expressed and Ni-NTA purified proteins were stable following freeze-drying by lyophilization. A) shows binding activity of recombinant anti-Norovirus VHH expressed in *Spirulina* exhibit no loss in binding activity against recombinant HuNoV GII.10 P domain following freeze-drying (SP833_lyo, SP834_Lyo, and SP1241_Lyo) when compared to purified protein stored at 4° C. after purification (SP833, SP834, and SP1241 respectively). Observed ELISA based binding as measured by EC50 is given in the accompanying table. B) shows binding activity of recombinant anti-Norovirus VHH expressed in *Spirulina* exhibit no loss in binding activity against recombinant HuNoV GI.1 P domain following freeze-drying (SP835_lyo, and SP864_Lyo) when compared to purified protein stored at 4° C. after purification (SP835, and SP864 respectively). Observed ELISA based binding as measured by EC50 is given in the accompanying table.

Figure 35:
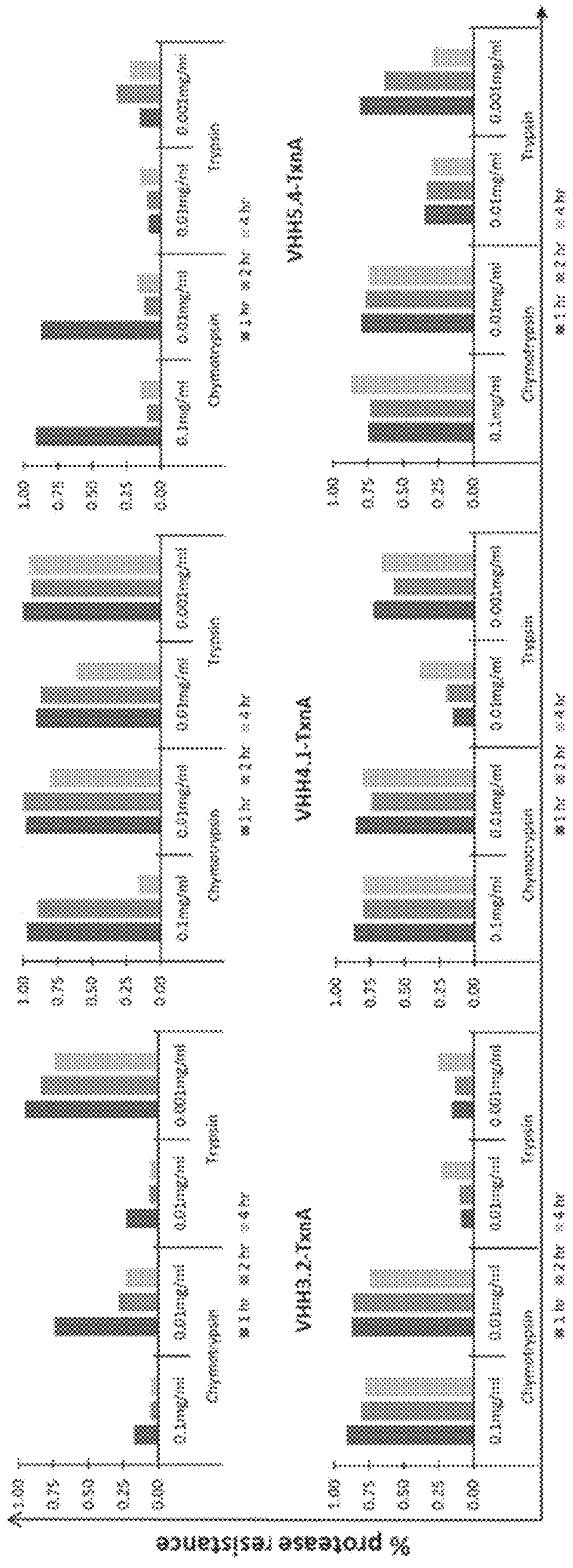

FIG. 35: Anti-Norovirus capsid protrusion domain (P) targeting VHHs show varying degrees of protease sensitivity, with the GII genogroup targeting loop grafted Nano85 exhibiting the best resistance against Chymotrypsin and Trypsin. Bacterial expressed recombinant VHHs (1 μg total protein) were incubated with 20 μL of chymotrypsin (0.1 mg/mL or 0.01 mg/mL) or Trypsin (0.01 mg/mL or 0.001 mg/mL) in digestion buffer (1 mM Tris pH 8.0, 20 mM CaCl2). Samples were incubated for 1 hour, 2 hours, or 4 hours. Protease sensitivity was assayed using ELISA based binding. High binding ELISA plates were coated with the recombinant GII.2 P domain. The level of active VHH post-protease digestion was determined by assessing VHH binding to antigen. The percentage of active VHH after digestion was calculated as a ratio of activity from VHH incubated with PBS.

Figure 36A:
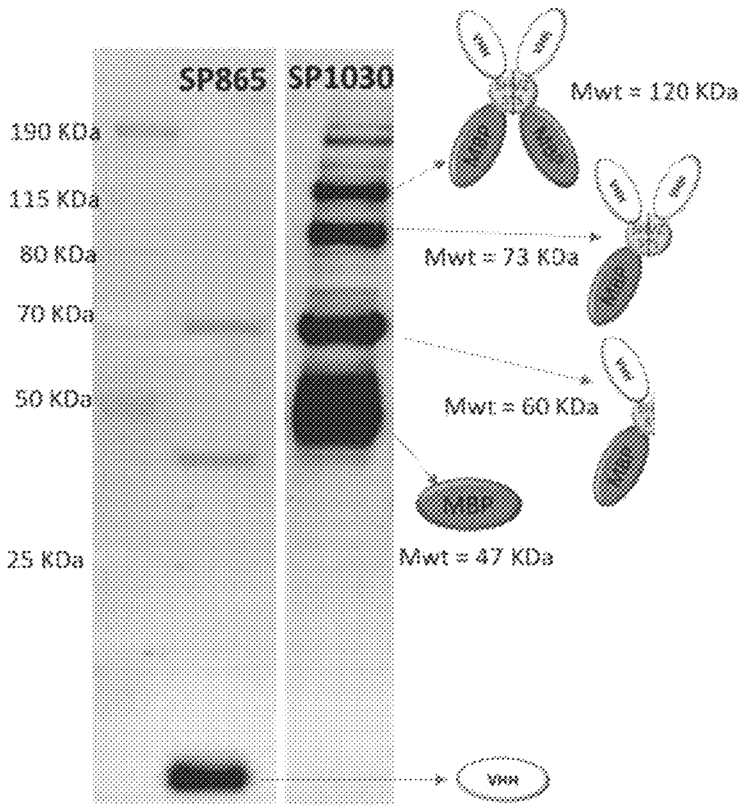
Figure 36B:
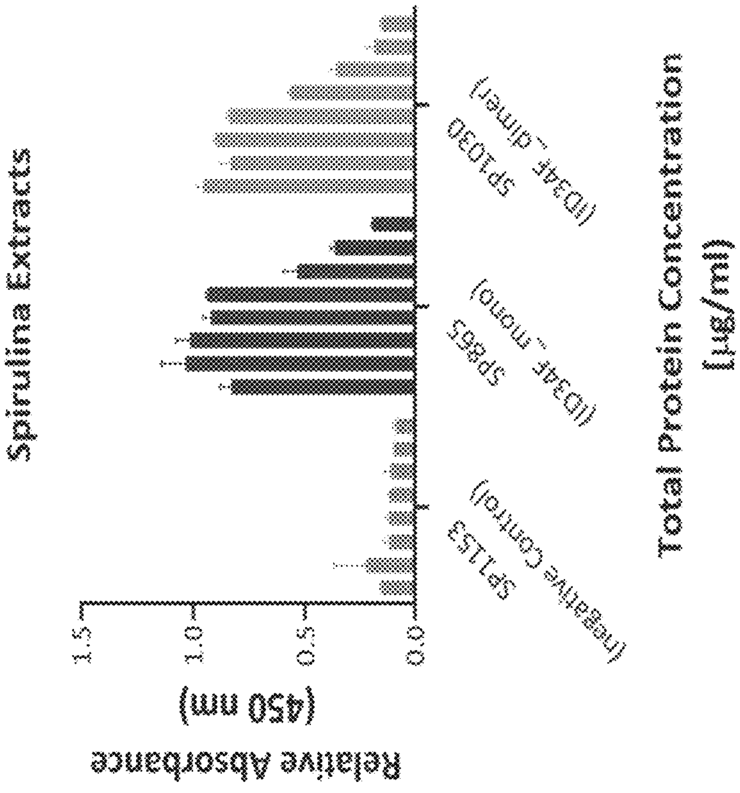
Figure 36C:
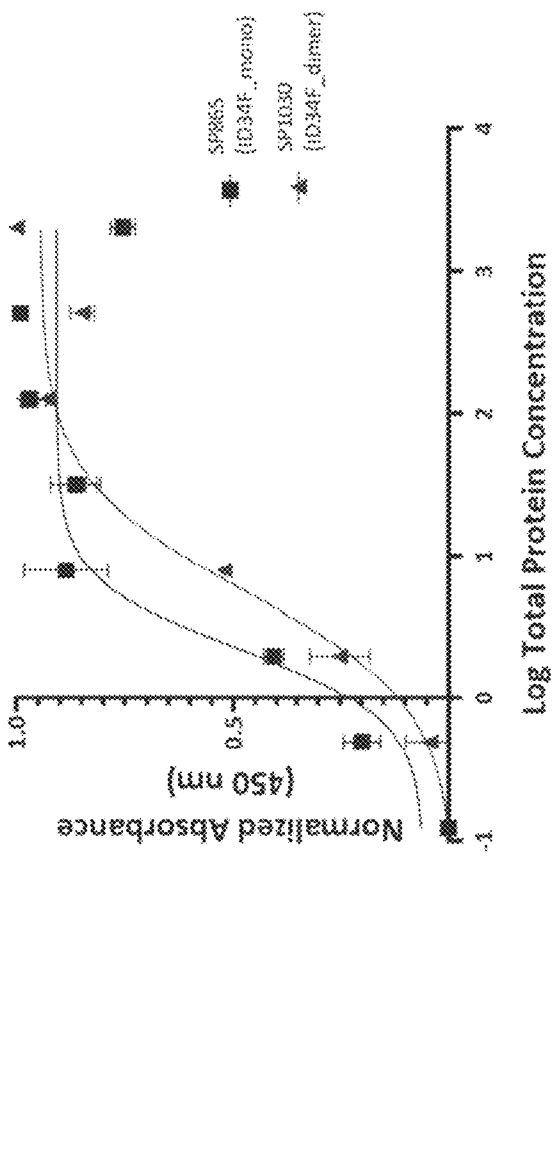

FIG. 36A-C shows anti-TNFα *Spirulina* Expression Constructs design, expression and activity. A) Anti-TNF-α VHH, ID34F designed as monomer (SP865) and dimer (SP1030) for *Spirulina* expression. Expression is confirmed by western blotting. B) *Spirulina* expressed VHHs exhibit binding activity against recombinant human TNF-α on ELISA plates where high affinity plates are coated with human TNF-α and VHHs in the form of *Spirulina* crude lysates were titrated in dilution series starting from 20,000 μg/ml. C) Binding efficiency was calculated as EC50. Both monomeric and dimeric forms of the VHH bind comparably.

Figure 37:
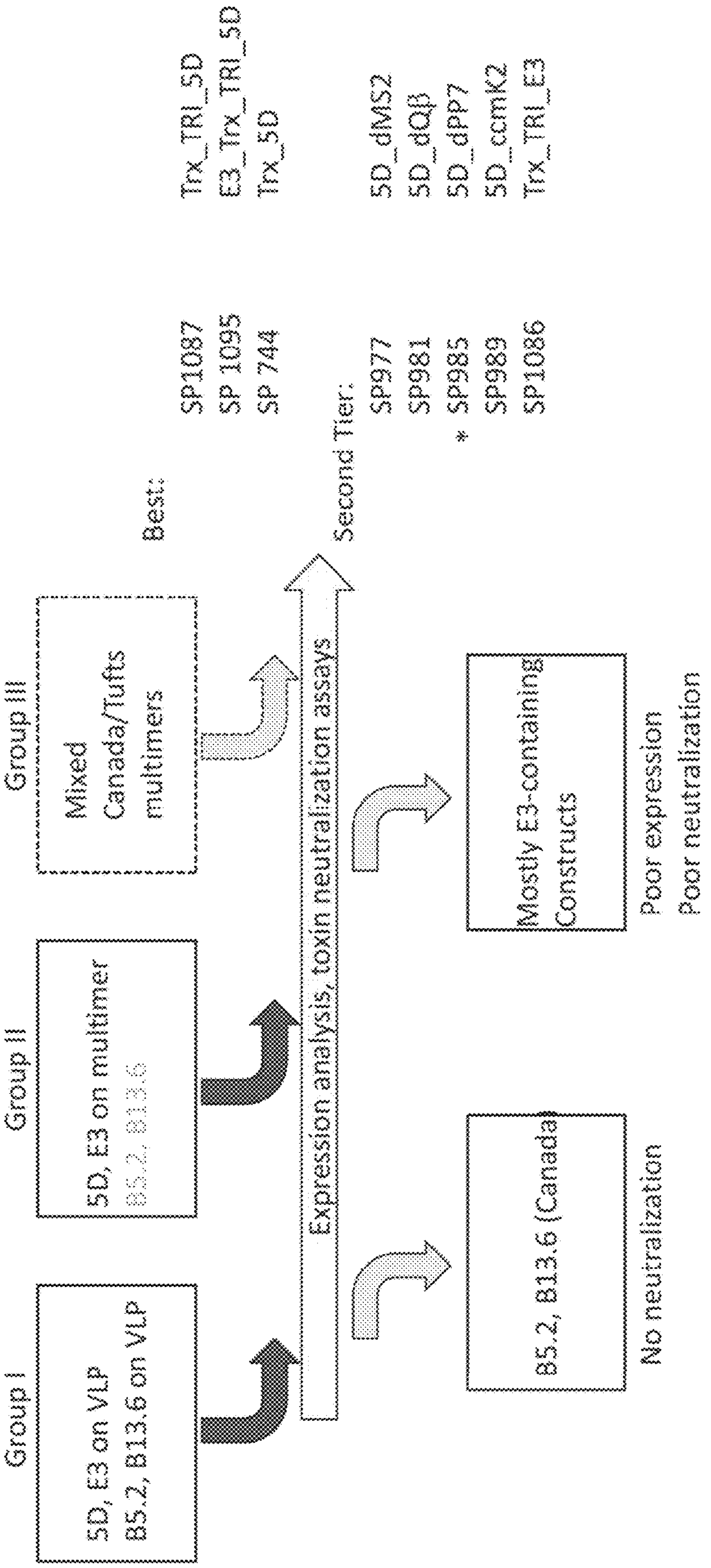

FIG. 37 shows an overview of the development and testing of anti-toxinB (*C. difficile*) VHHs.

FIGS. 38A-D: Western blot expression analysis of *Spirulina* strains expressing anti-TcdB VHHs 5D and E3 in various hybridization contexts. "ssPsbU" and "ssPsbP2" indicate the presence of putative thylakoid targeting signal sequences on the N-terminus of designated proteins, derived from the cyanobacterial photosystem proteins PsbU and PsbP2, respectively. pAP205, pMS2, pQb and PP7 are enforced single peptide dimers derived from the capsid protein of RNA phages AP205, MS2, Qb and PP7, respectively. CCMk2 denotes the *Spirulina* carboxysome shell protein CCMk2, which was circularly permuted to position N- and C-termini to face outward to allow genetic fusion with denoted VHH. Trx denotes thioredoxin. "Tri" and "pent" denote the synthetically designed non-covalent multimers 1na0C3 and DHR5C5_G2, respectively. Single and double VHHs are appended to said multimers in the orientations designated on the blots. SP 744, 745, 746, and 747 are thiredoxin fusions with 5D and E3 in both the N- and C-terminal orientations.

Figure 39A:
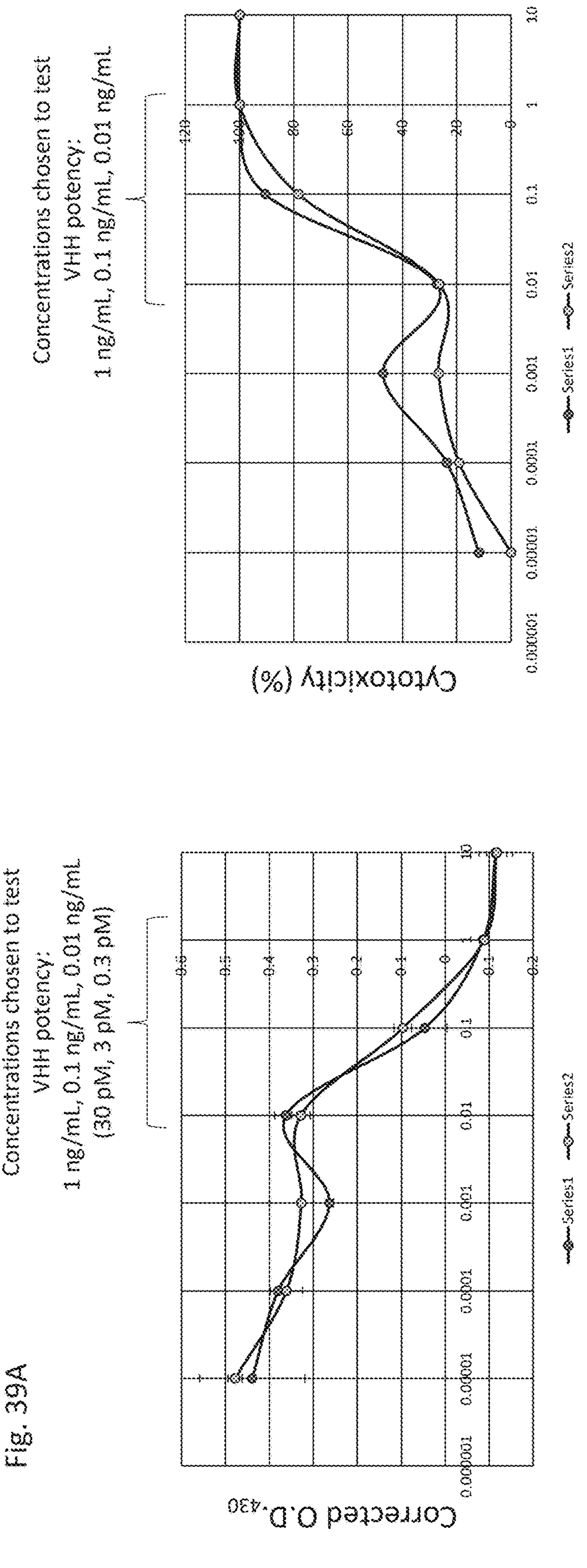

FIGS. 39A-B demonstrate the potency of various anti-tcdB VHH constructs.

Figure 40:
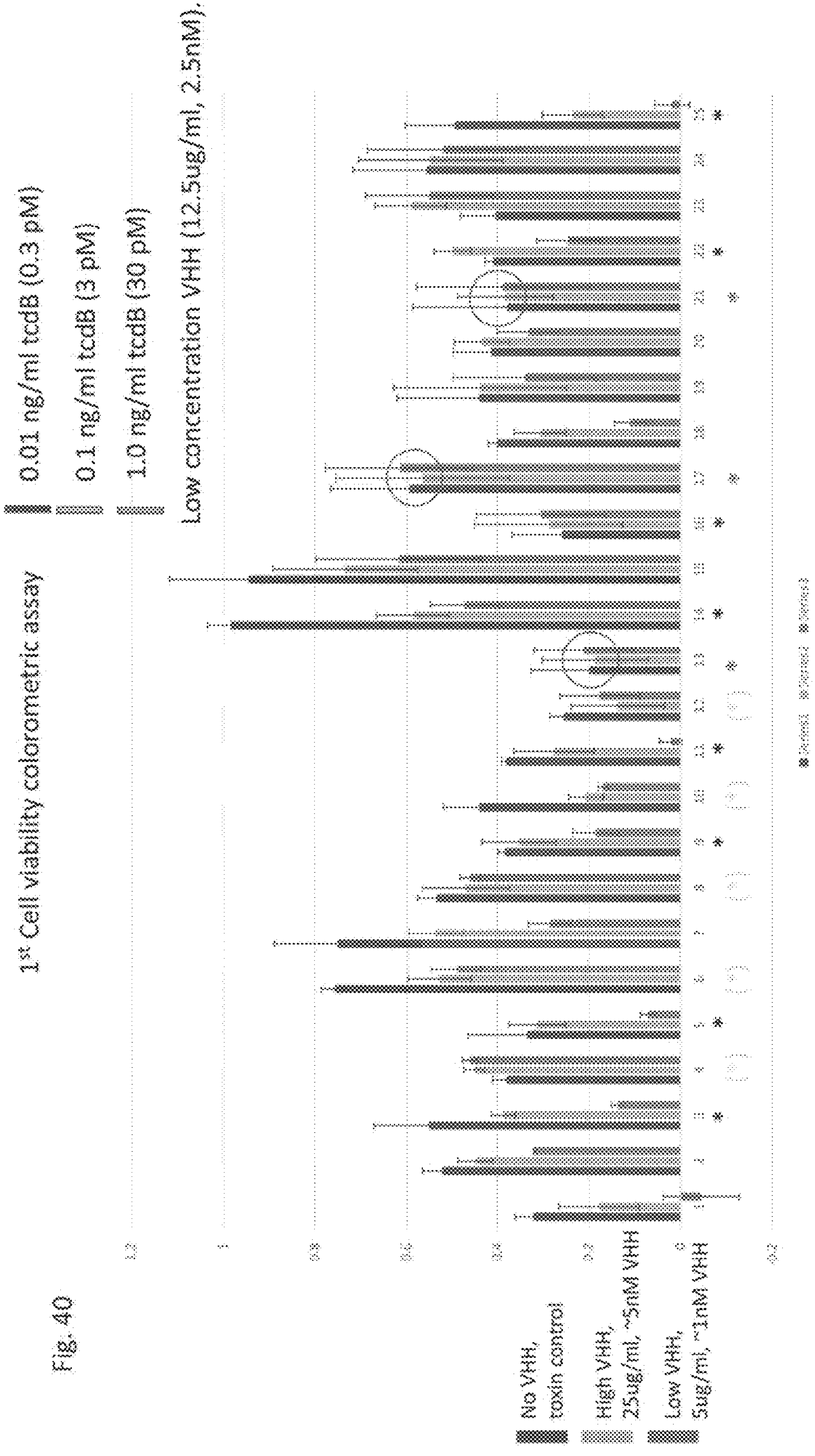

FIG. 40 demonstrates colorimetric assays testing the anti-tcdB VHH constructs.

Figure 41A:
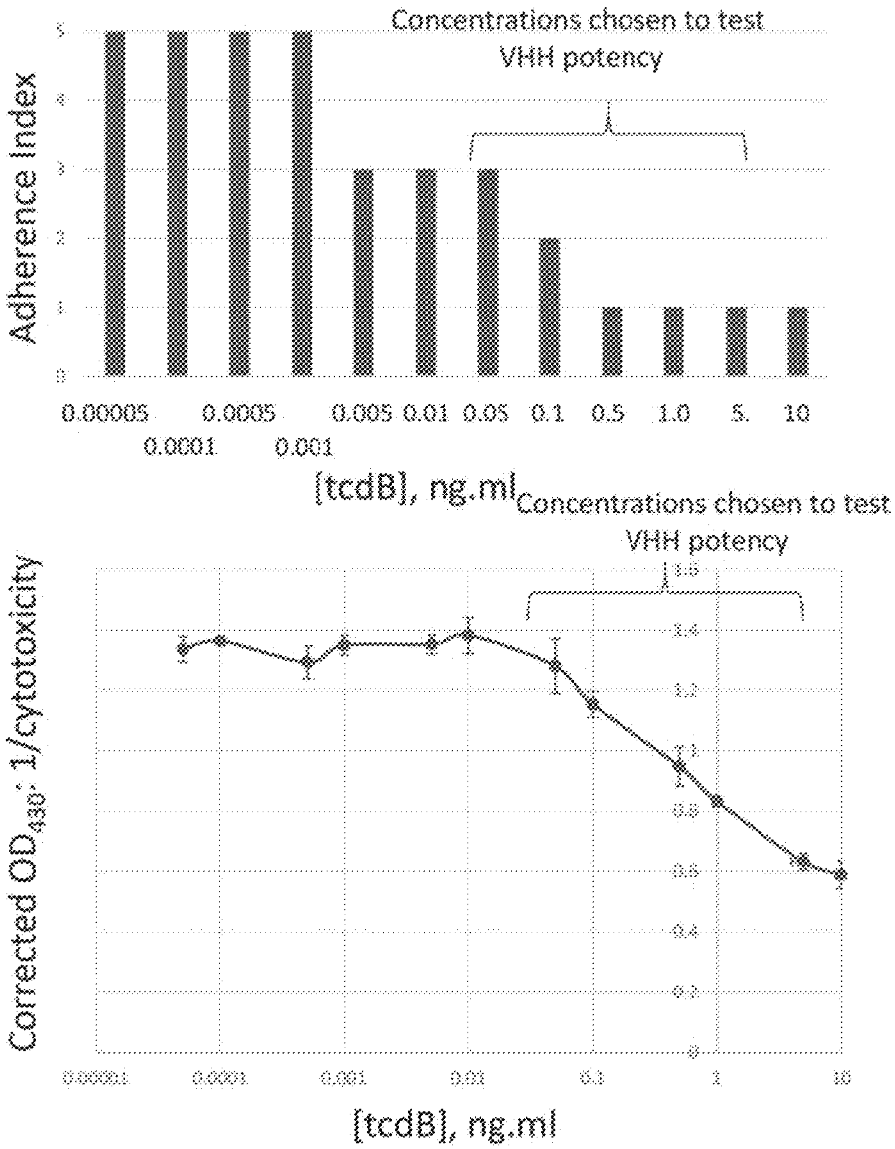
Figure 41B:
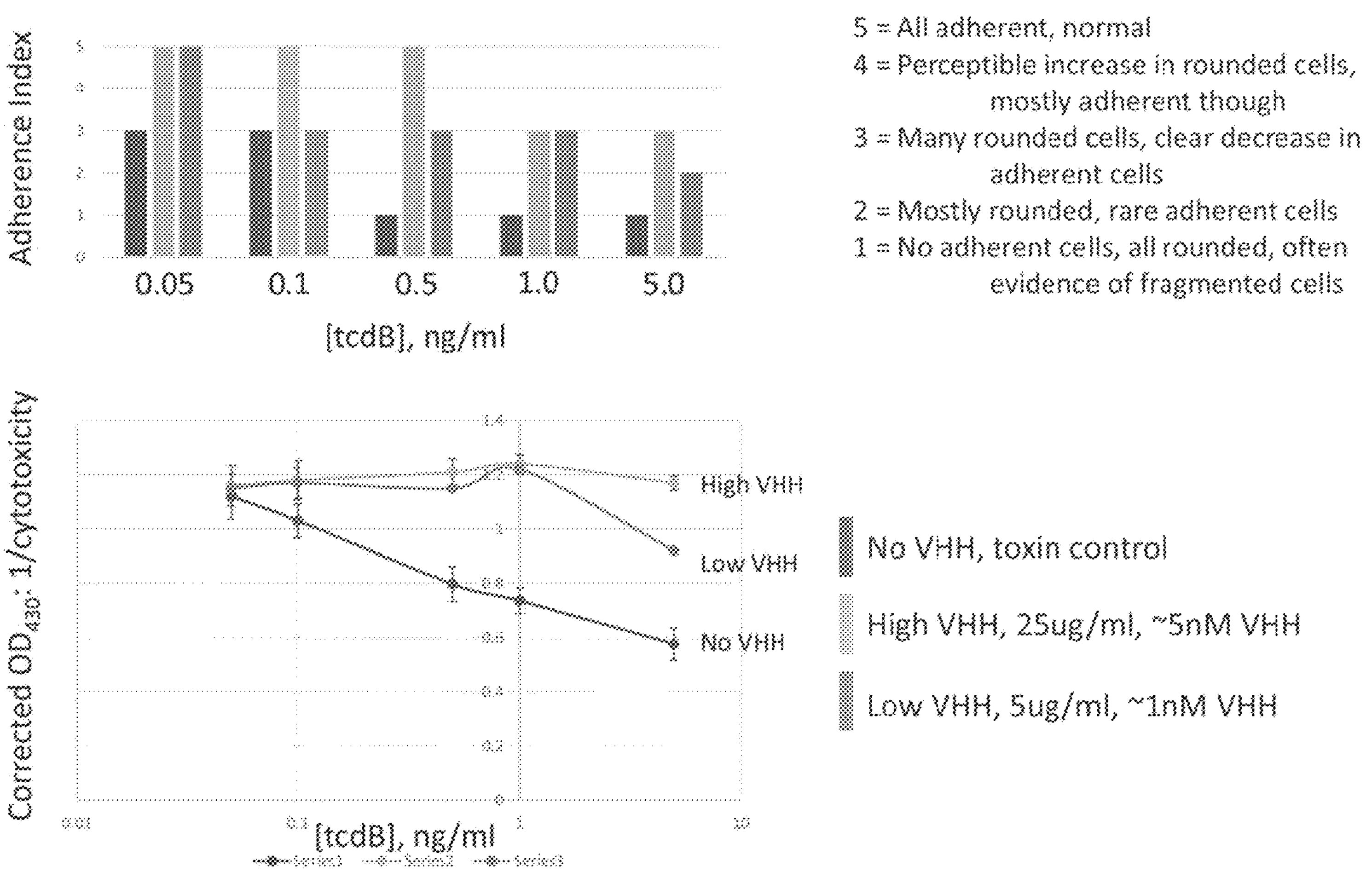
Figure 41C:
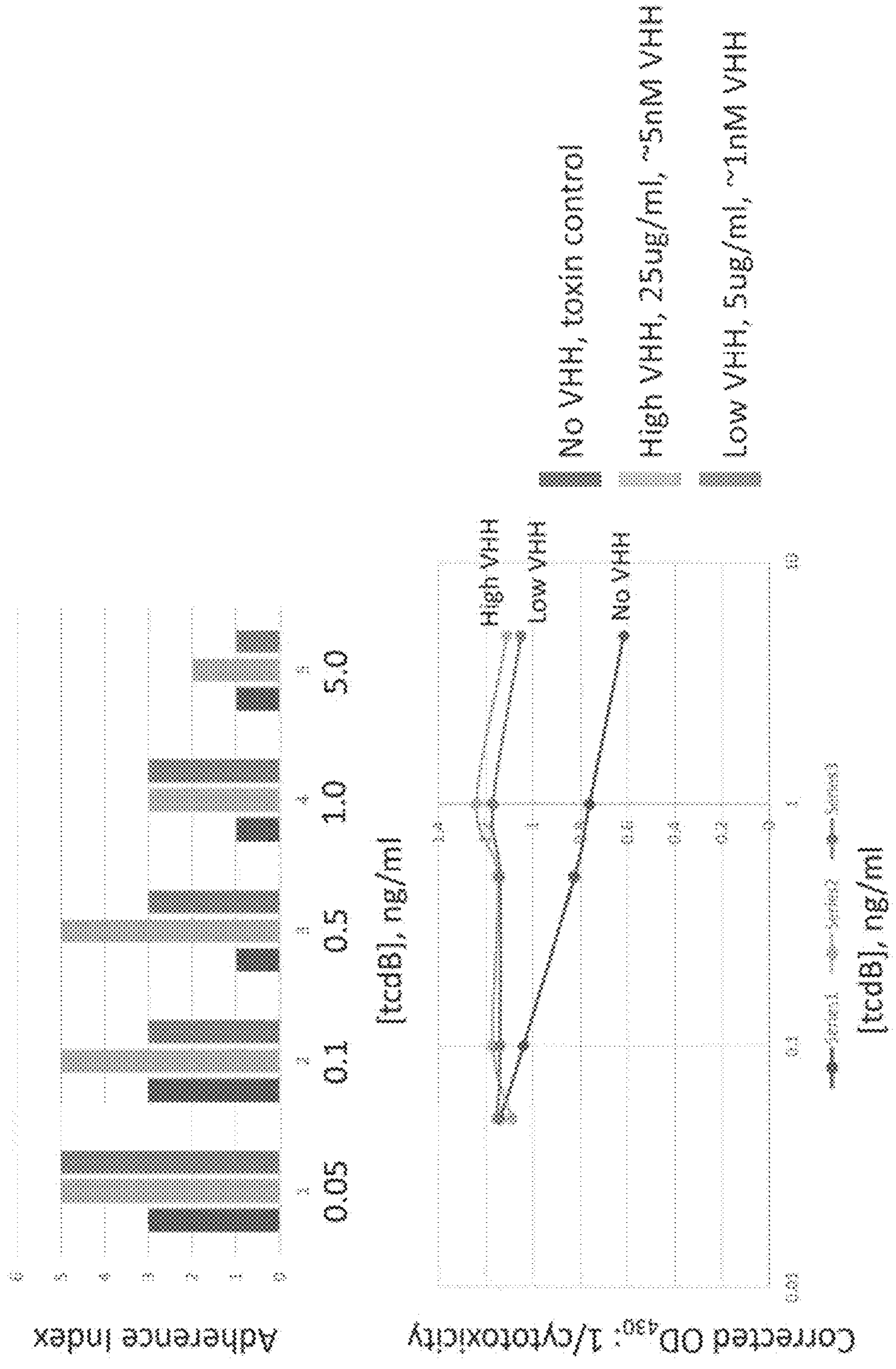
Figure 41D:
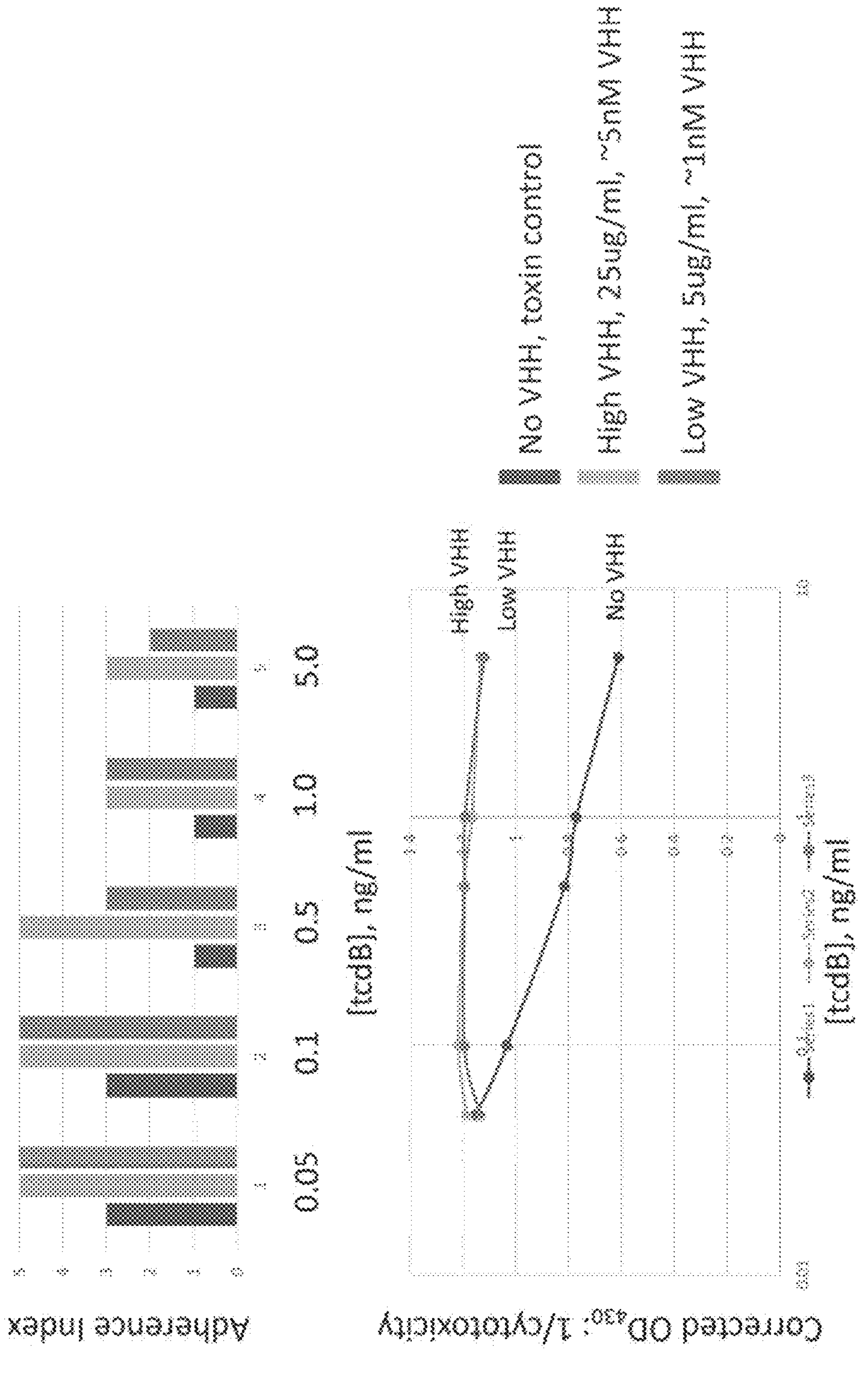
Figure 41E:
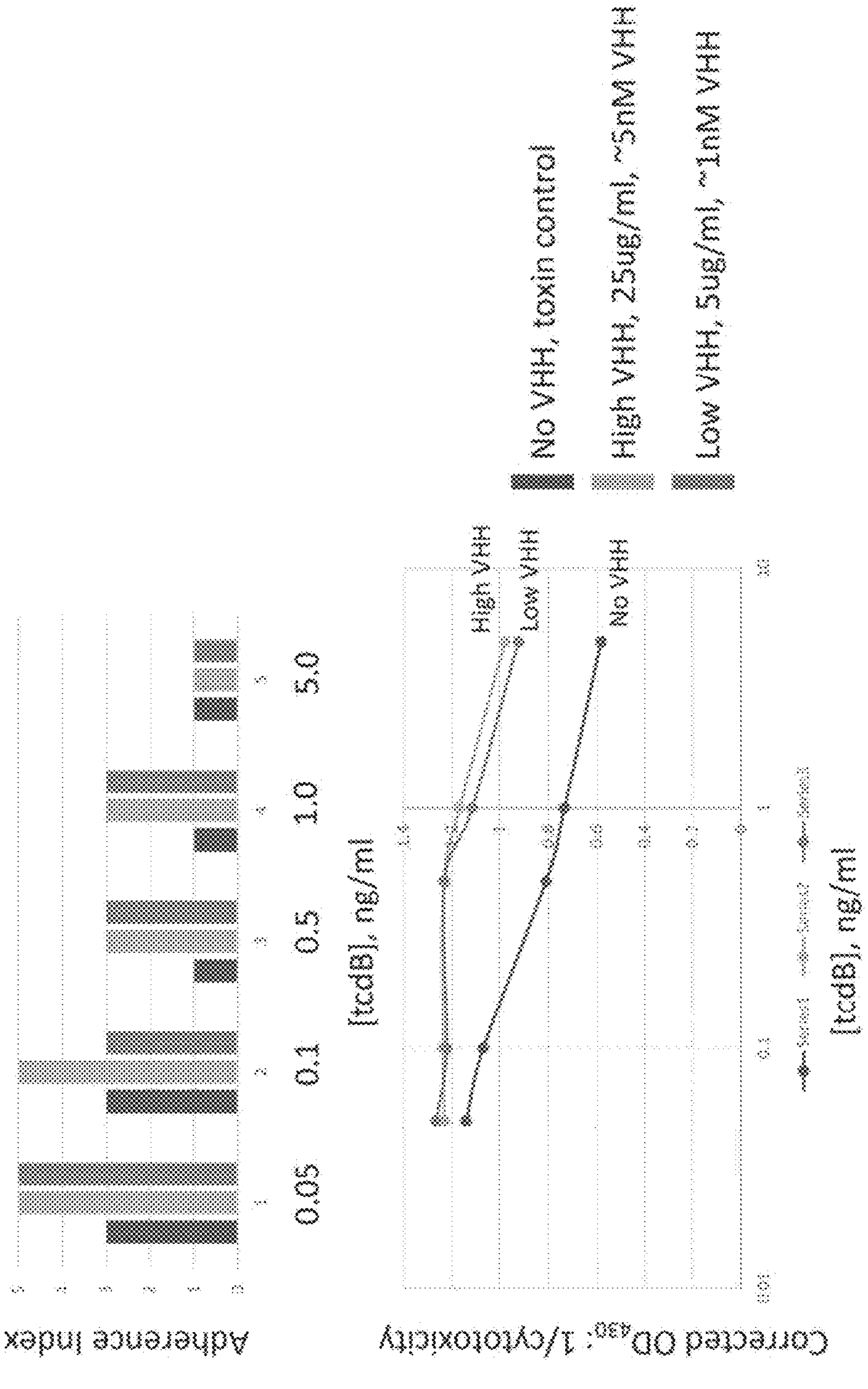
Figure 41F:
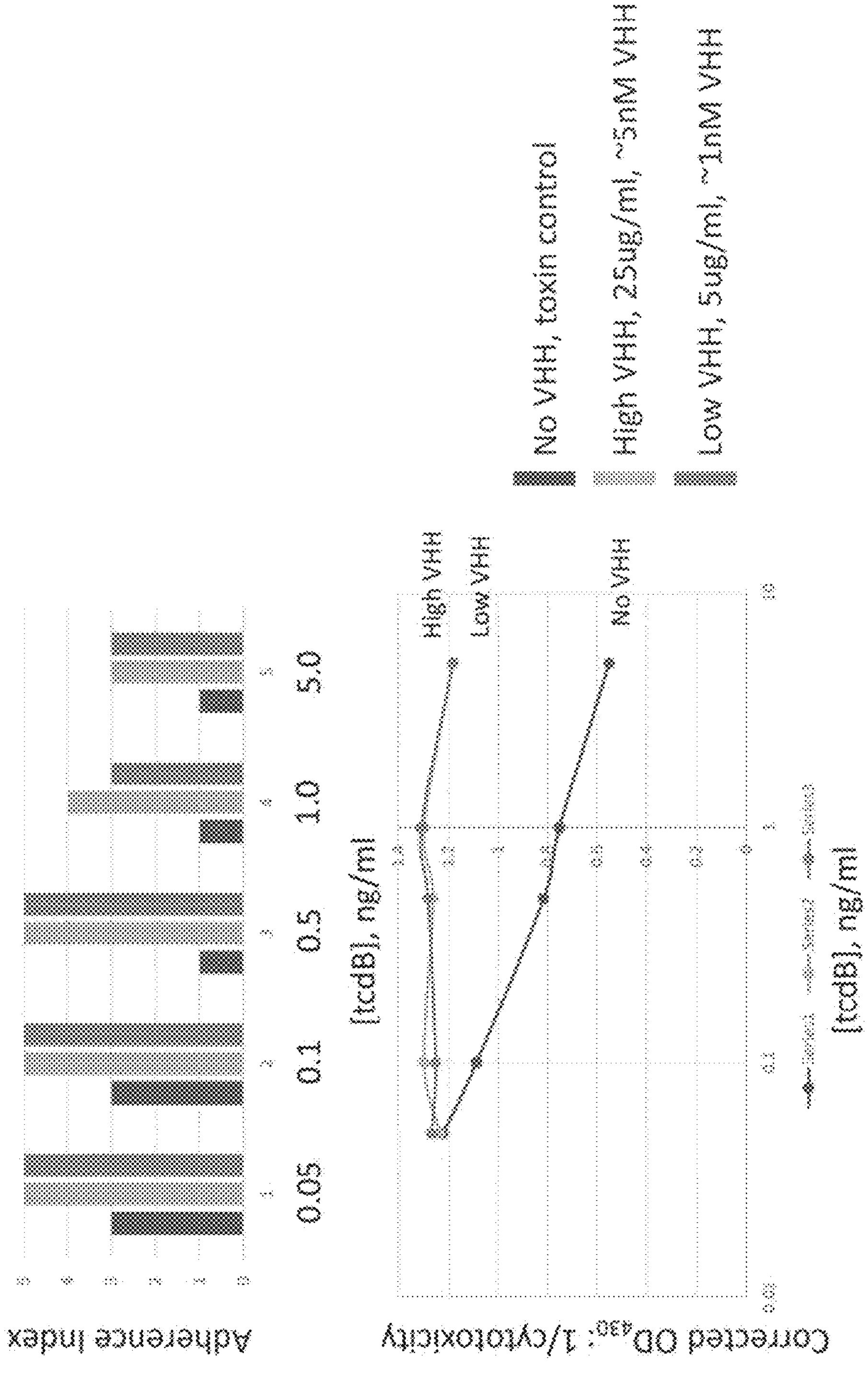
Figure 41G:
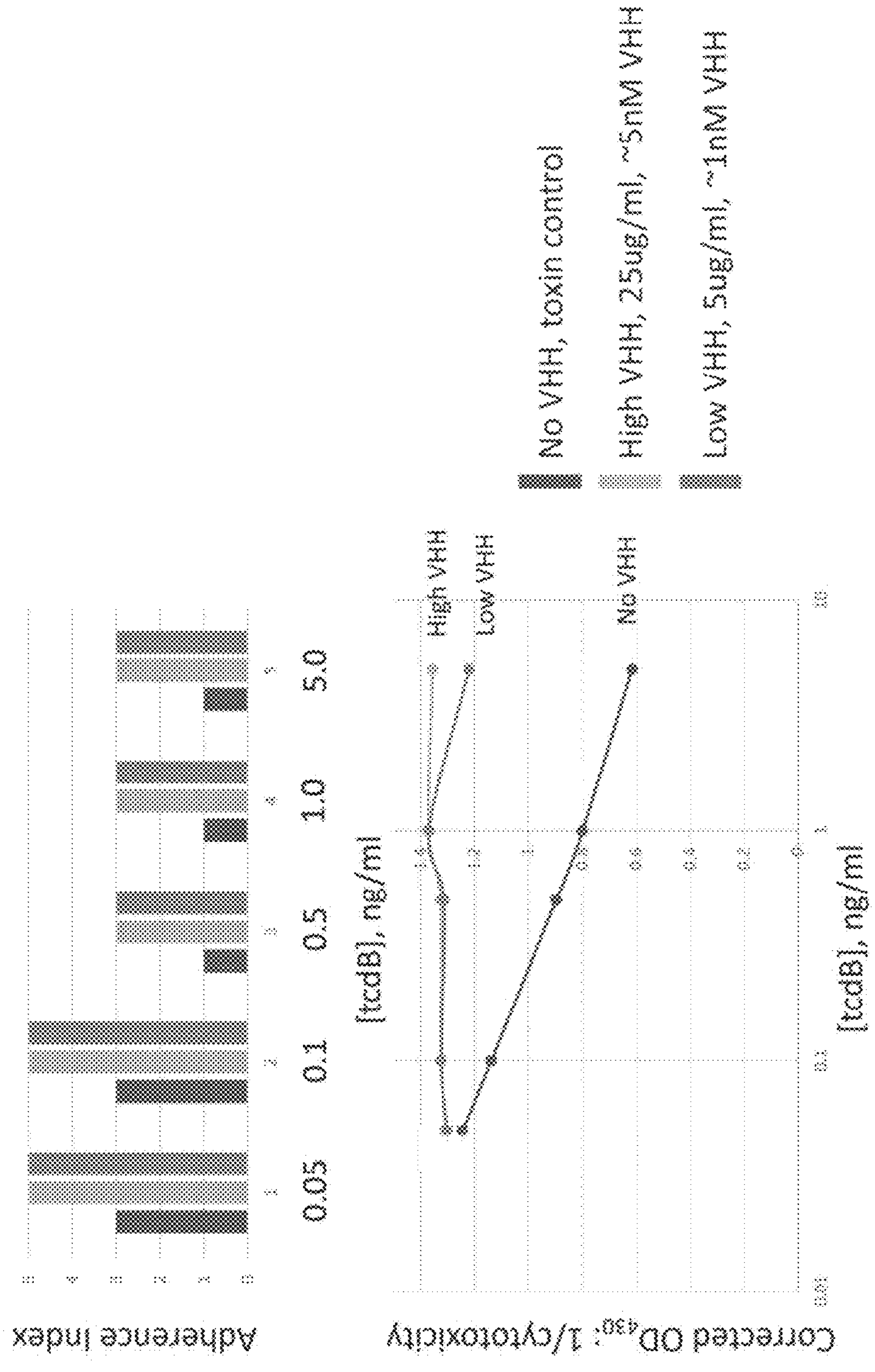
Figure 41H:
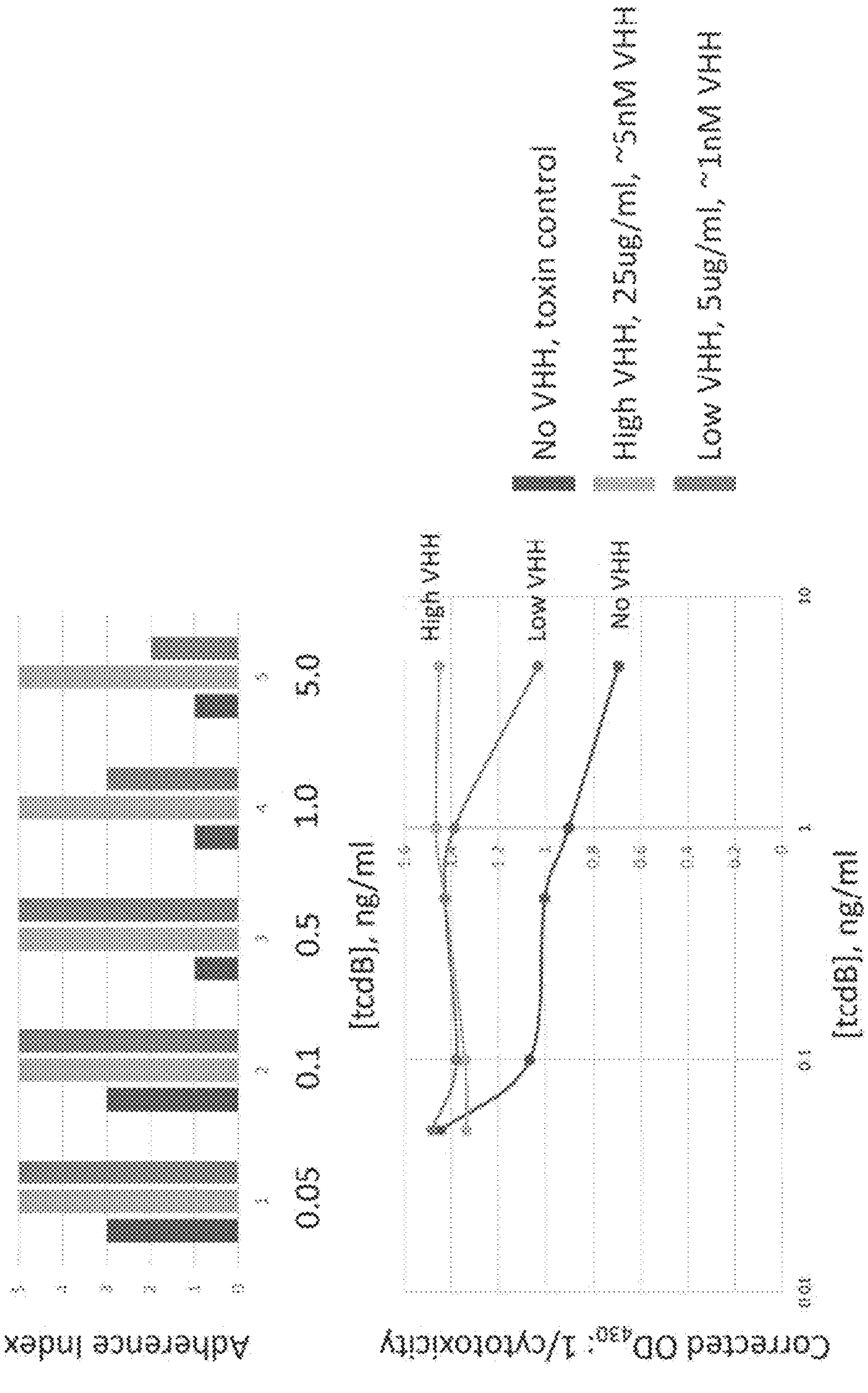
Figure 41J:
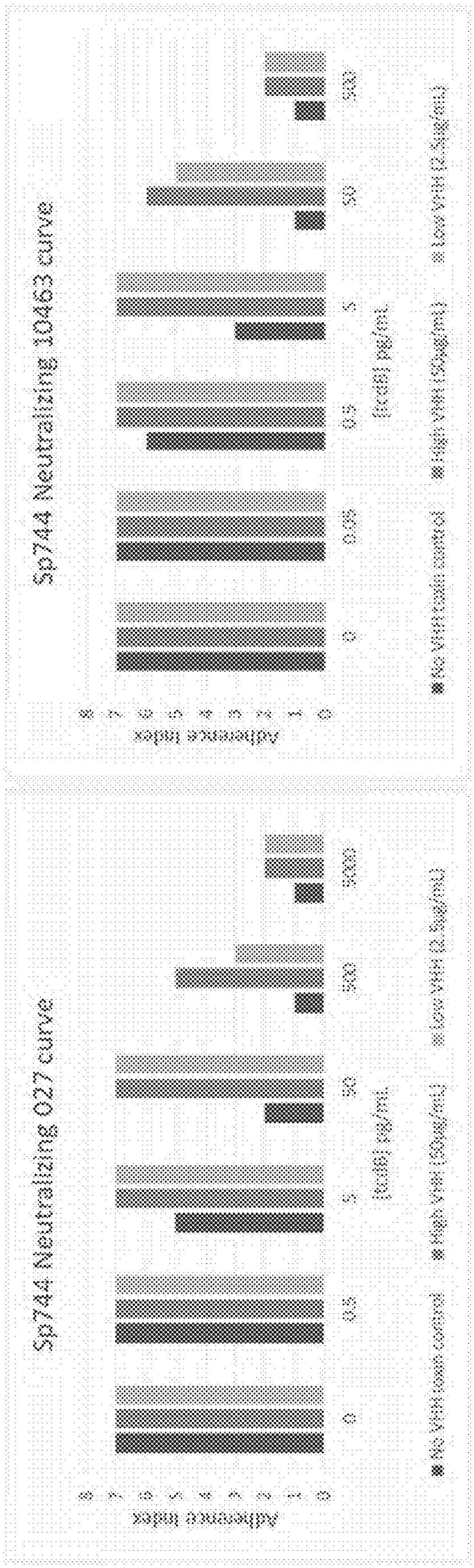
Figure 41J:
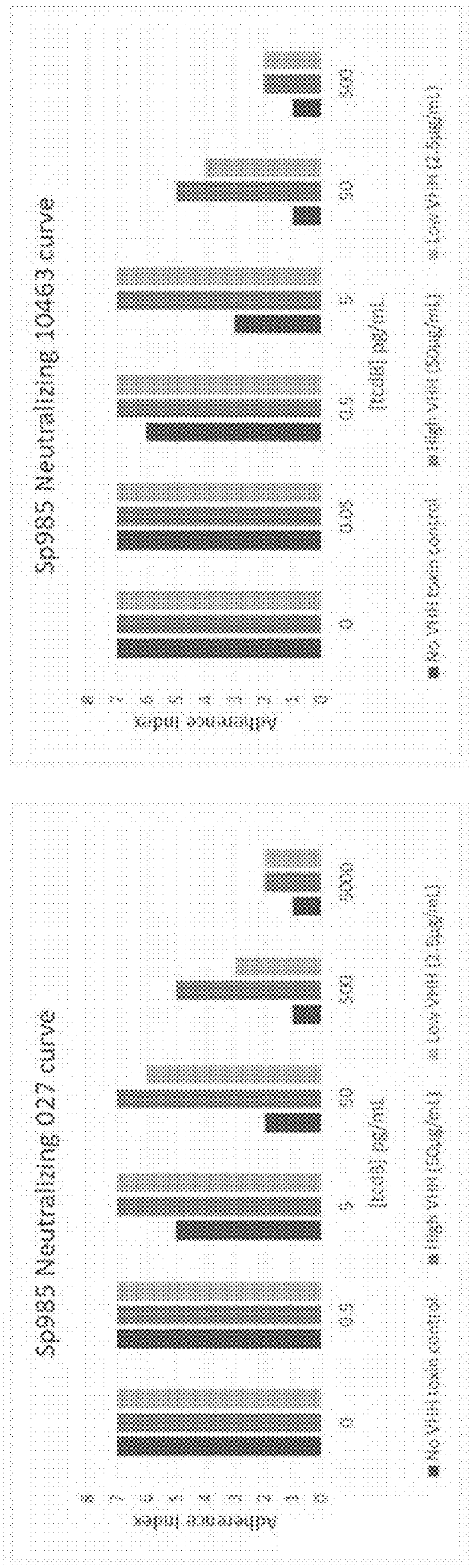
Figure 41L:
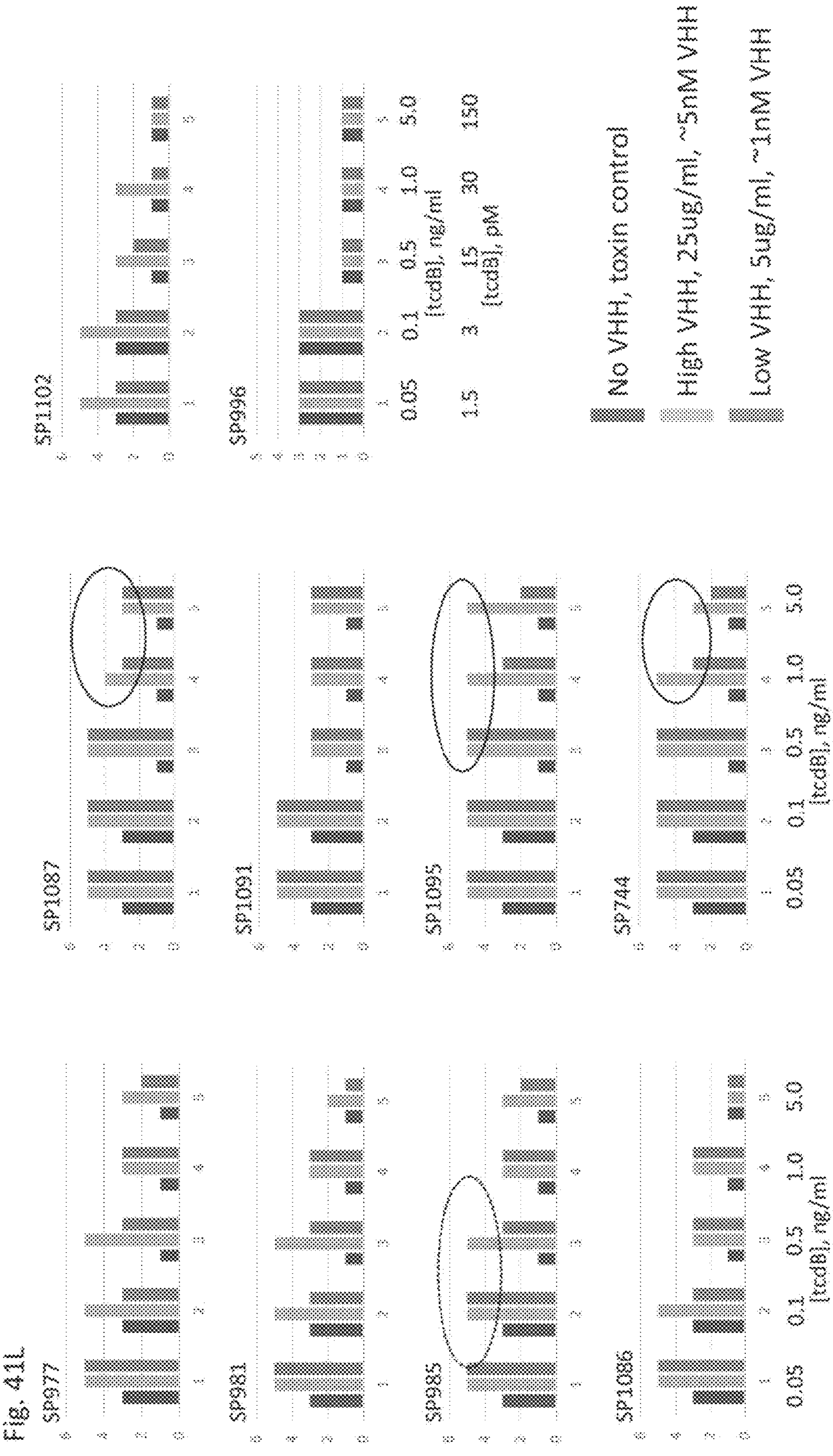

FIGS. 41A-O demonstrate morphology and cytotoxicity assays testing the anti-tcdB VHH constructs. FIGS. 41I-K and FIGS. 41M-O: Characterization of anti-TcdB neutralizing potency of high-performin *Spirulina* strains in the Vero cell rounding assay, using both the 027 and 10463 forms of TcdB. *Spirulina* lysates were normalized to transgene mass and compared in high and low concentration against a titration of toxin. FIG. 41I: SP744: VHH 5D-Trx neutralizing curves; FIG. 41J: SP985: VHH 5D-d.PP7 VLP neutralizing curves: FIG. 41K: SP1087: Trx-Trimer-VHH.5D neutralizing curves: FIG. 41M: SP1095: VHH.E3-Trx-Trimer-VHH.5D neutralizing curves; FIG. 41N: SP977: VHH.5D-dMS2 VLP neutralizing curves; FIG. 41O: SP1091: Trx-Pentamer-VHH.5D. FIG. 41L: Characterization of anti-TcdB neutralizing potency of select *Spirulina* strains in the Vero cell rounding assay, using the 027 form of TcdB. *Spirulina* lysates were normalized to transgene mass and compared in high and low concentration against a titration of toxin. Best performers are denoted with red ovals.

Figure 42:
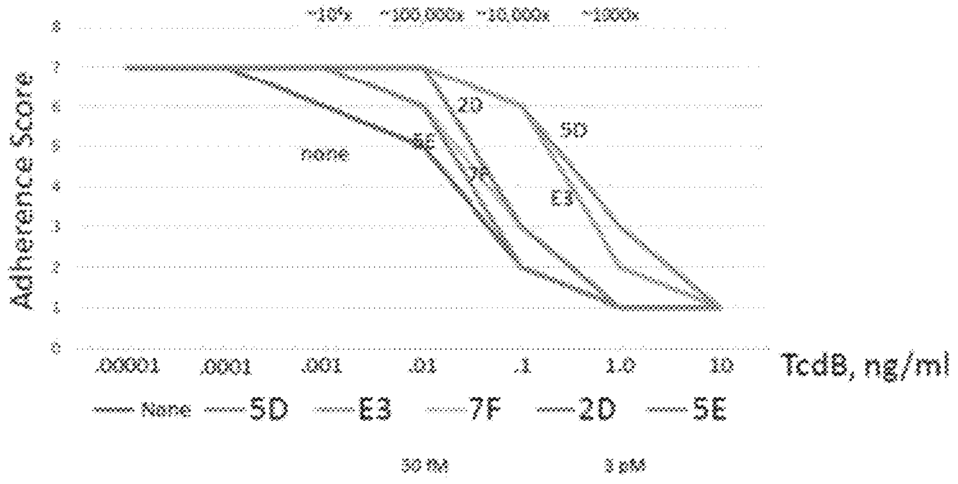

FIG. 42 demonstrates the binding strength of various VHH sequences to *C. difficile* TcdB toxin.

Figure 43:
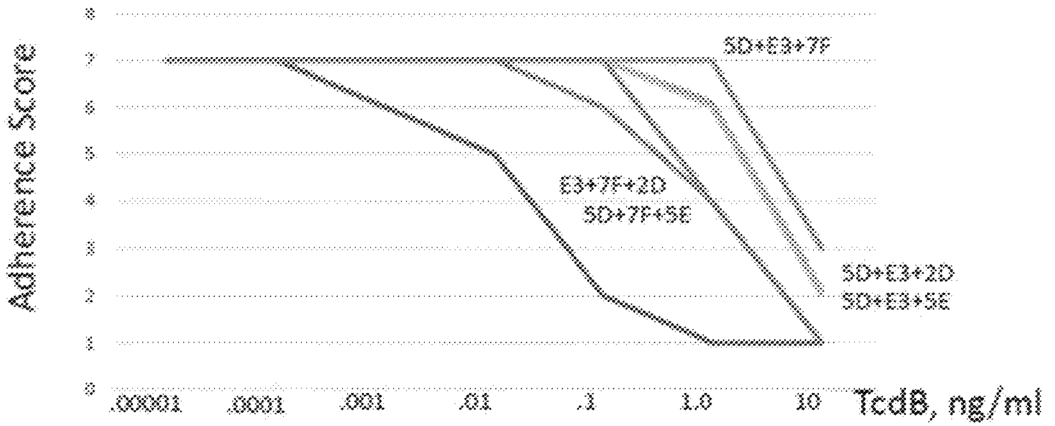

FIG. 43 demonstrates the binding strength of combinations of different VHH sequences to *C. difficile* TcdB toxin.

Figure 44A:
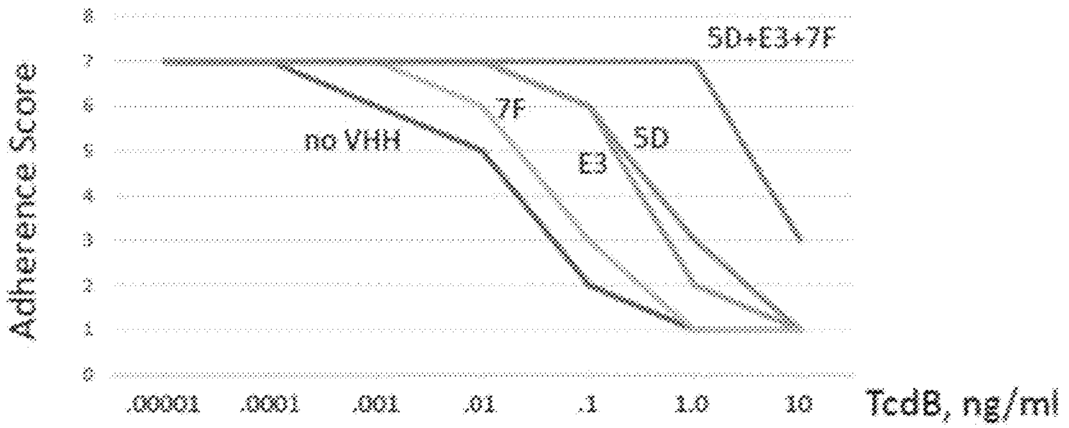
Figure 44B:
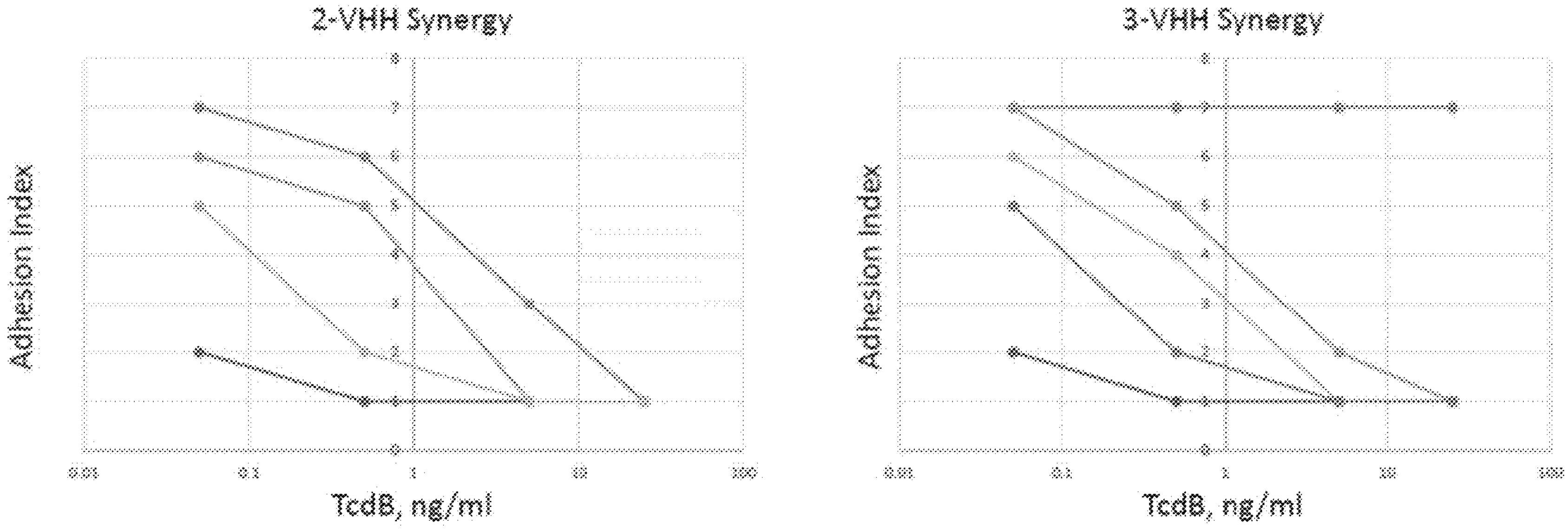

FIG. 44A-B demonstrates the binding strength of the combination of the 5D, E3, and 7F VHHs to *C. difficile* TcdB toxin both alone and in combination.

Figure 45B:
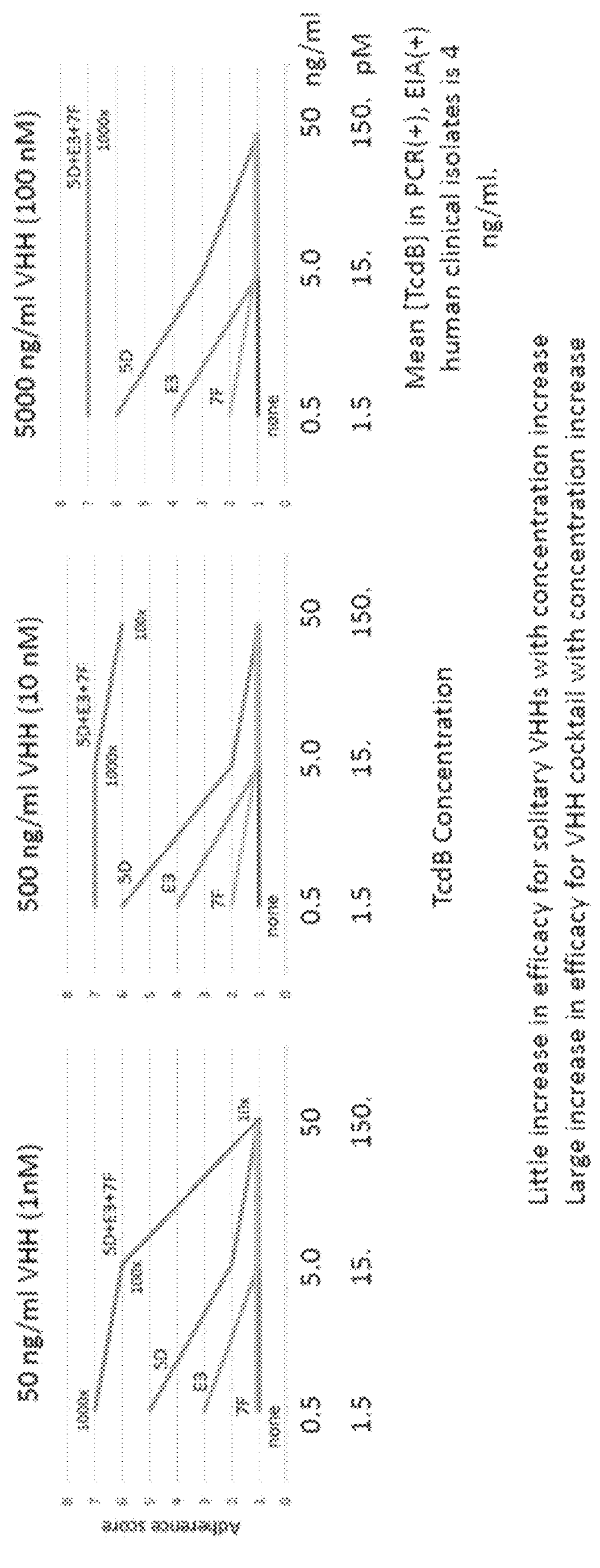

FIGS. 45A-B demonstrate the effect of VHH concentration on binding to *C. difficile* TcdB toxin. While concentration increases of any of the single VHH sequences had little effect on efficacy, surprisingly, concentration increases of the combination of VHH sequences showed a large increase in efficacy.

Figure 46:
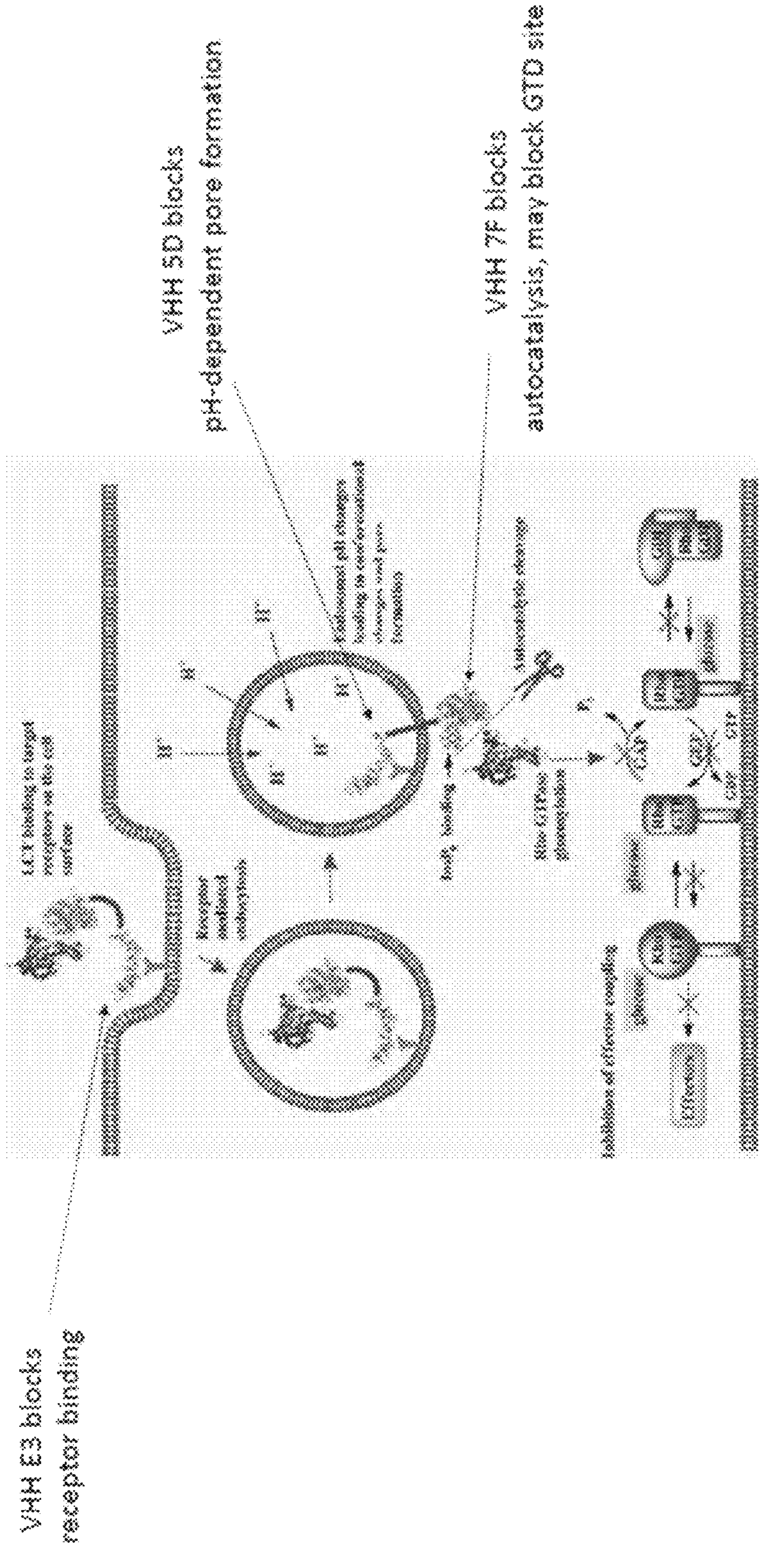

FIG. 46 shows putative synergistic action of different VHHs on *C. difficile* infection and signaling.

FIG. 47A-B: Two-way synergy among anti-TcdB VHHs. Scoring denotes cell rounding index: 7=normal, 1=100% rounding, 4=50% rounding, as determined by visual inspection. Scores of 5 and 6 are on a gradient from 50% round to 100% normal, and scores of 3 and 2 are on a similar gradient from 50% round to 100% round.

Figure 48:
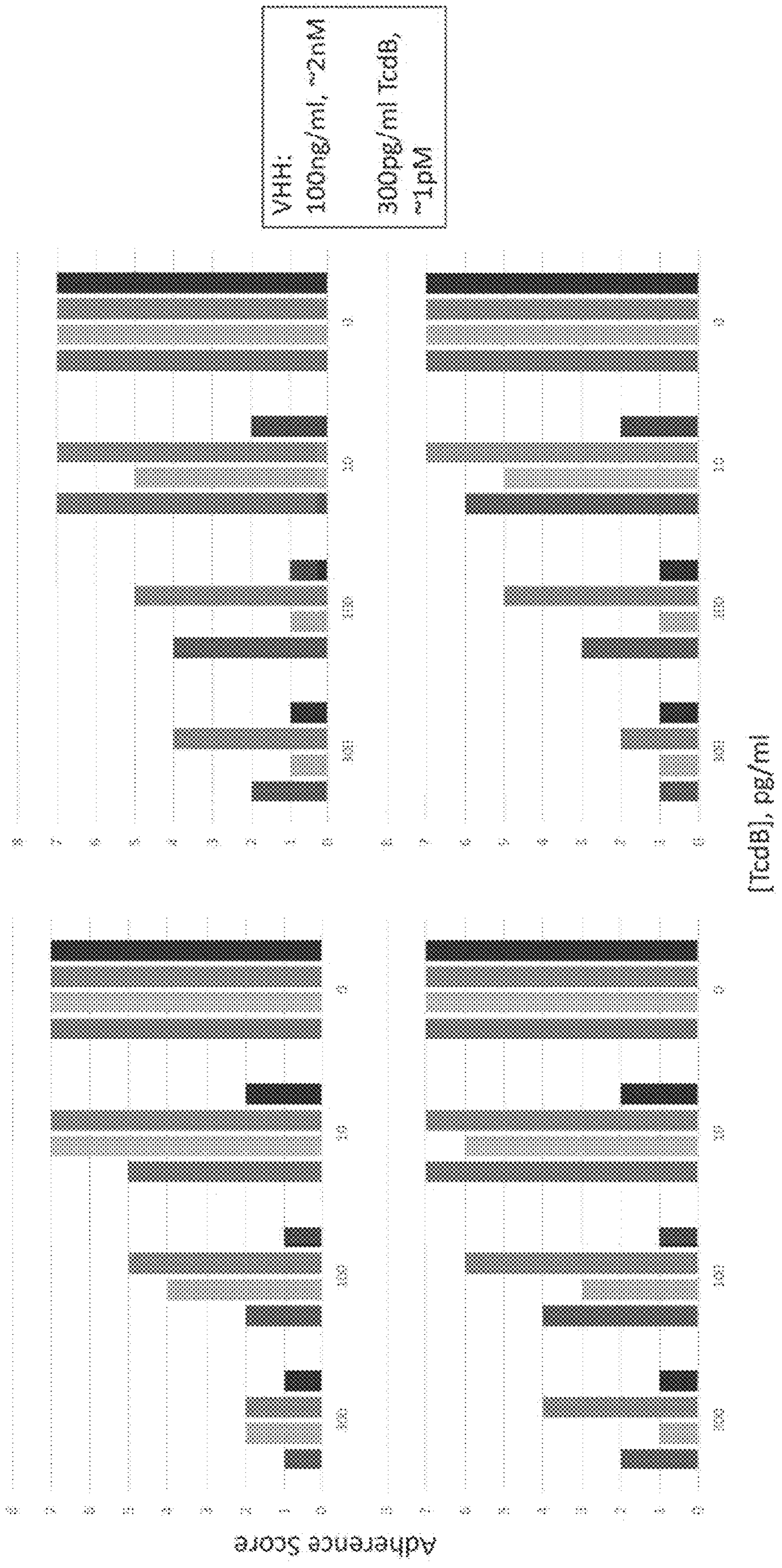

FIG. 48: Individual and 2-way synergy combinations of anti-TcdB VHHs, measured in Vero cell rounding assay using TcdB 027.

Figure 49:
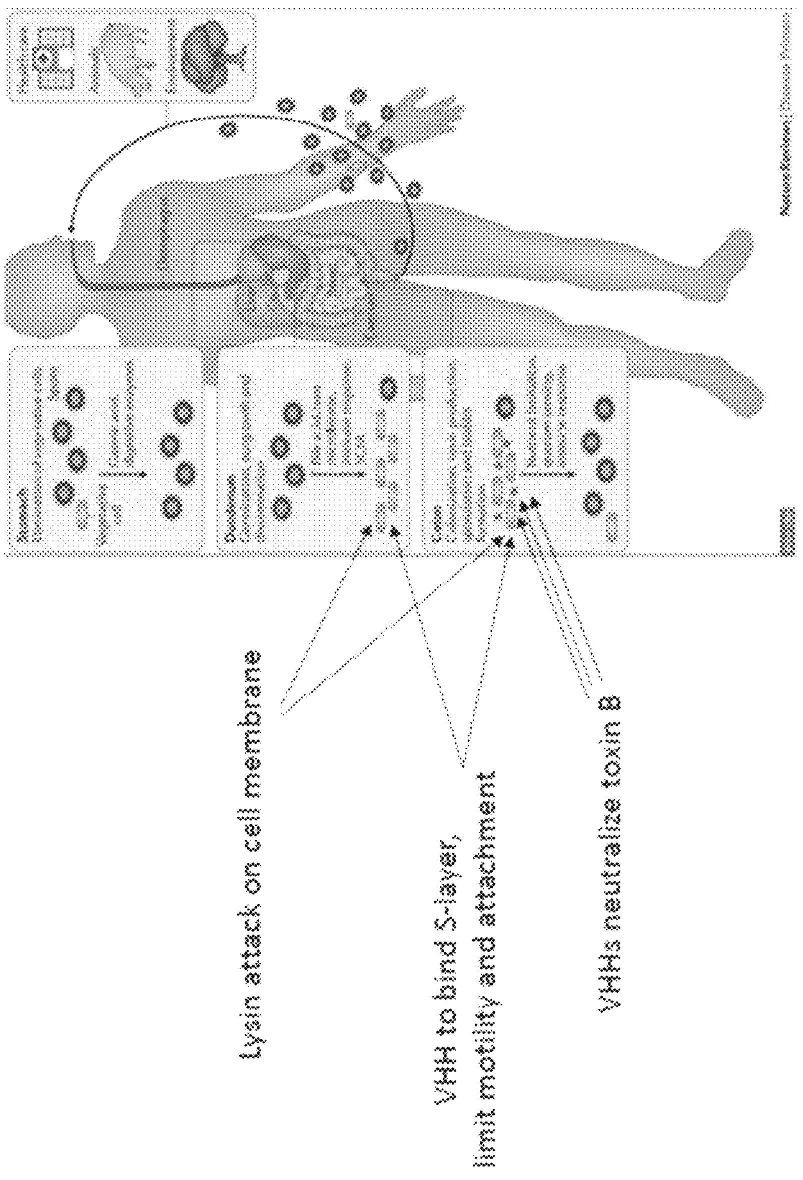

FIG. 49 describes a putative cocktail for preventing and/or treating a *C. difficile* infection.

Figure 50:
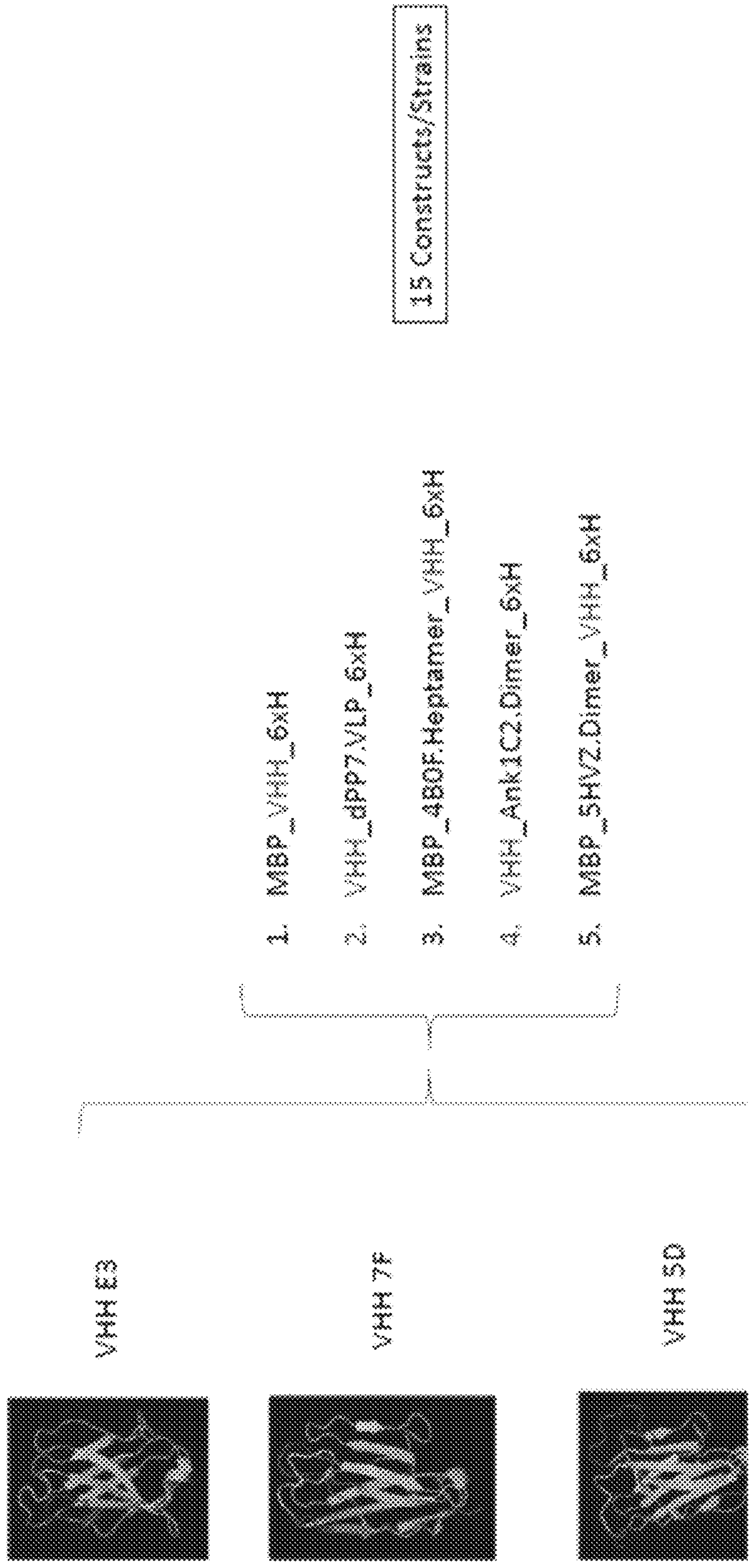

FIG. 50: Schema of VHH hybridization with candidate scaffold partners. VHHs were selected based on our evaluation, and published structure/function studies with TcdB.

Figure 51:
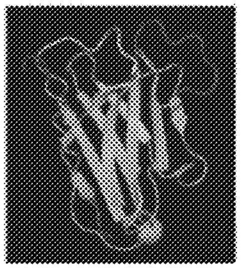

FIG. 51 shows constructs for assessment of rigid interdomain linkers.

Figure 52A:
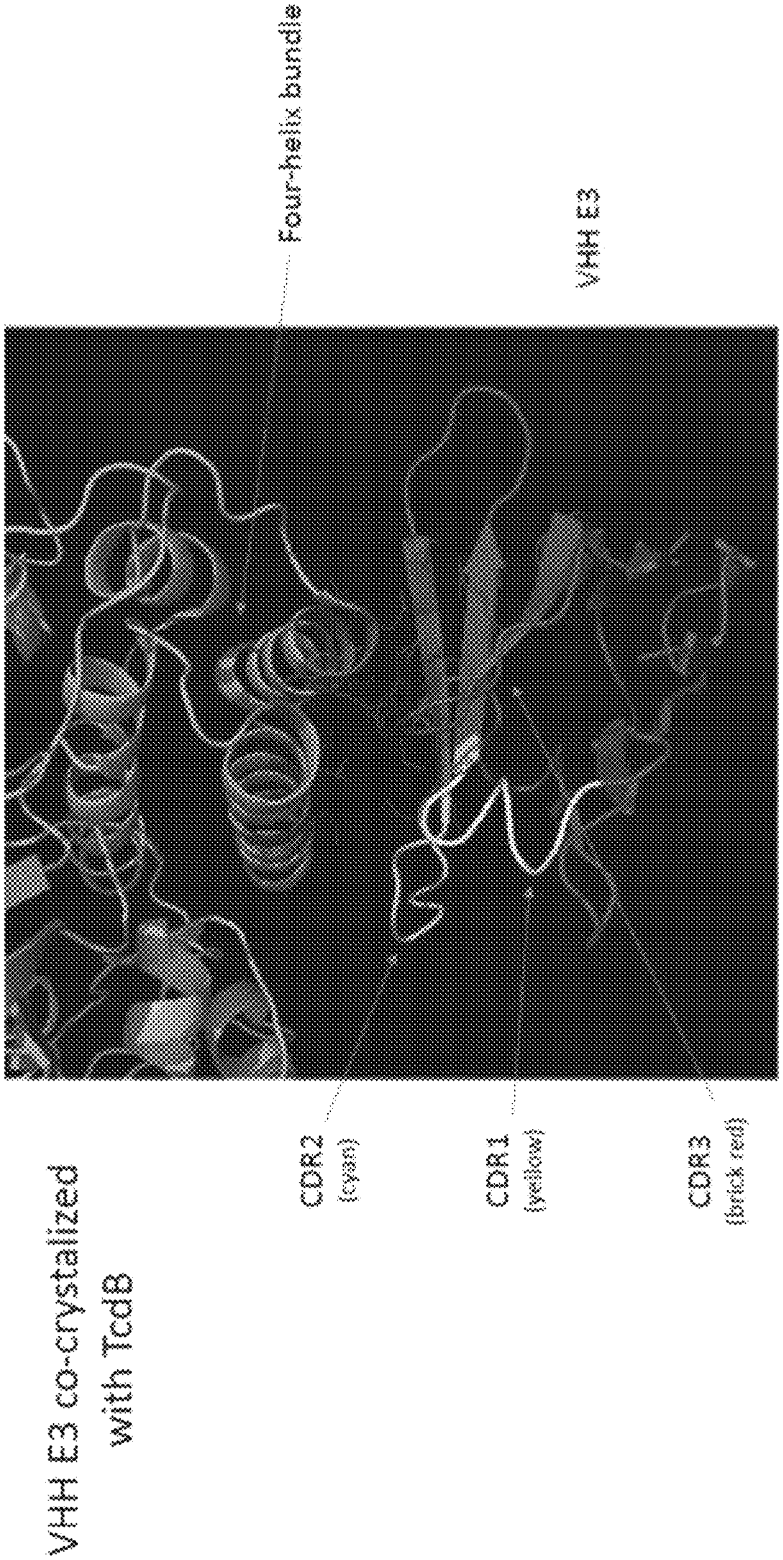
Figure 52B:
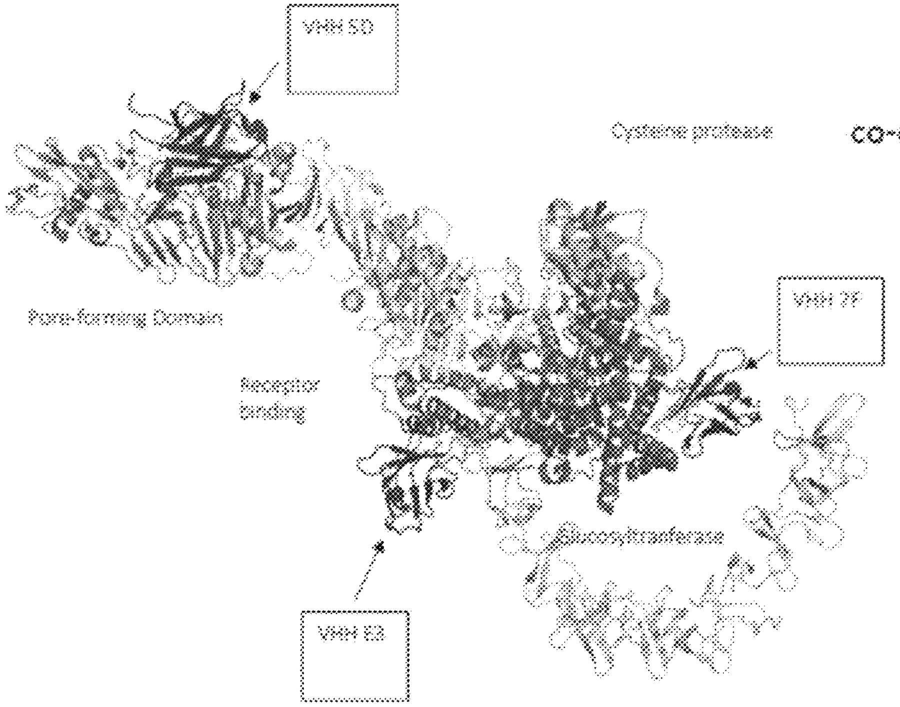

FIG. 52A-B shows the crystal structure of VHH E3 co-crystallized with TcdB.

Figure 53:
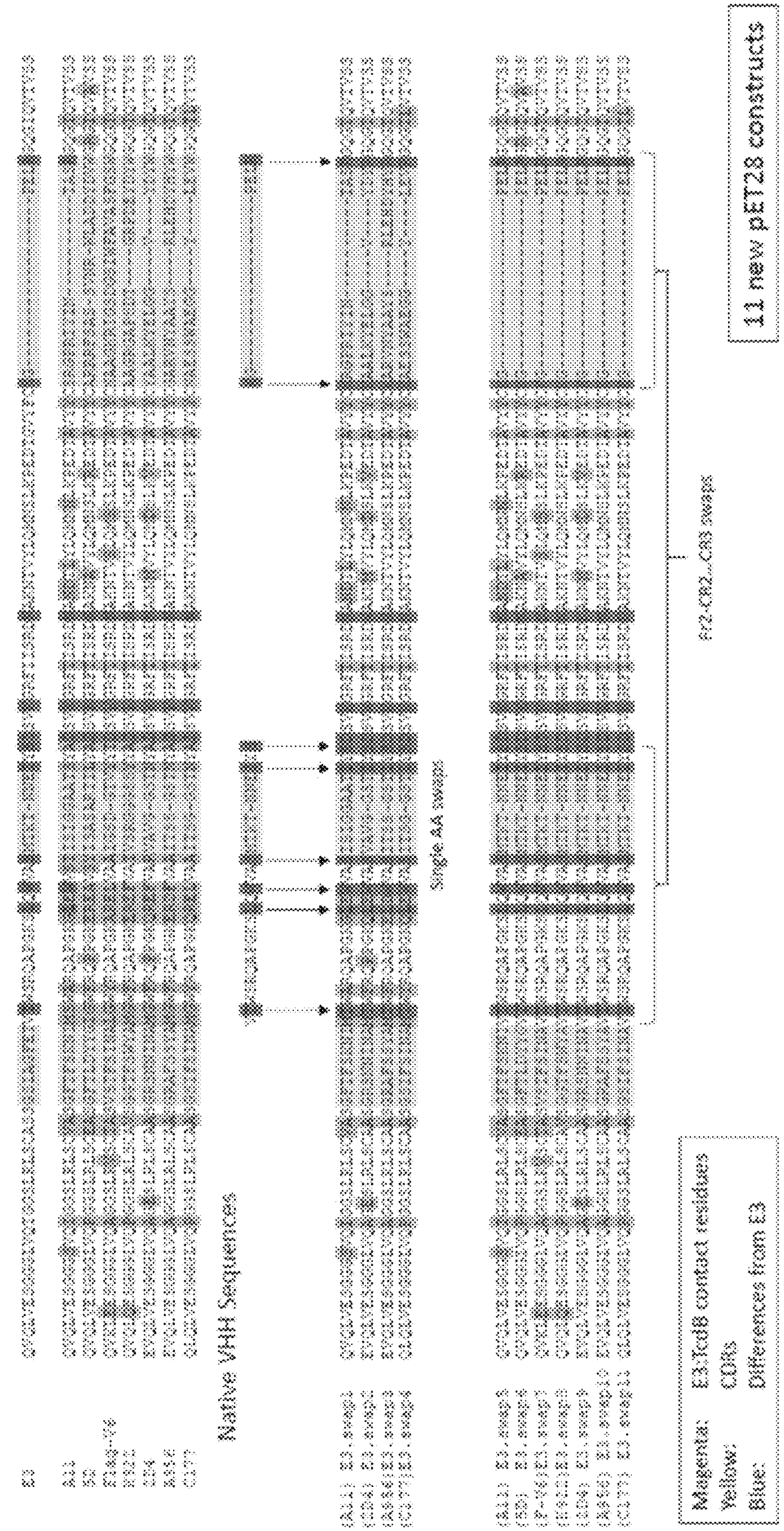

FIG. 53 shows exemplary sequences engineering VHH.E3-like activity onto other frameworks.

FIG. 54 shows adherence values for individual VHHs produced in *Spirulina.*

Figure 55:
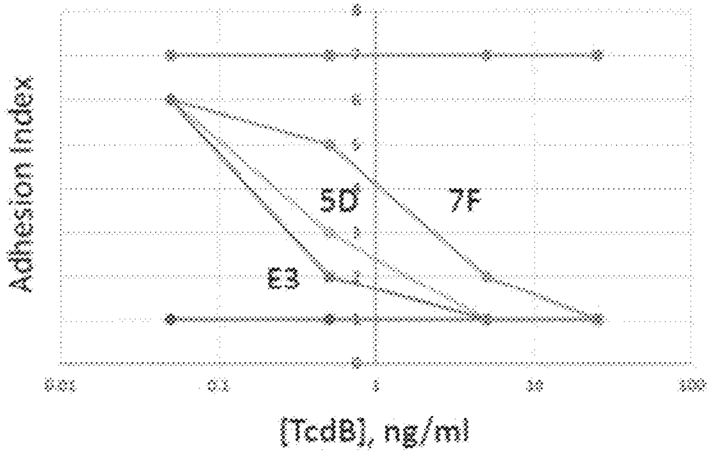

FIG. 55 demonstrates that a mixture of three *Spirulina*-expressed VHHs (5D+E3+7F) is substantially more potent than individual constituents.

Figure 56:
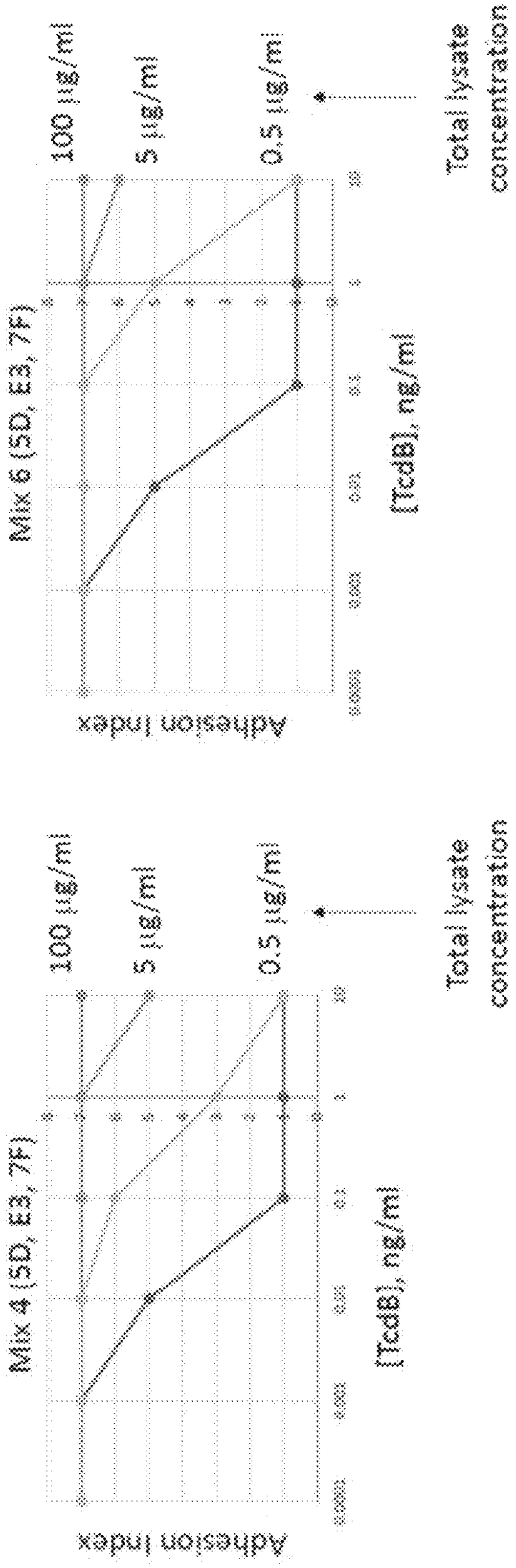

FIG. 56 shows adherence values for mixtures of *Spirulina*-produced VHHs.

FIG. 57 shows that mixtures of *Spirulina*-produced VHHs neutralizes high-doses of TcdB.

Figure 58:
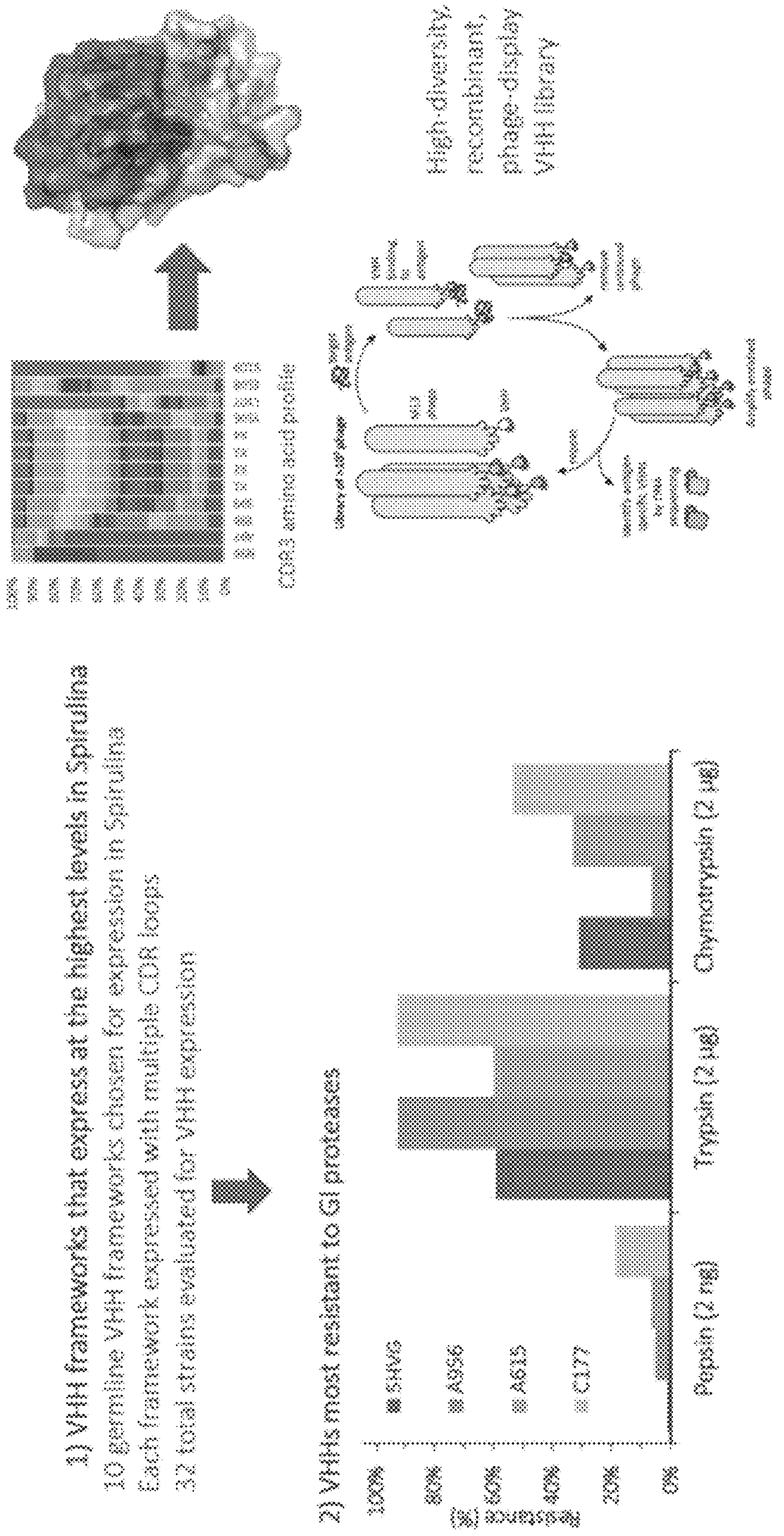

FIG. 58 shows how the present disclosure can be employed to rapidly discover antibodies tailor-made for oral delivery.

Figure 59:
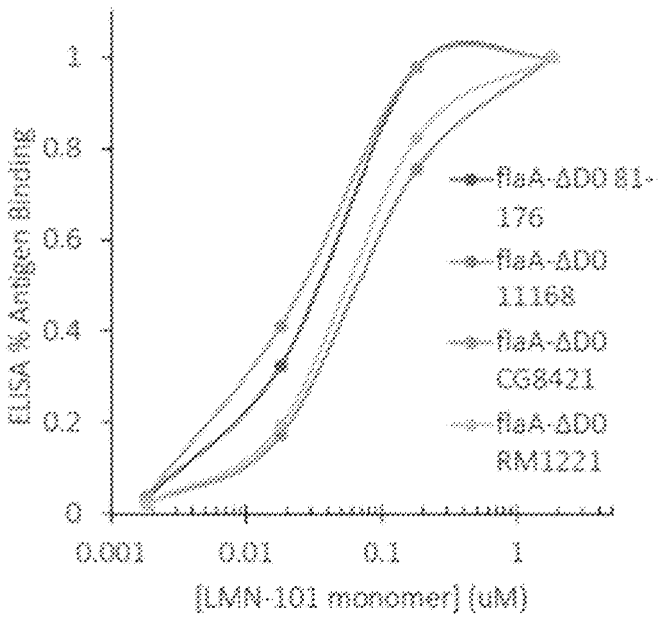

FIG. 59 shows maximized strain cross-reactivity. A comparison of the domain in FlaA targeted by LMN-101 from the Navy (NCBIC) *C. jejuni* database (>10,000 sequences) shows that 79% of the sequences share at least 75% homology suggesting that cross-reactivity of this one lead VHH may extend to 79% of *campylobacter* strains.

Figure 60:
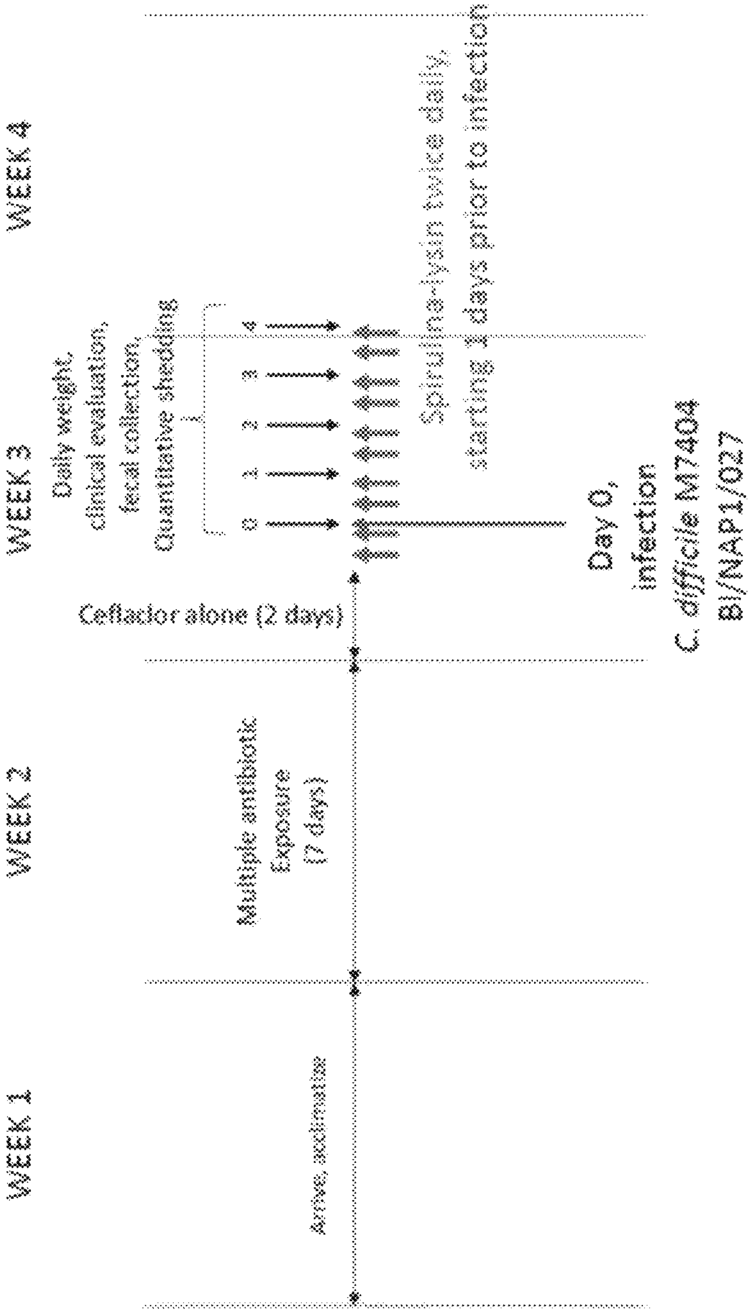

FIG. 60 shows a proposed model for prevention of *C. difficile* in mice.

Figure 61:
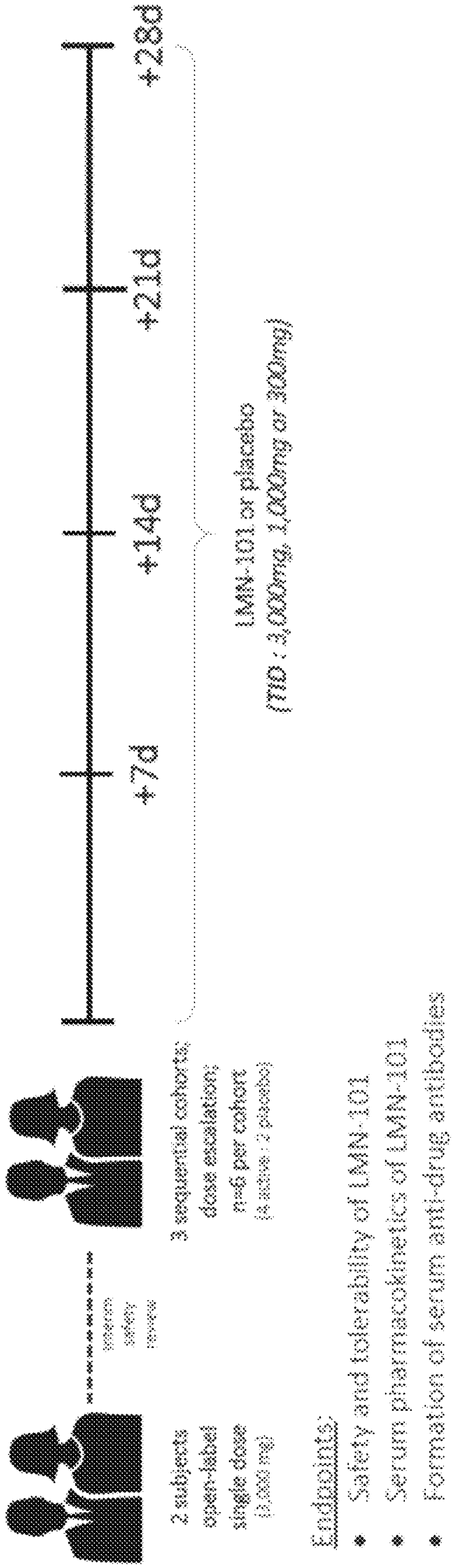

FIG. 61 shows an exemplary double-blind, placebo-controlled study to evaluate the safety and tolerability of LMN-101.

FIG. 62 shows an exemplary double-blind, placebo-controlled study to evaluate the safety and prophylactic activity of LMN-101 against *C. jejuni* CG8421 (human challenge strain.

Figure 63:
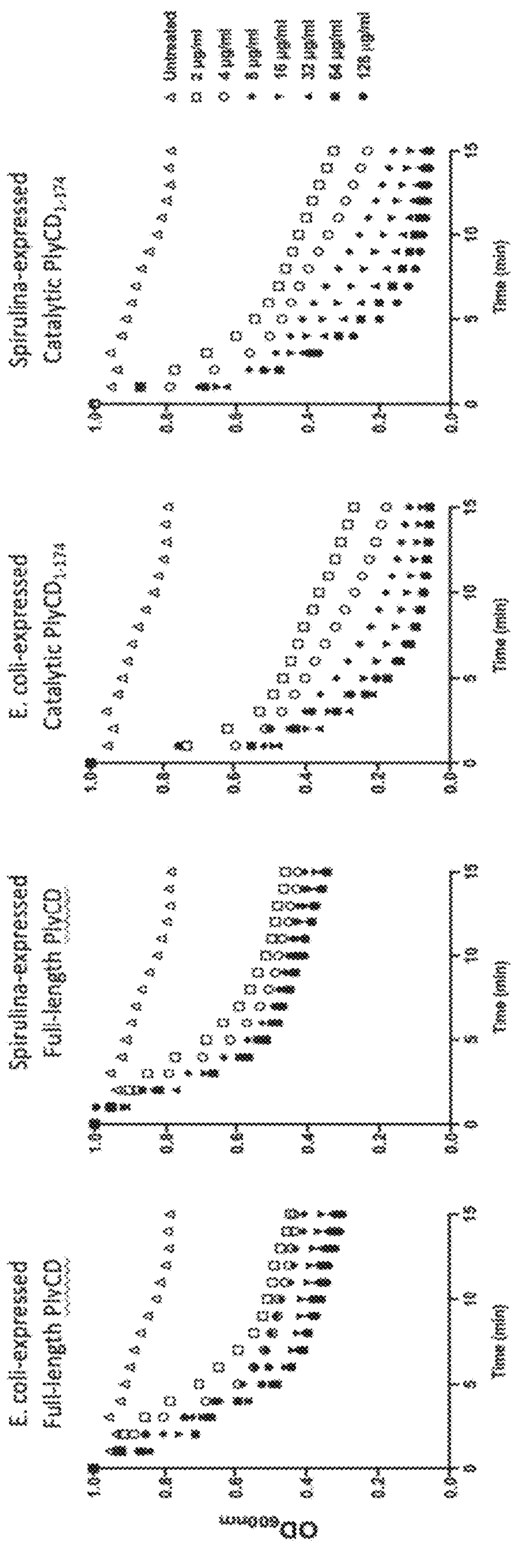

FIG. 63 shows cell lysis assay results for both *E. coli*-expressed and *Spirulina*-expressed proteins. Log-phase cultures, O.D.600=1, of *C. difficile* were treated with the indicated concentrations of lysin. Cell lysis was measured by reduction in optical density over time. *Spirulina*-expressed lysins are biologically active.

FIG. 64: the effect of rigid linkers on VHH 5D neutralizing activity. The assay has a numeric read out from 1 (totally detached and dying) to 7 (normal).

Figure 65:
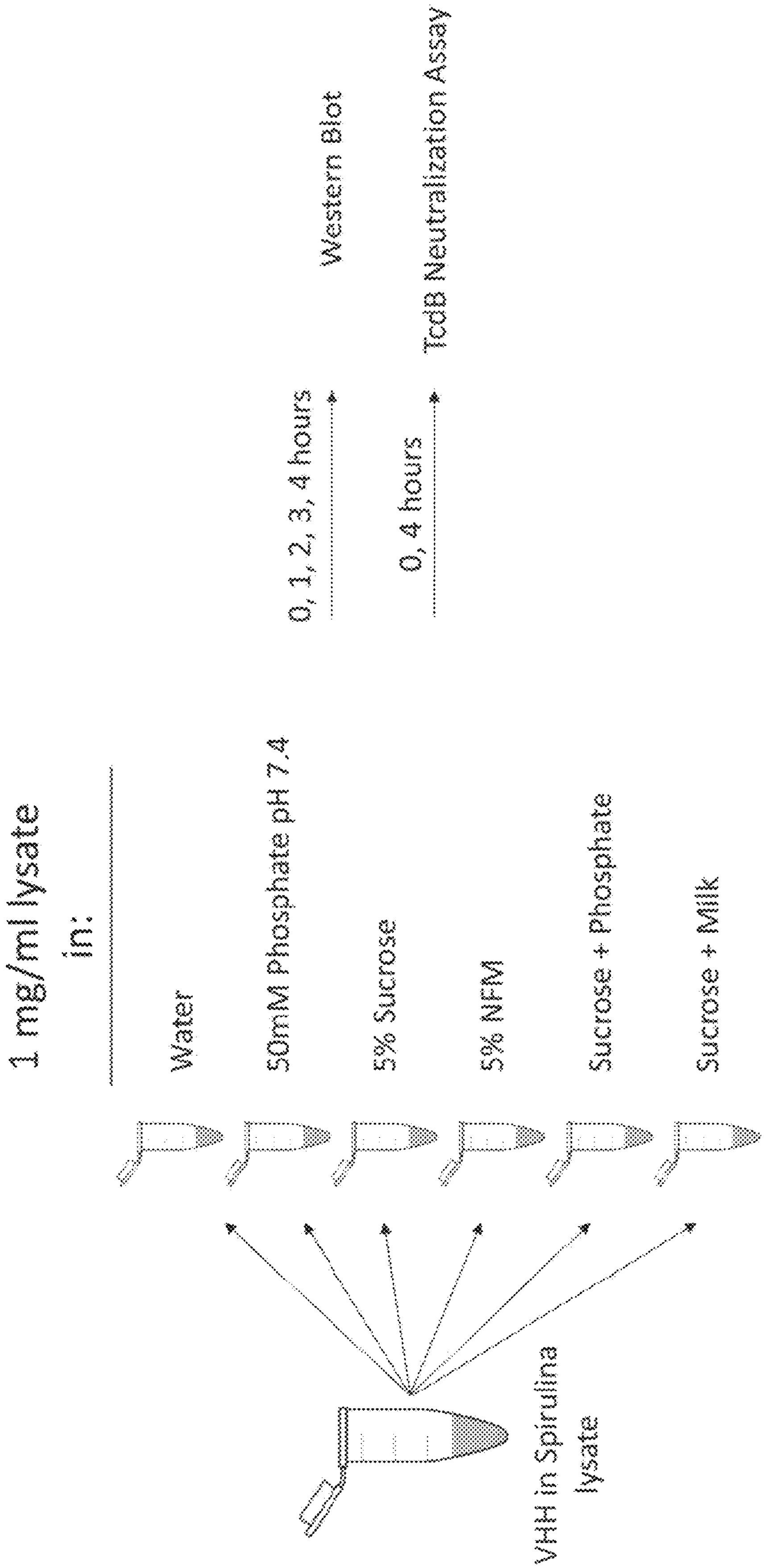

FIG. 65: overview of *Spirulina* stability assay

Figure 66:
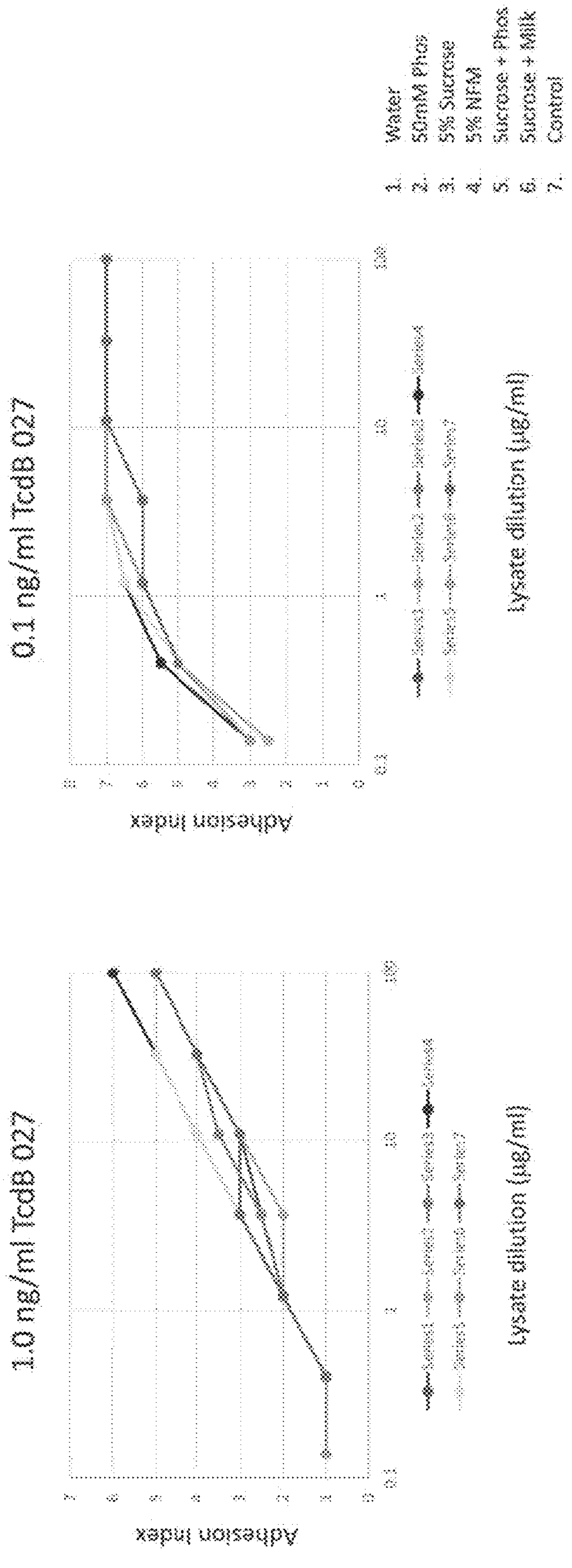

FIG. 66: aqueous stability study of SP1308, MBP-SHVZ-VHH 5D. The lysates were incubated in media for four hours.

Figure 67:
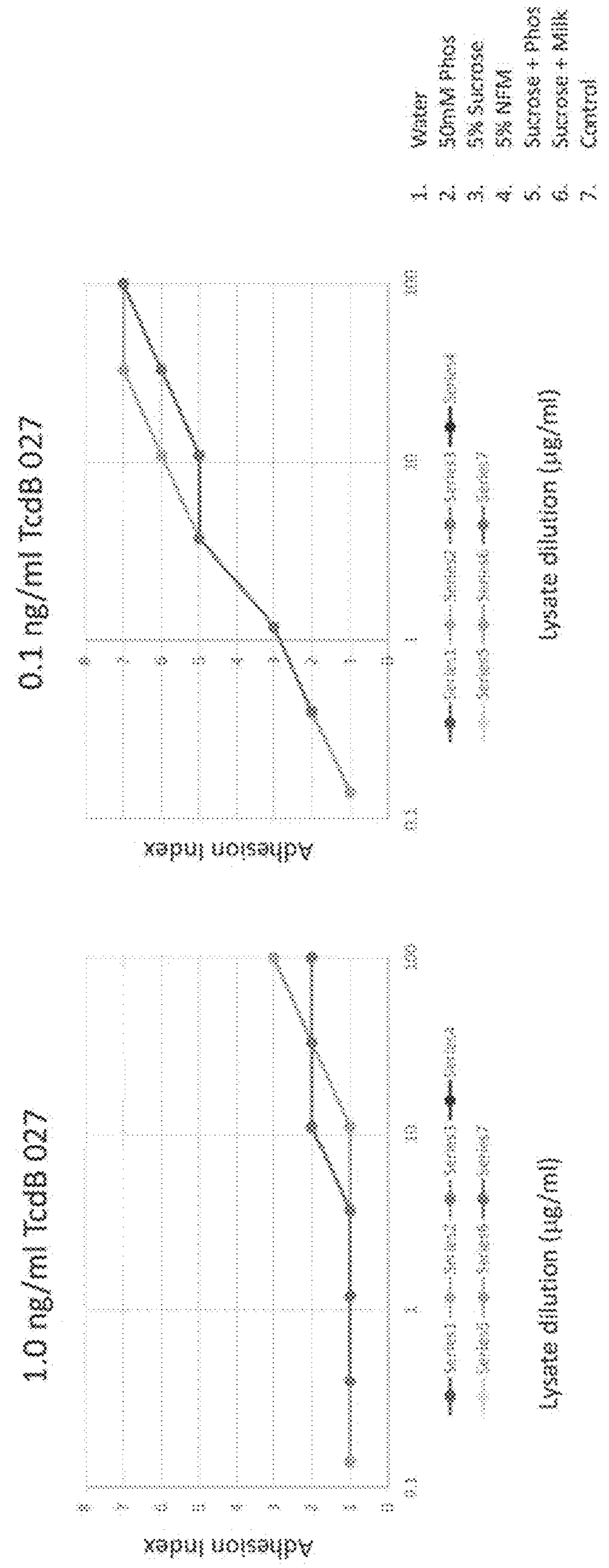

FIG. 67: aqueous stability study of SP1312, MBP-5HVZ-VHH E3. The lysates were incubated in media for four hours.

Figure 68:
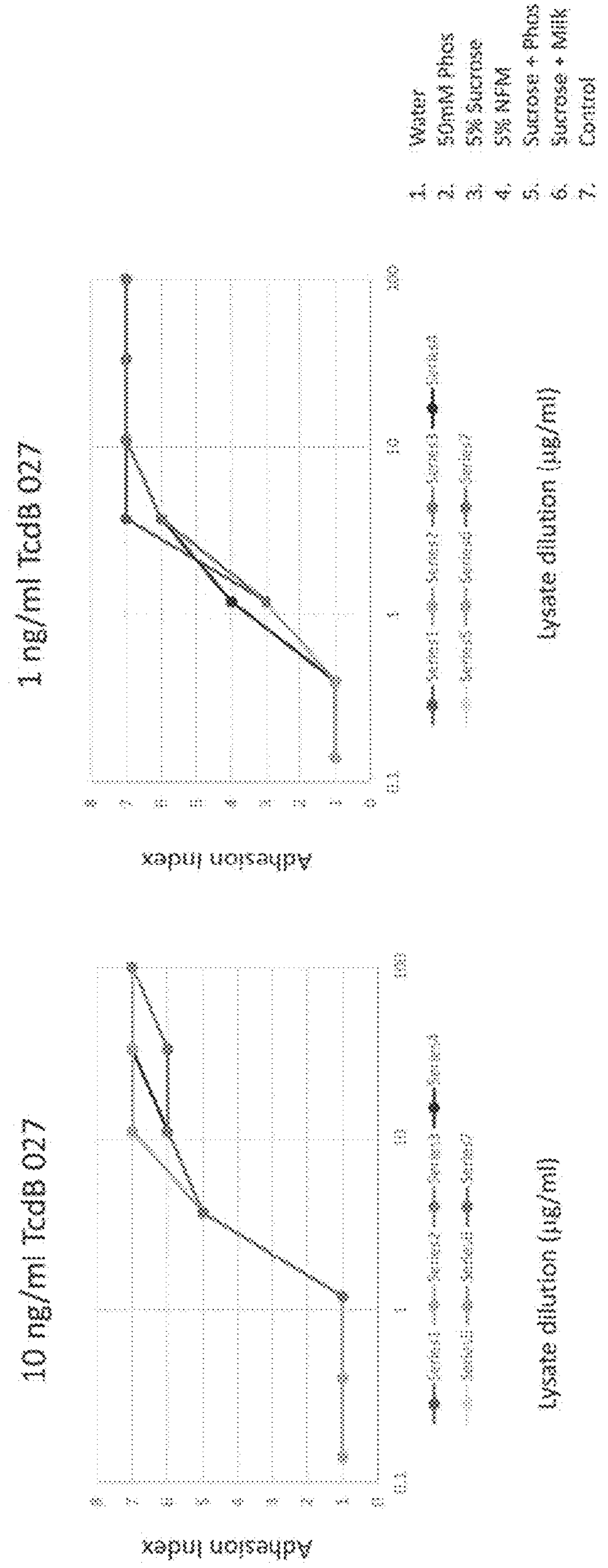

FIG. 68: aqueous stability study of SP1308+SP1312+SP1313. The lysates were incubated in media for four hours.

Figure 69A:
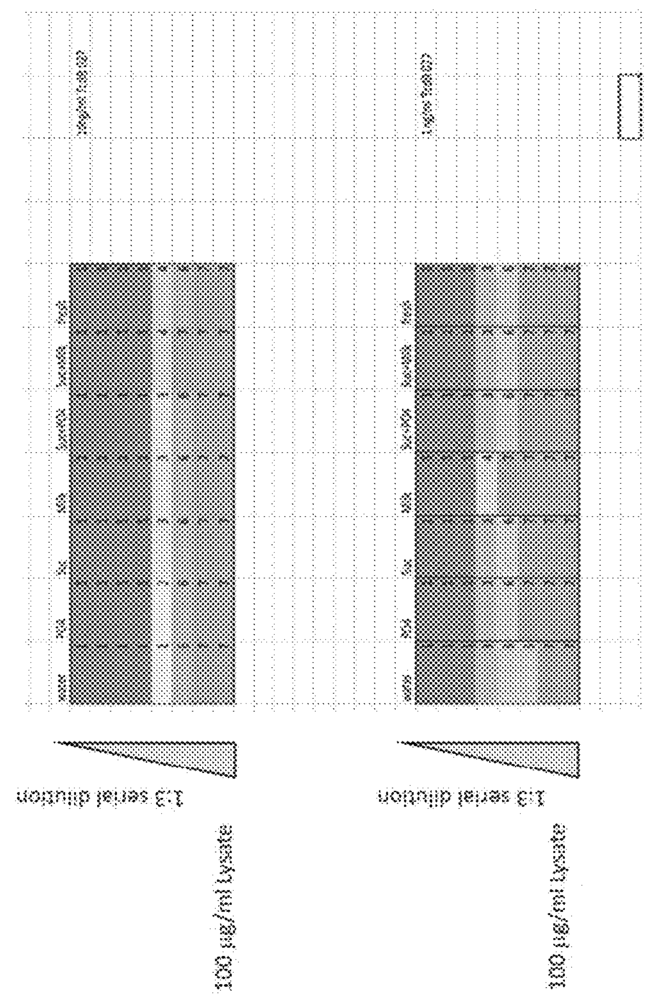
Figure 69B:
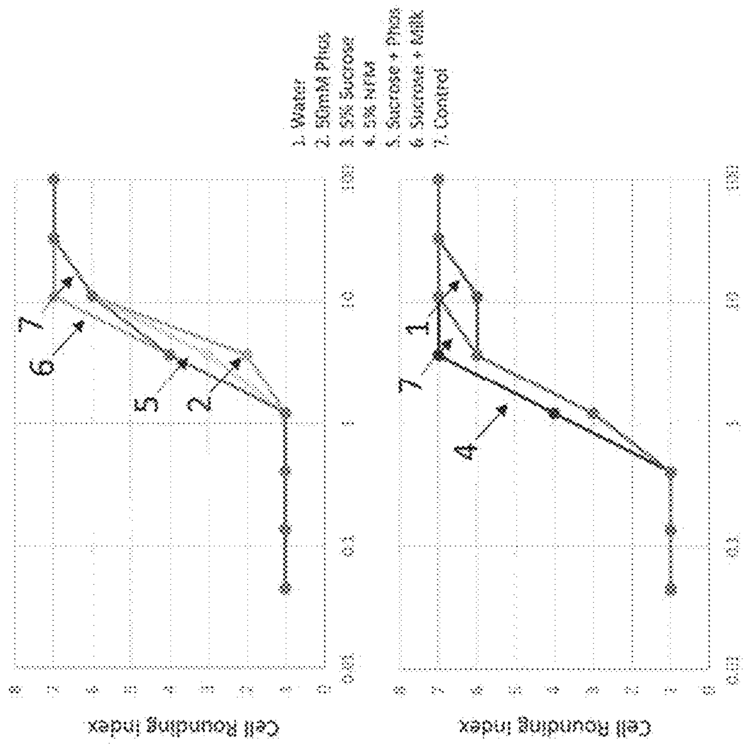

FIG. 69A-B: VHH aqueous stability. The aqueous stability of VHHs was measured at 12 hours using a VERO cell, cell rounding assay. FiA) shows neutralizing activity. B) shows the cell rounding assay.

Figure 70:
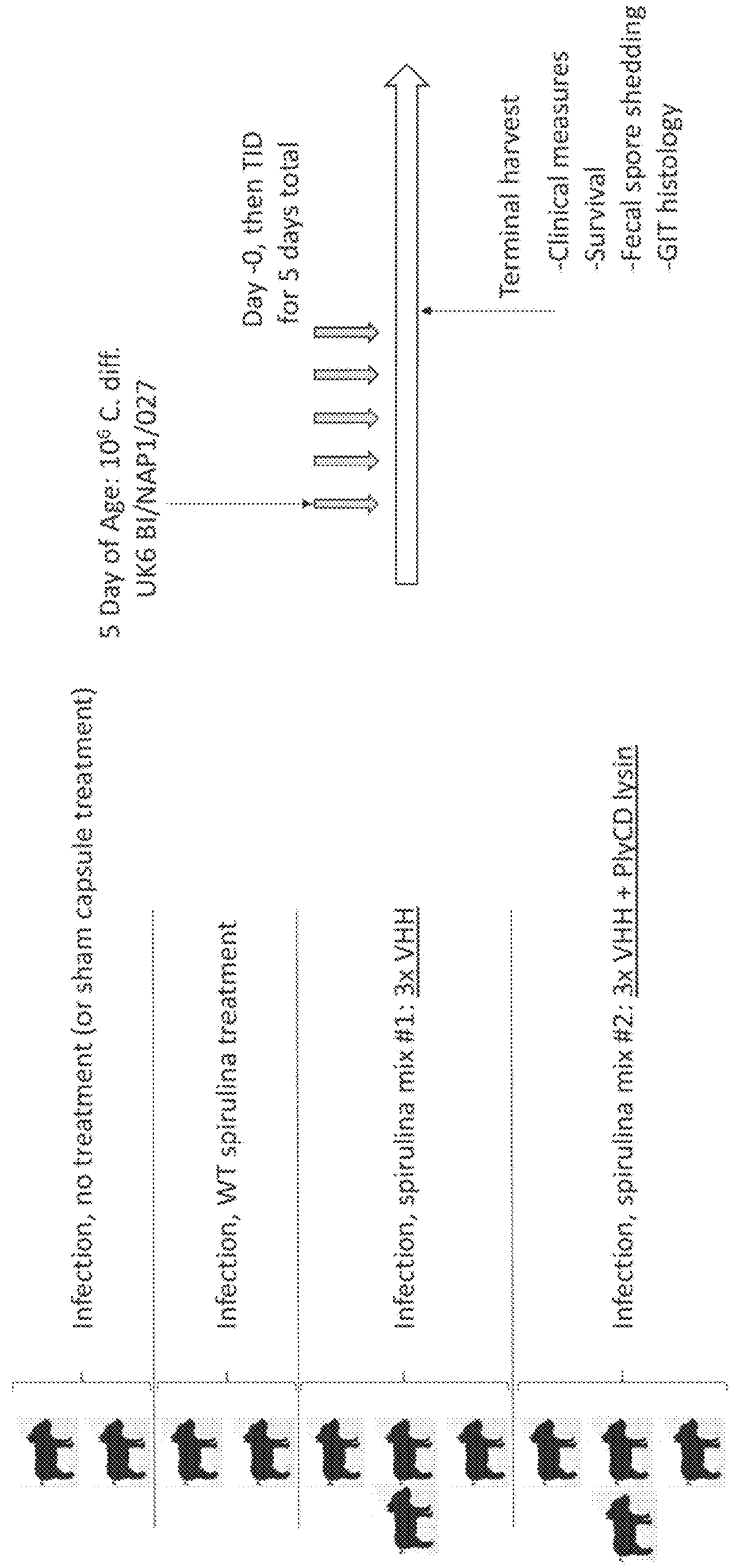

FIG. 70: Overview of gnotobiotic pig model to assess the effect of anti-TcdB VHH on *C. difficile* infection.

Figure 71A:
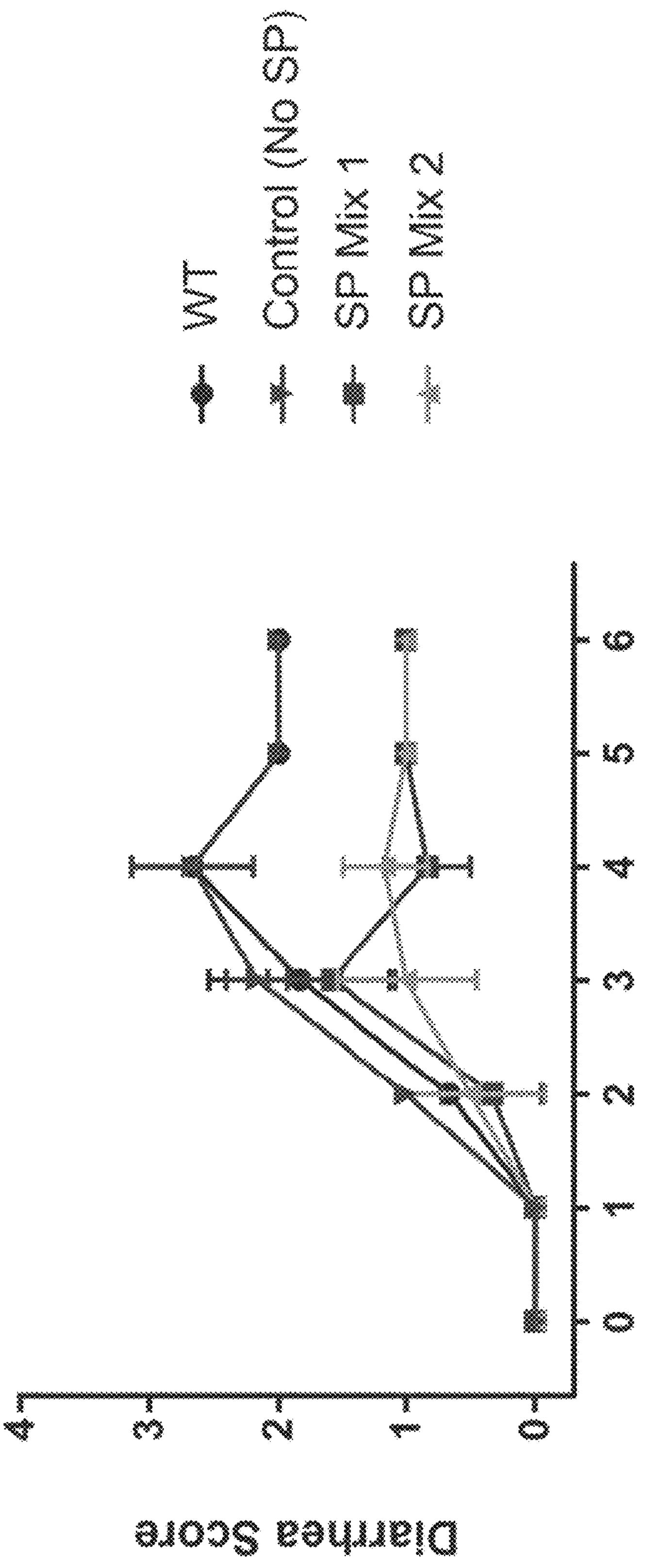
Figure 71B:
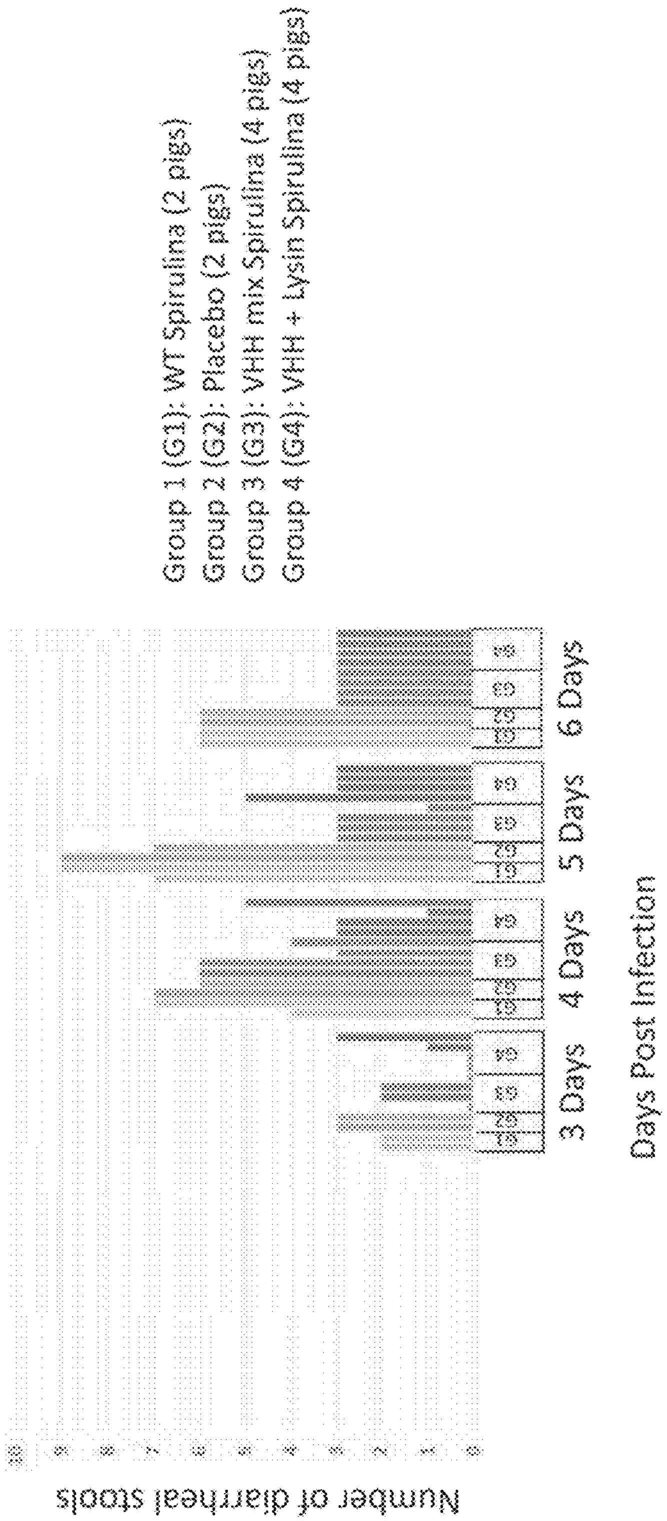

FIG. 71A-B: Clinical Data: Piglet III treated with 3-VHH combination+/−lysin. A) shows diarrhea burden among animals experimentally infected with 027-strain *Clostridium difficile*. B) shows diarrhea burden among individual animals. Animals were treated from day −1 until end of study with either PBS (negative control), wildtype *Spirulina* (negative control), or *Spirulina* containing three different anti-TcdB VHHs (Mix 1), or containing the same three VHHs and an anti-*clostridium* lysin (Mix 2).

Figure 72:
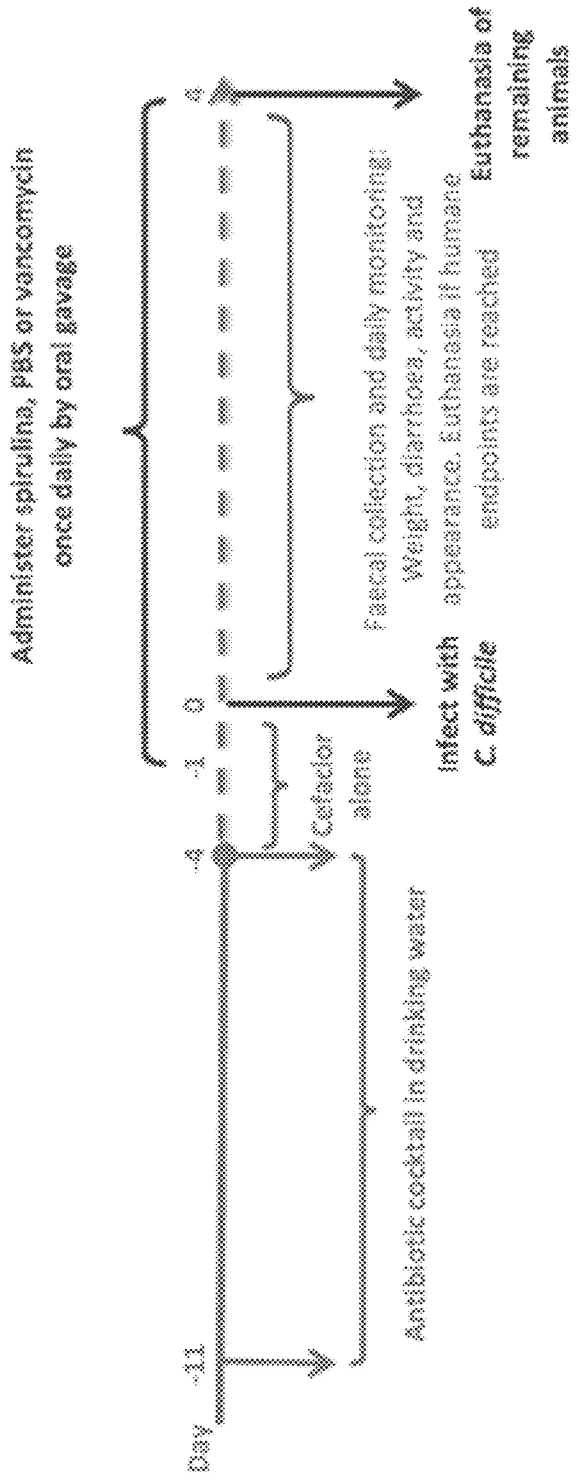

FIG. 72: overview of Monash mouse CDI model study of anti-TcdB VHHs

Figure 73A:
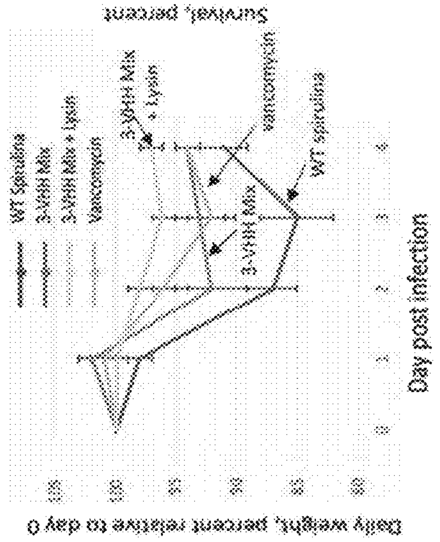
Figure 73B:
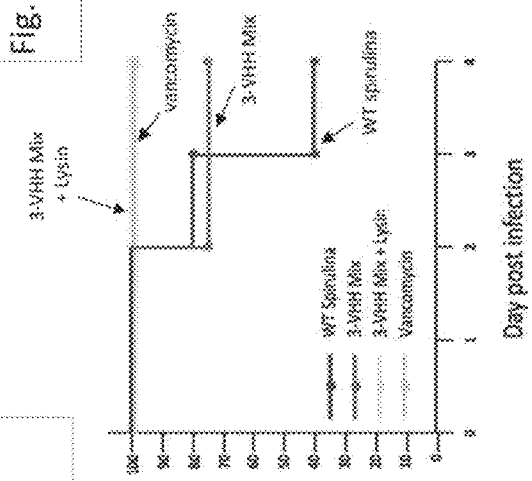
Figure 73C:
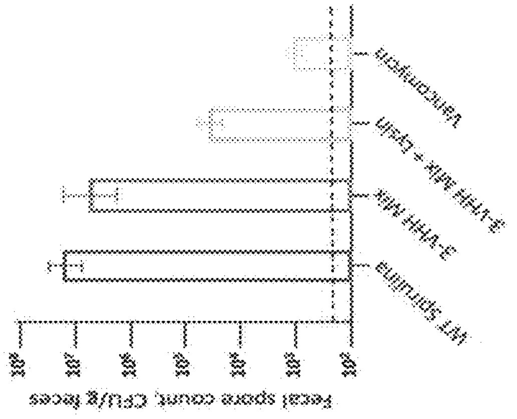

FIG. 73A-C: Prophylactic activity of anti-TcdB VHHs, with and without a *C. difficile* specific lysin, in a mouse model of CDI. Mice were treated daily, beginning on day −1 and continuing to day 4, with the indicated *Spirulina* biomass, or with vancomycin as a positive control. Mice were inoculated with pandemic 027 *C. difficile* on day 0. A) shows the effect on weight loss associated with CDI. B) shows the effect on survival. C) shows the effect on *C. difficile* spore shedding. (Dashed line is the limit of detection).

Figure 74:
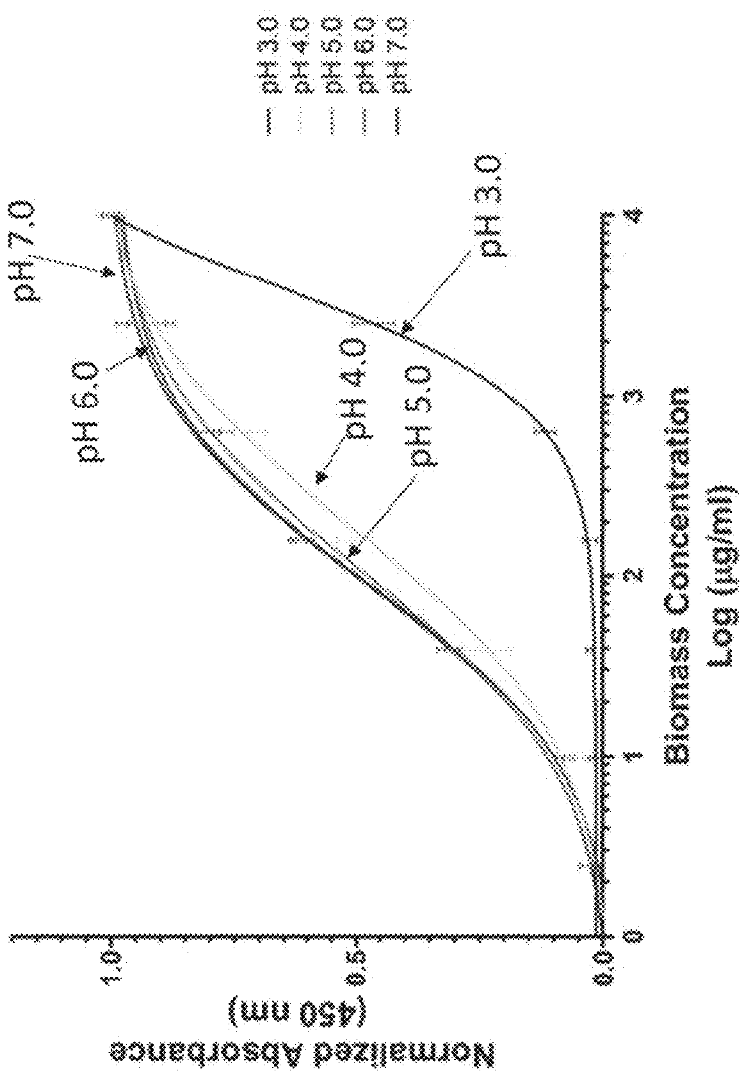

FIG. 74: ELISA titration curves of SP1182 extracts prepared in various pH buffers. Each binding curve represents 4-fold serial dilutions of protein extracts from *Spirulina* biomass (µg/mL) resuspended in a different pH. Each curve was internally normalized to 1, and results are the mean of two replicates.

Figure 75:
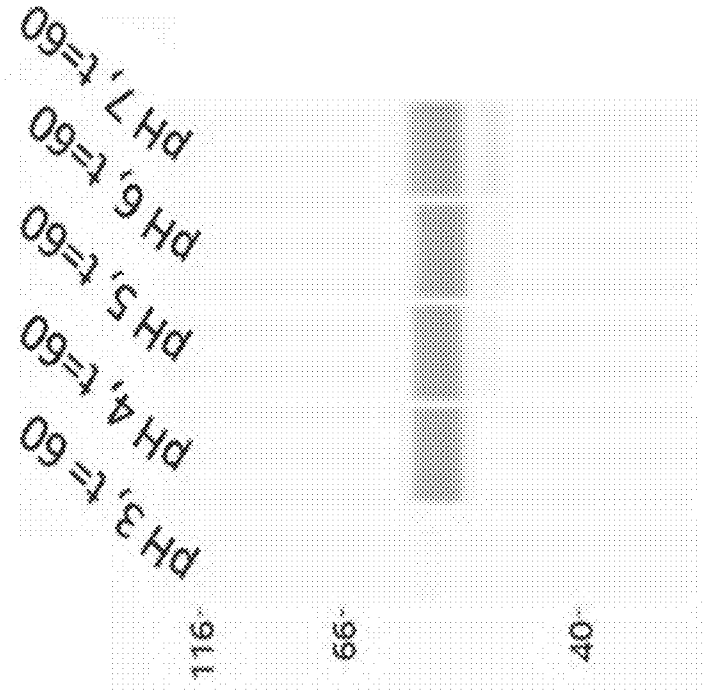

FIG. 75: Western blot gel analysis of SP1182 extracts prepared in various pH buffers. Lanes represent a 600-fold dilution of clarified *Spirulina* extracts from *Spirulina* biomass resuspended at 50 mg/mL and extracted in different pH buffers for 60 min.

Figure 76:
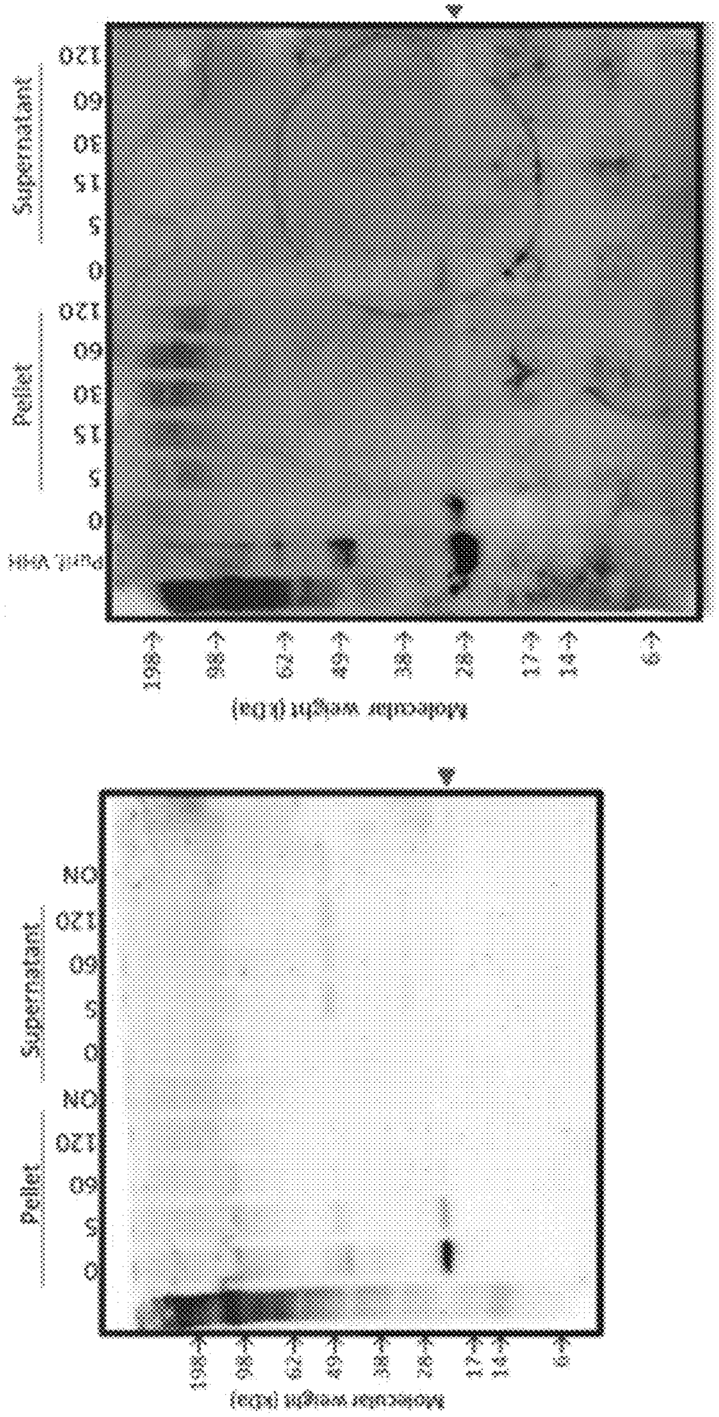

FIG. 76: Western blot of intestinal-phase digestion of dried *Spirulina*-VHH biomass. Spray-dried *Spirulina*-VHH of SP806 was incubated in SIF for the indicated times. All incubation times are shown in minutes or overnight (ON). The experiment was performed twice with different time points (left and right panels). Intact biomass (Pellet) was analyzed alongside released sample (Supernatant). Samples were run on a western blot and detected with an anti-VHH antibody. The arrows indicate expected band size for full-length VHH protein.

Figure 77:
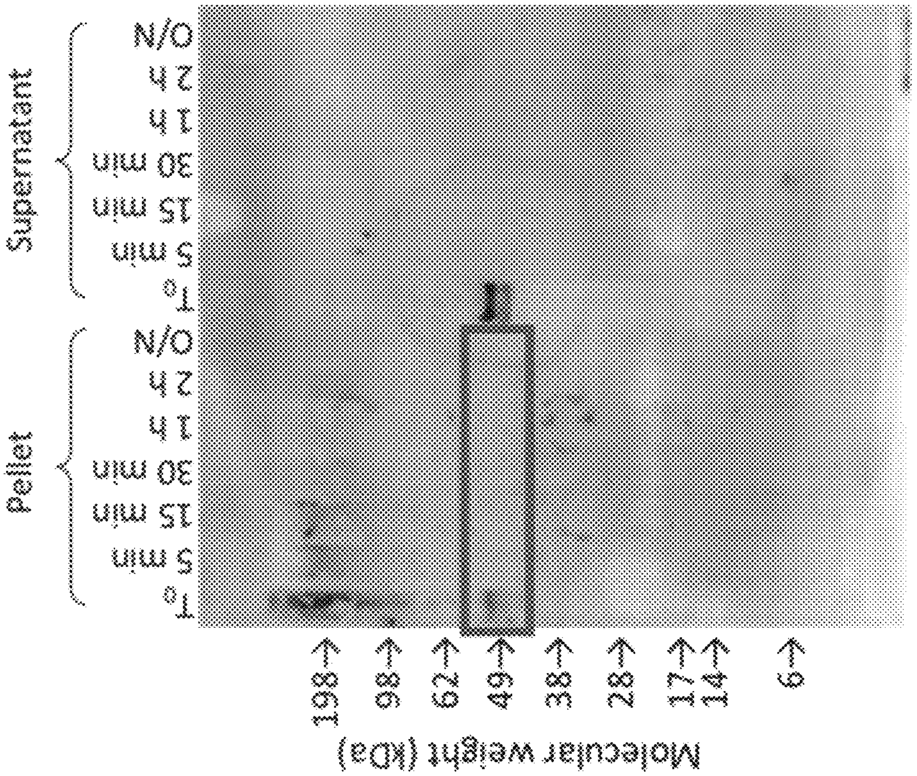

FIG. 77: Western blot of in vitro intestinal-phase digestion of SP1182 Drug Substance. Dried *Spirulina* biomass was incubated in SIF for the indicated times. Intact biomass (Pellet) was analyzed alongside released sample (Supernatant). Samples were run on a western blot and detected with an anti-VHH antibody. Red box indicates bands of VHH (aa682).

Figure 78:
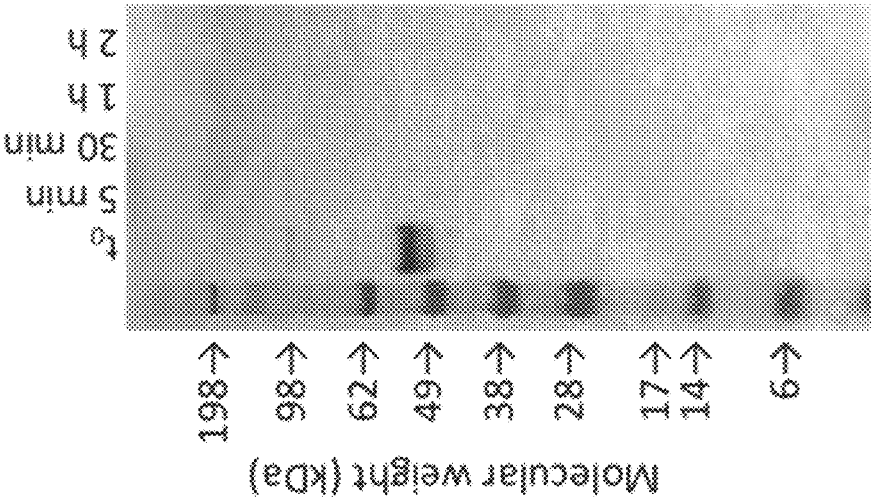

FIG. 78: Western blot of in vitro intestinal-phase digestion of aa682. Purified aa682 was incubated in simulated intestinal fluid for the indicated times. Samples were run on a western blot and detected with an anti-VHH antibody.

Figure 79:
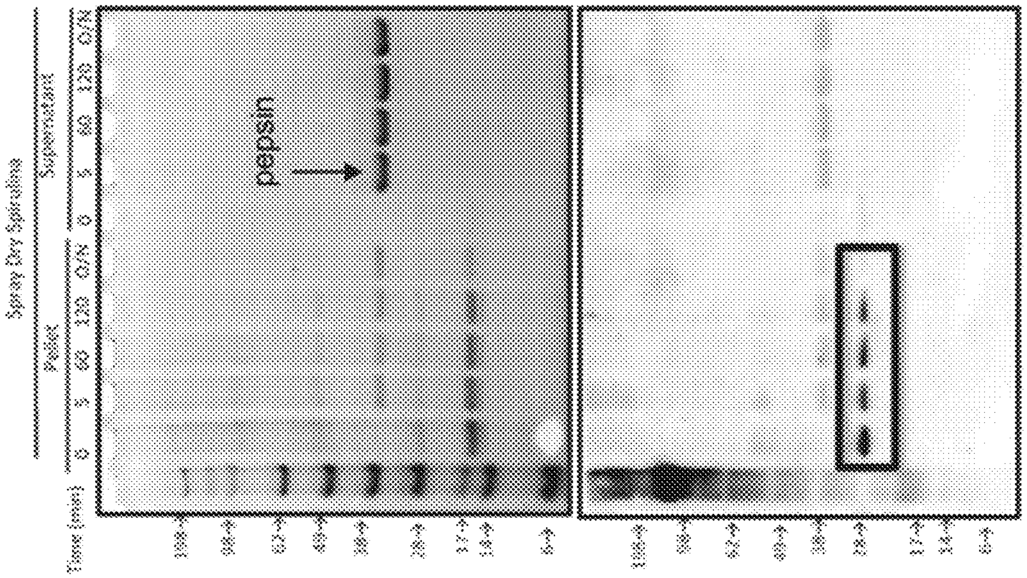

FIG. 79: SDS-PAGE analysis of gastric-phase digestion of dried *Spirulina* biomass. Spray-dried *Spirulina* biomass of (SP806, containing a trimeric VHH) was incubated in SGF for the indicated time periods or overnight (O/N). Intact biomass (Pellet) was analyzed alongside released sample (Supernatant). Samples were run on SDS-PAGE gels and analyzed by Coomassie stain (upper gel) and western blot (lower gel). Proteins were detected on the western blot with an anti-VHH antibody. The black box highlights bands corresponding to the VHH.

Figure 80:
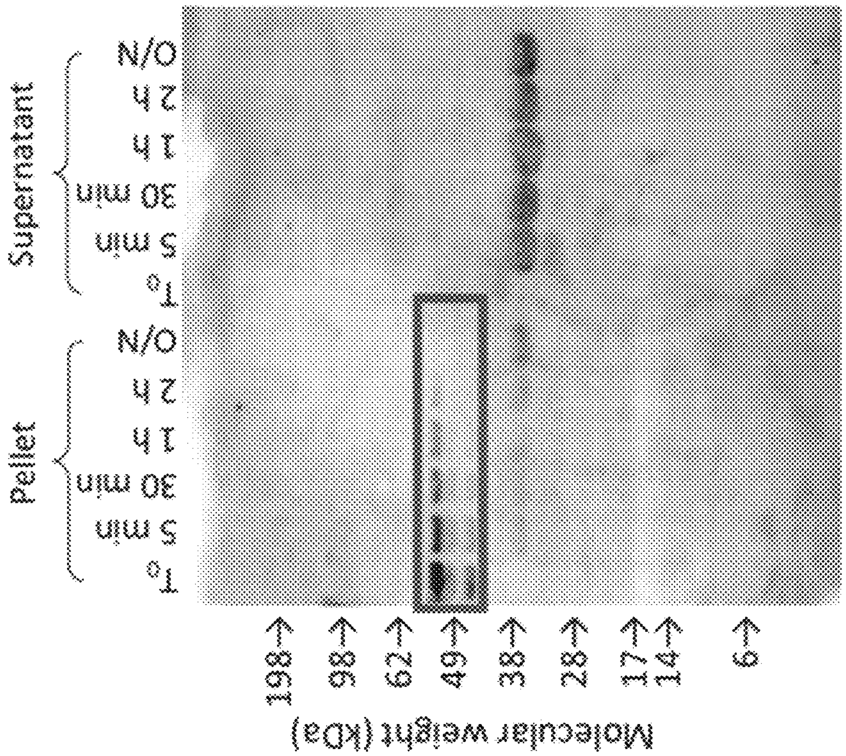

FIG. 80: Western blot of gastric-phase digestion of SP1182 drug substance. Dried *Spirulina* was incubated in SGF for the indicated times or overnight (O/N). Intact biomass (Pellet) was analyzed alongside released sample (Supernatant). Samples were run on a western blot and detected with an anti-VHH antibody. Red box indicates bands of VHH (aa682).

Figure 81:
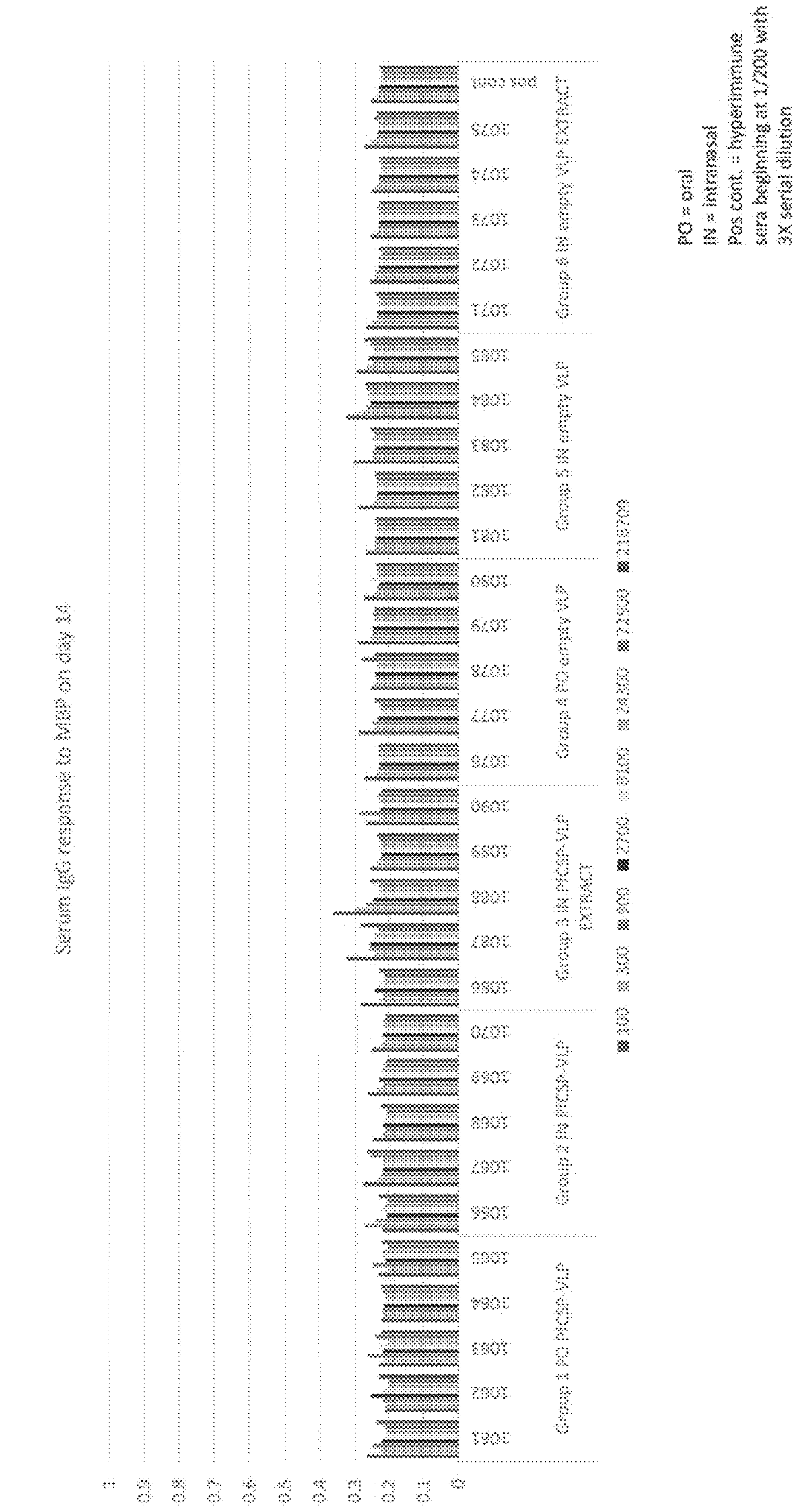

FIG. 81: Serum IgG response to maltose binding protein (MBP) on day 14. Sera was diluted as indicated. PO=oral administration; IN=intranasal administration. Pos. cont=the positive control of hyperimmune sera beginning at 1/200 with 3× serial dilution.

Figure 82:
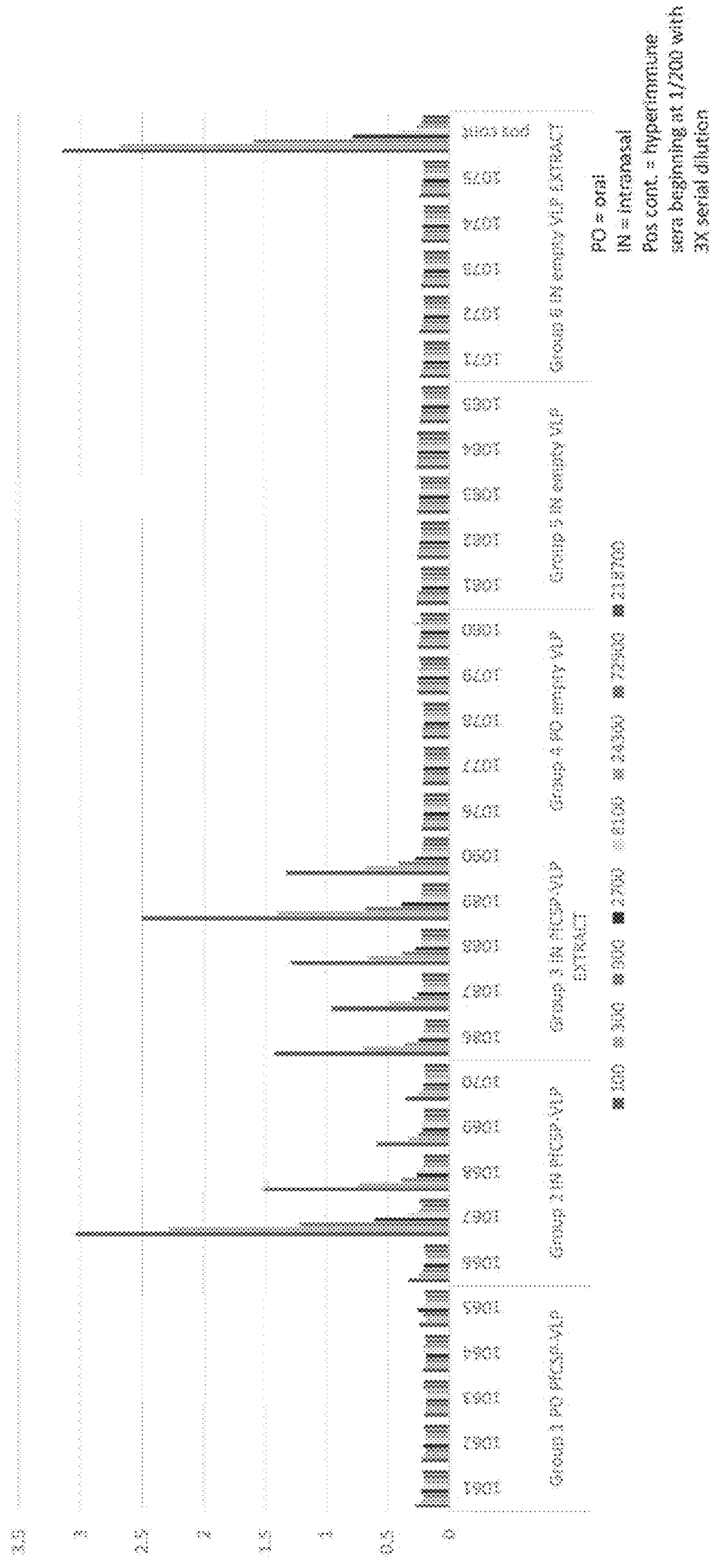

FIG. 82: Serum IgG response to NANP on day 14. Sera was diluted as indicated. PO=oral administration; IN=intranasal administration. Pos. cont=the positive control of hyperimmune sera beginning at 1/200 with 3× serial dilution. Groups 2 and 3 show production of IgG antibodies by day 14.

Figure 83:
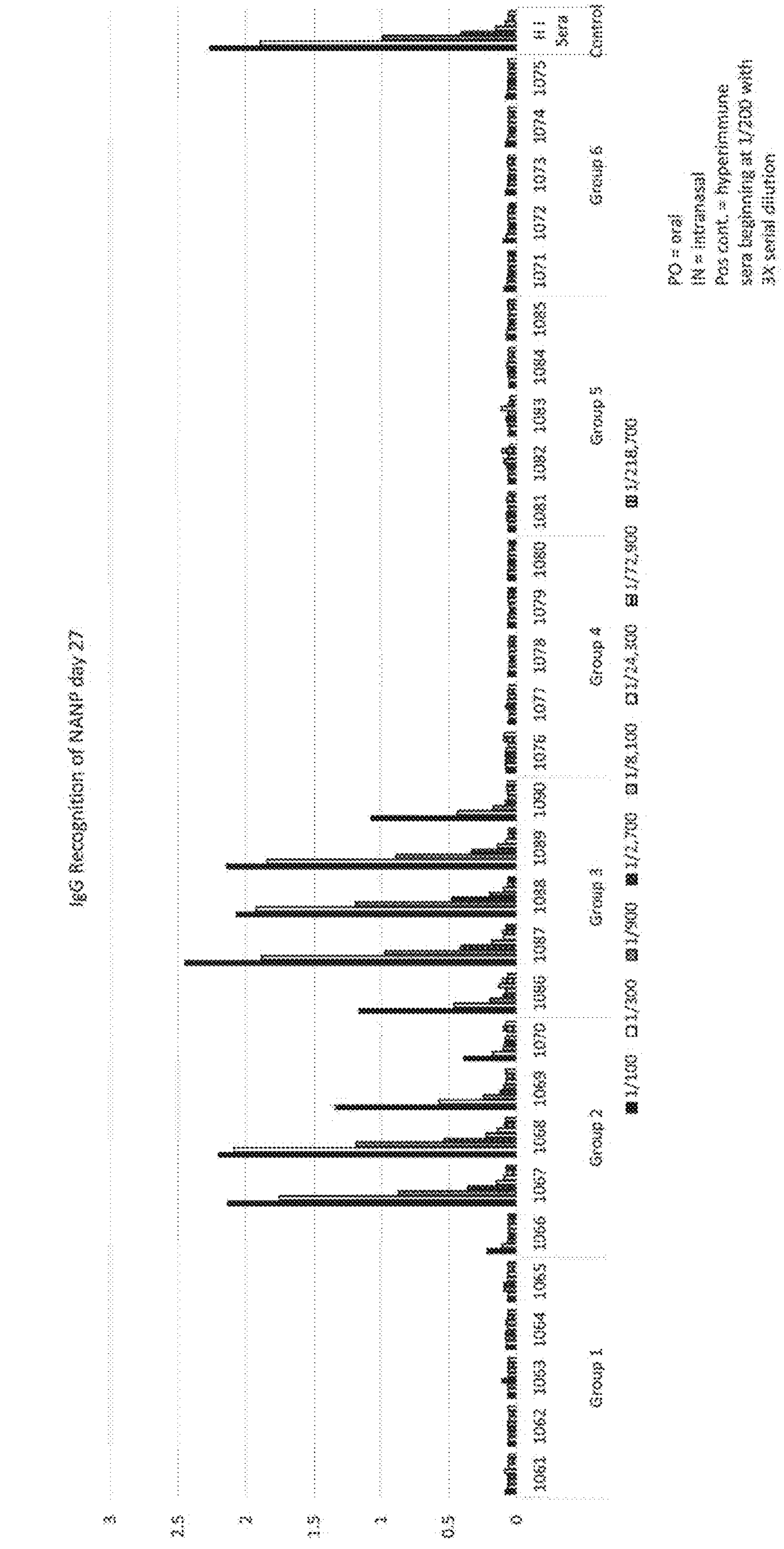

FIG. 83: Serum IgG response to NANP on day 27. Sera was diluted as indicated. PO=oral administration; IN=intranasal administration. Pos. cont=the positive control of hyperimmune sera beginning at 1/200 with 3× serial dilution. Groups 2 and 3 show production of IgG antibodies by day 27.

Figure 84:
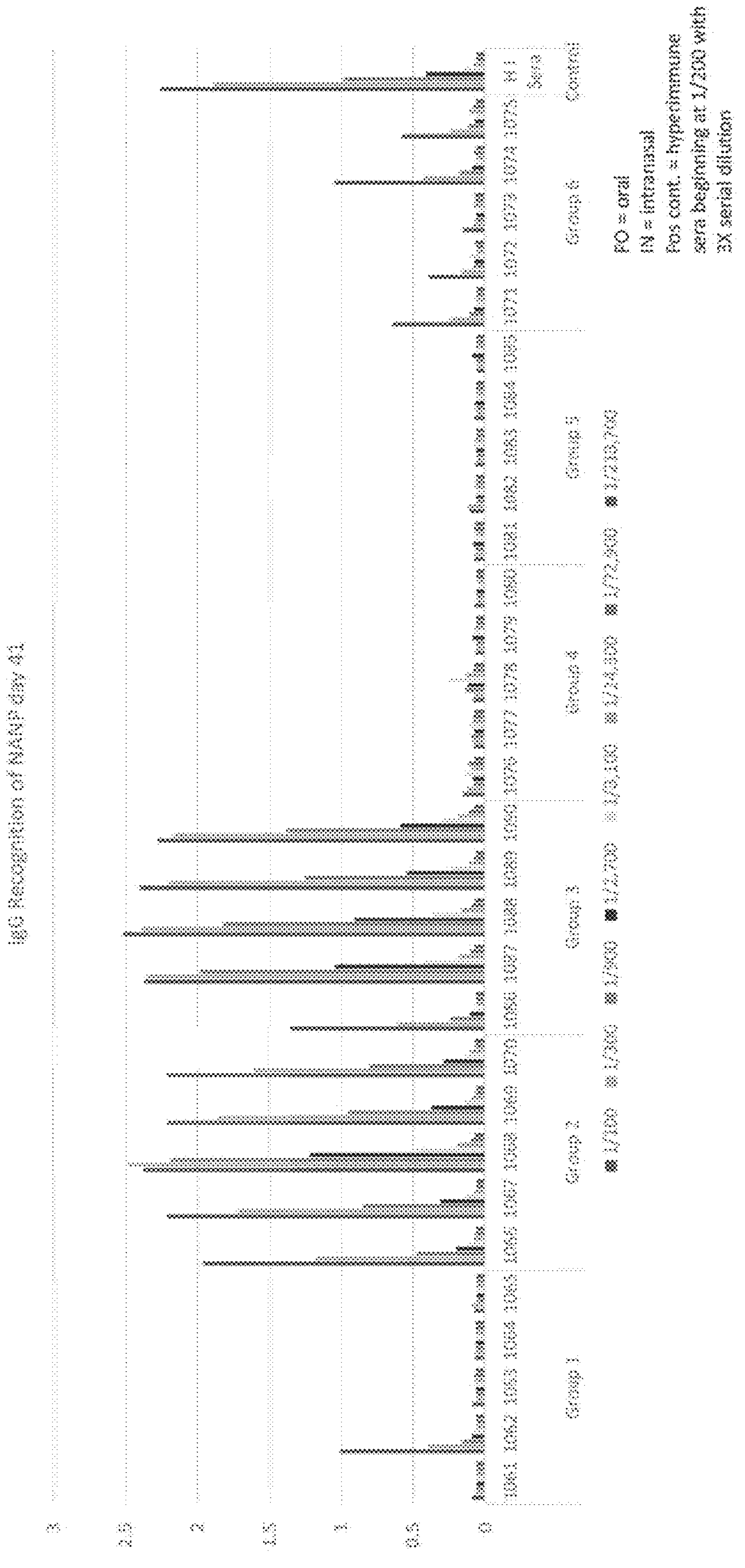

FIG. 84: Serum IgG response to NANP on day 41. Sera was diluted as indicated. PO=oral administration; IN=intranasal administration. Pos. cont=the positive control of hyperimmune sera beginning at 1/200 with 3× serial dilution. Groups 2 and 3 show production of IgG antibodies by day 41.

Figure 85:
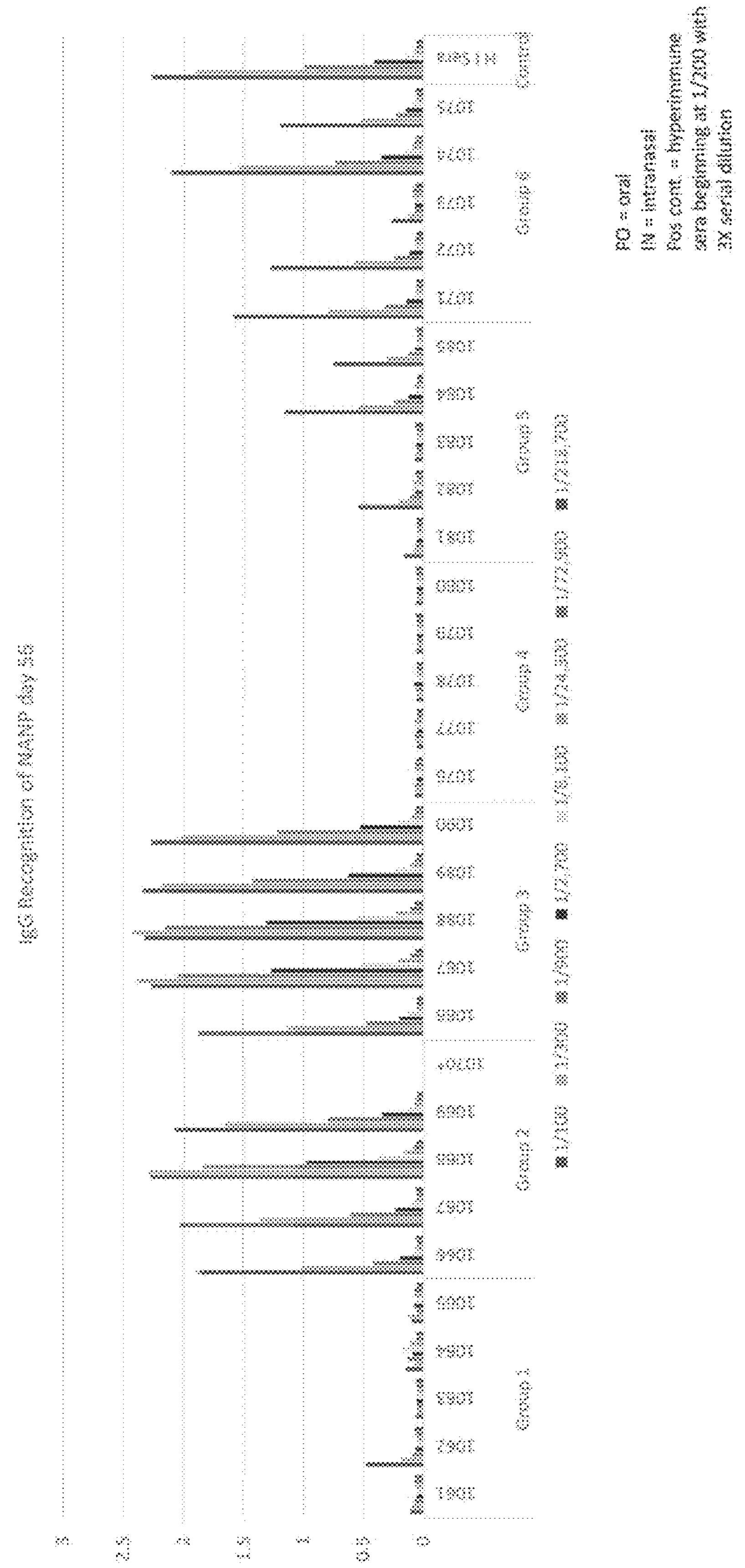

FIG. 85: Serum IgG response to NANP on day 56. Sera was diluted as indicated. PO=oral administration; IN=intranasal administration. Pos. cont=the positive control of hyperimmune sera beginning at 1/200 with 3× serial dilution. Groups 2 and 3 show production of IgG antibodies by day 56.

Figure 86:
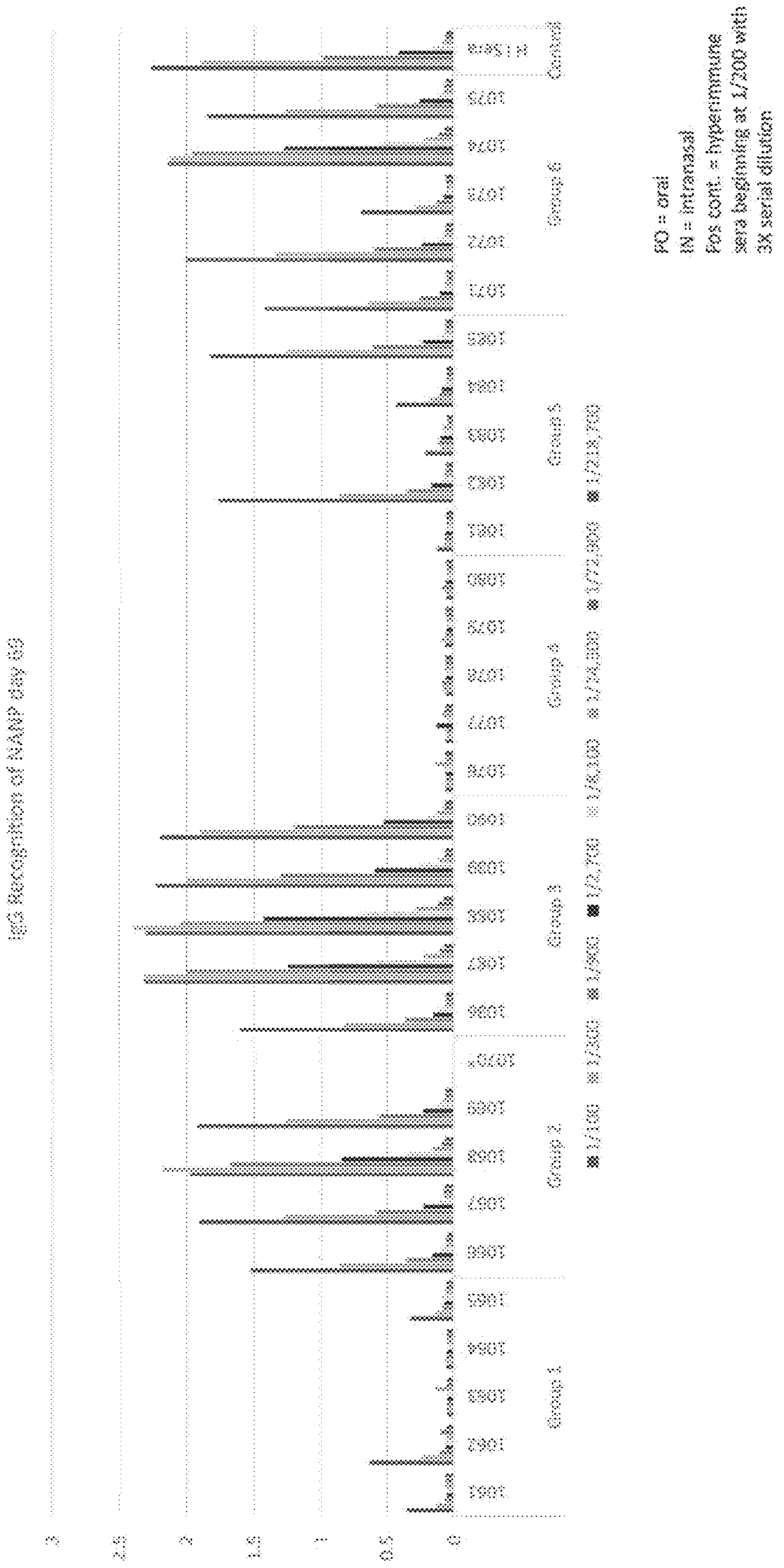

FIG. 86: Serum IgG response to NANP on day 69. Sera was diluted as indicated. PO=oral administration; IN=intranasal administration. Pos. cont=the positive control of hyperimmune sera beginning at 1/200 with 3× serial dilution. Groups 2 and 3 show production of IgG antibodies by day 69.

Figure 87:
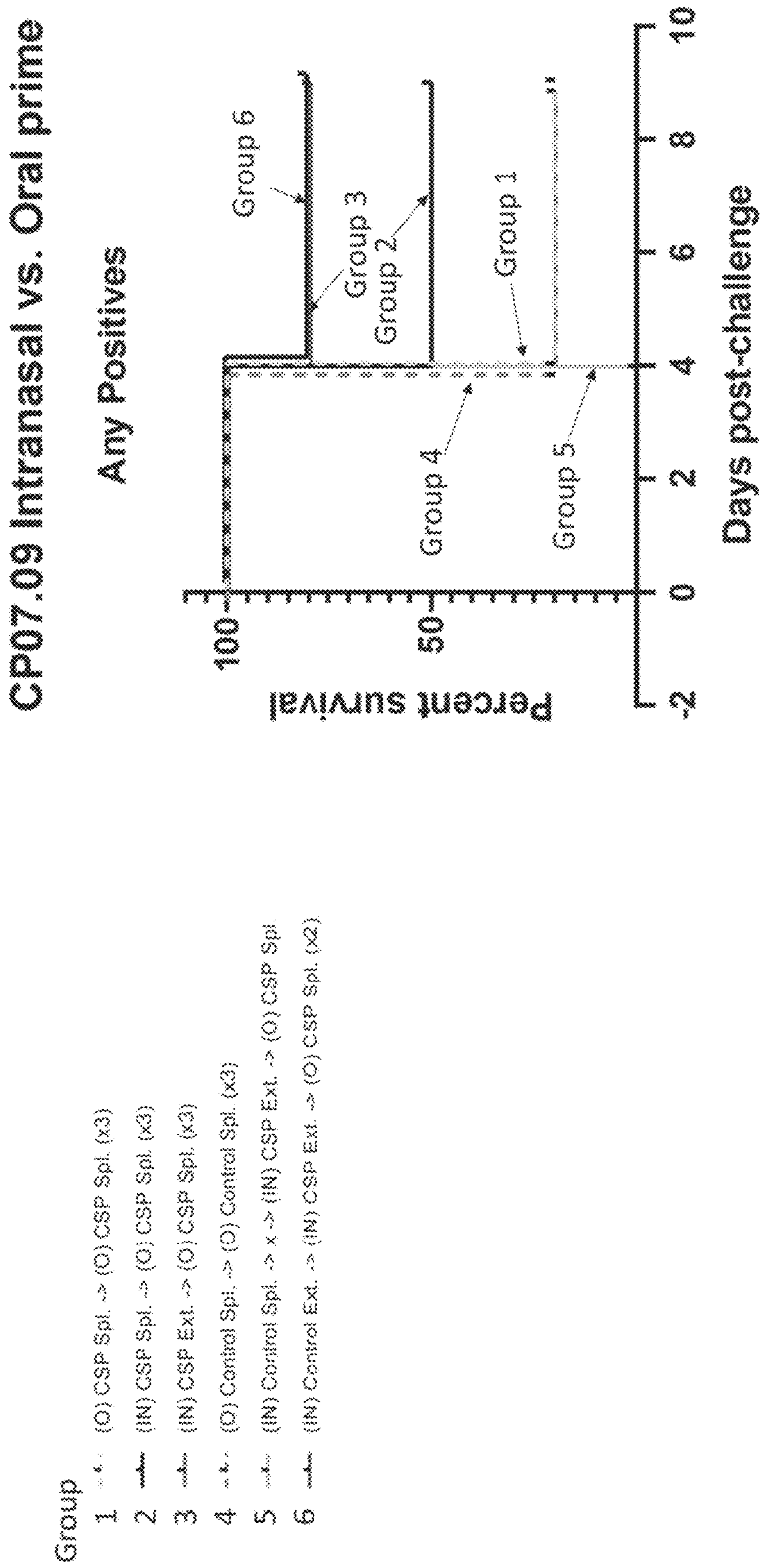

FIG. 87: Survival of vaccinated mice after challenge with *P. falciparum*.

DETAILED DESCRIPTION

The present disclosure teaches exogenous therapeutics or prophylactic molecules are packaged in prokaryotic algae and then administered by non-parenteral means to a subject. In some embodiments, the recombinant prokaryotic algae are edible and can serve as an edible composition for the delivery of the payload expressed in the algae. In the case of polypeptide therapeutics or prophylactic molecules (e.g. antibodies, antigens, etc.), the expression levels of the exogenous polypeptides in the *Spirulina* delivery systems of the present disclosure are 10 to 100-fold higher compared to other systems.

Provided herein are non-parenteral compositions comprising a recombinant *Spirulina* comprising at least one exogenous therapeutic or prophylactic molecule, methods of making, and use thereof.

Before describing certain embodiments in detail, it is to be understood that this disclosure is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this disclosure and in the specific context where each term is used. Certain terms are discussed below or elsewhere in the specification, to provide additional guidance to the practitioner in describing the compositions and methods of the disclosure and how to make and use them. The scope and meaning of any use of a term will be apparent from the specific context in which the term is used. As such, the definitions set forth herein are intended to provide illustrative guidance in ascertaining particular embodiments of the disclosure, without limitation to particular compositions or biological systems.

Following long-standing patent law convention, the terms "a", "an", and "the" refer to "one or more" when used in this application, including the claims, unless clearly indicated otherwise. By way of example, "an antigenic epitope" means one epitope or more than one epitope.

As use herein, the term "antigenic composition" refers to a preparation which, when administered to a subject will induce a protective immune response that provides immunity to a disease or disorder, or can be used to treat a disease or disorder as described herein.

The term "antigen" as used herein refers to a protein or a peptide that binds to a receptor of an immune cell and induces an immune response in a human or an animal. The antigen can be from infectious microorganisms including viruses, bacteria, parasite, or fungi or the antigen can be a tumor antigen or a self-antigen associated with an autoimmune disease.

The term "antigenic epitope" as used herein refers to a short amino acid sequence, for example, of about 4 to 1000 amino acids, of an antigen that is recognized by, and binds to, a receptor of an immune cell and induces an immune response in a human or an animal. The antigenic epitopes of the present disclosure are from the antigens described above.

The term "subject" as used herein refers to a vertebrate or an invertebrate, and includes mammals, birds, fish, reptiles, and amphibians. Subjects include humans and other primates, including non-human primates such as chimpanzees and other apes and monkey species. Subjects include farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like; and aquatic animals such as fish, shrimp, and crustaceans.

Non-Parenteral Therapeutic Compositions

Provided herein are non-parenteral compositions comprising a recombinant *Spirulina*, wherein the *Spirulina* is engineered to contain at least one exogenous therapeutic or fragment thereof. As used herein, the term "therapeutic" refers to any molecule that may be used to treat a disease or disorder and/or have a therapeutic effect in a subject. As used herein, the term "prophylactic" refers to any molecule that may be used to prevent the development of a disease or disorder in a subject.

There are several advantages to non-parenterally delivering therapeutics or prophylactic molecules encapsulated in *Spirulina*. One of these advantages is the increased resistance of the encapsulated therapeutic or prophylactic molecule to proteolysis. For example, when delivered orally, encapsulation in *Spirulina* protects the therapeutic or prophylactic molecule from the enzymes and conditions of the digestive tract, thereby allowing the therapeutic to be delivered to the portion of the digestive tract that digests the *Spirulina* cells and releases the therapeutic or prophylactic molecule. In some embodiments, the orally delivered compositions of the present disclosure survive (e.g. remain substantially intact) at a pH of about 1.3 to about 8.0. In some embodiments, the orally delivered compositions of the present disclosure survive in the oral cavity. In some embodiments, the orally delivered compositions of the present disclosure survive in the stomach. In some embodiments, the orally delivered compositions survive in the small and/or large intestine. In some embodiments, the orally delivered compositions survive in the colon. In some embodiments, the orally delivered compositions survive in a simulated stomach environment. In some embodiments, the simulated stomach environment has an acidic pH and contains pepsin. In some embodiments, the simulated stomach environment has a pH of about 3.0 and about 2000 U/mL of pepsin. In some embodiments, the orally delivered compositions can survive in the gastrointestinal conditions or simulated stomach environment for about 5 minutes to about 1 day. In some embodiments, the orally delivered compositions survive in the gastrointestinal conditions or simulated stomach environment for about 5 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 12 hours, about 24 hours. In some embodiments, the orally delivered compositions survive in the gastrointestinal conditions or simulated stomach environment overnight.

In some embodiments, the non-parenterally delivered compositions of the present disclosure survive (e.g. remain substantially intact) at a pH of about 5.0 to about 8.0. In some embodiments, the non-parenterally delivered compositions of the present disclosure survive (e.g. remain substantially intact) at a pH of about 5.5 to about 6.5. In some embodiments, the non-parenterally delivered compositions of the present disclosure survive in the oral cavity. In some embodiments, the non-parenterally delivered compositions of the present disclosure survive in the nose. In some embodiments, the non-parenterally delivered compositions survive in the pharynx. In some embodiments, the non-parenterally delivered compositions survive in the trachea. In some embodiments, the non-parenterally delivered compositions survive in the bronchi. In some embodiments, the non-parenterally delivered compositions survive in the lungs. In some embodiments, the non-parenterally delivered compositions survive in the alveoli. In some embodiments, the non-parenterally delivered compositions survive in the airway. In some embodiments, the non-parenterally delivered compositions survive in a simulated nasal cavity and/or respiratory tract environment. In some embodiments, the simulated nasal cavity environment has a pH of about 5 to about 7. In some embodiments, the simulated nasal cavity environment has a pH of about 5.5 to about 6.5. In some embodiments, the simulated respiratory tract environment has a pH of about 7 to about 8. In some embodiments, the simulated respiratory tract environment has a pH of about 7.3 to about 7.5. In some embodiments, the non-parenterally delivered compositions can survive in nasal cavity conditions, respiratory tract conditions, or a simulated respiratory tract environment for about 5 minutes to about 1 day. In some embodiments, the non-parenterally delivered compositions can survive in nasal cavity conditions, respiratory tract conditions, or a simulated respiratory tract environment for about 5 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 12 hours, about 24 hours. In some embodiments, the non-parenterally delivered compositions can survive in nasal cavity conditions, respiratory tract conditions, or a simulated respiratory tract environment overnight. In some embodiments, the non-parenterally delivered composition is an extract of a recombinant *Spirulina* biomass.

Another advantage of the non-parenterally delivered compositions of the present disclosure is their stability in storage. In some aspects, the non-parenterally delivered compositions of the present disclosure are stable at elevated temperatures (e.g. greater than room temperature). In some embodiments, the non-parenterally delivered compositions of the present disclosure are stable at 42° C. In some embodiments, the non-parenterally delivered compositions of the present disclosure are stable at 42° C. for about one day to 5 years. In some embodiments, the non-parenterally delivered compositions of the present disclosure are stable at 42° C. for about one day, two days, three days, four days, five days, six days, seven days, one week, two weeks, three weeks, four weeks, one month, two months, three months, four months, five months, six months, or one year. In some embodiments, the non-parenterally delivered compositions of the present disclosure are stable at 42° C. for one month or three months. In some embodiments, the non-parenterally delivered compositions of the present disclosure are stable at room temperature (e.g. about 20° to about 29° C.). In some embodiments, the non-parenterally delivered compositions of the present disclosure are stable at 27° C. In some embodiments, the non-parenterally delivered compositions of the present disclosure are stable at 27° C. for about one day to 5 years. In some embodiments, the non-parenterally delivered compositions of the present disclosure are stable at 27° C. for about one day, two days, three days, four days, five days, six days, seven days, one week, two weeks, three weeks, four weeks, one month, two months, three months, four months, five months, six months, or one year. In some embodiments, the non-parenterally delivered compositions of the present disclosure are stable at 27° C. for one month or three months.

Therapeutics

Any exogenous (i.e. non-*Spirulina*) therapeutic or prophylactic molecule appropriate for non-parenteral administration may be used in the compositions and methods of the present disclosure. In some embodiments, the therapeutic or prophylactic molecule is a small-molecule. In some embodiments, the therapeutic or prophylactic molecule is a polypeptide or a fragment thereof. In some embodiments, the recombinant *Spirulina* comprises a mixture of therapeutics, including a mixture of polypeptides or fragments thereof, a mixture of small molecules, or prophylactic molecules and/or a mixture of polypeptides or fragments thereof and small molecules.

In some embodiments, the therapeutic or prophylactic molecule is a small molecule is produced by a cell. In some embodiments, the small molecule is produced by a microorganism such as a bacteria, virus, fungus, or parasite. In some embodiments, the small molecule is produced by a plant.

In some embodiments, the small molecule has an anti-microbial effect. In some embodiments, the small molecule has an anti-fungal effect. In some embodiments, the small molecule has an anti-viral effect. In some embodiments, the small molecule has an anti-parasite effect. In some embodiments, the small molecule is selected from the group consisting of, but not limited to, antibiotics, malacidins, penicillin, streptomycin, polymyxin, colistin, circulin, bacillomycin, mycobacillin, fungistatin. tannins, terpenoids, saponins, alkaloids, flavonoids, polyphenols, saponins, chloroquine, quinine, amodiaquine, hydroxychloroquine, Metronidazole, tinidazole, iodoquinol, paromomycin, metronidazole and tinidazole, or a combination thereof.

In some embodiments, the exogenous therapeutic or prophylactic molecule is a polypeptide or a fragment thereof. In some embodiments, the polypeptide or prophylactic molecule is selected from the group consisting of, but not limited to, a receptor, an agonist, a hormone, a neurotransmitter, a secreted polypeptide, an anchored polypeptide, a transcription factor, an antimicrobial peptide, a chemokine, a cytokine, a pro-protein, a pre-pro-protein, an interferon, an antibody, a neuropeptide, an antigen, an epitope from an antigen, a self-antigen, a secretin, a G-protein coupled receptor, an opioid peptide, cell-surface protein, a cytoplasmic protein, a mitochondrial protein, a cell-signalling protein, insulin, C-peptide, amylin, interferon, a hormone, a receptor, a receptor agonist, a receptor antagonist, an incretin, GLP-1, glucose-dependent insulinotropic peptide (GIP), an immunomodulatory, an immunosuppressor, a peptide chemotherapeutic, an anti-microbial peptide, magainin, NRc-3, NRC-7, buforin IIb, BR2, p16, Tat, TNFalpha, and chlorotoxin, or a combination thereof.

In some aspects, the present disclosure does not comprise compositions or methods of *Spirulina* comprising an antigen, antigenic epitope, or fragment thereof. In some embodiments, the present disclosure does not comprise the subject matter of PCT/US2019/032998 filed May 17, 2019. In some embodiments, the present disclosure does not comprise compositions or methods to elicit or increase an immune response in a subject. In some embodiments, the present disclosure does not comprise compositions or methods to elicit or increase the production of antibodies or fragments thereof against the exogenous polypeptide contained in the *Spirulina*.

In some embodiments, the polypeptide is an antibody or fragment thereof. In some embodiments, the antibody or fragment thereof is selected from the group consisting of, but not limited to, full length antibody, a monospecific antibody, a bispecific antibody, a trispecific antibody, an antigen-binding region, heavy chain, light chain, VHH, VH, VL, a CDR, a variable domain, scFv, Fc, Fv, Fab, $F(ab)_2$, reduced IgG (rIgG), monospecific $Fab_2$, bispecific $Fab_2$, trispecific $Fab_3$, diabody, bispecific diabody, trispecific triabody, minibody, nanobody, IgNAR, V-NAR, HcIgG, or a combination thereof.

In some embodiments, the therapeutic peptide is associated with, or derived from, or treats or prevents infection by any microorganism, including, but not limited to, *E. coli*, Enterotoxigenic *E. coli* (ETEC), anthrax, EHEC, EAEC, *Shigella, Mycobacterium, Streptococcus, Staphylococcus, Shigella, Campylobacter, Salmonella, Clostridium, Corynebacterium, Pseudomonas, Neisseria, Listeria, Vibrio, Bordetella, Legionella*, bacteriophage, RNA bacteriophage (e.g. MS2, AP205, PP7 and Qβ), *Helicobacter pylori*, Infectious Haematopoietic Necrosis Virus, Parvovirus, Herpes Simplex Virus, Hepatitis A virus, Hepatitis B virus, Hepatitis C virus, Measles virus, Mumps virus, Rubella virus, HIV, Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, White Spot Syndrome Virus, a coronavirus, SARS, MERS, SARS-CoV-2, *Aspergillus, Candida, Blastomyces, Coccidioides, Cryptococcus, Histoplasma, Plasmodium, P. falciparum, P. malariae, P. ovale, P. vivax, Trypanosoma, Toxoplasma, Giardia, Leishmania Cryptosporidium*, helminthic parasites: *Trichuris* spp., *Enterobius* spp., *Ascaris* spp., *Ancylostoma* spp. and Necatro spp., *Strongyloides* spp., *Dracunculus* spp; *Onchocerca* spp. and *Wuchereria* spp., *Taenia* spp., *Echinococcus* spp., and *Diphyllobothrium* spp., *Fasciola* spp., and *Schistosoma* spp. or a combination thereof.

In some embodiments, the exogenous polypeptide is an antigen or a self-antigen. In some embodiments, the self-antigen is associated with an autoimmune disease or disorder. In some embodiments, the self-antigen is a tumor antigen. In some embodiments, the exogenous polypeptide binds to an antigen or self-antigen.

In various embodiments, the compositions of the present disclosure comprise a recombinant *Spirulina* comprising at least one exogenous polypeptide derived from (e.g. a portion or fragment thereof, or antigenic variant thereof) an infectious microorganism, a tumor antigen or a self-antigen associated with an autoimmune disease.

In some embodiments, the compositions comprise a recombinant *Spirulina* comprising at least one exogenous antigenic epitope derived from an infectious microorganism such as a virus, bacterium, parasite, or fungus. The infectious microorganism can be a microorganism that causes infections in a human or an animal such as a species of livestock, poultry, and fish.

In some embodiments, the compositions of the present disclosure comprise a recombinant *Spirulina* comprising at least one polypeptide, antigen, or antigenic epitope from a virus including but not limited to, bacteriophage, RNA bacteriophage (e.g. MS2, AP205, PP7 and Qβ), *Helicobacter pylori*, infectious haematopoietic necrosis virus (IHNV), parvovirus, Herpes Simplex Virus, Hepatitis A virus, Hepatitis B virus, Hepatitis C virus, Measles virus, Mumps virus, Rubella virus, Human Immunodeficiency Virus (HIV), Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, White Spot Syndrome Virus, a coronavirus, MERS, SARS, and SARS-CoV-2. In some embodiments, the compositions of the present disclosure comprise a recombinant *Spirulina* comprising at least one polypeptide, antigen, or antigenic epitope from IHNV. In some embodiments, the compositions of the present disclosure comprise the recombinant *Spirulina* SP105 or SP113. In some embodiments, the compositions of the present disclosure comprise a recombinant *Spirulina* comprising at least one polypeptide, antigen, or antigenic epitope from a coronavirus. In some embodiments, the compositions of the present disclosure comprise a recombinant *Spirulina* comprising at least one polypeptide, antigen, or antigenic epitope from SARS-CoV-2. In some embodiments, oral compositions of the present disclosure comprise a recombinant *Spirulina* comprising at least one polypeptide, antigen, or antigenic epitope from a parvovirus, e.g., canine parvovirus. In some embodiments, the compositions of the present disclosure comprise the recombinant *Spirulina* SP673 or SP678.

In some embodiments, the compositions of the present disclosure comprise a recombinant *Spirulina* comprising at least one polypeptide or fragment thereof that binds to a virus or portion thereof, including but not limited to, bacteriophage, RNA bacteriophage (e.g. MS2, AP205, PP7 and Qβ), *Helicobacter pylori*, infectious haematopoietic necrosis virus (IHNV), parvovirus, Herpes Simplex Virus, Hepatitis A virus, Hepatitis B virus, Hepatitis C virus, Measles virus, Mumps virus, Rubella virus, Human Immunodeficiency Virus (HIV), Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, White Spot Syndrome Virus, a coronavirus, MERS, SARS, and SARS-CoV-2.

In some embodiments, the recombinant *Spirulina* comprises a polypeptide or fragment thereof that binds to a Norovirus polypeptide or antigen. In some embodiments, the recombinant *Spirulina* comprises a polypeptide or fragment thereof that binds to a norovirus P domain. In some embodiments, the polypeptide or fragment thereof is a VHH. In some embodiments, the recombinant *Spirulina* comprises a VHH that binds to a Norovirus polypeptide. In some embodiments, the recombinant *Spirulina* comprises a VHH that binds to a norovirus P domain. In some embodiments, the recombinant *Spirulina* comprises a polypeptide or fragment thereof that binds to a GII genotype, a G1 genotype, a G11.10 genotype. In some embodiments, the recombinant *Spirulina* comprises a polypeptide or fragment thereof that binds to a polypeptide from two or more norovirus genotypes. In some embodiments, the recombinant *Spirulina* comprises a VHH comprising a Nano85 nanobody, a Nano26 nanobody, a Nano94 nanobody, a K922 antibody or a modified sequence or fragment thereof. In some embodiments, the recombinant *Spirulina* comprises a VHH comprising Nano85 and/or a loop grafted modification thereof. In some embodiments, the VHH comprises the amino acid sequence of any of SEQ ID NOs: 40-79 or a fragment thereof. In some embodiments, the recombinant *Spirulina* comprises a polypeptide or fragment thereof that binds a Norovirus polypeptide or antigen, or fragment thereof in fusion with a chaperone polypeptide. In some embodiments, the recombinant *Spirulina* comprises multiple copies of a polypeptide or fragment thereof that binds a Norovirus polypeptide or antigen, or fragment thereof in fusion with a chaperone polypeptide. In some embodiments, the chaperone polypeptide is maltose binding protein (MBP) or Thioredoxin A (TxnA). In some embodiments, the recombinant *Spirulina* comprises a monomer, dimer, or heptamer of a polypeptide or fragment thereof that binds an anti-*Clostridium* toxin or fragment thereof. I In some embodiments, the recombinant *Spirulina* comprises a VHH comprising a Nano85 and/or a loop grafted modification thereof in fusion with a chaperone polypeptide. In some embodiments, the chaperone polypeptide is maltose binding protein (MBP) or Thioredoxin A (TxnA). In some embodiments, the recombinant *Spirulina* comprises multiple copies of VHH comprising a Nano85 and/or a loop grafted modification thereof in fusion with a chaperone polypeptide. In some embodiments, the recombinant *Spirulina* is SP833, SP834, SP835, SP864, SP1241, SP1371 or SP1372.

In some embodiments, the compositions comprise a recombinant *Spirulina* comprising at least one antigenic epitope from a bacterium including but not limited to, *Mycobacterium, Streptococcus, Staphylococcus, Shigella, Campylobacter, Salmonella, Clostridium, Corynebacterium, Pseudomonas, Neisseria, Listeria, Vibrio, Bordetella, E. coli* (including pathogenic *E. coli*), and *Legionella.*

In some embodiments, the recombinant *Spirulina* comprises a polypeptide that binds to a ETEC polypeptide or antigen or fragment thereof. In some embodiments, the recombinant *Spirulina* comprises a polypeptide that binds to a fimbriae polypeptide or fragment thereof. In some embodiments, the recombinant *Spirulina* comprises a VHH that binds to a ETEC polypeptide. In some embodiments, the recombinant *Spirulina* comprises a VHH that binds to a fimbriae polypeptide or fragment thereof. In some embodiments, the recombinant *Spirulina* comprises a VHH that binds to an adhesion or fragment thereof. In some embodiments, the recombinant *Spirulina* comprises a VHH that binds to a polypeptide from two or more adhesions. In some embodiments, the recombinant *Spirulina* comprises a polypeptide or fragment thereof that binds to the F4+ adhesin domain FaeG or the F18+ adhesin domain FedF. In some embodiments, the recombinant *Spirulina* comprises a polypeptide or fragment thereof that binds one or more of the adhesins K88 (also called F4), K99 (F5), 987P (F6), F41, and F18 or a modification or a fragment thereof. In some embodiments, the recombinant *Spirulina* comprises a polypeptide or fragment thereof that binds K88. In some embodiments, the recombinant *Spirulina* comprises a polypeptide or fragment thereof that binds an ETEC polypeptide or antigen or fragment thereof in fusion with a chaperone polypeptide. In some embodiments, the chaperone polypeptide is maltose binding protein (MBP) or Thioredoxin A (TxnA). In some embodiments, the recombinant *Spirulina* comprises multiple copies of a polypeptide or fragment thereof that binds an ETEC polypeptide or antigen or fragment thereof in fusion with a chaperone polypeptide. In some embodiments, the recombinant *Spirulina* comprises a monomer, dimer, or heptamer of a polypeptide or fragment thereof that binds an ETEC polypeptide or fragment thereof or of an ETEC polypeptide or antigen or fragment thereof. In some embodiments, the dimer or heptamer is homodimer or homoheptamer. In some embodiments, the dimer or heptamer is a heterodimer or heteroheptamer. In some embodiments, the recombinant *Spirulina* is SP795 or SP1156.

In some embodiments, the recombinant *Spirulina* comprises a polypeptide that binds to an anti-*Clostridium* toxin. In some embodiments, the *Clostridium* is *C. difficile*. In some embodiments, the recombinant *Spirulina* comprises a VHH that binds to an anti-*Clostridium* toxin. In some embodiments, the polypeptide or fragment thereof binds to a *Clostridium* component, toxin A, or toxin B, or both. In some embodiments, the polypeptide is a VHH comprising the amino acid sequence of any of SEQ ID NO:s 5-17 or fragment thereof. In some embodiments, the recombinant *Spirulina* comprises a *Clostridium* antigen or fragment thereof or a polypeptide or fragment thereof that binds an anti-*Clostridium* toxin or fragment thereof in fusion with a chaperone polypeptide. In some embodiments, the recombinant *Spirulina* comprises multiple copies of or a *Clostridium* antigen or fragment thereof or a polypeptide or fragment thereof that binds an anti-*Clostridium* toxin or fragment thereof in fusion with a chaperone polypeptide. In some embodiments, the chaperone polypeptide is maltose binding protein (MBP) or Thioredoxin A (TxnA). In some embodiments, the recombinant *Spirulina* comprises a monomer, dimer, or heptamer of or a *Clostridium* antigen or fragment thereof or a polypeptide or fragment thereof that binds an anti-*Clostridium* toxin or fragment thereof. In some embodiments, the dimer or heptamer is homodimer or homoheptamer. In some embodiments, the dimer or heptamer is a heterodimer or heteroheptamer. In some embodiments, the recombinant *Spirulina* is SP744, SP977, SP985, SP1087, SP1091, or SP1095.

In some embodiments, the recombinant *Spirulina* comprises a polypeptide that binds to a *Campylobacter* polypeptide or antigen or fragment thereof. In some embodiments, the *Campylobacter* is *C. jejuni*. In some embodiments, the recombinant *Spirulina* comprises a polypeptide that binds to a flagellin component. In some embodiments, the recombinant *Spirulina* comprises a polypeptide or fragment thereof that binds to a flagellin polypeptide or fragment thereof. In some embodiments, the recombinant *Spirulina* comprises a polypeptide or fragment thereof that binds to flaA or a fragment thereof. In some embodiments, the recombinant *Spirulina* comprises a VHH that binds to a *Campylobacter* polypeptide or antigen or fragment thereof. In some embodiments, the recombinant *Spirulina* comprises a VHH that binds to a flagellin polypeptide. In some embodiments, the recombinant *Spirulina* comprises a VHH that binds flaA or fragment thereof. In some embodiments, the recombinant *Spirulina* comprises a polypeptide or fragment thereof that binds a *Campylobacter* or antigen or fragment thereof in fusion with a chaperone polypeptide. In some embodiments, the chaperone polypeptide is maltose binding protein (MBP) or Thioredoxin A (TxnA). In some embodiments, the recombinant *Spirulina* comprises multiple copies of a polypeptide or fragment thereof that binds a *Campylobacter* polypeptide or antigen or fragment thereof in fusion with a chaperone polypeptide. In some embodiments, the recombinant *Spirulina* comprises a monomer, dimer, trimer, pentamer, or heptamer of a polypeptide or fragment thereof that binds a *Campylobacter* polypeptide, antigen, or fragment thereof. In some embodiments, the dimer, trimer, pentamer, or heptamer is homodimer, homotrimer, homopentamber, or homoheptamer. In some embodiments, the dimer, trimer, pentamer, or heptamer is a heterodimer, heterotrimer, heteropentamer, or heteroheptamer. In some embodiments, the recombinant *Spirulina* is SP526, SP651, SP742, or SP806.

In some embodiments, the recombinant *Spirulina* comprises a polypeptide that binds to a malaria polypeptide or antigen or fragment thereof. In some embodiments, the malaria is *P. falciparum*. In some embodiments, the recombinant *Spirulina* comprises a polypeptide that binds to a Circumsporozoite protein (CSP) or fragment thereof. In some embodiments, the recombinant *Spirulina* comprises a polypeptide or fragment thereof that binds to a polypeptide comprising one or more NANP repeats. In some embodiments, the recombinant *Spirulina* comprises a VHH that binds to a malaria polypeptide or antigen or fragment thereof. In some embodiments, the recombinant *Spirulina* comprises a VHH that binds to a CSP polypeptide. In some embodiments, the recombinant *Spirulina* comprises a VHH that binds a polypeptide comprising one or more NANP repeats. In some embodiments, the recombinant *Spirulina* comprises malaria antigen. In some embodiments, the malaria is *P. falciparum*. In some embodiments, the recombinant *Spirulina* comprises a Circumsporozoite protein (CSP) or fragment thereof. In some embodiments, the recombinant *Spirulina* comprises a polypeptide comprising one or more NANP repeats. In some embodiments, the polypeptide or fragment thereof is a VHH comprising the amino acid sequence of any of SEQ ID NOs: 26-31 or a fragment thereof. In some embodiments, the recombinant *Spirulina* comprises a polypeptide or fragment thereof that binds a malaria or antigen or fragment thereof in fusion with a chaperone polypeptide. In some embodiments, the chaperone polypeptide is maltose binding protein (MBP) or Thioredoxin A (TxnA). In some embodiments, the recombinant *Spirulina* comprises multiple copies of a polypeptide or fragment thereof that binds a malarai polypeptide or antigen or fragment thereof in fusion with a chaperone polypeptide. In some embodiments, the recombinant *Spirulina* comprises a monomer, dimer, trimer, pentamer, or heptamer of a polypeptide or fragment thereof that binds a malaria polypeptide, antigen, or fragment thereof. In some embodiments, the dimer, trimer, pentamer, or heptamer is homodimer, homotrimer, homopentamber, or homoheptamer. In some embodiments, the dimer, trimer, pentamer, or heptamer is a heterodimer, heterotrimer, heteropentamer, or heteroheptamer. In some embodiments, the recombinant *Spirulina* is SP648, SP803, or SP856.

In some embodiments, the at least one exogenous polypeptide is expressed in *Spirulina* by itself, i.e., the polypeptide is not fused to another protein.

In some embodiments, the at least one exogenous polypeptide expressed in *Spirulina* is comprised in an exogenous antigen. In some embodiments, the exogenous antigen is a natural antigen. For example, a recombinant *Spirulina* may express the entire circumsporozoite protein containing one or more antigenic epitopes or a portion or a domain of the circumsporozoite protein that contains one or more antigenic epitopes. In this case, the exogenous antigen is considered a natural antigen. Other examples of natural antigens that can be expressed in *Spirulina* to prepare oral antigenic compositions include hemagglutinin (HA), neuraminidase (NA), and matrix (M1) proteins of an influenza virus.

In addition to immunogenic epitopes, the present disclosure provides structures and/or ligands to stimulate the innate immune system (e.g. by engineering the epitopes into VLP structures). The innate immune system can be activated by adjuvant-like properties inherent in the VLP and/or adjuvants added to vaccine compositions. In some embodiments, these structures and/or ligands that stimulate the innate immune system include, but are not limited to, fragments of *Salmonella* flagellin, fliC, human and mouse TNF-alpha, and human and mouse CD40-Ligand. In some embodiments, the exogenous polypeptide is a fusion protein. For example, in some embodiments, a recombinant *Spirulina* may express a fusion protein comprising at least one exogenous polypeptide and a portion of another protein such as a viral protein or a scaffold protein. In some embodiments, the exogenous polypeptide or fragment thereof is in a fusion protein. In some embodiments, the fusion protein is a fusion of two or more polypeptides or fragments thereof. In some embodiments, the fusion protein is one or more polypeptides or fragments thereof attached to one or more scaffolding polypeptides. In some embodiments, the fusion protein is one or more polypeptides or fragments thereof attached to one or more chaperone polypeptides. In some embodiments, the fusion protein comprises a tag for separation and/or purification (e.g. a 6× His tag). In some embodiments, the fusion protein comprises one or more targeting signals or polypeptides. In some embodiments, the fusion protein comprises one or more VHH sequences in fusion with one or more chaperone polypeptides. In some embodiments, the fusion protein comprises one or more VHH sequences in fusion with one or more chaperone polypeptides and one or more scaffolding polypeptides.

In some embodiments, the exogenous antigenic epitopes can be from different antigens that activate different types of immunity (e.g. innate, cellular, or humoral). In some embodiments, the one or more exogenous antigenic epitopes from different antigens are from at least one B-cell antigen and at least one T-cell antigen. In some embodiments, the one or more exogenous antigenic epitopes are in a fusion protein with a viral protein (e.g. a coronavirus spike protein). In some embodiments, the one or more exogenous antigenic epitopes are in a fusion protein with a viral protein (e.g. a coronavirus spike protein) with one epitope at either terminus. In some embodiments, the one or more exogenous antigenic epitopes are a B-cell epitope fused to one terminus of a virus protein and a T-cell epitope fused to the other terminus of the virus protein.

In some embodiments, the compositions of the present disclosure comprise a recombinant *Spirulina* comprising multiple copies of one or more therapeutic and/or prophylactic molecules. In some embodiments, the compositions of the present disclosure comprise a recombinant *Spirulina* comprising a combination of therapeutic and/or prophylactic molecules. In some embodiments, oral compositions of the present disclosure comprise a recombinant *Spirulina* comprising multiple copies of one therapeutic or prophylactic and at least one other therapeutic or prophylactic molecule. In some embodiments, the compositions of the present disclosure comprise a recombinant *Spirulina* comprising at least one antibody and at least one other therapeutic or prophylactic molecule. In some embodiments, the compositions of the present disclosure comprise at least one VHH and at least one other therapeutic or prophylactic molecule. In some embodiments, the compositions of the present disclosure comprise at least one VHH and a polypeptide. In some embodiments, the compositions of the present disclosure comprise at least one VHH and a lysin polypeptide.

In some embodiments, one or more therapeutic and/or prophylactic molecule is an enzyme. In some embodiments, the enzyme is a hydrolytic enzyme. In some embodiments, the hydrolytic enzyme cleaves the wall of a cell. In some embodiments, the hydrolytic enzyme targets the bonds in peptidoglycan. In some embodiments, the hydrolytic enzyme includes, but is not limited to, lysin, a phage lysin, a cytolysin, an egg lysin, hemolysin, NK-lysin, streptolysin, an autolysin, a LytC amidase, a LytD glucosaminidase, a N-acetylmuramolyl-L-alanine amidase, a polypeptide comprising or consisting of one or more catalytic domains from a lysin or autolysin, or a combination and/or fragment thereof Fusion Proteins In some aspects of the disclosure, the therapeutic or prophylactic molecule may reside in the *Spirulina* as part of a complex. In some embodiments, the *Spirulina* comprise multiple copies of the one or more therapeutic and/or prophylactic molecule in a complex. In some embodiments, the *Spirulina* comprise a combination of one or more therapeutic and/or prophylactic molecules in a complex. In some embodiments, the *Spirulina* comprise one or more therapeutic and/or prophylactic molecules in a fusion protein.

In some embodiments, the *Spirulina* comprise one or more therapeutic and/or prophylactic molecules in a complex containing a linker. In some embodiments, the construct inserted into the recombinant *Spirulina* comprises a linker. In some embodiments, the polypeptide expressed from the recombinant *Spirulina* comprises a linker. In some embodiments, the linker is a rigid linker. In some embodiments, the linker is a flexible linker. In some embodiments, the linker attaches two or more VHH sequences. In some embodiments, the linker attaches one or more VHH sequences with another polypeptide. In some embodiments, the other polypeptide is selected from, but not limited to, a chaperone protein, a targeting protein, a scaffold, an oligomerization domain, an enzyme, or a lysin. In some embodiments, the linker is a helix 1 linker (SEQ ID NO: 19), helix 2 linker (SEQ ID NO: 20), helix 4 linker (SEQ ID NO: 21), a PA5 linker (SEQ ID NO: 22), a PA10 lin25).

In some embodiments, at least one exogenous polypeptide is expressed in *Spirulina* as a fusion protein, wherein the fusion protein forms a three-dimensional structure (sometimes referred to herein as "particles"). In some embodiments, the fusion protein that forms a three-dimensional structure may comprise multiple functional domains and one or more exogenous polypeptide. Such fusion proteins can be engineered in a number of ways. In some embodiments, a fusion protein is a single polypeptide with multiple modular domains. An example of this is the woodchuck hepadnavirus core antigen (WHcAg) engineered with a B cell antigen at the Major Insertion Region/spike position, and a T cell epitope at the C-terminus. Another example is an RNA bacteriophage (ie, MS2, PP7, AP205 or $Q_\beta$), engineered to be a tandem dimer, with an antigen at the N-terminus, and a fragment of *Salmonella* flagellin at the C-terminus, thus combining an immunogenic epitope with an innate immune system stimulant to act as an intrinsic adjuvant, which self-organizes into a three-dimensional structure with two functional domains displayed on its surface. In some embodiments, recombinant *Spirulina* may express two heterologous polypeptides. For example, a recombinant *Spirulina* may express one gene that encodes a tandem RNA bacteriophage capsid protein dimer with an N-terminal antigenic structure, and a second gene that encodes an identical capsid dimer but with an adjuvant like *Salmonella* flagellin at its C-terminus. These two nearly identical polypeptides expressed in *Spirulina* can cooperatively form a three-dimensional mosaic particle in which the two polypeptides contribute to the "tiling" that forms a VLP capsid. Another example of this is to express a gene encoding a viral capsid protein like WHcAg or one of the RNA phage particles with a polypeptide genetically linked, and a second gene with the native viral protein. This allows for the avoidance of stearic conflicts that might arise if every particle had a bulky hybrid partner attached. The particles formed in this example can self-organize forming further higher-order structures.

In some embodiments, the recombinant *Spirulina* comprises a fusion protein comprising at least one exogenous polypeptide and a trimerization domain of certain proteins that naturally exist as trimers. Exemplary proteins that comprise trimerization domains are described below. For example, the HA protein from influenza virus (either the whole ectodomain or the minimal stem region) naturally forms trimers, and interfaces between monomeric subunits are considered to be important immunodominant epitopes. The fusion protein (F protein) from respiratory syncytial virus (RSV) is an obligate trimer. Similarly, Tumor Necrosis Factor alpha (TNFα) and the ligand for CD40 (CD40L) are obligate trimers. A recombinant *Spirulina* comprising a fusion protein comprising at least one exogenous antigenic epitope and a trimerization domain of any of these proteins is encompassed by the present disclosure. In exemplary embodiments, to facilitate trimerization, the inventors have genetically linked the WHcAg monomer to a number of coiled-coil domains that both facilitate trimer formation and situate bulky domains like influenza HA away from the potential stearic interference by the spike domains of the WHcAg. The inventors have used a trimerization derivative of the *Saccharomyces cerevisiae* transcription factor GCN4, a parallel trimeric-coiled coil, and a related structure based on CGN4 with the addition of mutations informed by the HIV GP41 trimer structure. The inventors have genetically linked these two trimers, with varying length linker sequences, to WHcAg, as well as to a number of RNA bacteriophages.

In some embodiments, the recombinant *Spirulina* comprises a fusion protein comprising at least one exogenous polypeptide and a viral protein capable of forming a virus-like particle (VLP). In these embodiments, the exogenous polypeptide is expressed in *Spirulina* as a protein macromolecular particle, such as virus-like particles (VLPs). VLPs mimic the overall structure of a virus particle by retaining the three-dimensional structure of a virus without containing infectious material. VLPs have the ability to stimulate B-cell and T-cell mediated responses. When viral proteins are expressed in a heterologous system, such as *Spirulina*, they can spontaneously form VLPs. Accordingly, in some embodiments, the at least one exogenous antigenic epitope is fused to a VLP-forming viral protein. When this fusion protein is expressed in *Spirulina*, it forms a VLP.

In some embodiments, tethering the exogenous polypeptide to a VLP-forming viral protein (or other protein that forms tertiary structures) allows the expression of hundreds of monomer proteins per VLP (e.g. 180-240 monomer proteins per VLP when using the hepatitis VLP). This allows the expression of thousands of millions of VLPs per cell. In some embodiments, the exogenous polypeptide is tethered to a VLP-forming viral protein. In some embodiments, the exogenous antigenic epitope is tethered to a VLP-forming viral protein at the C-terminus or the N-terminus of the viral protein. That is, the amino acid sequence for the polypeptide is preceded by (attachment of the viral protein at the N-terminus of the antigen or the epitope), or followed by (attachment of the viral protein at the N-terminus of the antigen or the epitope), the amino acid sequence of the viral protein. In some other embodiments, the exogenous antigenic epitope is inserted into a VLP-forming viral protein. For example, the at least one exogenous polypeptide can be inserted between two adjacent amino acid residues of the viral protein. Alternatively, a region of the viral protein that is not required for the formation of a VLP can be replaced by inserting the at least one exogenous polypeptide in that region. Throughout this disclosure, when it is said that the at least one exogenous polypeptide is comprised in a VLP or is present in a VLP, it refers to the fusion protein comprising at least one exogenous polypeptide and a VLP-forming viral protein described herein.

Viral proteins that can be used to form polypeptide-containing VLPs of the present disclosure include capsid proteins of various viruses. Exemplary capsid proteins that can be used in the VLPs of the present disclosure include capsid proteins of viruses from the Hepadnaviridae family, papillomaviruses, picornaviruses, caliciviruses, rotaviruses, and reoviruses. In some embodiments, viral proteins that can be used to form polypeptide, antigen- or antigenic epitope-expressing VLPs of the present disclosure include the Hepadnaviridae core antigen (HBcAg). An exemplary HBcAg that can be used in the present disclosure is Woodchuck Hepadnaviral core antigen (WHcAg) from the Woodchuck Hepadnavirus (also referred to herein as Woodchuck Hepatitis Virus).

In some embodiments, the recombinant *Spirulina* comprises a fusion protein comprising at least one exogenous therapeutic and a protein that forms a trimer. In some embodiments, the trimer-forming protein is from an RNA bacteriophage or *Helicobacter pylori*. In some embodiments, the trimer-forming protein is the *Helicobacter pylori* ferritin protein. The at least one exogenous polypeptide, antigen, or antigenic epitope can be attached at the C-terminus or the N-terminus, or within the body of the protein that forms a trimer. In some embodiments, these proteins that form a trimer include but are not limited to, GCN4 polypeptides from *S. cerevisiae* and/or HIV or fragments, mutants or variants thereof.

In some embodiments, the recombinant *Spirulina* comprises a fusion protein comprising at least one exogenous polypeptide, antigen, or antigenic epitope and a scaffold protein. The term "scaffold protein" as used herein refers to a protein that acts as a docking protein and facilitates the interaction between two or more proteins. For example, a fusion protein comprising at least one exogenous polypeptide and a scaffold protein can facilitate the binding of the exogenous polypeptide with a receptor on a cell. In some embodiments, the exogenous polypeptide is tethered to a scaffold protein at the C-terminus or the N-terminus of the scaffold protein. In some other embodiments, the exogenous polypeptide is inserted into a scaffold protein (e.g. in the body of the scaffold protein). For example, the at least one exogenous polypeptide can be inserted between two adjacent amino acid residues of the scaffold protein. Alternatively, a region of the scaffold protein that is not required for the scaffolding function can be replaced by inserting the at least one polypeptide in that region. For example, in a recombinant *Spirulina* comprising multiple copies of the exogenous polypeptide and a scaffold protein, the exogenous antigenic epitope and the scaffold protein can be arranged in any one of the following patterns: (E)n-(SP), (SP)-(E)n, (SP)-(E)n-(SP), $(E)n_1$-(SP)-$(E)n_2$, (SP)-$(E)n_1$-(SP)-$(E)n_2$, and (SP)-$(E)n_1$-(SP)-$(E)n_2$-(SP), wherein E is the exogenous polypeptide, SP is the scaffold protein, and n, $n_1$, and $n_2$ represent the number of copies of the exogenous polypeptide. It is understood that the recombinant *Spirulina* may comprise more than one exogenous polypeptide and one or more scaffold proteins, where the multiple exogenous polypeptide and the scaffold proteins can be arranged in various patterns as described above.

In some embodiments, recombinant *Spirulina* may comprise a fusion protein comprising at least one exogenous polypeptide, a scaffold protein, a VLP-forming viral protein, and/or a trimer-forming protein. In these embodiments, the at least one exogenous polypeptide can be tethered to or inserted into one or more scaffold proteins as described above and the fusion protein comprising the scaffold proteins and the at least one exogenous polypeptide is tethered to or inserted into a VLP-forming viral protein and/or the trimer-forming protein.

Exemplary scaffold proteins include the oligomerization domain of C4b-binding protein (C4BP), a cholera toxin b subunit, or oligomerization domains of extracellular matrix proteins. In some embodiments, a scaffold protein used in the oral antigenic compositions of the present disclosure comprises a sequence from the oligomerization domain of C4BP selected from the group consisting of:

```
                                        (SEQ ID NO: 1)
SAGAHAGWETPEGCEQVLTGKRLMQCLPNPEDVKMALEVYKLSLEIEQL
ELQRDSARQSTLDKEL,

                                        (SEQ ID NO: 2)
WVIPEGCGHVLAGRKVMQCLPNPEDVKMALEVYKLSLEIELLEIQRDKA
RDPAMD,

                                        (SEQ ID NO: 3)
WEYAEGCEQVVKGKKLMQCLPTPEEVRLALEVYKLYLEIQKLELQKDEA
KQA,
and

                                        (SEQ ID NO: 4)
WVVPAGCEQVIAGRELTQCLPSVEDVKMALELYKLSLEIELLELQKDKA
KKSTLESPL.
```

In some embodiments, the exogenous polypeptide binds to a target or target molecule. In some embodiments, multimers of the exogenous polypeptide bind to the target or target molecule with a higher affinity than monomers or smaller multimers. For example, heptameric VHH may bind with higher affinity to a target than a dimer of the same exogenous polypeptide. In some embodiments, multimers are heteromeric. In some embodiments, the different components of the heteromer bind to different targets or target molecules.

The recombinant *Spirulina* present in the non-parenteral compositions of the present disclosure can comprise multiple copies of the at least one exogenous polypeptide. In some embodiments, the recombinant *Spirulina* expresses an exogenous polypeptide, or a fusion protein as described above, wherein the exogenous polypeptide comprises at least 1, 2, 3, 4, 5, 6, 7, 8, 9, or 10 copies of the at least one exogenous polypeptide per single molecule of the exogenous antigen. In some embodiments, the recombinant *Spirulina* expresses an exogenous polypeptide, wherein the exogenous polypeptide comprises 1-5, 2-5, 2-4, 3-6, 3-8, or 4-5 copies of the at least one exogenous polypeptide per single molecule of the exogenous antigen. In some embodiments, the recombinant *Spirulina* comprises at least 1, 2, 3, 4, 5, 6, 7, 8, 9, 10, 15, 20, 25, 30, 35, 40, 45, 50, 55, or 60 copies of the at least one exogenous polypeptide per single molecule of the exogenous antigen. In some embodiments, the recombinant *Spirulina* expresses an exogenous polypeptide, wherein the exogenous polypeptide comprises 1-10, 1-15, 1-20, 1-25, 1-30, 1-40, 1-50, 5-10, 5-15, 5-20, 5-25, 5-30, 5-40, 5-50, 10-25, 10-50, 10-60, 15-30, 15-45, 15-60, 20-50, 20-60, 20-70, 25-50, 25-60, 30-60, or 2-100 copies of the at least one exogenous polypeptide epitope per single molecule of the exogenous polypeptide. In some embodiments, the recombinant *Spirulina* cell can comprise thousands of copies of the at least one exogenous polypeptide (e.g. by expressing the corresponding nucleic acid sequences via one or more vectors in the cell or via integration into the *Spirulina* genome).

The recombinant *Spirulina* present in the non-parenteral compositions of the present disclosure can comprise multiple copies of a nucleic acid sequence encoding the at least one exogenous polypeptide. The multiple copies of the nucleic acid sequence encoding the at least one exogenous polypeptide can be integrated into the genome of the *Spirulina* or can be present on one or more vectors introduced into the *Spirulina*. In some embodiments, the recombinant *Spirulina* comprises between 2 and 100 copies of the nucleic acid sequence encoding the at least one exogenous polypeptide. In some embodiments, the recombinant *Spirulina* comprises at least 1, 2, 3, 4, 5, 6, 7, 8, 9, or 10 copies of a nucleic acid sequence encoding the at least one exogenous polypeptide integrated into its genome or present on one or more vectors. In some embodiments, the recombinant *Spirulina* comprises 1-5, 2-5, 2-4, 3-6, 3-8, or 4-5 copies of a nucleic acid sequence encoding the at least one exogenous polypeptide integrated into its genome or present on one or more vectors. In some embodiments, the recombinant *Spirulina* comprises at least 1, 2, 3, 4, 5, 6, 7, 8, 9, 10, 15, 20, 25, 30, 35, 40, 45, 50, 55, or 60 copies of a nucleic acid sequence encoding the at least one exogenous polypeptide integrated into its genome or present on one or more vectors. In some embodiments, the recombinant *Spirulina* comprises 1-10, 1-15, 1-20, 1-25, 1-30, 1-40, 1-50, 5-10, 5-15, 5-20, 5-25, 5-30, 5-40, 5-50, 10-25, 10-50, 10-60, 15-30, 15-45, 15-60, 20-50, 20-60, 20-70, 25-50, 25-60, or 30-60 copies of a nucleic acid sequence encoding the at least one exogenous polypeptide integrated into its genome or present on one or more vectors.

In some embodiments, multiple copies of the at least one exogenous polypeptide are linked in tandem, i.e., the first copy is immediately followed by the second copy without being separated by any amino acids, the second copy is immediately followed by the third copy, and so on. In some embodiments, where the recombinant *Spirulina* comprises more than one exogenous polypeptide, the individual polypeptide can be similarly linked in tandem to the other antigenic epitope. For example, in a recombinant *Spirulina* comprising E1 and E2 as exogenous polypeptide, these two polypeptides can be linked in tandem in the following ways: (E1E2)x, (E2E1)x, (E1)x(E2)y, (E1)x(E2)y(E1)z, (E2)x(E1)y(E2)z, where x, y, and z represent the number of copies of the polypeptides. Similar arrangement patterns for more than two exogenous polypeptides are contemplated.

In some embodiments, multiple copies of the at least one exogenous polypeptide present in a protein can be separated by spacer sequences. In some embodiments, multiple copies of the exogenous polypeptide can be separated by about 1 to about 50 amino acid space sequences. For example, in some embodiments, multiple copies of the exogenous polypeptide can be separated by about 1, 2, 3, 4, 5, 6, 7, 8, 9, 10, 15, 20, 30, 40, or 50 amino acid spacer sequences. It is understood that in these embodiments, when more than 2 copies of the exogenous polypeptide are present, some copies can be linked in tandem and some copies can be separated by spacer sequences. For example, in a recombinant *Spirulina* comprising multiple copies of E1 as the at least one exogenous polypeptide, the multiple copies of this epitope can be separated in the following ways: (E1)x-S-(E1)y, (E1)(E1)x-S-(E1)y, (E1)x-S-(E1)y-S-(E1)z, where S represents the spacer sequence and x, y, and z represent the number of copies of the exogenous polypeptide. When multiple spacer sequences are present, these sequences can be identical or different in length and/or the amino acid sequence.

In embodiments, where the recombinant *Spirulina* comprises a protein comprising more than one exogenous polypeptide, the first exogenous polypeptide can be separated from the other polypeptide epitope by spacer sequences of about 1, 2, 3, 4, 5, 6, 7, 8, 9, 10, 15, 20, 30, 40, or 50 amino acids. If multiple copies of each of the exogenous polypeptide are present, some of the copies can be linked in tandem with the other polypeptide while some copies can be separated by spacer sequences; alternatively, all copies of one polypeptide can be linked in tandem followed by a spacer sequence followed by all copies of the second polypeptide, and the like. For example, in a recombinant *Spirulina* comprising E1 and E2 as exogenous polypeptide, the two polypeptides can be arranged in the following ways: (E1)x-S-(E2)y, (E2)x-S-(E1)y, (E1)x-S-(E2)y-S(E1)z-S-(E2)v, (E1)x-S-(E2)y(E1)z, (E1)x-S-(E2)y-S-(E1)z, (E2)x-S-(E1)y(E2)z, and the like, where v, x, y, and z represent the number of copies of the polypeptide.

In some embodiments, a recombinant *Spirulina* may comprise one or more exogenous polypeptide and multiple copies thereof in the arrangement patterns described above directly, i.e., without being part of or fused to another protein.

In some embodiments, recombinant *Spirulina* comprises a fusion protein comprising a VLP-forming viral protein or a trimer-forming protein and one or more exogenous polypeptide, antigen, and/or antigenic epitopes, where the exogenous polypeptide, antigen, and/or antigenic epitopes and multiple copies thereof, if present, can be arranged within the fusion protein in various patterns as described above. In some other embodiments, recombinant *Spirulina* may comprise a fusion protein comprising a scaffold protein and one or more exogenous polypeptides, antigens, and/or antigenic epitopes, where the exogenous antigenic epitopes and multiple copies thereof, if present, can be arranged within the fusion protein in various patterns as described above. In some other embodiments, recombinant *Spirulina* may comprise a fusion protein comprising a VLP-forming viral protein, a trimer-forming protein, and/or a scaffold protein, and one or more exogenous polypeptides, antigens, and/or antigenic epitopes, where the exogenous polypeptide, antigens, and/or antigenic epitopes and multiple copies thereof, if present, can be arranged within the fusion protein in various patterns as described above.

The non-parenteral compositions provided by the present disclosure comprise a recombinant *Spirulina*, wherein the recombinant *Spirulina* comprises at least one exogenous polypeptide, small molecule, antigen or epitope in any of the ways described above.

*Spirulina*

Non-parenteral compositions of the present disclosure comprise recombinant *Spirulina* in a non-living form. These non-living *Spirulina* containing an expressed exogenous polypeptide, small molecule, antigen or epitope are then administered to a subject to elicit an immune response in the subject. In some embodiments, non-living recombinant *Spirulina* comprising at least one exogenous polypeptide, antigen, or at least one exogenous antigenic epitope is prepared by drying the live culture of the recombinant *Spirulina*. Methods of drying include heat drying, e.g., drying in an oven; air-drying, spray drying, lyophilizing, or freeze-drying. Accordingly, in some embodiments, non-parenteral compositions of the present disclosure comprise a dried biomass of a recombinant *Spirulina* comprising at least one exogenous polypeptide, antigen, or at least one exogenous antigenic epitope as described herein.

As used herein "*Spirulina*" is synonymous with "*Arthrospira*." Non-parenteral compositions of the present disclosure can comprise any one of the following species of *Spirulina: A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri Stizenberger, A. jenneri* f. *purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata* f. *acutissima, A. neapolitana, A. nordstedtii, A. oceanica, A. okensis, A. pellucida, A. platensis, A. platensis* var. non-constricta, *A. platensis* f. *granulate, A. platensis* f. *minor, A. platensis* var. *tenuis, A. santannae, A. setchellii, A. skujae, A. spirulinoides* f. *tenuis, A. spirulinoides, A. subsalsa, A. subtilissima, A. tenuis, A. tenuissima*, and *A. versicolor.*

Pharmaceutical Compositions and Dosing

As used herein, the terms "oral composition" or "orally delivered composition" comprise compositions administered or delivered to the gastrointestinal tract (e.g. orally, compositions administered to the stomach via a feeding tube, etc.). Any appropriate area of the gastrointestinal tract may be targeted by the compositions of the present disclosure.

In some aspects, the compositions of the present disclosure are administered via the airway. In some embodiments, the compositions of the present disclosure are administered by inhalation. In some embodiments, the compositions of the present disclosure are administered intranasaly. In some embodiments, the compositions of the present disclosure are administered by a nebulizer, an inhaler, or a mist. In some embodiments, the compositions of the present disclosure are lyophilized and delivered as a powder or a powder resuspended in a liquid.

In some embodiments, the compositions of the present disclosure are formulated for administration via the airway. In some embodiments, the compositions of the present disclosure are formulated for administration by inhalation. In some embodiments, the compositions of the present disclosure are formulated for intranasal administration. In some embodiments, the compositions of the present disclosure are formulated for administration by a nebulizer, an inhaler, or a mist.

In some embodiments, compositions of the present disclosure can comprise one or more pharmaceutically acceptable excipients. Pharmaceutically acceptable carriers include but are not limited to saline, buffered saline, dextrose, water, glycerol, sterile isotonic aqueous buffer, and combinations thereof. In some embodiments, a pharmaceutically acceptable excipient is sodium bicarbonate.

In some embodiments, compositions of the present disclosure may comprise an adjuvant. As known in the art, the immunogenicity of a particular composition can be enhanced by the use of non-specific stimulators of the immune response, known as adjuvants. Exemplary adjuvants include a water-in-oil (W/O) emulsion composed of a mineral oil and a surfactant from the mannide monooleate family (e.g. MONTANIDE™ class of adjuvants) and flagellin adjuvants.

In some embodiments, compositions of the present disclosure comprise about 0.1% to about 5% of the total *Spirulina* biomass. In some embodiments, compositions of the present disclosure comprise about 1 mg to about 50 mg of the exogenous antigenic epitope per gram of dried *Spirulina* biomass. In some embodiments, compositions of the present disclosure comprise at least about 1 mg, 5 mg, 10 mg, 25 mg, 50 mg, 100 mg, 200 mg, 300 mg, 500 mg, 750 mg, 1 mg, 5 mg, 10 mg, or 50 of the exogenous antigenic epitope per gram of dried *Spirulina* biomass.

Uses of Compositions

In some embodiments, compositions of the present disclosure can be used to reduce the severity of a disease or disorder in a subject in need thereof. In some embodiments, compositions can be used to prevent a disease or disorder in a subject. In some embodiments, compositions can be used to prevent initiation of a disease or disorder in a subject. In some embodiments, compositions can be used to reduce the severity of a disease or disorder in a subject. In some embodiments, compositions can be used to prevent or delay recurrence of a disease in a subject. In some embodiments, compositions can be used to treat, prevent, or delay recurrence of a cancer in a subject.

Compositions of the present disclosure can be used as a vaccine. In some embodiments, compositions can be used to induce an immune response in a subject. For example, compositions can be used to induce an immune response directed to an infectious microorganism, a tumor antigen, or a self-antigen.

In some embodiments, provided herein are methods of inducing an immune response in a subject in need thereof comprising administering to the subject any of the compositions described herein. Without wishing to be bound to a theory, it is expected that when the composition of the present disclosure is administered to a subject, the at least one exogenous antigenic epitope is recognized by immune cells of the subject, such as T cells or B cells, thereby activating an immune response against the exogenous antigenic epitope. In some embodiments, administration of compositions described herein can induce a humoral immune response and/or a cellular immune response.

The compositions of the present disclosure may be administered daily, weekly, biweekly, every other week, monthly, etc. In some embodiments, the compositions of the present disclosure are administered to a subject for about 1 day to about 1 year. In some embodiments, the compositions of the present disclosure are administered to a subject for about 1 day, 2 days, 3 days, 4 days, 5 days, 6 days, 7 days, 8 days, 9 days, 10 days, one week, two weeks, three weeks, four weeks, five weeks, six weeks, one month, two months, three months, four months, five months or more. In some embodiments, the compositions of the present disclosure are administered on consecutive days. In some embodiments, the compositions of the present disclosure are administered on non-consecutive days. In some embodiments, the compositions of the present disclosure are administered once a day. In some embodiments, the compositions of the present disclosure are administered multiple times a day. In some embodiments, the compositions of the present disclosure are administered twice a day, three times a day, four times a day, or more. In some embodiments, the compositions of the present disclosure are administered continuously (e.g. via a feeding tube). In some embodiments, the compositions of the present disclosure are administered with meals. In some embodiments, the compositions of the present disclosure are administered when the subject is in a fasting state.

Compositions of the present disclosure can be administered according to a schedule, for example, administering a priming dose of an antigenic composition and subsequently administering one or more booster doses of the antigenic composition. In some embodiments, a first booster dose of the antigenic composition can be administered anywhere from about two weeks to about 10 years after the priming dose. In some embodiments, a first booster dose of the antigenic composition can be administered anywhere from about two weeks, 1 month, 2 months, 3 months, 4 months, 6 months, 9 months, 1 year, 2 years, 3 years, or 5 years after the priming dose. A second booster dose of the antigenic composition can be administered after the first booster dose and anywhere from about 3 months to about 10 years after the priming dose. In some embodiments, a second booster dose of the antigenic composition can be administered after the first booster dose and from about 3 months, 4 months, 6 months, 9 months, 1 year, 2 years, 3 years, or 5 years after the priming dose. The third booster dose may be optionally administered when no or low levels of specific immunoglobulins are detected in the serum and/or other bodily fluids of the subject after the second booster dose.

In some embodiments, compositions other than the compositions of the present disclosure can be administered prior to the administration of the present compositions to prime the subject's immune response. In these embodiments, methods of the present disclosure comprise administering an composition other than the present antigenic composition as a priming dose and subsequently administering one or more booster doses of the present composition.

Compositions of the present disclosure can be used to treat and/or prevent or reduce the severity of a disease or disorder. In some embodiments, the disease or disorder is selected from the group including, but not limited to, Type 1 diabetes, Type 2 diabetes, cancer, an inflammatory disorder, a gastrointestinal disease, an autoimmune disease or disorder, an endocrine disorder, gastroesophageal reflux disease (GERD), ulcers, high cholesterol, inflammatory bowel disorder, irritable bowel syndrome, crohn's disease, ulcerative colitis, constipation, and diarrhea.

Compositions of the present disclosure can be used as a vaccine or to treat and/or prevent or reduce the severity of a disease or an infection caused by a virus, bacterium, parasite, or fungus.

In some embodiments, compositions can be used as a vaccine or to treat, and/or reduce the severity of an infection such as tetanus, diphtheria, pertussis, pneumonia, meningitis, campylobacteriosis, mumps, measles, rubella, polio, flu, hepatitis, chickenpox, malaria, toxoplasmosis, giardiasis, or leishmaniasis.

In some embodiments, compositions described herein can be used to induce an immune response to, to treat and/or reduce the severity of an infection caused by a virus including, but not limited to, bacteriophage, RNA bacteriophage (e.g. MS2, AP205, PP7 and Qβ), *Helicobacter pylori*, infectious haematopoietic necrosis virus (IHNV), parvovirus, Herpes Simplex Virus, Hepatitis A virus, Hepatitis B virus, Hepatitis C virus, Measles virus, Mumps virus, Rubella virus, HIV, Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, White Spot Syndrome Virus, a coronavirus, SARS, MERS, and SARS-CoV-2.

In some embodiments, the compositions described herein can be used to induce an immune response to, to treat, and/or reduce the severity of an infection caused by IHNV.

In some embodiments, the compositions described herein can be used to induce an immune response to and/or reduce the severity of an infection caused by a parvovirus, e.g., canine parvovirus.

In some embodiments, the compositions described herein can be used to induce an immune response to and/or reduce the severity of an infection caused by a coronavirus, e.g., ARDS, COVID-19.

In some embodiments, compositions described herein can be used to induce an immune response to, to treat and/or reduce the severity of an infection caused by a bacterium including, but not limited to, *Mycobacterium, Streptococcus, Staphylococcus, Shigella, Campylobacter, Salmonella, Clostridium, Corynebacterium, Pseudomonas, Neisseria, Listeria, Vibrio, Bordetella*, and *Legionella*.

In some embodiments, compositions described herein can be used to induce an immune response to and/or reduce the severity of an infection caused by a parasite including, but not limited to, *Plasmodium, Trypanosoma, Toxoplasma, Giardia*, and *Leishmania, Cryptosporidium*, helminthic parasites: *Trichuris* spp. (whipworms), *Enterobius* spp. (pinworms), *Ascaris* spp. (roundworms), *Ancylostoma* spp. and Necatro spp. (hookworms), *Strongyloides* spp. (threadworms), *Dracunculus* spp. (Guinea worms), *Onchocerca* spp. and *Wuchereria* spp. (filarial worms), *Taenia* spp., *Echinococcus* spp., and *Diphyllobothrium* spp. (human and animal cestodes), *Fasciola* spp. (liver flukes) and *Schistosoma* spp. (blood flukes).

In some embodiments, compositions described herein can be used to induce an immune response to and/or reduce the severity of an infection caused by *Plasmodium*. In some embodiments, compositions of the present disclosure can be used to induce an immune response to and/or reduce the severity of an infection caused by a *Plasmodium* selected from the group consisting of: *P. falciparum, P. malariae, P. ovale* and *P. vivax*.

In some embodiments, compositions described herein can be used to induce an immune response to and/or reduce the severity of an infection caused by a fungus including but not limited to *Aspergillus, Candida, Blastomyces, Coccidioides, Cryptococcus*, and *Histoplasma*. In some embodiments, compositions can be used to induce an immune response to and/or reduce the severity of a *Candida albicans* or a *Candida auris* infection.

In some embodiments, compositions described herein can be used to induce an immune response to a tumor antigen. In some embodiments, the compositions can be used to induce an immune response to a tumor antigen expressed on a cancer cell including but not limited to breast cancer cell, colon cancer cell, brain cancer cell, pancreatic cancer cell, lung cancer cell, cervical cancer cell, uterine cancer cell, prostate cancer cell, ovarian cancer cell, melanoma cancer cell, lymphoma cancer cell, myeloma cancer cell, and leukemic cancer cell.

In some embodiments, compositions described herein can be used to induce an immune response to a self-antigen. In some embodiments, the compositions can be used to induce an immune response to a self-antigen associated with an autoimmune disease including but not limited to ulcerative colitis, rheumatoid arthritis, systemic lupus erythematosus (SLE), celiac disease, inflammatory bowel disease, Hashimoto's disease, Addison's disease, Grave's disease, type I diabetes, autoimmune thrombocytopenic purpura (ATP), idiopathic pulmonary fibrosis, idiopathic thrombocytopenia purpura (ITP), Crohn's disease, multiple sclerosis, and myasthenia gravis.

In some embodiments, compositions of the present disclosure are administered orally. In some embodiments, compositions of the present disclosure are administered via the respiratory tract (e.g. intranasally or via inhalation). In some embodiments, compositions of the present disclosure are administered as *Spirulina* biomass. In some embodiments, compositions of the present disclosure are administered as lyophilized *Spirulina* biomass. In some embodiments, compositions of the present disclosure are administered as extracts of *Spirulina* biomass.

The dosage of the composition can be determined readily by the skilled artisan, for example, by first identifying doses effective to elicit a prophylactic or therapeutic effect. Said dosages can be determined from animal studies. A non-limiting list of animals used to study the efficacy of vaccines include the guinea pig, hamster, ferrets, chinchilla, mouse and cotton rat. Study animals may not be the natural hosts to infectious agents but can still serve in studies of various aspects of the disease. For example, any of the above animals can be dosed with an composition of the present disclosure, e.g. a recombinant *Spirulina* comprising a VLP comprising a polypeptide.

In some embodiments, administration of the compositions of the present disclosure decreases infectious agent burden. In some embodiments, administration of the compositions of the present disclosure decreases colonization of the infection agent. In some embodiments, administration of the compositions of the present disclosure decrease shedding of the infectious agent (e.g. viral shedding). In some embodiments, administration of the compositions of the present disclosure decrease shedding of the infectious agent. In some embodiments, administration of the compositions of the present disclosure increase shedding for one period (e.g. 24 hours) and then decrease shedding afterward (e.g. at 72 hours). In some embodiments, administration of the compositions decreases expression of a biomarker. In some embodiments, the biomarker is a marker of inflammation.

In some embodiments, administration of the compositions of the present disclosure neutralizes or blocks the activity of a target. In some embodiments, administration of the present disclosure neutralizes or blocks the activity of the target by about 1%, about 2%, about 3%, about 4%, about 5%, about 6%, about 7%, about 8%, about 9%, about 10%, about 15%, about 20%, about 30%, about 40%, about 50%, about 60%, about 70%, about 80%, about 90%, about 95%, about 98%, about 99%, or about 100%.

In addition, human clinical studies can be performed to determine the preferred effective dose for humans by a skilled artisan. Such clinical studies are routine and well known in the art. Effective doses may be extrapolated from dose-response curves derived from in vitro studies, animal studies, and/or clinical studies.

Methods of Making Non Parenteral Compositions

Provided are methods of making non-parenteral compositions described herein. Methods of making non-parenteral compositions comprise introducing into a *Spirulina* a nucleic acid sequence encoding the at least one exogenous polypeptide, antigen, and/or antigenic epitope. In some embodiments, the methods of making non-parenteral compositions comprise introducing into a *Spirulina* a polypeptide, antigen, and/or antigenic epitope. In some embodiments, methods of making non-parenteral compositions comprise introducing into a *Spirulina* a small molecule.

Any appropriate means for transforming *Spirulina* may be used in the present disclosure. Exemplary methods for transforming *Spirulina* to express a heterologous protein are described in U.S. Pat. No. 10,131,870, which is incorporated by reference herein in its entirety.

In some embodiments, methods of making an non-parenteral composition comprising introducing an expression vector having a nucleic acid sequence encoding the at least one exogenous polypeptide, antigen, and/or antigenic epitope into a *Spirulina* cell. In some embodiments, the vector is not integrated into the *Spirulina* genome. In some embodiments, the vector is a high copy or a high expression vector. In some embodiments the nucleic acid sequence encoding the at least one exogenous polypeptide, antigen, and/or antigenic epitope is under the control of a strong promoter. In some embodiments the nucleic acid sequence encoding the at least one exogenous polypeptide, antigen, and/or antigenic epitope is under the control of a constitutive promoter. In some embodiments the nucleic acid sequence encoding the at least one exogenous polypeptide, antigen, and/or antigenic epitope is under the control of an inducible promoter.

In some embodiments, methods of making a composition comprise introducing a vector (e.g. via homologous recombination) having homology arms and a nucleic acid sequence encoding the at least one exogenous polypeptide antigen, and/or antigenic epitope into a *Spirulina* cell.

In some embodiments, a vector having homology arms and a nucleic acid sequence encoding the at least one exogenous polypeptide, antigen, and/or antigenic epitope can be introduced into *Spirulina* using electroporation. The electroporation is preferably carried out in the presence of an appropriate osmotic stabilizer.

Prior to introduction of the vector into *Spirulina, Spirulina* may be cultured in any suitable media for growth of cyanobacteria such as SOT medium. SOT medium includes $NaHCO_3$ 1.68 g, $K_2HPO_4$ 50 mg, $NaNO_3$ 250 mg, $K_2\mathbf{50}_4$ 100 mg, NaCl 100 mg, $MgSO_4.7H_2O$, 20 mg, $CaCl_2.2H_2O$ 4 mg, $FeSO_4.7H_2O$ 1 mg, Na2EDTA.$2H_2O$ 8 mg, As solution 0.1 mL, and distilled water 99.9 mL. As solution includes $H_3BO_3$ 286 mg, $MnSO_4.5H_2O$) 217 mg, $ZnSO_4.7H_2O$ 22.2 mg, $CuSO_4.5H_2O$ 7.9 mg, $Na_2MoO_4.2H_2O$ 2.1 mg, and distilled water 100 mL. Cultivation may occur with shaking (e.g., 100-300 rpm) at a temperature higher than room temperature (e.g. 25-37° C.) and under continuous illumination (e.g. 20-2,000, 50-500, or 100-200 μmol photon $m^{-2}$ $s^{-1}$). The growing cells may be harvested when the optical density at 750 nm reaches a predetermined threshold (e.g., $OD_{750}$ of 0.3-2.0, 0.5-1.0, or 0.6-0.8). A volume of the harvested cells may be concentrated by centrifugation then resuspended in a solution of pH balancer and salt. The pH balancer may be any suitable buffer that maintains viability of *Spirulina* while keeping pH of the media between 6 and 9 pH, between 6.5 and 8.5 pH, or between 7 and 8 pH. Suitable pH balancers include HEPES, HEPES-NaOH, sodium or potassium phosphate buffer, and TES. The salt solution may be NaCl at a concentration of between 50 mM and 500 mM, between 100 mM and 400 mM, or between 200 mM and 300 mM. In an embodiment between 1-50 mL of 1-100 mM pH balance may be used to neutralize the pH.

Cells collected by centrifugation may be washed with an osmotic stabilizer and optionally a salt solution (e.g. 1-50 mL of 0.1-100 mM NaCl). Any amount of the culture may be concentrated by centrifugation. In an embodiment between 5-500 mL of the culture may be centrifuged. The osmotic stabilizer may be any type of osmotic balancer that stabilizes cell integrity of *Spirulina* during electroporation. In an embodiment, the osmotic stabilizer may be a sugar (e.g. w/v 0.1-25%) such as glucose or sucrose. In an embodiment the osmotic stabilizer may be a simple polyol (e.g. v/v 1-25%) including glycerine, glycerin, or glycerol. In an embodiment the osmotic stabilizer may be a polyether including (e.g. w/v 0.1-20%) polyethylene glycol (PEG), poly(oxyethylene), or poly(ethylene oxide) (PEO). The PEG or PEO may have any molecular weight from 200 to 10,000, from 1000 to 6000, or from 2000 to 4000. In an embodiment the pH balancer or buffer may be used instead of or in addition to the osmotic stabilizer.

A vector having homology arms and a nucleic acid sequence encoding the at least one exogenous polypeptide, antigen, and/or antigenic epitope can be introduced into *Spirulina* cells that are cultured and washed with an osmotic stabilizer as described above. Electroporation can be used to introduce the vector.

Electroporation may be performed in a 0.1-, 0.2- or 0.4-cm electroporation cuvette at between 0.6 and 10 kV/cm, between 2.5 and 6.5 kV/cm, or between 4.0 and 5.0 kV/cm; between 1 and 100 μF, between 30 and 70 μF, or between 45 and 55 μF; and between 10 and 500 mΩ, between 50 and 250 mΩ, or between 90 and 110 mΩ. In some embodiments, electroporation may be performed at 4.5 kV/cm, 50 μf, and 100 mΩ.

Following electroporation the cells may be grown in the presence of one or more antibiotics selected based on resistance conferred through successful transformation with the plasmid. Post-electroporation culturing may be performed at reduced illumination levels (e.g. 5-500, 10-100, or 30-60 μmol photon $m^{-2}$ $s^{-1}$). The culturing may also be performed with shaking (e.g. 100-300 rpm). The level of antibiotics in the media may be between 5 and 100 μg/mL. Post-electroporation culturing may be continued for 1-5 days or longer. Successful transformants identified by antibiotic resistance may be selected over a time course of 1 week to 1 month on plates or in 5-100 mL of SOT medium supplemented with 0.1-2.0 μg of appropriate antibiotics.

A vector used in the methods can be a plasmid, bacteriophage, or a viral vector into which a nucleic acid sequence encoding the at least one exogenous polypeptide, antigen, and/or antigen can be inserted or cloned. A vector may comprise one or more specific sequences that allow recombination into a particular, desired site of the *Spirulina*'s chromosome. These specific sequences may be homologous to sequences present in the wild-type *Spirulina*. A vector system can comprise a single vector or plasmid, two or more vectors or plasmids, some of which increase the efficiency of targeted mutagenesis, or a transposition. The choice of the vector will typically depend on the compatibility of the vector with the *Spirulina* cell into which the vector is to be introduced. The vector can include a reporter gene, such as a green fluorescent protein (GFP), which can be either fused in frame to one or more of the encoded antigenic epitopes, or expressed separately. The vector can also include a positive selection marker such as an antibiotic resistance gene that can be used for selection of suitable transformants. The vector can also include a negative selection marker such as the type II thioesterase (tesA) gene or the *Bacillus subtilis* structural gene (sacB). Use of a reporter or marker allows for identification of those cells that have been successfully transformed with the vector.

In some embodiments, the vector includes one or two homology arms that are homologous to DNA sequences of the *Spirulina* genome that are adjacent to the targeted locus.

The sequence of the homology arms can be partially or fully complementary to the regions of *Spirulina* genome adjacent to the targeted locus.

The homology arms can be of any length that allows for site-specific homologous recombination. A homology arm may be any length between about 2000 bp and 500 bp. For example, a homology arm may be about 2000 bp, about 1500 bp, about 1000 bp, or about 500 bp. In some embodiments having two homology arms, the homology arms may be the same or different length. Thus, each of the two homology arms may be any length between about 2000 bp and 500 bp. For example, each of the two homology arms may be about 2000 bp, about 1500 bp, about 1000 bp, or about 500 bp.

A portion of the vector adjacent to one homology arm or flanked by two homology arms modifies the targeted locus in the *Spirulina* genome by homologous recombination. The modification may change a length of the targeted locus including a deletion of nucleotides or addition of nucleotides. The addition or deletion may be of any length. The modification may also change a sequence of the nucleotides in the targeted locus without changing the length. The targeted locus may be any portion of the *Spirulina* genome including coding regions, non-coding regions, and regulatory sequences.

EXAMPLES

Example 1: Oral *Spirulina*-VHH Provides Complete Protection Against *Campylobacter*

*Spirulina* Expressing a Monomeric VHH

Mice were inoculated with $10^7$ *Campylobacter jejuni*. *Spirulina* were transfected with vectors expressing monomeric VHH antibodies targeting *campylobacter*. After growth of the *Spirulina* to allow expression of the monomeric VHH antibodies, the *Spirulina* were dried, and *campylobacter* infected mice were administered a daily gavage of 200 μl of PBS and 10% *Spirulina* biomass (13 mg) for five days. The 13 mg of *Spirulina* contains 425 μg of monomeric VHH per dose. As controls, mice were administered with daily gavage of either 1) PBS; 2) wild type *Spirulina*, or 3) *Spirulina* expressing an irrelevant VHH As shown in FIG. 1A, 100% of *campylobacter*-infected mice treated with any one of the control treatments presented with diarrhea. In contrast, no mice administered the *Spirulina* expressing the monomeric anti-*campylobacter* VHH presented with diarrhea. Further, at 7 days after inoculation, mice treated with the *Spirulina* expressing the monomeric anti-*campylobacter* VHH demonstrated a four-log reduction in *Campylobacter* shedding (FIG. 1B).

Example 2: *Spirulina* Expressing Trimeric VHH

Oral *Spirulina*—VHH has anti-inflammatory activity in *Campylobacter* infection. Mice were inoculated with $10^8$ *Campylobacter jejuni*. *Spirulina* were transfected with vectors expressing trimeric VHH antibodies targeting *Campylobacter*. After growth of the *Spirulina* to allow expression the trimeric VHH antibodies, the *Spirulina* were dried, and *Campylobacter*-infected mice were administered a daily gavage of 400 μl of PBS+0.5% *Spirulina* biomass (1.3 mg) for three days. The 1.3 mg of *Spirulina* contains 19 μg of trimeric VHH per dose. As controls, mice were administered with a daily gavage of *Spirulina* expressing an irrelevant VHH.

Figure 2A:
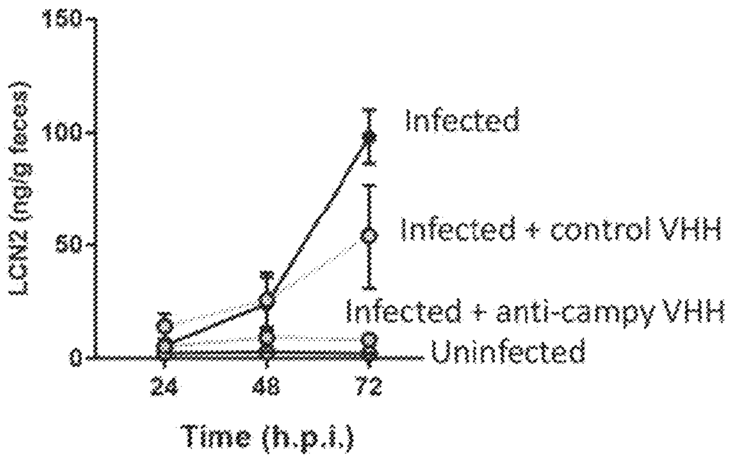
FIG. 2A-B demonstrates *Spirulina* expressing trimeric anti-*campylobacter* VHH have an anti-inflammatory effect in *Campylobacter*-infected mice. Administration of an oral gavage containing 0.5% *Spirulina* biomass (19 μg of the trimeric VHH per dose) daily for three days decreases markers of inflammation, stool lipocalin (Panel A) and myeloid cell infiltration of gut lamina propria (Panel B).
Figure 2B:
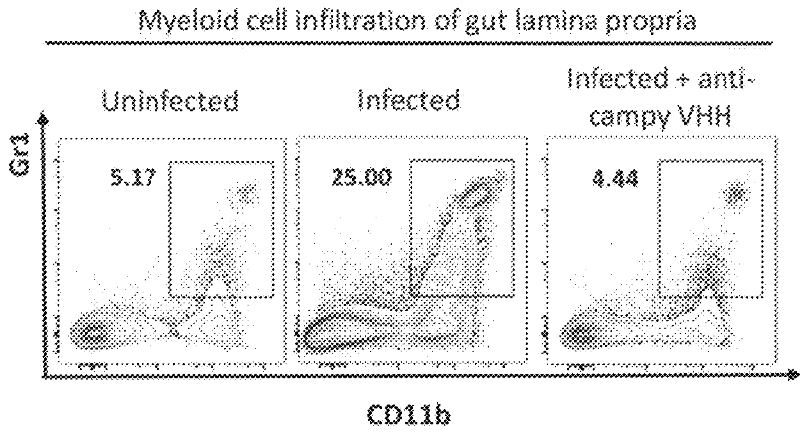

As shown in FIG. 2A, the expression of stool lipocalin, a marker of inflammation, is reduced in mice treated with the *Spirulina* expressing trimeric anti-*campylobacter* VHH compared to controls, and indeed stool lipocalin in these treated mice mirror that of uninfected mice. Further, FIG. 2B demonstrates that treatment of the infected mice with *Spirulina* expressing trimeric anti-*campylobacter* VHH prevents myeloid cell infiltration of gut lamina propria.

Example 3: Prophylactic Effect of *Spirulina*-VHH in Mice Challenged with *C. jejuni* Strain 81-176

Test Article:

*Spirulina* strain SP257 (irrelevant VHH)
*Spirulina* strain SP526 (anti-*C. jejuni* VHH FlagV6)
*Spirulina* strain SP651 (anti-*C. jejuni* VHH FlagV6)

A mouse model of *C. jejuni* infection was used to assess the prophylactic efficacy of an anti-*C. jejuni* VHH expressed in *Spirulina* [Giallourou et al]. *Spirulina* strains expressing either the VHH FlagV6 (SP526), a protease-resistant form of FlagV6 (FlagV6-F23) (SP806), or an irrelevant VHH (SP257) were tested. Biomass was prepared by spray drying a 4% *Spirulina*-VHH biomass resuspension in a solution containing 2% trehalose.

To prepare for *C. jejuni* infection, 21-day-old C57BL/6 female mice were treated with vancomycin 48, 24, and 12 hours prior to treatment. On day 0, mice were given an inoculum of $10^8$ *C. jejuni* strain 81-176 resuspended in PBS. Food and water were provided ad libitum throughout the trial.

To determine how well the mice tolerated being administered *Spirulina*-VHH by gavage, a high, three-dose regimen was tested. *Spirulina*-VHH was resuspended in PBS, and 400 μL of the slurry was delivered by oral gavage at 90 min before, and 24 and 48 hours after inoculation with *C. jejuni*. Mice were separated into four different groups:

- 13.3 mg *Spirulina*-VHH (670 mg/kg) containing an irrelevant VHH;
- 13.3 mg of an anti-*campylobacter* VHH on a trimeric scaffold (SP651);
- 13.3 mg of an anti-*campylobacter* VHH on a pentameric scaffold (SP737)
- Control group treated with PBS.

Relative to the infected control group treated with PBS, all mice treated with a *Spirulina*-VHH demonstrated non-specific flushing of *C. jejuni* in stool at 24 hours, followed by reduced bacterial burden at 48 and 72 hours (data not shown). No adverse events were observed in any mice at this dose.

To identify a dose regimen of *Spirulina*-VHH conferring a specific anti-*campylobacter* effect, mice were tested as below:

- Administration of a single 400-μL dose of SP561 5% *Spirulina*-VHH powder w/v resuspended in PBS, gavaged 1.5 hours before inoculation (equivalent to 13.3 mg *Spirulina*-VHH per dose);
- Administration of three 400-μL doses of SP561 0.5% *Spirulina*-VHH powder w/v resuspended in PBS, gavaged at 1.5 hours before and 24 and 48 hours after inoculation (equivalent to 1.33 mg *Spirulina*-VHH per dose);
- Administration of one 400-μL dose of SP257, an irrelevant VHH 0.5% *Spirulina*-VHH powder w/v resuspended in PBS, gavaged at 1.5 hours before and 24 and 48 hours after inoculation (equivalent to 1.33 mg *Spirulina*-VHH per dose);

Administration of three 400-μL doses of SP257, an irrelevant VHH 0.5% *Spirulina*-VHH powder w/v resuspended in PBS, gavaged at 1.5 hours before and 24 and 48 hours after inoculation (equivalent to 1.33 mg *Spirulina*-VHH per dose);

Control mice administered PBS gavage.

Figure 3A:
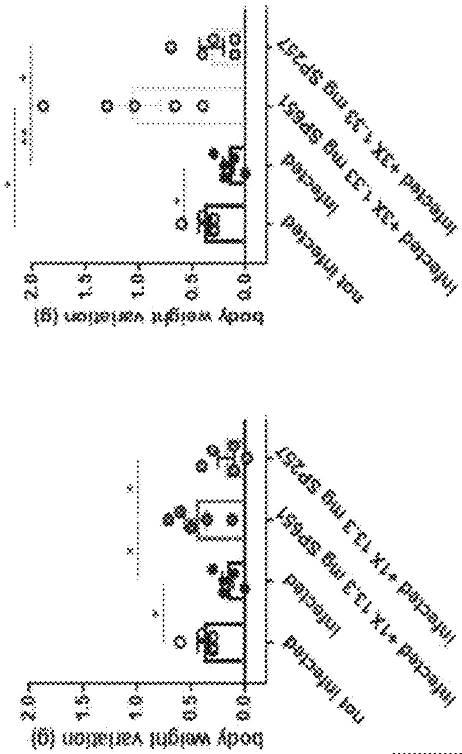
FIG. 3A-B: Weight changes and histology scores for mice pretreated with *Spirulina* and infected with *C. jejuni*. Mice were pretreated with one dose (left) or three doses (right) of *Spirulina*.

There were five mice in each experimental group. Three days after *campylobacter* inoculation, control infected mice (PBS gavage) showed a significant weight deficit compared to uninfected mice (FIG. 3A). Infected mice treated with SP257 showed a similar weight deficit. In contrast, infected mice treated under both dosing regimens with SP651, which expresses the anti-*campylobacter*-binding protein on a trimeric scaffold, showed a weight gain comparable to or significantly better than uninfected mice (FIG. 3A).

Figure 3B:
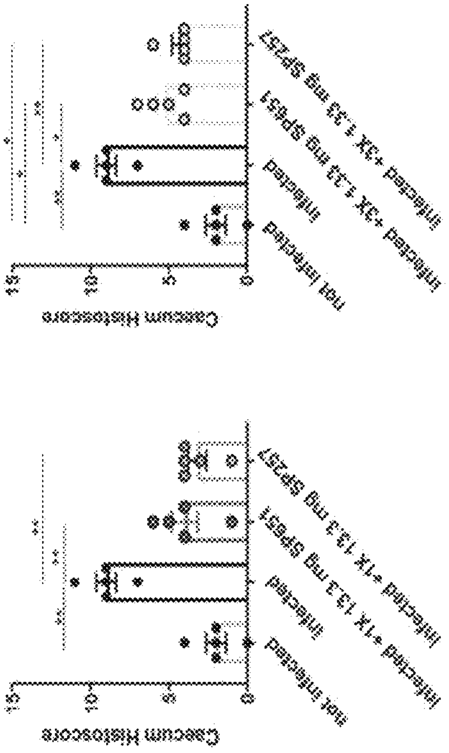

Caeca from all animals were examined at necropsy 72 hours after infection. Tissue sections were processed and scored in a blinded manner by a histopathologist on a scale of 0-24. Each section was assessed for submucosal edema, crypt hyperplasia, goblet cell depletion, epithelial integrity, mucosal mononuclear cell infiltration, and submucosal PMN and mononuclear cell infiltration. Animals that were treated with either SP651 or SP257 scored significantly lower than the infected control and closer to uninfected control (FIG. 3B). These results suggested that *Spirulina* itself had a positive impact on reducing the histopathology of the *C. jejuni*-infected animals. Without wishing to be bound by theory, this effect could be due to *Spirulina's* inherent health benefits (i.e. it is considered a superfood).

*Spirulina*-VHH was well tolerated, and no adverse effects were observed in mice treated with the highest dose of 13.3 mg *Spirulina*-VHH.

In a second experiment, a single 1.33-mg dose of *Spirulina*-VHH (SP651) was used to determine the efficacy of an anti-*C. jejuni* VHH strain compared to *Spirulina* expressing an irrelevant VHH (SP257).

1.5 hours before infection with *C. jejuni*, mice were given a single 400-μL dose containing 1.33 mg of *Spirulina*-VHH in PBS. Four cohorts, each containing 5 mice, were treated as below:

uninfected, infected and treated with PBS gavage, infected and treated with SP257 gavage, infected and treated with SP651 gavage.

Figures 4A, 4B, 4C:
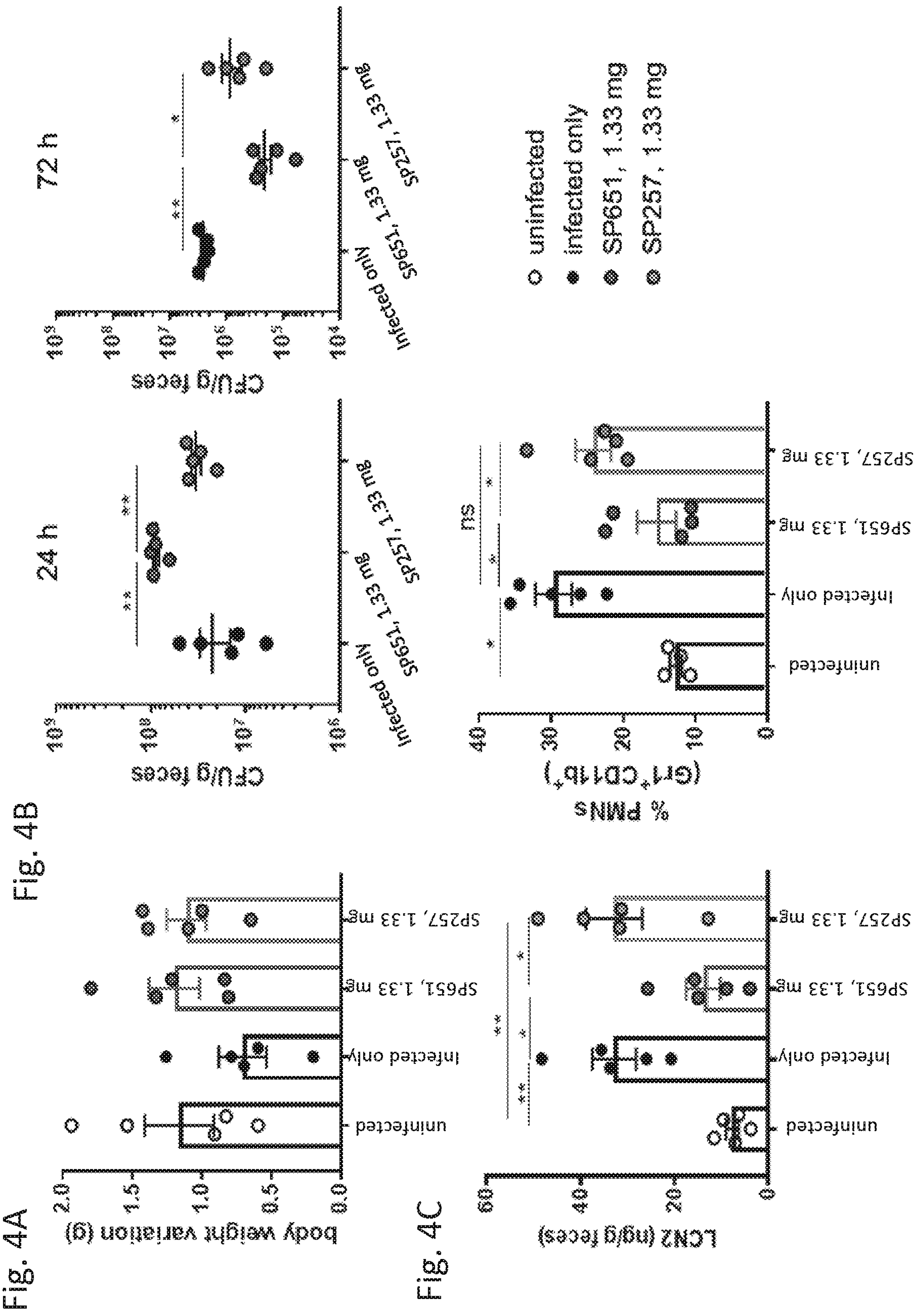
FIG. 4A-C: Weight changes and pathogen shedding in mice pretreated with a single dose of *Spirulina* and infected with *C. jejuni*. Mice were pretreated with 1.33 mg of *Spirulina*, inoculated with $10^8$ CFU *C. jejuni* at time 0, and treated with PBS (infected), *Spirulina* SP651 (anti-*C. jejuni* VHH), or SP257 (irrelevant VHH).

Treatment with this single prophylactic dose of *Spirulina* containing an anti-campylobacter VHH was sufficient to significantly accelerate campylobacter flushing at 24 hours post infection and reduce campylobacter shedding at 72 hours post infection as measured by fecal campylobacter CFUs. (FIG. 4B). Inflammation following infection was measured by stool lipocalin amounts and by flow cytometric quantitation of myeloid cell infiltration in the cecal lamina propria. *Campylobacter* infection caused a significant increase in both inflammation biomarkers (FIG. 4C). This increase was prevented by the single prophylactic dose of SP651 (expressing the anti-campylobacter binding VHH), whereas a prophylactic dose of SP257 (expressing the irrelevant VHH) was without effect (FIG. 4). Also, as in the previous experiment, the weight deficit caused by campylobacter infection was prevented by the prophylactic dose of SP651. (FIG. 4A) However, in this experiment, *Spirulina* expressing the irrelevant VHH also suppressed the infection-associated weight deficit, again suggesting a possible nutritional benefit of *Spirulina* per se. Importantly, the *Spirulina* expressing the irrelevant VHH did not exert an effect on the biomarkers of inflammation or myeloid cell infiltration in the cecal lamina propria.

In a third experiment, increasingly dilute single doses of *Spirulina*-VHH were tested to determine the minimal effective dose (MED) of *Spirulina*-VHH required to observe a positive result. Two *Spirulina*-VHH strains were compared: SP526 and SP806. SP526 exhibits a high expression level of the anti-*C. jejuni* FlagV6 VHH, and SP806 expresses a protease-resistant form of FlagV6 (FlagV6-F23) which contains two mutations in the VHH reported to confer resistance to chymotrypsin (Hussack et al. 2014). The results were also compared retrospectively to the efficacy of SP651 in the previous experiment.

Figures 5A, 5B:
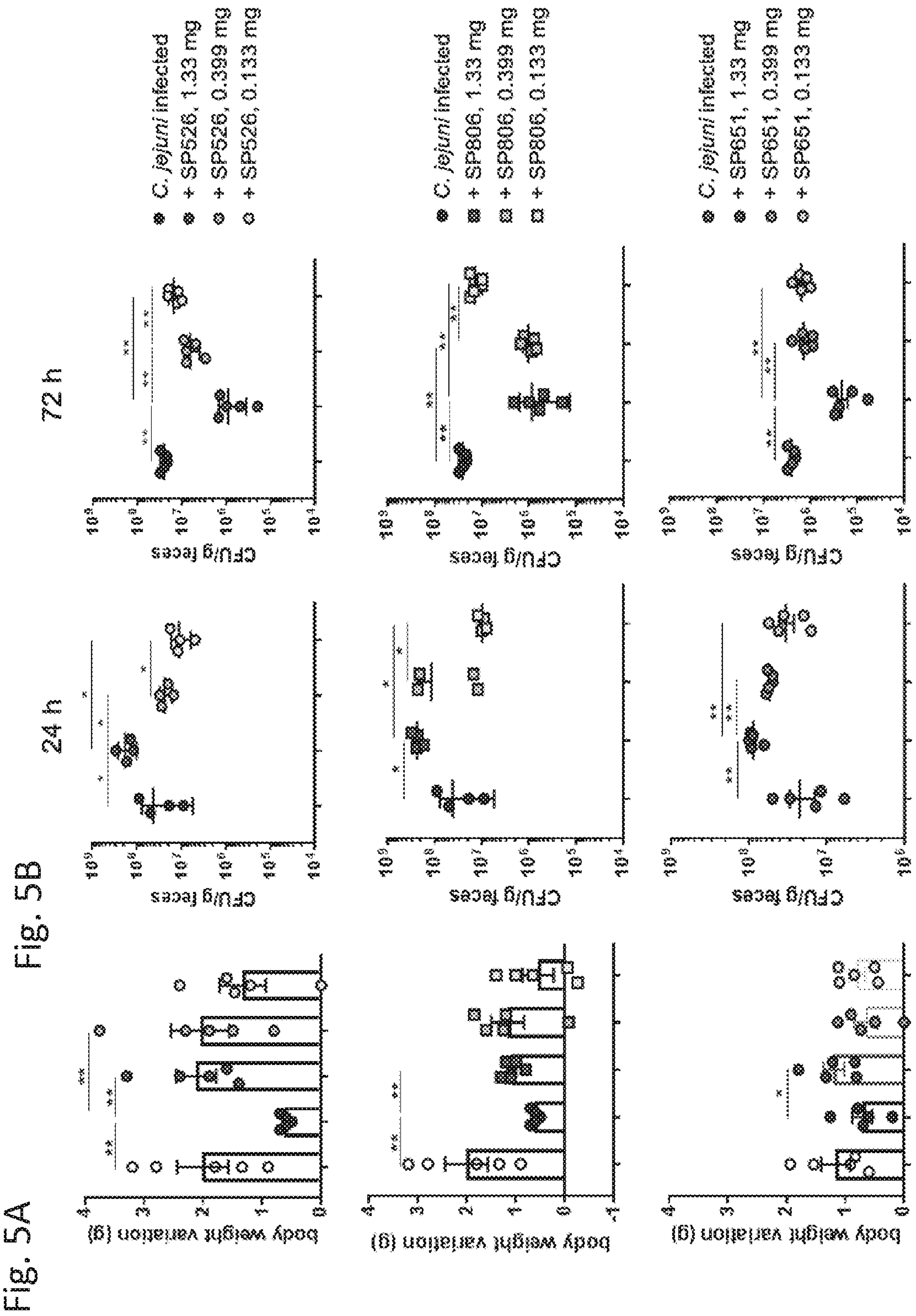
FIG. 5A-B: Weight changes and pathogen shedding in mice pretreated with a protease-resistant VHH variant in *Spirulina* and infected with *C. jejuni*. Mice were pretreated with a single dose of varying concentration of *Spirulina*-VHH, and infected with $10^8$ CFU of *C. jejuni*. Each row of data represents a different treatment strain (SP526, SP806, or SP651).

1.5 hours prior to infection with *C. jejuni*, mice were given a single 400-μL dose containing 1.33 mg, 0.399 mg, or 0.133 mg of *Spirulina*-VHH (SP526, SP806, or SP651) in PBS. Measurements of body weight variation showed, as in previous experiments, that campylobacter caused a weight gain deficit at 72 hours post infection. Treatment with each of the three *Spirulina*-VHH strains suppressed this loss at the 1.33-mg dose (FIG. 5A). In this assay the minimal effective dose (MED) for SP526 was 0.133 mg (6.7 mg/kg), for SP806 it was 0.399 mg (20 mg/kg), and for SP651 it was 1.33 mg (67 mg/kg).

Measurements of fecal campylobacter CFUs showed, as in previous experiments, that all three *Spirulina*-VHH strains accelerated campylobacter flushing at 24 hours post treatment and reduced long-term shedding at 72 hours after treatment (FIG. 5B). Again, VHH expression level and protease resistance independently increased efficacy, with SP526 and SP806 both showing a MED, in this assay, of 0.399 mg (20 mg/kg).

Figures 6A, 6B:
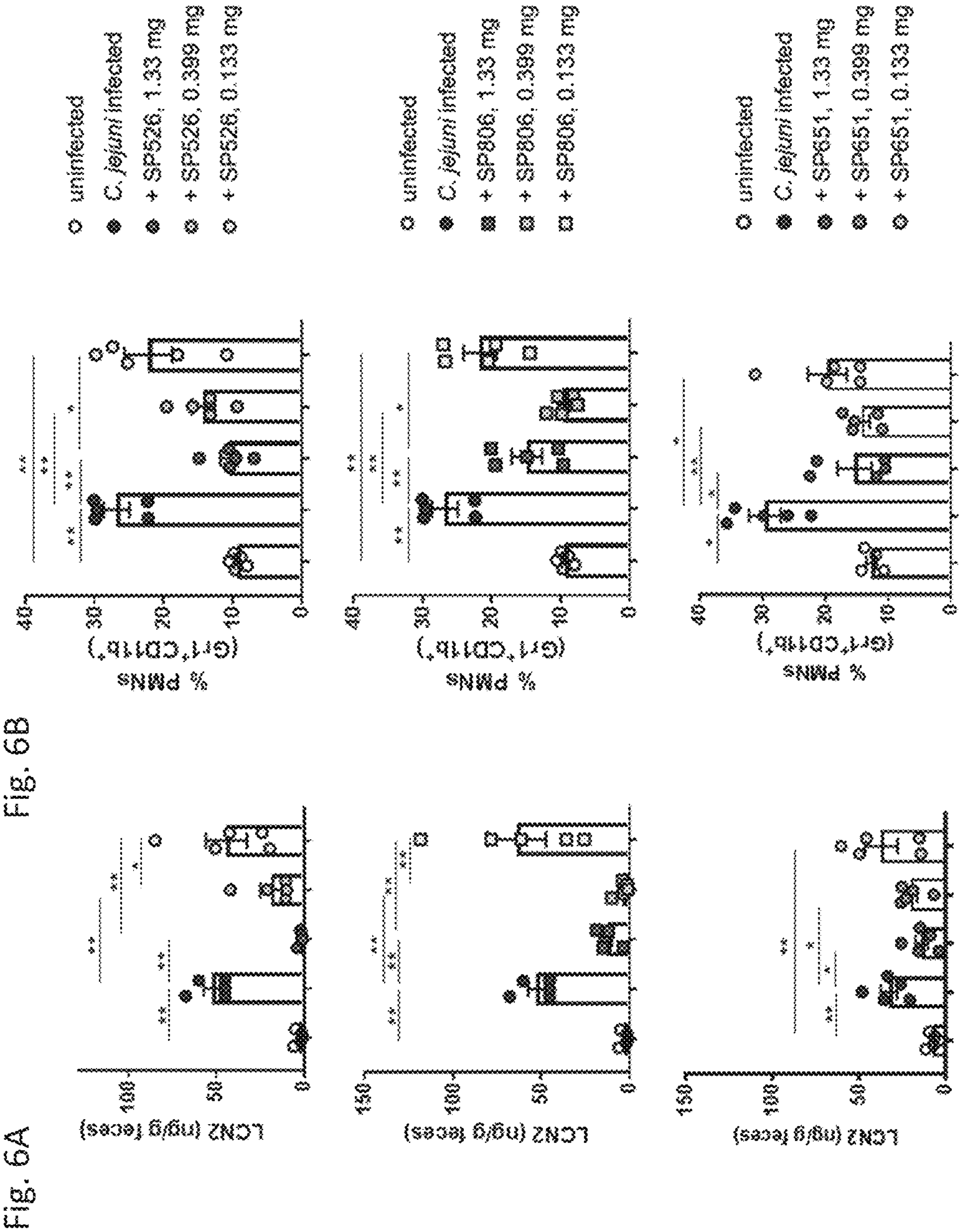
FIG. 6A-B: Inflammatory markers and lamina propria leukocyte infiltration in mice pretreated with *Spirulina* and infected with *C. jejuni*. Mice were pretreated with a single dose of varying concentrations of *Spirulina*-VHH and infected with $10^8$ CFU of *C. jejuni*. Each row of data represents a different treatment strain (SP526, SP806, or SP651). A), stool lipocalin-2 (LCN2) levels 72 hours post-infection. B), Gr1+, CD11b+ myeloid cells infiltrating lamina propria (% PMNs) were identified by FACS. White circles represent uninfected control mice. Mice treated with SP526 and SP806 were treated concurrently and therefore used the same uninfected and infected control groups.

Biomarkers of inflammation—stool lipocalin and myeloid cell infiltration of the cecal lamina propria—showed, as in previous experiments, that all three strains suppressed intestine inflammation following campylobacter infection (FIG. 6). The protease-resistant strain (SP806) conferred the greatest reduction in both lipocalin-2 levels and lamina propria infiltrating myeloid cells. The MED for all three strains was 0.399 mg (20 mg/kg), with partial efficacy at 0.133 mg (6.7 mg/kg).

Caeca from all animals were examined at necropsy 72 hours after infection. Tissue sections were processed and scored in a blinded manner by a histopathologist as before. The only group to demonstrate a significant reduction in histopathology relative to the infected control was treatment with 1.33 mg (67 mg/kg) of SP526. Below this dose or in groups treated with different *Spirulina*-VHH (SP806 or SP651), the positive effect of treatment was determined with other metrics of efficacy (i.e., bacterial shedding, inflammatory biomarkers, etc.).

Conclusion: Administration of all *Spirulina*-VHH strains expressing the anti-*C. jejuni* VHH FlagV6 gave favorable results for treating *C. jejuni*-infected mice with a single dose of 1.33 or 0.399 mg *Spirulina*-VHH. Compared to mice receiving no treatment, these mice had better weight gain and reduced levels of inflammatory markers.

No adverse events were observed in these experiments, up to the highest biomass dose administered. The drug material was well tolerated and no signs of toxicity were observed.

The most significant new observation made using the Grassi model is that the minimally effective dose was 0.399 mg dried *Spirulina*-VHH. A single oral dose administered by gavage 90 minutes prior to campylobacter inoculation was sufficient to prevent infection-associated weight loss, reduce fecal shedding of campylobacter at day three, and maintain control (baseline) levels of both molecular and cellular metrics of infection-associated intestine inflammation (stool lipocalin and myeloid cell infiltration of the intestinal lamina propria).

Example 4—Effect of Post-Challenge Treatment with Anti-Campylobacter Spirulina-VHH in Mice Challenged with *C. jejuni* Strain CG8421

Figure 7:
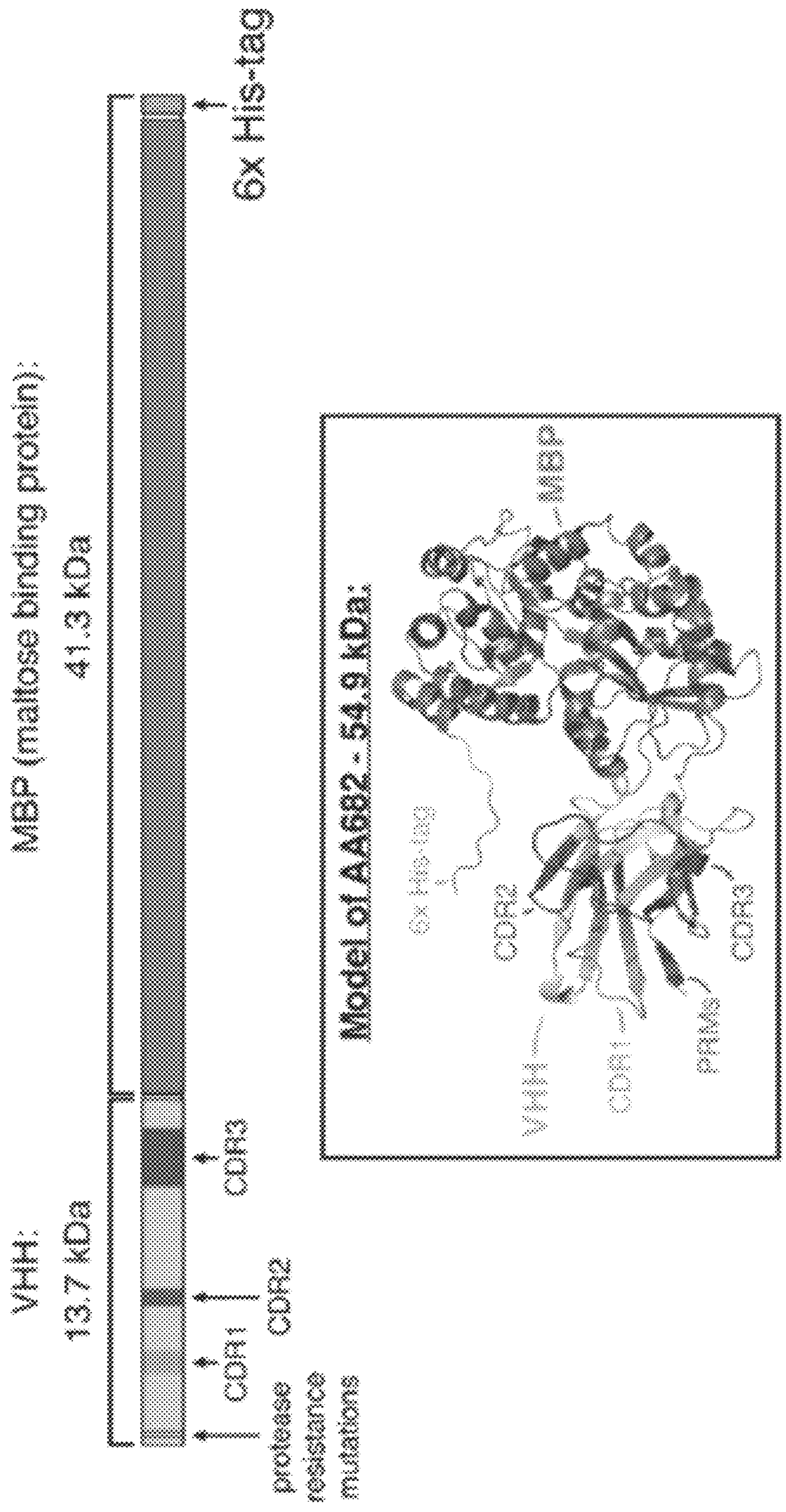
FIG. 7: SP1182 construct both as schematic and ribbon structure.
Figure 8:
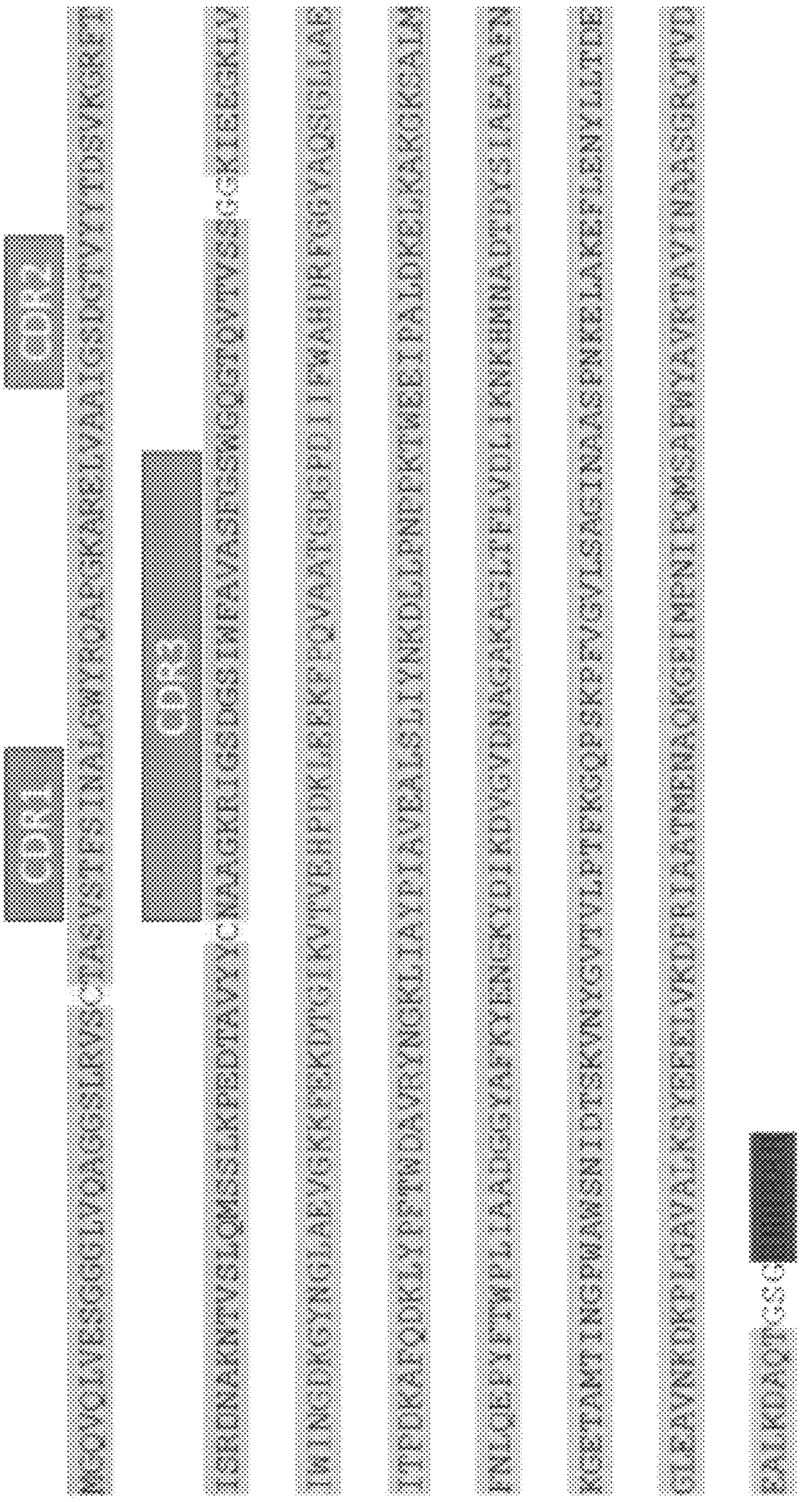
FIG. 8: Sequence of SP1182 construct. The VHH binds to the flagellin protein flaA from *C. jejuni*. The CDR1, CDR2, and CDR3 are noted above the corresponding segment of the VHH sequence. Mass spectrometry data of the intact protein indicates that the N-terminal methionine is removed. The maltose binding protein serves to increase expression levels and solubility of the fused VHH, while the hexahistidine tae serves as an affinity tag for detection reagents. Two short flexible linkers, a G-G and a G-S-G bridge the VHH and MBP and the MBP and hexahistidine tag respectively.

The SP1182 construct is described in FIGS. 7 and 8. This fusion protein comprises a camelin VHH FLAGV6-F23 that binds the flagellin protein flaA from *C. jejuni*. As the SP1182 fusion protein does not contain a targeting protein, it remains in the cytoplasm of the *Spirulina* cell.

A mouse campylobacter challenge experiment was performed to test the efficacy of orally delivered SP1182 administered in a treatment modality.

Twenty-one-day-old C57BL/6 mice were given a 48-hour vancomycin conditioning regimen and then challenged with $10^8$ CFU of *C. jejuni* CG8421 (in PBS). Food and water were provided ad libitum throughout the trial. Three cohorts containing 5 mice each were treated as below beginning 24 hours after the campylobacter challenge:

- Two treatment doses at 24 hours and 48 hours post challenge of 67 mg/kg SP1182;
- Three treatment doses at 24, 36, and 48 hours post-challenge of 67 mg/kg SP1182;
- Two doses at 24 hours and 48 hours of 67 mg/kg wild-type *Spirulina* (SP3);
- Three doses at 24, 36, and 48 hours of 67 mg/kg wild-type *Spirulina* (SP3).

Figure 9:
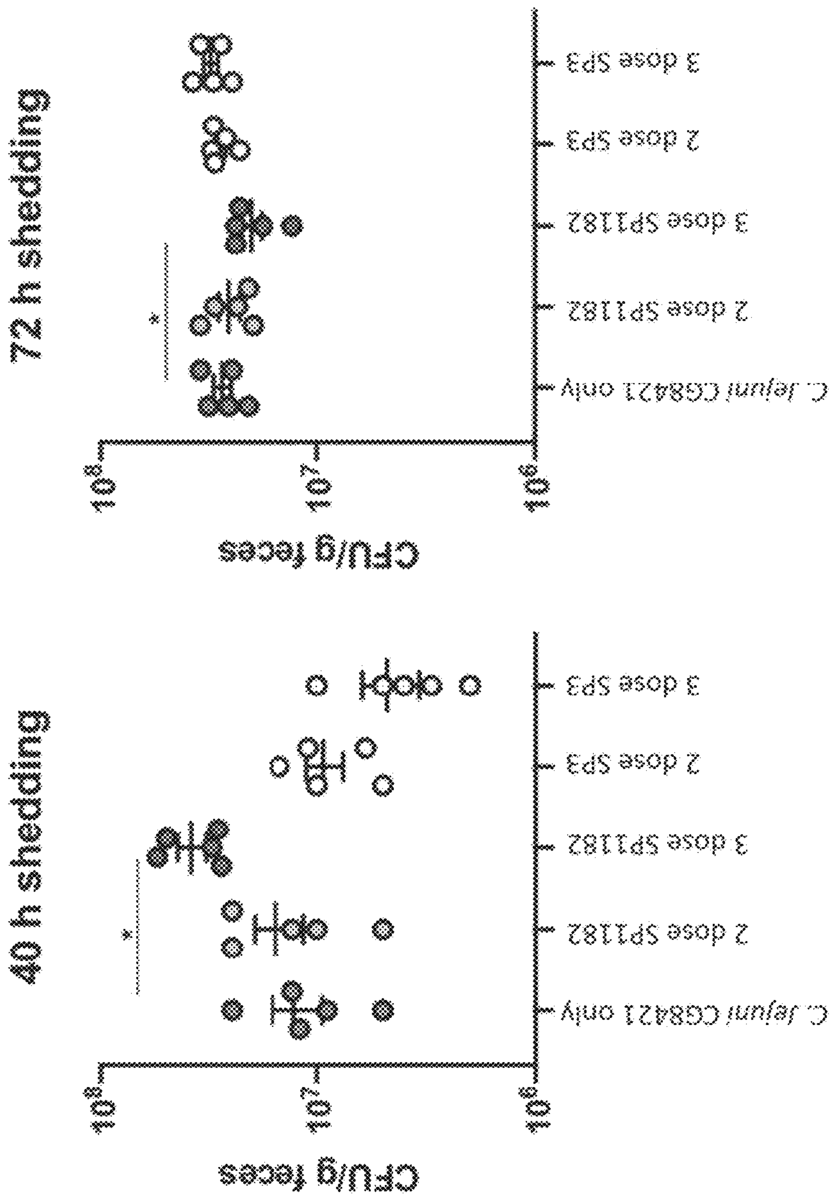
FIG. 9: Bacterial shedding (CFU/g feces) measured in stool at 40 and 72 hours after infection. *C. jejuni*-only mice received no treatment. Two-dose (24 and 48 hours after infection) and three-dose (24, 36, and 48 hours after infection) mice received 1.33 mg of the indicated *Spirulina*-VHH per dose.
Figure 10:
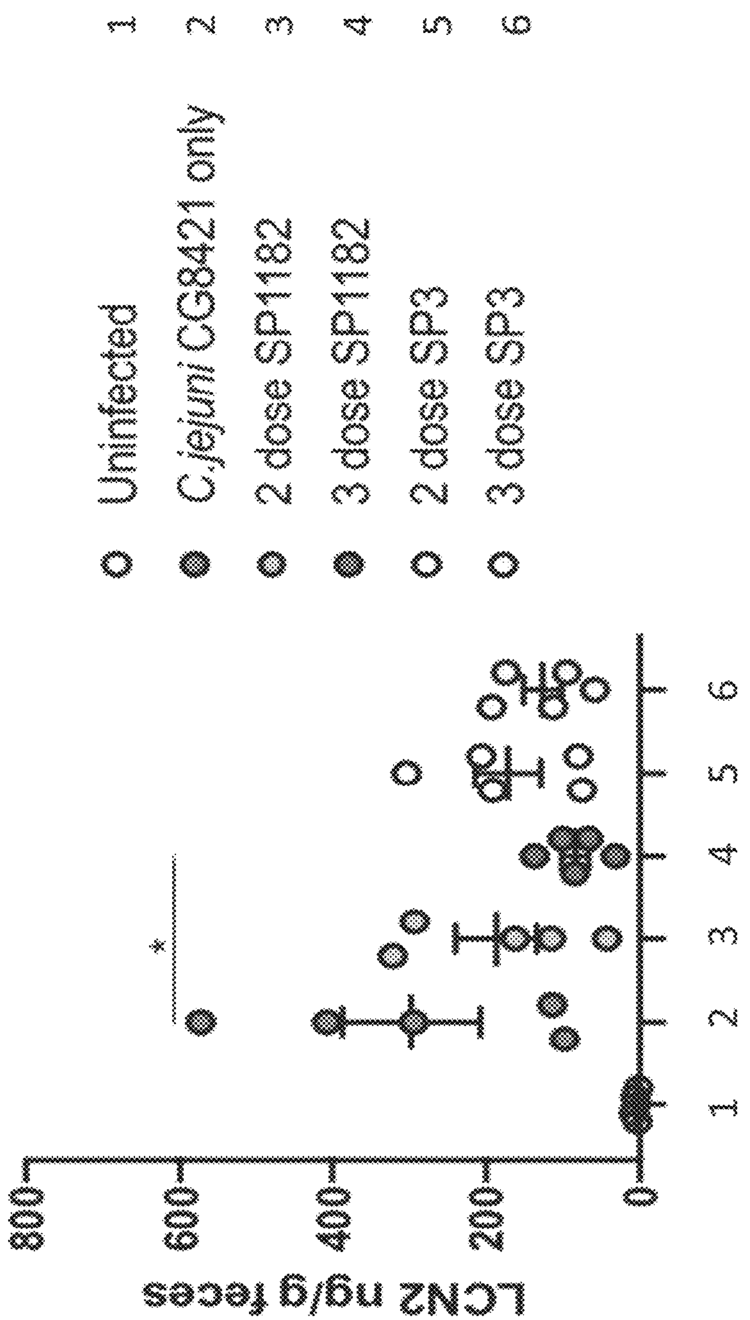
FIG. 10: Lipocalin (LCN2) levels measured in stool at 72 hours after infection. Uninfected and *C. jejuni*-only mice received no treatment. Two-dose (24 and 48 hours post infection) and three-dose (24, 36, and 48 hours after infection) mice received 1.33 mg of the indicated *Spirulina*-VHH per dose.

Fecal campylobacter shedding was measured at 40 and 72 hours after infection. At the 40-hour time point there was a significant ($p<0.05$) burst of campylobacter expulsion only in the 3-dose cohort that received SP1182 at 36 hours (FIG. 9). At 72 hours after infection there was a significant ($p<0.05$) reduction in fecal campylobacter shedding. Further, there was a significant ($p<0.05$) reduction in stool lipocalin (a metric for inflammation) only in the cohort of mice that received 3 doses of SP1182 (FIG. 10). Overall these results were very similar to the effect of a single pre-inoculation (prophylactic) dose of SP1182.

Caeca from all animals were examined at necropsy 72 hours after infection. Tissue sections were processed and scored in a blinded manner by a histopathologist on a scale of 0-24. Each section was assessed for submucosal edema, crypt hyperplasia, goblet cell depletion, epithelial integrity, mucosal mononuclear cell infiltration, and submucosal PMN and mononuclear cell infiltration. No treatment group exhibited a reduction in histopathology, with all treatment groups scoring similarly to *C. jejuni*-infected control.

Figure 11A:
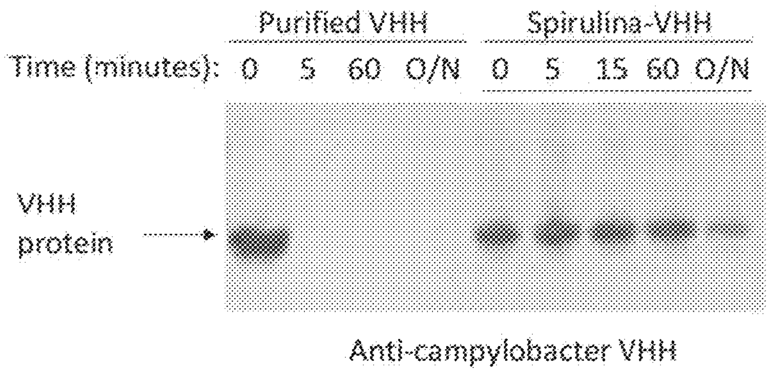
FIG. 11A-B demonstrates that encapsulation of anti-*campylobacter* VHH in *Spirulina* protects the polypeptide in a simulated stomach environment. The anti-*campylobacter*
Figure 11B:
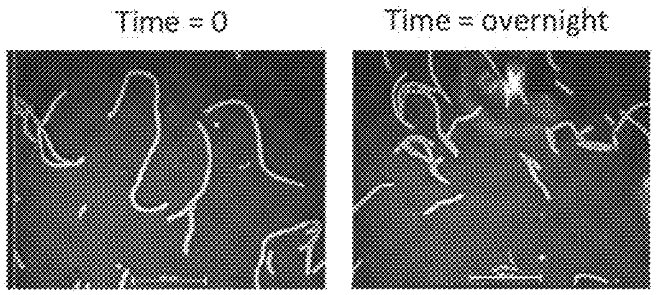

Example 5: Encapsulation by *Spirulina* Protects Polypeptides in the Stomach To demonstrate the protective effect of *Spirulina* on polypeptides, *Spirulina* were transfected to express an anti-campylobacter VHH. These *Spirulina* along with the purified anti-campylobacter VHH were subjected to a simulated stomach environment (pH of 3; pepsin at 2,000 U/ml) overnight. Samples were collected at 0 minutes, 5 minutes, 60 minutes, and overnight. As shown in FIG. 11A, the VHH protein encapsulated in *Spirulina* could be detected after overnight treatment, while those of purified VHH could not be detected after 5 minutes of exposure to the simulated stomach environment. FIG. 11B shows microscopic images of the anti-campylobacter VHH expressing *Spirulina* at times 0 and overnight; the *Spirulina* maintained their integrity in the simulated stomach environment.

Example 6: Polypeptides Expressed in *Spirulina* are Stable Long-Term in Dried Biomass To test the effect of long-term storage of dried biomass on polypeptide stability, *Spirulina* expressing monomeric anti-campylobacter VHH were spray dried and stored: 1) 1 month at 27° C.; 2) 3 months at 27° C.; 3) 1 month at 42° C.; or 4) 3 months at 42° C. At the various time points, the VHH was purified from the *Spirulina* and tested for binding activity. As shown in FIG. 12, no decrease in anti-campylobacter VHH bioactivity was observed with prolonged incubation at elevated temperatures.

Example 7: Preclinical Efficacy of Multiple Doses in Mice Challenged with Campylobacter Test Articles:

- *Spirulina* strain SP651 (expressed anti-*C. jejuni* VHH FlagV6)
- *Spirulina* strain SP806 (expressed anti-*C. jejuni* VHH FlagV6-F23)
- *Spirulina* strain SP257 (expressed irrelevant VHH)
- *Spirulina* strain SP526 (expressed anti-*C. jejuni* VHH FlagV6)

Using a mouse model of *C. jejuni* infection developed at the Institute Research in Biomedicine in Switzerland, the efficacy of prophylactic treatment with anti-*C. jejuni* VHH expressing *Spirulina* was assessed. Several *Spirulina* strains expressing either the anti-*C. jejuni* VHH FlagV6, a protease-resistant form of FlagV6 (FlagV6-F23) (Hussack et al. 2014; Riazi et al. 2013), or an irrelevant VHH were tested. Biomass was prepared by spray drying a 3% *Spirulina* biomass resuspension in a solution containing 2% trehalose. To prepare for *C. jejuni* infection, 21-day old C57BL/6 mice were treated with vancomycin from 48-12 hours prior to treatment. On day 0, mice were given an inoculum of $10^8$ *C. jejuni*, strain 81-176.

To determine how well the mice would tolerate being given *Spirulina* by gavage, two dosing regimens were tested: 1) a single 400 μL dose of 5% *Spirulina* powder w/v resuspended in phosphate buffer saline (PBS), gavaged 1.5 h before inoculation (equivalent to 12 mg *Spirulina* per dose), 2) three 400 μL doses of 0.5% *Spirulina* powder w/v resuspended in PBS, gavaged at 1.5 h before and 24 and 48 h after inoculation (equivalent to 1.2 mg *Spirulina* per dose). Under both regimens, infected mice treated with *Spirulina* (either SP257 or SP651) showed weight gain similar to the uninfected control group (FIG. 16). *Spirulina* was considered well tolerated because no adverse effects were observed in mice treated with the highest dose of 12 mg *Spirulina* .

A single 1.2 mg dose of *Spirulina* was used to determine the efficacy of an anti-*C. jejuni* VHH strain (SP651) compared to *Spirulina* expressing an irrelevant VHH (SP257). 1.5 h before infection with *C. jejuni*, mice were given a single 400 μL dose containing 1.2 mg of *Spirulina* in PBS. Compared to untreated, infected mice, mice that received anti-*C. jejuni Spirulina* demonstrated good weight gain, an increase in shedding at 24 h followed by a decrease at 72 h, and reduced levels of biomarkers of inflammation (FIG. 17A-C). *Spirulina* containing an irrelevant VHH had little to no effect on shedding and inflammatory biomarker reduction.

Increasingly dilute single doses of *Spirulina* were tested to determine the limiting amount of *Spirulina* required to observe a positive result. Three *Spirulina* strains expressing the anti-*C. jejuni* FlagV6 VHH in different forms were compared for potency. Notably, SP526 was selected for its high expression level of the anti-*C. jejuni* FlagV6 VHH, and SP806 was identical to SP651, with the exception that SP806 contained two mutations in the VHH reported to confer resistance to chymotrypsin (Hussack et al. 2014). 1.5 h prior to infection with *C. jejuni*, mice were given a single 400 μL dose containing 1.2 mg, 0.36 mg, or 0.12 mg of *Spirulina* in PBS. All three strains showed good efficacy at the 1.2 mg dose and varying degrees of reduced effectiveness at the 0.36 mg and 0.12 mg doses. Mice treated with SP526 exhibited the best weight gain, while SP806 reduced shedding at 72 h at the intermediate dose concentration (FIG. 18A-C). All three strains significantly reduced levels of biomarkers of inflammation at a 0.36 mg dose (FIG. 19A-B), but the protease resistant strain (SP806) conferred the greatest reduction in both lipocalin-2 levels and lamina propria infiltrating myeloid cells. At the 0.12 mg dose of *Spirulina*, all strains behaved similarly to the *C. jejuni*-only control, suggesting that this amount was below the effective therapeutic dose.

In summary, all *Spirulina* strains expressing the anti-*C. jejuni* VHH FlagV6 gave positive results for treating *C. jejuni* infected mice with a single dose of 1.2 mg *Spirulina*-VHH. Compared to mice receiving no treatment, these mice had better weight gain and reduced levels of inflammatory markers.

No adverse events were observed in these experiments, up to the highest biomass dose administered. The drug material was well tolerated and no signs of toxicity were observed.

Example 8: Effect of Spirulina-VHH in Chickens Challenged with *C. jejuni* Strain 81-176

Test Article:

*Spirulina* strain SP257 (irrelevant VHH)

*Spirulina* strain SP526 (anti-*C. jejuni* VHH FlagV6)

*Spirulina* strain SP651 (anti-*C. jejuni* VHH FlagV6)

The efficacy of orally delivered *Spirulina*-VHH in blocking the colonization of the chicken intestinal tract was investigated. A chicken model of *C. jejuni* enteric colonization was used to assess the prophylactic efficacy of an anti-*C. jejuni* VHH expressed in *Spirulina. Spirulina* strains expressing either a monomeric anti-campylobacter VHH (SP526), a homotrimeric multimer of the VHH (SP651), or an irrelevant VHH (SP257) were tested. Strains were cultivated and spray dried at a concentration of 3% biomass in 2% trehalose. This experiment was designed to assess the therapeutic efficacy of different *Spirulina* strains on their ability to block gastrointestinal tract colonization with *C. jejuni*, a very common occurrence in commercial flocks and a major source of human food-borne illness.

Study animals were 14-day old SPF leghorn mixed-sex chicks. A 13.3-mg *Spirulina*-VHH dose (150 mg/kg) was administered in 200 μL PBS by oral gavage 1 hour prior to a challenge inoculum of $10^8$ *C. jejuni*, strain 81-176. Chicks were randomly assigned into negative control, positive control, and treatment groups, housed in isolator units and provided standard feed and water ad libitum. Two days following isolation, chicks were treated with one dose by gavage with PBS or with *Spirulina* suspended in PBS. One hour later birds were inoculated with 108 CFU of *C. jejuni* 81-176, or sham inoculated with PBS, by gavage. Body weights were measured at 24, 48 and 72 hours post-inoculation. At 72 hours, birds were euthanized and cecal contents were aseptically collected for quantitative assessment of *C. jejuni* colonization.

Figure 20:
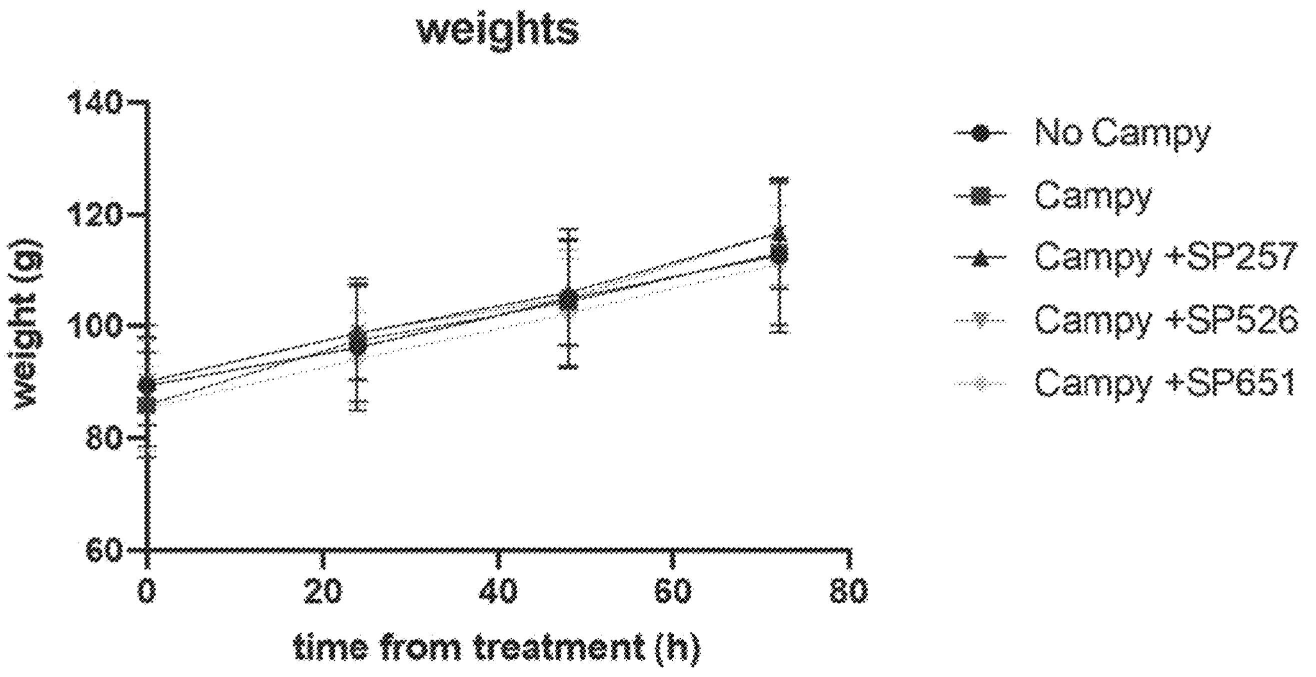

Birds were observed to gain weight normally, without deficit independent of *Campylobacter* inoculation or prophylactic therapy (FIG. 20). Cecal colony counts were used to assess bacterial burden. Cecal colonization with *Campylobacter* significantly reduced following pretreatment with *Spirulina* SP651, a strain expressing anti-*Campylobacter* FlagV6 in homotrimeric configuration. Treatment with SP257, expressing an irrelevant VHH, and SP526, expressing monomeric VHH FlagV6, resulted in reduced *Campylobacter* colonization, though to an insignificant degree compared to no *Spirulina* treatment (FIG. 21).

Example 9: ETEC Therapeutics: *Spirulina* Expressed Anti Adhesion VHHs

Enterotoxigenic *Escherichia coli* (ETEC) is one of the causative agents of diarrhea in children in developing countries and traveler's diarrhea in persons who travel to areas where ETEC is endemic. According to the WHO, the pathogen is responsible for over 200 million illnesses and around 0.5 million deaths worldwide annually. ETEC caused diarrhea has a long-lasting effect on young patients, including stunted growth, decreased intellectual aptitude, and associated long term economic disadvantages. The adverse impact of ETEC pathogenesis necessitates effective preventive post-infection treatment or preventive therapeutics like passive immunization. The two main virulence factors in ETEC infection targeted by vaccine development or prophylactic therapy are the enterotoxins and colonization factors (CFs) or pili. Enterotoxins are directly responsible for causing diarrhea following bacterial colonization of gut intestinal epithelial cells. In the other hand, ETEC CFs allow the organisms to readily colonize the small intestine and subsequently result in the expression of enterotoxins close to mucosal cells causing diarrhea.

The Inventors have developed single-domain camelid antibody (VHH)-based therapeutics that target ETEC fimbriae tip domain and inhibit bacterial attachment to host intestinal epithelial cells and hence block bacterial colonization. The VHHs are derived from either Llama Immunization with the fimbriae tip adhesion protein CfaE or screened against the same antigen from a yeast-based synthetic library. VHHs that exhibit higher antigen binding and bacterial inhibition in hemagglutination or cell-based assay were designed for *Spirulina* expression as monomers, dimers, trimers, tetramers, pentamers, heptamers and displayed on nanoparticles. Chaperone proteins like Maltose Binding Protein (MBP), Thioredoxin A (TxnA) and Neutrophil Gelatinase-Associated Lipocalin (LCN) were used to increase heterologous protein solubility which can result in higher protein expression levels of therapeutic VHH in *Spirulina.*

*Spirulina* strains expressing the anti-CfaE VHHs show good binding activity to the Adhesion domain of CFA/I fimbriae tip. An increased multimeric state of VHHs correspond to increased binding activity ELISA.

Example 10: Pig ETEC Therapeutics: *Spirulina* Expressed Anti Adhesion VHHs

Porcine Enterotoxigenic *Escherichia coli* (ETEC) is the number one cause of piglet diarrhea. The infection of ETEC in nursery pigs may induce diarrhea during the first 1 or 2 weeks of postweaning periods usually resulting in dehydration, reduced weight gain, and death. The economic challenge on the porcine industry makes Post-weaning diarrhea and the causative agent ETEC, an economically significant disease in the pig farming industry. The main virulence factor in ETEC strains is the adhesins expressed as part of the fimbriae (pili) structures where the most common in porcine ETEC are adhesins K88 (also called F4), K99 (F5), 987P (F6), F41, and F18 of which K88 and F18 are the most prevalent in the swine industry.

The Inventors have developed a system to cost-effectively produce a multivalent camelid single domain antibodies (VHHs) targeting the virulence factors in K88 and F18 in the *Spirulina* platform, which enable oral delivery of protein therapeutics to farm animals to protect the gastrointestinal tract through passive immunization without the need for purification or expensive preservatives and delivery methods. The therapeutics can be incorporated as part of animal feed.

The Inventors have designed VHHs that target the ETEC virulence factor important in the attachment to host cells for *Spirulina* expression as monomers, dimers, and, heptamers. To achieve higher protein expression levels of therapeutic VHH in *Spirulina*, chaperone proteins like Maltose Binding Protein (MBP), or Thioredoxin A (TxnA) are used to increase heterologous protein solubility. Expression constructs are designed with affinity tags to facilitate downstream protein expression, purification, and ELISA assays.

The expression level of protein of interest is determined by Western Blotting using anti-tag or anti-VHH primary and appropriate secondary antibody combinations. Binding activity of protein expressed in *Spirulina* strains are assessed using ELISA where the antigen is coated onto high binding plates, and antibody-expressing *Spirulina* strain crude cell lysate titrated in dilutions. We have expressed monomeric, dimeric and hetero-heptameric anti-adhesin VHHs in *Spirulina*. (FIG. 22A-C). VHH binding activity against antigen by ELISA shows that the VHHs are active as *Spirulina* crude lysates. The hetero-pentameric construct the express VHHs targeting the F4+ and F18+ adhesin bind both the F4+ adhesin domain FaeG and the F18+ adhesin domain FedF. (FIG. 23A-C).

Example 11: VHHs that Target the ETEC Fimbrial Domain Inhibit Bacterial Attachment in the Gnobiotic Piglet Model VHHs were designed that target the fimbrial domain of the ETEC strain K88ac+, an ETEC strain that causes post-weaning diarrhea in piglets. This VHH was expressed in *Spirulina* as a homodimer (SP795) and heteroheptamer (SP1156). (FIG. 22A). The *Spirulina* biomass was dried, and protein expression confirmed. (FIG. 25A). The VHH in *Spirulina* slurry from spray-dried and freeze-dried powder show comparable ELISA based binding. (FIG. 25B). The antigen binding efficiency of *Spirulina* expressed VHH was further assessed using BLI based kinetics measurement. (FIG. 25C).

Table 2 shows the total VHH expression per mass of dried *Spirulina* biomass assessed using Western Blot. Binding strength was assessed using ELISA EC50, and KD as measured from BLI based kinetic measurements. The level of active VHH was determined by comparing observed activity from *Spirulina* biomass to binding activity by purified protein.

TABLE 2

| Strain (protein) | EC50 (μg/ml) | Active VHH % | KD (nM) | Total VHH % |
|---|---|---|---|---|
| SP1156 (purified Protein) | 0.14 | 100 | | |
| SP1156 (Spray dried biomass (SD)) | 28.01 | 0.5 | | |
| SP1156 (Freeze dried biomass (FD)) | 18.65 | 0.7 | ~8.9 | ~1.3 |
| SP795 (purified protein) | 0.11 | 100 | | |
| SP795 (Freeze dried Biomass (FD)) | 7.78 | 1.4 | ~1.4 | ~3.5 |

The level of active protein in SP1156 was determined to be 0.5%, while the level of activity in SP795 is determined from 1.4%.

Further, VHHs that target the fimbrial domain of the ETEC strain K88ac+(F4+ac), an ETEC strain that causes post-weaning diarrhea in piglets, affect bacterial load in gnotobiotic piglets. Surgically delivered gnotibiotic piglets were treated with wild type or therapeutic VHH expressing *Spirulina* powder slurry by oral gavage twice a day from day 0 onward. The piglets were then challenged with $10^{10}$ ETEC one day later. (FIG. 26A). K88 (F4ac)-susceptible piglets were administered the 0.5 g *Spirulina* biomass in 10 ml of aqueous diluent VH795 *Spirulina*, SP1156 *Spirulina*, or wild type *Spirulina*. K88 (F4ac)-resistant piglets were administered *Spirulina* containing either an SP795 or the SP1156 VHH by oral gavage twice a day, from day 0 onward.

On Day 1, the piglets, both K88 susceptible and K88 resistant piglets, showed signs of infection and symptoms at 12-18 hours post-infection. The bacterial dose used was too high, and susceptible piglets had to be euthanized at Day 2. The K88 susceptible piglets were necropsied due to severe symptoms, and intestinal samples were assayed for bacterial load. Piglets treated with therapeutic *Spirulina* powder containing the SP1156 VHH showed decreased bacterial load in all tissues assayed. (FIG. 26B).

The high bacterial dose lead even the resistant piglets to exhibit symptoms. K88-resistant piglets were maintained for four days, and bacterial shedding was assessed by taking fecal swabs. Piglets treated with the *Spirulina* strain SP1156 showed decreased bacterial load after challenge. (FIG. 26C). These piglets, while showing symptoms, were still healthy enough to stop the treatment after the challenge to divert them to a different study.

Example 12: Norovirus Therapeutics: *Spirulina* Expressed Anti Norovirus Capsid Protrusion Domain VHHs Human Norovirus (HuNoV) is one of the most important causative agents of gastroenteritis with about one-fifth of all acute infections attributed to this virus. HuNoV is the primary causative agent of acute gastroenteritis. According to a study that looked at the burden of diarrheal diseases in the US, HuNoV infections result in approximately 2 million outpatient visits, 800 deaths, 70,000 hospitalizations, and nearly 400,000 emergency room visits per year in the US. According to the CDC, HuNoV is the leading cause of food-borne illnesses. HuNoV is a single strand RNA virus where its genome has genes that encode for the viral capsid protein (VP1). Based on the sequence diversity in the gene that encodes for the capsid (VP1), Noroviruses are classified into various genogroups (GI-GVII). The genogroups are further divided into genotypes. The most prominent genogroups isolated from recent incidents of human infection are Genogroup GI, GII, and GIV. of which over 25 genotypes have been identified. The most prevalent genotypes in recent HuNoV outbreaks are GI.1, GII.4, and GII.10.

Orally delivered single domain antibody (VHH) based prophylactic therapeutics will be developed. The approach combines the favorable VHH properties that make these class of antibody suitable for oral delivery (properties like high solubility, increased pH stability, and resistance to enzymatic degradation) and *Spirulina*-based oral delivery of therapeutics. VHHs that target the viral Capsid protein where in some disassemble viral particles upon binding and neutralize infective virus are designed for expression in *Spirulina.*

Multivalent camelid single domain antibodies (VHHs) targeting the viral capsid protein will be developed to enable oral delivery of protein therapeutics against HuNoV to protect the gastrointestinal tract through passive immunization without the need for purification of the therapeutic agent or expensive preservatives and delivery methods. VHHs that are designed for *Spirulina* expression as monomers with or without chaperone proteins like Maltose Binding Protein (MBP), or Thioredoxin A (TxnA) to increase heterologous protein solubility. Expression constructs are engineered with affinity tags.

The expression level of protein of interest is determined by Western Blotting using anti-tag or anti-VHH primary and appropriate secondary antibody combinations. Binding activity of protein expressed in *Spirulina* strains are assessed using ELISA where the antigen is coated onto high binding plates, and antibody-expressing *Spirulina* strain crude cell lysate is titrated in dilutions.

We have expressed monomeric anti HuNoV capsid protrusion protein VHHs with and without chaperone fusion partners in *Spirulina*. (FIG. 27A-C) ELISA based binding assay show that *Spirulina* expressed VHHs are active as *Spirulina* crude lysates. (FIG. 28A-C). Furthermore, VHHs purified from *Spirulina* crude lysate exhibit the expected virus Capsid disassembly and block virus attachment to tissue biopsy that mimic intestinal environment. (FIG. 29A-B).

Example 13: Development of VHHs to Treat Norovirus Infection

To create novel VHHs that target norovirus, Nano85, an anti-human Norovirus (HuNoV) protrusion (P) domain antibody was modified by grafing the binding regions of Nano85 onto the framework of the K922 antibody (SEQ ID NO: 18) which is known to be resistant to gut proteases and allow increased expression in *Spirulina*. (FIG. 30). Constructs comprising the unmodified Nano85 having a C-terminal maltose binding protein (MPB) (SP1371) and the modified Nano85 having a C-terminal MPB (SP1372) were expressed in *Spirulina*. (FIG. 31A). Further, SP1371 and SP1372 bind to various recombinant P domains derived from different human norovirus Gii strains (GII.2, GII.4, and GII.17). (FIGS. 31B and 31C). The purified proteins also show measurable binding to irrelevant antigens, including the campylobacter flagellin protein FlaA, Swine ETEC adhesin protein FaeG, and Human ETEC fimbrial adhesion domain CfaE.

Moreover, the binding kinetics and cross-reactivity of various recombinant anti-human P domain targeting VHH sequences was studied. Nano26 (SEQ ID NO: 73) and Nano85 (SEQ ID NO: 71) show broad cross-reactivity, while VHH3.2, VHH4.1, and VHH5.4 show no binding against the GII.17 P domain. (FIG. 32A-B)

TABLE 3

ELISA based binding against HuNoV GII.2, GII.3, GII.4, GII > 4, GII.10 and GII.17 P domains.

| EC50 (nM) | VHH3.2 - TxnA | VHH4.1 - TxnA | VHH5.4 TxnA | Nano85_loop-grafted-TxnA | Nano26-TxnA |
|---|---|---|---|---|---|
| GII.2 | 2.45 | 5.31 | 3.43 | 2.14 | 3.38 |
| GII.3 | 2.93 | 15.62 | 2.52 | 8.67 | 4.46 |
| GII.4 | 0.77 | 2.05 | 1.07 | 0.91 | 15.45 |
| GII.10 | 2.58 | 7.34 | 3.46 | 1.99 | 1.46 |
| GII.17 | ND | ND | ND | 4.32 | 2.52 |

TABLE 4

BLI based binding kinetics to HuNoV GII.2 P domain

| | KD (nM) | ka (1/Ms) | kdis (1/s) |
|---|---|---|---|
| VHH3.2 -TxnA | 7.12 | 1.18E6 | 8.41E−3 |
| VHH4.1 -TxnA | 5.51 | 6.70E5 | 3.70E−3 |
| VHH5.4 TxnA | 8.73 | 7.73E5 | 6.75E−3 |
| Nano85_loopgrafted-MBP | 10.1 | 1.36E5 | 1.38E−3 |
| Nano26-MBP | 21.9 | 1.72E5 | 3.78E−3 |

Additionally, the binding and cross-reactivity of anti-Human Norovirus (HuNoV) P domain targeting VHHs Nano94 (SEQ ID NO: 75), VHH10, VHH6.3, and VHH7.3 were assessed. The VHHs tested exhibit binding EC50 ranging from 0.21 nM to 50.07 nM, where *Spirulina* expressed recombinant nano94-TxnA shows the weakest binding. (FIG. 33A) The VHH7.3 was cross-reactive binding against the GI.3 P domain. (FIG. 33B)

TABLE 5

EC50 values from ELISA based binding against HuNoV GI.1 and GI.3

| EC50 (nM) | VHH10.4 - TxnA | VHH6.3 - TxnA | VHH7.3 TxnA | Nano94-TxnA |
|---|---|---|---|---|
| GI.1 | 0.21 | 4.75 | 1.34 | 50.07 |
| GI.3 | ND | ND | 66.28 | ND |

To create effective *Spirulina* expressing anti-human norovirus VHHs, the stability of the recombinant *Spirulina* when lyophilized was determined. The constructs from the SP833, SP834, SP835, SP864, and SP1241 were lyophilized and tested for stability. (FIG. 33A-B). Comparison of the stability of the lyophilized proteins with that of purified protein stored at 4° C. show no loss in binding activity.

The protease sensitivity of various anti-human norovirus P domain VHH constructs was assessed by incubating 1 μg bacterial expressed recombinant VHHs with 20 μL of chymotrypsin (0.1 mg/mL or 0.01 mg/mL) or Trypsin (0.01 mg/mL or 0.001 mg/mL) in digestion buffer (1 mM Tris pH 8.0, 20 mM $CaCl_2$)) for one hour, two hours, or 4 hours. Protease sensitivity was measured using ELISA-based binding as shown in Figure BB6. The loop-grafterd Nano85 exhibits the best protease resistance compared to recombinant Nano85 and the other tested. VHH3.2, VHH4.1, and VHH5.4 show resistance against chymotrypsin while exhibiting varying sensitivity to Trypsin.

Example 14: Inflammatory Bowel Disease Therapeutics: *Spirulina* Expressed Anti TNF Alpha VHHs Inflammatory bowel diseases (IBD) are chronic disorders of the gastrointestinal tracts. IBD, which include Chron's disease and ulcerative colitis, are relapsing diseases with a tendency of being progressive. IBD treatments include anti-inflammatory drugs, immunosuppressive drugs, and anti-TNF α biologics. Tumor Necrosis Factor alpha (TNF-α) is a cytokine involved in inflammation. In chronic IBD, TNF α accumulated in the lamina propria of the gut mucosa. Increased accumulation of TNF α is responsible for chronic inflammation and subsequent damage to the intestinal epithelial cells. Current anti-TNF α biological therapeutics under investigation include infliximab, adalimumab, golimumab, and certolizumab. Given the chronic nature of IBD, oral delivery of biologics is ideal for patient comfort, ease of treatment, willingness to adhere to prescription regimen and cost. However, biologics that are developed for IBD are currently delivered intravenously or subcutaneously due to physiological barriers that render biologics not effective for oral delivery. These challenges include instability of protein-based therapeutics in the GI tract, extreme pH environments, and high enzymatic activity in the GI tract.

Singe domain Llama antibodies (VHHs) possess properties that make them amenable for oral delivery. VHHs retain antigen binding specificity and potency comparable to traditional IgG antibodies. The small size of VHHs and rigid structural nature, solubility, ease of expression and stability under the GI environment makes VHHs suitable for oral-based therapeutics. Given these properties, VH Squared had developed VHH (V565) that can bind TNF α and can be used for the management of IBD through oral delivery.

The anti-TNF-α VHH from VH squared as monomer and dimer has been expressed. (FIG. 36A-C) The expression level of anti-TNF-α VHH is determined by Western Blotting using anti-tag or anti-VHH primary and appropriate secondary antibody combinations. Binding activity of protein expressed in *Spirulina* strains are assessed using ELISA where the antigen is coated onto high binding plates, and antibody-expressing *Spirulina* strain crude cell lysate is titrated in dilutions. Both monomeric and dimeric forms of the VHH show good binding to recombinant human TNF-α.

Example 15: *Clostridium difficile* Toxin B (tcdB) Specific VHHs in *Spirulina*

Anti-tcdB VHHs 5D (SEQ ID NO: 5) and E3 (SEQ ID NO: 6) were constructed into various scaffolds and expressed in *Spirulina*. (FIG. 37) Scaffolds include *E. coli*-derived thioredoxin (Trx), virus-like particles derived from a number of RNA phages (MS2, $Q_\beta$, PP7 and AP205), and computationally-designed trimers and pentamers.

For the trimers and pentamers, thioredoxin was always used in the scaffold structure; some are designed as homo-multimers (eg. Trx-Trimer-VHH), some as homo-multivalent structures (eg E3.VHH-Trx-TRIMER-E3.VHH) and some as hetero-multivalent structures (eg. E3.VHH-Trx-TRIMER-5D.VHH).

Figure 38A:
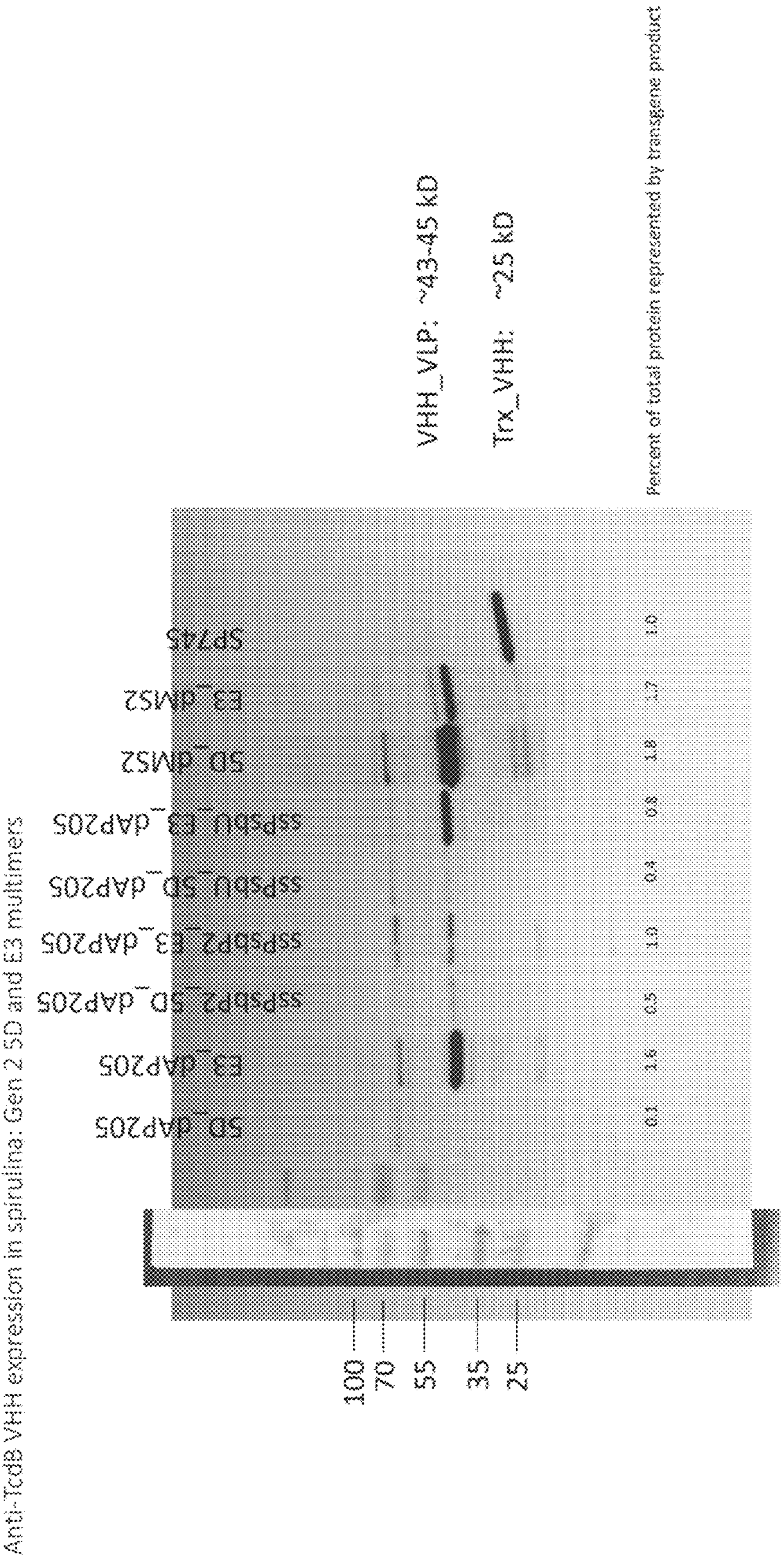
Figure 38B:
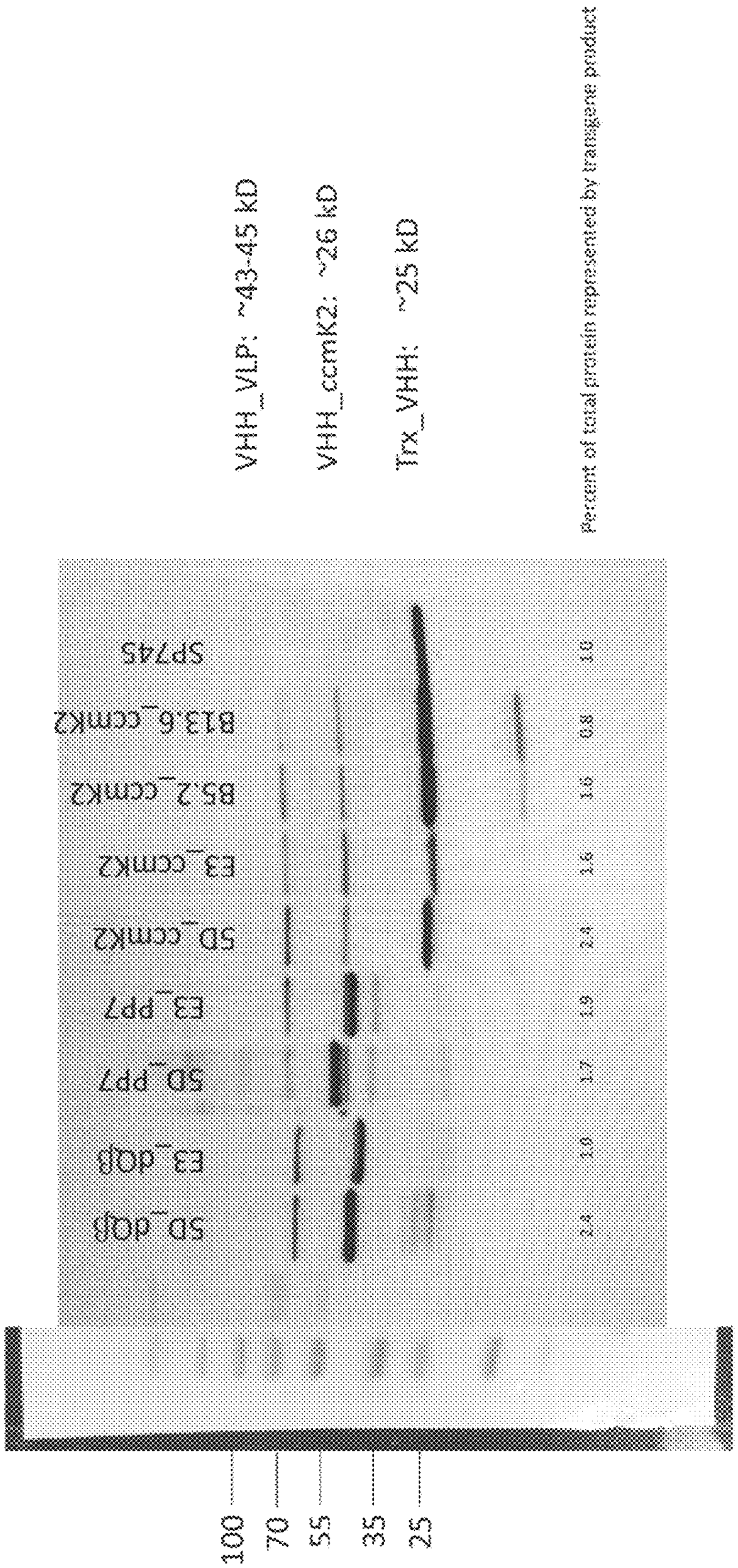
Figure 38C:
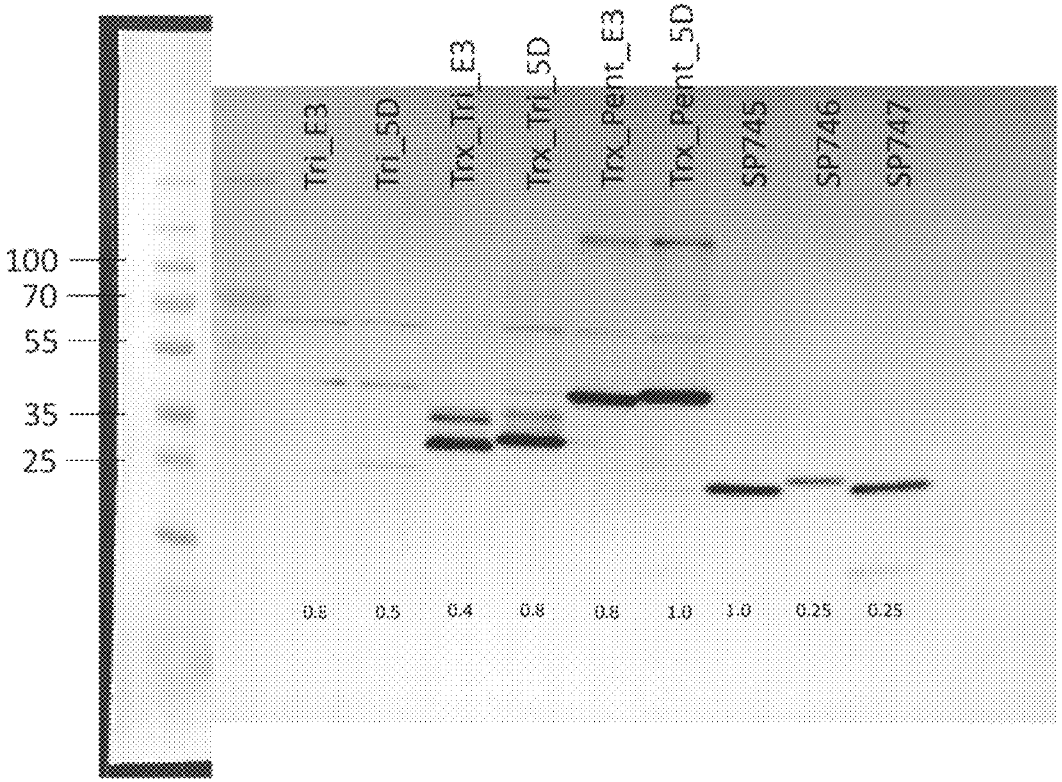
Figure 38D:
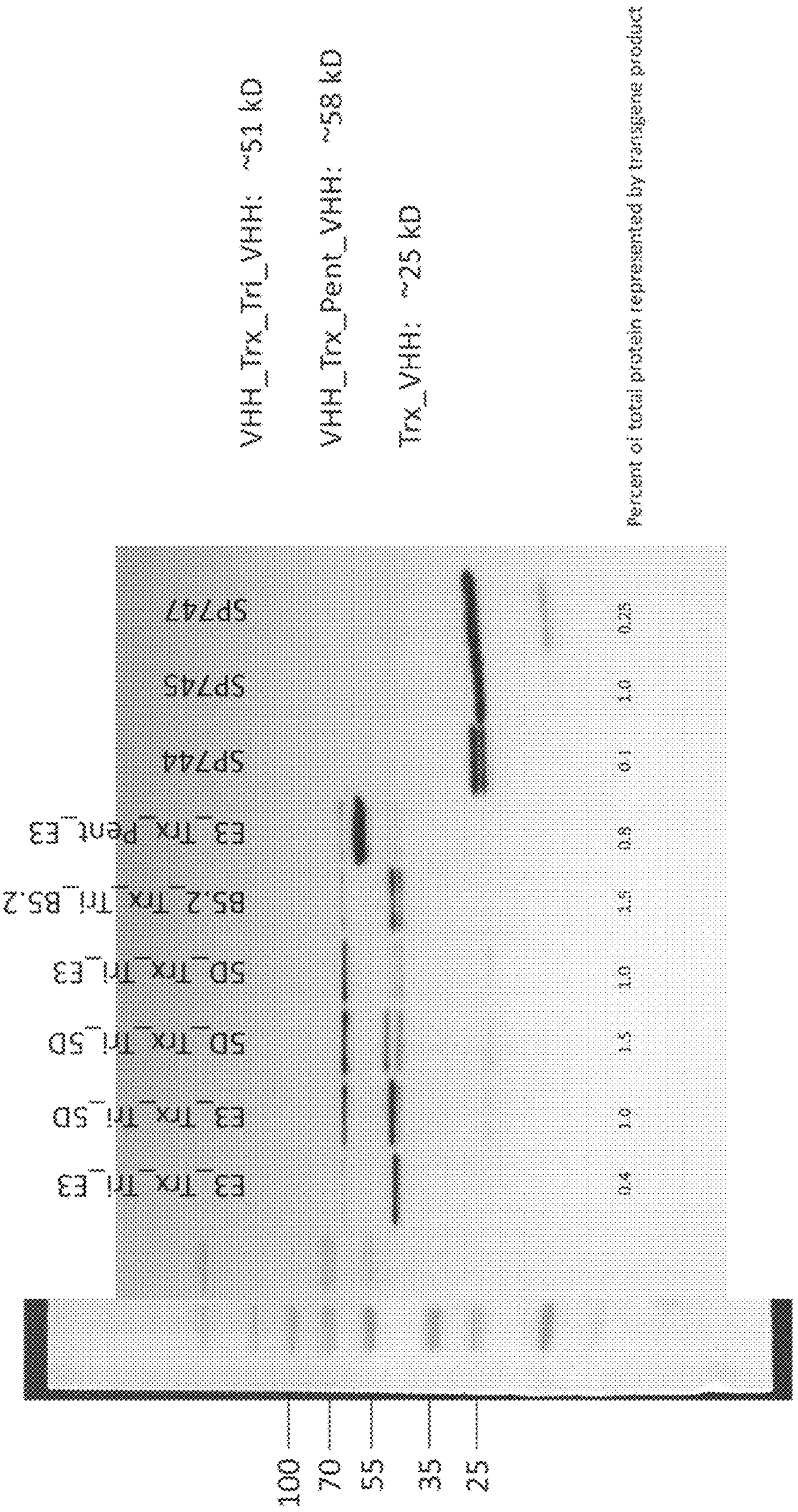

Constructs containing VHH.5D express at higher levels than those with VHH.E3. Certain hetero-multivalent structures express at higher level if E3 is at the N-terminus as opposed to 5D. (FIG. 38A-C)

Constructs were evaluated for their neutralizing activity against tcdB in vitro. (FIG. 39). Vero cells (African green monkey epithelial cells) were exposed to dose ranges of tcdB with or without the addition of *Spirulina* extracts containing VHHs. The biologic effect was measured in two ways: first, a colormetric reagent that linearly reacts with heathy, metabolizing cells was used as a quantitative measure (FIG. 40) second, visual microscopy was used to assess the degree of "rounding", that is, the degree to which the normally adherent and angulated Vero cells detach from the plastic substrate and appear round. (FIGS. 41A-O). These methods generally agree, though the visual rounding assay was consistently more sensitive.

Results i. B5.2, B13.6 VHHs (Canada) do not neutralize when expressed on VLPs.

ii. Tufts VHHs E3 and 5D both demonstrate neutralizing activity iii. Generally, 5D-containing constructs express more abundantly, and demonstrate more potent neutralizing activity.

iv. The best in vitro activity was shown by the following strains:

SP1095, a heterobifunctional trimer construct, E3_Trx_TRI_5D

SP747, monomeric Trx_5D

SP1087, trimer construct Trx_TRI_5D

Slightly less potent in vitro were:

SP985, RNA phage VLP PP7 hybridized to VHH 5D

SP1091, pentamer construct Trx_PENT_5D.

VHH-5E (SEQ ID NO: 7) constructs were also constructed. VHH.5E-containing constructs performed more potently than those bearing VHH.E3, though the most potent, on a per-mole basis was a trimer containing both VHH.E3 and VHH.5D. Potency generally followed expression level, though the most effective/potent structure was VHH.E3-Trx-Trimer-VHH.5D, which expressed at only ~0.1% total protein, and was more potent than Trx-VHH.5D, which expressed at −2% total protein and was the next most potent extract. *Spirulina* extracts with no VHH displayed no inherent neutralizing activity.

The three or four best performing strains will be expanded for bioreactor and spray drying. Further, next generation constructs will be designed and new strains will be built (e.g. markerless versions of present strains, native Arthrospira thioredoxin, hetero-multimers with 5D and new Tufts VHHs directed at RBD). Also, animal studies will be initiated using the present hit strains: 1) Mouse model I: Lyras/Australia; 2) Mouse model II: Guerrant/Virginia; 3) Pig model: Tzipori/Tufts.

Example 16—Combinations of VHHs Exhibit a Synergistic Increase in Binding to *C. difficile* Toxin The binding strength of various VHHs alone and in combination to *C. difficile* TcdB toxin was tested. The VHHs were produced in *E. coli* and tested in vitro. FIG. 42 shows the binding strength of the VHHs 5D (SEQ ID NO: 5), E3 (SEQ ID NO: 6), 7F (SEQ ID NO: 13), 2D (SEQ ID NO: 65), and 5E (SEQ ID NO: 7) alone to TcdB at various concentrations. The 5D VHH shows the greatest binding, with 2D showing the least binding. FIG. 43 shows the binding strength of different combinations of the VHHs 5D, E3, 7F, 2D, and 5E. FIG. 44 shows the binding strength of the VHHs 5D, E3, and 7F alone and in combination. FIGS. 45A-B show the binding strength of the VHHs 5D, E3, and 7F alone and in combination at different concentrations. An increase of the concentration of solitary VHHs had little increase in efficacy. In contrast, higher concentrations of the combination VHH (i.e. a VHH cocktail) showed a surprising increase in efficacy with increased concentration.

The increased efficacy of the combination of VHHs may be explained by the different targets of the different VHHs. For example, as shown in FIG. 46, the VHHs may act at different points of the process of the TcdB signalling pathway. The VHH E3 blocks the receptor binding, the VHH 5D blocks the pH-dependent pore formation, and the VHH 7F blocks autocatalysis, and potentially the GTD site. This could explain the synergistic effect of the VHH cocktail over the effect of a single VHH.

TABLE 6 anti-TcdB VHHs

| Name | KD | Target Domain (Crystal) | Target Domain (Reported) |
|---|---|---|---|
| **5D** | **0.65 mM** | **PFD** | **GTD** |
| **E3** | **0.03 nM** | **GTD/FHD** | **GTD** |
| **2D** | **Nd** | | **GTD** |
| 2Ds | Nd | | |
| **5E** | **0.03 nM** | | **PFD** |
| **7F** | **8.8 nM** | **GTD** | **GTD** |
| A1 | Nd | | RBD/CHOP |
| A11 | Nd | | RBD/CHOP |
| AB8 | Nd | | |
| B12 | 0.07 nM | | RBD/CHOP |
| C6 | 0.89 nM | | GTD |

Bacterial lysates of VHHs constructed in fusion with maltose binding protein (MBP) in a MBP-VHH orientation (with the exception of 5D, which was used as *Spirulina* lysate expressing a PP7 particle decorated with VHH 5d), were used at the concentrations indicated in Figures 47A-47B. Individual VHHs were used at 100 ng/ml, and 2-way combinations were used at 50 ng/ml each, for a total VHH concentration of 100 ng/ml. VHHs were tested against 3 concentrations of TcdB 027-type, as indicated.

Example 17—Anti-TcdB (*Clostridium difficile* Toxin B) VHHs Produced in *Spirulina*

Multimerizing single-domain antibodies in a single polypeptide chain increases avidity, and often biologic activity. Multi-VHH single polypeptides have been produced in *E. coli*, though have proven very challenging to express in *Spirulina*. Recently, the crystal structure of the TcdB protein in its entirety (~300 kDa) was solved with three VHHs bound (VHHs 5D, E3, and 7F). See FIG. 52 which shows TcdB bound to E3. Each VHH bound to a distinct domain spatially distant from one another. Two of the three domains have had essential biologic activities identified in the intoxication process, and the bound VHHs were shown to disrupt structural changes necessary for these functions. The third bound a domain that in homologous toxins has been linked to localization to the target cell's membrane. Each VHH had previously been shown to have some degree of toxin neutralizing activity on its own.

A single polypeptide containing the three VHHs will be sterically disfavored to either bind all three epitopes on one toxin, or to bind distinct epitopes on multiple toxin molecules. Given their demonstrated individual neutralizing activities, a simple mixture of the three VHHs will have neutralizing activity in excess of simply additive effects. Using bacterially-expressed protein, mixtures of two VHHs from a panel of 10 were tested, and it was identified independently that VHHs E3, 5D and 7F were particularly active when mixed in 2-member mixtures with each other, or with a number of other less active VHHs. Following on with 3-fold, 4-fold and 5-fold mixtures of the 10 VHHs, maximal neutralizing activity was found to coincide with any combination containing E3, 5D and 7F, the simplest being those three together.

Each of the three VHHs were engineered into hybrid structures with known solubility- or folding-optimizing partners (chaperones), to maximize accumulation of biologically active VHHs in *Spirulina*. *Spirulina* lysates containing individual constructs containing E3, 5D or 7F were assayed for TcdB neutralizing activity in isolation (FIG. 54), and in various combinations containing all three VHHs (FIGS. 55 and 56). Surprisingly, lysate combinations containing all three VHHs appeared to have >1000-fold greater neutralizing activity than any single VHH lysate. Complete neutralization of TcdB was seen at toxin concentrations far in excess of that seen in human clinical isolates, by concentrations of VHHs well below that predicted to be available following human administration (FIG. 57).

Example 18—Administration of VHHs with Other Therapeutic Molecules

In addition to different VHHs, other therapeutics may be present in the recombinant *Spirulina* to further increase the efficacy of the orally-delivered therapeutic. The effect of multi-drug cocktails has been demonstrated for numerous organisms, including *M tuberculosis*, where therapeutics that target cell wall synthesis, replication and transcription, energy metabolism, and translation may be combined to target different parts of the pathogen life-cycle (see FIG. 49). In the same way, targeting different aspects of the *C. difficile* receptor activation and the cell membrane may increase efficacy of an orally-delivered therapeutic. To demonstrate this, a recombinant *Spirulina* is produced that expresses one or more VHHs that bind to the S-layer of the *C. difficile*, one or more VHHs that neutralize toxin B, and a polypeptide such as a lysin to attack the cell membrane (see FIG. 50).

Example 19: Lysin Expressed from *Spirulina* is Active

PlyCD and the catalytic domain fragment PlyCD1-174 have previously been expressed in *E. coli* and shown to be bacteriocidal in vitro and in vivo. To determine whether phage-derived anti-*Clostridium* cell wall digesting lysin PlyCD expressed from *Spirulina* was active, the genes for PlyCD and PlyCD1-174 were inserted into *Spirulina* under the control of the cpc600 promoter and expression was confirmed by Western blot. Various concentrations were tested in a standard cell-lysis assay. FIG. 63 shows cell lysis assay results for both *E. coli*-expressed and *Spirulina*-expressed proteins. The *Spirulina*-expressed lysins are catalytically active.

Example 20: Effect of Linkers on Neutralizing Ability of Anti-TcdB VHH Sequences Various constructs were made containing different rigid linkers joining a series of transgenes encoding the anti-TcdB VHH 5D to chaperone partners. (FIG. 51) The particular constructs tested in this experiment are listed in FIG. 59.

The control strain uses a flexible (GGS)x linker between 5D and a computationally designed dimer.

FIG. 64 demonstrates neutralization data for the strains expressing the array of linkers joining 5D to MBP, as well as a single strains with an IgA-derived linker joining 5D and the PP7 VLP.

Example 21: Stability of *Spirulina* Constructs in Water and Potable Liquids The recombinant *Spirulina* may be administered orally, and addition of VHHs to drinking water would greatly increase the dose of VHH deliverable to animals. To test the stability and activity of VHHs held at room temperature in various buffers palatable to mice, rats, or pigs, 1 mg/mL *Spirulina* lysate was mixed into water, 50 mM phosphate pH 7.4, 5% sucrose, 5% Non-fat milk (NFM), sucrose+phosphate, or sucrose+milk. (FIG. 65) Western Blots were performed at 0, 1, 2, 3, and 4 hours. TcdB neutralization assays were performed at 0 and 4 hours.

Western blotting showed no decrease in his-tagged protein abundance over the timecourse. No decrease was observed in TcdB-neutralizing potency in any aqueous medium at either the 4 or 12 hour timepoint. (FIG. 66 and FIG. 67) Similar results were obtained for the individual VHHs 5D and E3, and for the 3-way synergistic combination of 5D, E3, and 7F. (FIG. 68).

Example 22: Study of *C. difficile* Protection in Gnotobiotic Pig Model

To study the effect of *Spirulina* expressing anti-TcdB VHHs on protection from *C. difficile* challenge, the gnotobiotic pig model was used. (FIG. 70) In this study, pigs were divided into 4 groups as indicated below:

- Group 1 (two pigs)—infection, no treatment (or sham capsule treatment)
- Group 2 (two pigs)—infection, wild-type *Spirulina* treatment
- Group 3 (four pigs)—infection, *Spirulina* mix #1: 3× VHH
- Group 4 (four pigs)—infection, *Spirulina* mix #2: 3× VHH+PlyCD lysin.

At five days of age, the animals were infected with $10^6$ *C. diff.* UK6 BI/NAP1/027. After infection, the animals were treated three times a day for five days starting at Day −0. After treatment, animals were measured for clinical measures, survival, fecal spore shedding, and GIT histology.

FIG. 71A-B shows that after day 4, the animals in both Groups 3 and 4 demonstrated reduced incidence of diarrhea compared to infected animals treated with wild type *Spirulina* or PBS.

Example 23: Study of the Effect of Prophylactic Administration of Anti-TcdB VHHs on *C. difficile* Infection in the Monash Mouse CDI Model Mice were administered an antibiotic cocktail in the drinking water from Day −11 to Day −4. From Day −4 to Day 0, the mice were administered cefaclor alone, and on Day 0 infected with *C. difficile*. From day −1 to day 4, mice were administered *Spirulina* (3× VHH mix or 3× VHH mix+lysin), PBS, or vancomycin once daily by oral gavage. During this period, the mice were monitored daily for weight diarrhea, activity, and appearance, and feces collected. (FIG. 72). Administration of an anti-TcdB VHH mix reduced weight loss associated with *C. difficile* infection. (FIG. 73A). Mice treated with the VHHs alone had improved survival over those treated with wild type *Spirulina*, and those treated with the 3× VHH mix+PlyCD lysin achieved 100% survival comparable to vancomycin. (FIG. 73B). Finally, administration of the 3× VHH mix+lysin reduced fecal *C. difficile* spore shedding by >2 logs. (FIG. 73C).

Example 24: Effect of pH on Release of VHH from LMN-101

Therapeutic VHHs encapsulated in *Spirulina* biomass are not released to gastric-fluid-simulating buffers. Bioencapsulation also prevents enzymatic degradation of VHHs under simulated gastric-digest conditions To analyze the effect of low pH on the release of VHH from *Spirulina* biomass, dried *Spirulina*-VHH biomass was resuspended in different pH buffers. Spray-dried *Spirulina*-VHH biomass used in LMN-101 (strain SP1182) was resuspended in citrate phosphate buffers ranging from pH 3 to pH 7, at 50 mg/mL, and incubated with gentle agitation at room temperature for 60 minutes. Resuspended biomass was clarified by centrifugation at 14,000 RPM for 1 min in a refrigerated microcentrifuge. The clarified extracts were used in an ELISA-based binding assay with recombinant *C. jejuni* flagellin to determine the amount of aa682 present. High-binding ELISA plates were coated with antigen, and SP1182 extracts were assayed as 4-fold serial dilutions in PBS supplemented with 0.05% Tween-20, and 5% non-fat dried milk. Bound aa682 was detected using a mouse anti-His-tag primary antibody and a goat anti-mouse-HRP secondary antibody.

In this ELISA, the relative binding activity of extracts corresponds to the amount of aa682 extracted at each pH. Calculated EC50 values indicated a comparable amount of aa682 binding activity when *Spirulina* biomass was resuspended in pH 5, pH 6, and pH 7 buffer solutions (FIG. 74 and Table 7). The amount of binding activity decreased by 50% when *Spirulina* biomass was extracted in pH 4 buffer. In contrast, the extract prepared in pH 3 buffer demonstrated a relatively small amount of binding activity. The EC50 of extract from biomass resuspended in pH 3 suggested that 40-fold less aa682 was released relative to release in pH 7 buffer. To assess the effect of pH on VHH stability and activity, purified aa682 was incubated in pH 3 buffer and VHH integrity was assessed by an ELISA-based binding assay as above. No measurable loss of binding was observed due to exposure to low pH buffer (data not shown).

TABLE 7

EC50s for SP1182 biomass resuspended in various pH buffers

| Buffer pH: | pH 3 | pH 4 | pH 5 | pH 6 | pH 7 |
|---|---|---|---|---|---|
| EC50 (μg biomass/mL) | 3921 | 190.7 | 107.7 | 92.96 | 97.25 |

To further demonstrate that the difference in binding activities was the result of a difference in VHH concentration, clarified *Spirulina* extracts were also assayed using a capillary electrophoresis immunoassay. Clarified extracts were prepared as above. VHHs were detected using mouse anti-His-tag primary antibody (Genscript), and HRP-conjugated anti-mouse secondary antibody (ProteinSimple). The amount of VHH protein released from *Spirulina* biomass increased with an increase in pH, with minimal VHH observed at pH 3 (FIG. 75).

These results suggest that at low pH, gastric-like conditions, the VHH may remain encapsulated in the *Spirulina* biomass and protected from the harsh environment of the stomach until transiting to the higher pH conditions of the small intestine.

Example 25—Phase 1 Clinical Trial of LMN-101

A Phase 1 safety and tolerability study was conducted in healthy volunteers with LMN-101 (SP1182), a single *Spirulina* strain that has been engineered to express a binding protein that inhibits *C. jejuni* (CG8421) infection. Part A of the study was an open-label oral administration of a single 3000-mg dose of LMN-101. Part B was a randomized, double-blind, placebo-controlled, dose-escalation study of 3 dose levels of LMN-101: 300 mg, 1000 mg, or 3000 mg. (FIG. 61 & FIG. 62) Wild type *Spirulina* was used as a control. In Part B, healthy volunteers took LMN-101 or placebo orally at one of these three dose levels three times daily for 28 days. No significant adverse events were reported. In addition, pharmacokinetic data showed that there was no significant systemic absorption, indicating that the *Spirulina* was able to pass through the stomach and deliver the VHH to the gastrointestinal tract. Orally delivered LMN-101 was safe and well tolerated at doses up to 3000 mg TID for 28 days, and no significant adverse events due to LMN-101 were observed.

Example 26: In Vitro Stability of Spirulina-VHH Biomass in Simulated Intestinal Fluids To model the intestinal phase of delivery, dried *Spirulina*-VHH biomass was incubated in simulated intestinal fluid (SIF): 50 mM citrate-phosphate buffer, pH 7.0, 164 mM NaCl, 85 mM $NaHCO_3$, 3 mM $CaCl_2$, and 1 mg/L Pancreatin with 10 mM Porcine Bile Extract, incubated at 37° C. Integrity of the intact anti-campylobacter-binding protein was determined by western blot. In two independent experiments using a dried biomass of anti-campylobacter *Spirulina*-VHH expressing a trimeric VHH (strain SP806), it was observed that more than 80% of the binding protein was released from the biomass within 5 minutes and more than 95% within 30 minutes (FIG. 76). In a similar experiment using the *Spirulina*-VHH present in LMN-101 (strain SP1182), more than 95% of the binding protein was released in 5 minutes (FIG. 77). A fully intact released binding protein did not accumulate to measurable levels in the simulated intestinal fluid in either case, indicating that its rate of proteolytic cleavage was faster than its release rate. The limit of detection in this experiment was approximately 20% recovery of released, intact anti-campylobacter-binding protein. Consistent with this interpretation, purified anti-campylobacter-binding protein added directly to the simulated intestinal fluid had a half-life for proteolytic cleavage of less than 5 minutes (FIG. 78).

The rapid release in the simulated intestinal environment suggests that aa682 is released in the proximal small intestine and be accessible to bind campylobacter in that milieu. The rapid degradation of aa682 suggests that detectable levels does remain in fecal contents.

Example 27: In Vitro Stability of Spirulina-VHH Biomass in Simulated Gastric Fluids

*Spirulina* biomass protects the campylobacter-binding protein while in transit through the harsh environment of the stomach. Dried biomass of an anti-campylobacter *Spirulina*-VHH was incubated in a simulated gastric fluid (SGF): 10 mM citrate-phosphate buffer, pH 3.5, 94 mM NaCl, 13 mM KCl, and 2,000 units/mL pepsin, incubated at 37° C. Western blotting of digested *Spirulina*-VHH biomass demonstrated that the campylobacter-binding protein expressed within this biomass was 50% intact for 120 minutes (FIG. 79). The analysis was repeated with the *Spirulina*-VHH present in LMN-101 (strain SP1182) but otherwise under identical conditions. Western blotting demonstrated that the campylobacter-binding protein expressed within this biomass was 20% intact after 120 minutes (FIG. 80).

Example 28: Intranasal Administration of SP648 Elicits Production of Antibodies in Murine Model Mice were tested to determine whether intranasal administration of a *Spirulina* expressing a malarial antigen, NANP, or *Spirulina* extract containing the malarial antigen, NANP, demonstrate an IgG response to NANP. The mice were further analyzed for survival of a malaria infection.

Mice were immunized with PfCSP-VLP (SP648—a malaria vaccine based on the NANP repeat region of *P. falciparum* CSP fused within a virus-like particle or empty VLP (SP79). Mice were assigned to 6 groups (5 mice/group) and treated as indicated in Table 8.

TABLE 8

| | | DAY | | | | | | | | | | |
|---|---|---|---|---|---|---|---|---|---|---|---|---|
| | | Day −1 | D 0 | D 14 | Day 27 | D 28 | Day 41 | D 42 | Day 56 | D 57 | Day 69 | D 70 |
| Grp 1 | Oral PfCSP-VLP Spirulina −> 3x Oral PfCSP-VLP Spirulina | Draw | Prime | Draw | Draw | Boost 1 | Draw | Boost 2 | Draw | Boost 3 | Draw | Challenge |
| Grp 2 | Intranasal PfCSP-VLP Spirulina −> 3x Oral PfCSP-VLP Spirulina | Draw | Prime | Draw | Draw | Boost 1 | Draw | Boost 2 | Draw | Boost 3 | Draw | Challenge |
| Grp 3 | Intranasal PfCSP-VLP Extract −> 3x Oral PfCSP-VLP Spirulina | Draw | Prime | Draw | Draw | Boost 1 | Draw | Boost 2 | Draw | Boost 3 | Draw | Challenge |
| Grp 4 | Oral Control-VLP Spirulina −> 3x Oral Control-VLP Spirulina | Draw | Prime | Draw | Draw | Boost 1 | Draw | Boost 2 | Draw | Boost 3 | Draw | Challenge |
| Grp 5 | Intranasal Control-VLP Spirulina −> IN PfCSP Extract −> Oral PfCSP Spirulina | Draw | Prime | Draw | Draw | NO Tx | Draw | RE-Prime IN sp648 | Draw | Boost 1 | Draw | Challenge |

TABLE 8-continued

| | | DAY | | | | | | | | | | |
|---|---|---|---|---|---|---|---|---|---|---|---|---|
| | | Day −1 | D 0 | D 14 | Day 27 | D 28 | Day 41 | D 42 | Day 56 | D 57 | Day 69 | D 70 |
| Grp 6 | Intranasal Control Extract –> IN PfCSP extract –> 2x Oral PfCSP Spirulina | Draw | Prime | Draw | Draw | RE-Prime IN sp648 | Draw | Boost 1 | Draw | Boost 2 | Draw | Challenge |

PfCSP-VLP whole biomass resuspended in PBS - oral administration (PO)
PfCSP-VLP whole biomass resuspended in PBS - intranasal administration (IN)
PfCSP-VLP extract - intranasal administration (IN)
Empty VLP whole biomass resuspended in PBS - oral administration (PO)
Empty VLP whole biomass resuspended in PBS - intranasal administration (IN)
Empty VLP extract - intranasal administration (IN)

Groups 5 and 6 both had a period of re-priming on a day Groups 1-4 may have received a boost. At the time Groups 1-4 received a first boost, Group 5 was not treated. When Groups 1-4 received their second boost, Group 5 was given a “Re-priming” with intranasal administration of PfCSP-VLP extract which was followed by one boost with orally administered PfCSP *Spirulina* biomass. At the time Groups 1-4 received their first boost, Group 6 was given a “Re-priming” with intranasal administration of PfCSP-VLP extract which was followed by two boosts with orally administered PfCSP *Spirulina* biomass. This re-priming was done to determine if the number of boosts administered to the mice influenced IgG production. Group 3 received three oral boosts; Group 6 received two; and Group 5 received only one.

IgG Measurement

Sera was collected at days 14, 27, 41, 56, and 69 as indicated in Table 8. The amount of IgG produced in the different groups was measured by indirect ELISA. The antigen coated on the plate, NANP, is covered by mouse sera containing varying amounts of antibodies specific for the NANP antigen followed by a secondary antibody that is conjugated to horseradish peroxidase (HRP). The substrate was added in the presence of hydrogen peroxide as an indirect way to measure how much antibody specific for NANP is present in each serum sample. ELISAs were performed on serial dilutions of the sera of each animal to detect the lowest amount of sera that can still generate a positive response to the antigen.

Results

The results shown in FIGS. 81 to 86 show the serum IgG response NANP at various timepoints after administration of the malaria vaccines or controls as outlined above. Measuring IgG response to Maltose Binding Protein (MBP) acted as the control. The Y axis on each is the absorbance value measure from the plate reader. Positive responses are those that approach the amount of IgG found in the positive control, hyperimmune sera. The dilutions for the hyperimmune sera are different from those for the experimental groups since the hyperimmune sera is so potent, and greater amounts are not required to detect IgG.

The data shown in FIG. 76 (day 14) measures serum IgG response against a different substrate (MBP) as a control. Since the NANP protein is fused to MBP, it is important that the sera not be reacting to MBP. FIG. 76 shows no IgG response to MBP at Day 14 after vaccination with the malaria vaccines tested here. Similar results were obtained for the other days tested (data not shown).

Previous reports demonstrated that after oral administration, mice showed production of IgG in response to NANP by 28 days, but as seen here, not by day 14. In contrast, intranasal administration offers a fairly robust serum IgG response against NANP even by day 14.

As shown in FIG. 81-FIG. 86, the serum IgG production in the mice of Group 3 was more uniform than that of Group 2 which may reflect the difference between administration of an extract and administration of a resuspended biomass. The extract is a homogenous solution, whereas the resuspended biomass may not be, leading mice within a given group to inadvertently receive different amounts of *Spirulina.*

Further, mice inoculated with the extract are readily exposed to the vaccine antigen, whereas those administered the *Spirulina* biomass might not be exposed to the vaccine antigen as efficiently or evenly. The encapsulation of the vaccine antigen in the *Spirulina* may not be an important component of vaccines administered nasally as opposed to orally where protection of the vaccine is important for crossing the stomach.

Importantly, nasal administration of extract yields a more robust and uniform response than administration of *Spirulina* biomass, whether given orally or intranasaly.

Challenge with Malaria

FIG. 87 shows the survival rate of the various groups after challenge with *P. falciuparum.*

Some mice appear to be protected from challenge even though they have a lower detectable serum IgG response indicating other elements play a role in the immune response, including other types of antibody response. The data shown here looks only at serum IgG—the mice also produce serum IgA and IgM. Further, an analysis of fecal samples will yield information regarding mucosal IgA which is an indicator that there has been a good mucosal response. Generally, however, a high serum IgG titer indicates protection from challenge, and indeed the 50% protection observed in Group 2 is quite good as it is hard to protect a mouse from malaria. Thus, the demonstrated protection of up to 80% is surprising.

EXAMPLES OF NON-LIMITING EMBODIMENTS OF THE DISCLOSURE

Embodiments, of the present subject matter disclosed herein may be beneficial alone or in combination, with one or more other embodiments. Without limiting the foregoing description, certain non-limiting embodiments of the disclosure, are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below.

Embodiment 1. A non-parenterally delivered composition comprising a recombinant *Spirulina*, wherein the recombinant *Spirulina* comprises at least one therapeutic or prophylactic molecule.

Embodiment 2. The non-parenterally delivered composition of embodiment 1, wherein the therapeutic or prophylactic molecule is delivered to the gastrointestinal tract.

Embodiment 3. The non-parenterally delivered composition of embodiment 1, wherein the therapeutic or prophylactic molecule is delivered systemically.

Embodiment 4. The non-parenterally delivered composition of any of embodiments 1-3, wherein the therapeutic or prophylactic molecule is an endogenous *Spirulina* molecule.

Embodiment 5. The non-parenterally delivered composition of embodiment 4, wherein the endogenous *Spirulina* molecule is found in higher concentrations than found in naturally-occurring *Spirulina*.

Embodiment 6. The non-parenterally delivered composition of any of embodiments 1-3 wherein the therapeutic or prophylactic molecule is exogenous to *Spirulina*.

Embodiment 7. The non-parenterally delivered composition of embodiment 6, wherein the exogenous molecule is produced by a different bacteria or plant.

Embodiment 8. The non-parenterally delivered composition of embodiment 7, wherein the exogenous therapeutic is a malacidin.

Embodiment 9. The non-parenterally delivered composition of embodiment 6, wherein the exogenous molecule is a polypeptide or a fragment thereof.

Embodiment 10. The non-parenterally delivered composition of embodiment 9, wherein the exogenous polypeptide is an antibody or fragment thereof.

Embodiment 11. The non-parenterally delivered 1 composition of embodiment 10, wherein the antibody or fragment thereof is selected from the group consisting: of full length antibody, a monospecific antibody, a bispecific antibody, a trispecific antibody, an antigen-binding region, heavy chain, light chain, VHH, VH, VL, a CDR, a variable domain, scFv, Fc, Fv, Fab, $F(ab)_2$, reduced IgG (rIgG), monospecific $Fab_2$, bispecific $Fab_2$, trispecific $Fab_3$, diabody, bispecific diabody, trispecific triabody, minibody, IgNAR, V-NAR, HcIgG, or a combination thereof.

Embodiment 12. The non-parenterally delivered composition of embodiment 9, wherein the exogenous polypeptide is selected from the group consisting of: insulin, C-peptide, amylin, interferon, a hormone, a receptor, a receptor agonist, a receptor antagonist, an incretin, GLP-1, glucose-dependent insulinotropic peptide (GIP), an immunomodulatory, an immunosuppressor, a peptide chemotherapeutic, an antimicrobial peptide, magainin, NRc-3, NRC-7, buforin IIb, BR2, p16, Tat, TNFalpha, and chlorotoxin.

Embodiment 13. The delivered composition of embodiment 9, wherein the exogenous polypeptide is an antigen or epitope.

Embodiment 14. The non-parenterally delivered composition of embodiment 13, wherein the antigen or epitope is derived from an infectious microorganism, a tumor antigen or a self-antigen associated with an autoimmune disease Embodiment 15. The non-parenterally delivered composition of any of embodiments 1-14, wherein administration of the recombinant *Spirulina* to a subject prevents, treats or ameliorates a disease or disorder.

Embodiment 16. The non-parenterally delivered composition of embodiment 15, wherein the disease or disorder is selected from the group consisting of: Type 1 diabetes, Type 2 diabetes, cancer, an inflammatory disorder, a gastrointestinal disease, an autoimmune disease or disorder, an endocrine disorder, gastroesophageal reflux disease (GERD), ulcers, high cholesterol, inflammatory bowel disorder, irritable bowel syndrome, crohn's disease, ulcerative colitis, constipation, vitamin deficiency, iron deficiency, and diarrhea.

Embodiment 17. The non-parenterally delivered composition of embodiment 15, wherein administration of the recombinant *Spirulina* to a subject treats, prevents, or ameliorates an infection.

Embodiment 18. The non-parenterally delivered composition of embodiment 17, wherein the infection is bacterial, viral, fungal, or parasitical.

Embodiment 19. The non-parenterally delivered composition of embodiment 18, wherein the bacteria causing the infection is selected from the group consisting of: *E. coli*, Enterotoxigenic *E. coli* (ETEC), *Shigella, Mycobacterium, Streptococcus, Staphylococcus, Shigella, Campylobacter, Salmonella, Clostridium, Corynebacterium, Pseudomonas, Neisseria, Listeria, Vibrio, Bordetella*, heliobacteter, anthrax, ETEC, EHEC, EAEC, and *Legionella*.

Embodiment 20. The non-parenterally delivered composition of embodiment 18, wherein the virus causing the infection is selected from the group consisting of: bacteriophage, RNA bacteriophage (e.g. MS2, AP205, PP7 and Qβ), *Helicobacter pylori*, Infectious Haematopoietic Necrosis Virus, Parvovirus, Herpes Simplex Virus, Hepatitis A virus, Hepatitis B virus, Hepatitis C virus, Measles virus, Mumps virus, Rubella virus, HIV, Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, White Spot Syndrome Virus, a coronavirus, MERS, SARS, and SARS-CoV-2.

Embodiment 21. The non-parenterally delivered composition of embodiment 18, wherein the fungus causing the infection is selected from the group consisting of: *Aspergillus, Candida, Blastomyces, Coccidioides, Cryptococcus*, and *Histoplasma*.

Embodiment 22. The non-parenterally delivered composition of embodiment 18, wherein the parasite causing the infection is selected from the group consisting of: *Plasmodium, P. falciparum, P. malariae, P. ovale, P. vivax, Trypanosoma, Toxoplasma, Giardia, Leishmania Cryptosporidium*, helminthic parasites: *Trichuris* spp., *Enterobius* spp., *Ascaris* spp., *Ancylostoma* spp. and *Necatro* spp., *Strongyloides* spp., *Dracunculus* spp; *Onchocerca* spp. and *Wuchereria* spp., *Taenia* spp., *Echinococcus* spp., and *Diphyllobothrium* spp., *Fasciola* spp., and *Schistosoma* spp.

Embodiment 23. The non-parenterally delivered composition of any of embodiments 9-22, wherein the exogenous polypeptide or a fragment thereof is in a fusion protein.

Embodiment 24. The non-parenterally delivered composition of any of embodiments 9-22, wherein the recombinant *Spirulina* comprises a nucleic acid encoding the exogenous polypeptide or fragment thereof.

Embodiment 25. The non-parenterally delivered composition of embodiment 24, wherein at least 2, at least 3, at least 4, or at least 5 copies of a nucleic acid sequence encoding the at least one exogenous polypeptide or fragment thereof are present in the recombinant *Spirulina*.

Embodiment 26. The non-parenterally delivered composition of any of embodiments 24-25, wherein 2, 3, 4, 5, 6, 8, 10, 15, 20, 25, 30, 40, or 50 copies of a nucleic acid sequence encoding the at least one exogenous polypeptide or fragment thereof are present in the recombinant *Spirulina*.

Embodiment 27. The non-parenterally delivered composition of embodiment 25, wherein at least 2, at least 3, at least 4, or at least 5 copies of the at least one exogenous polypeptide or fragment thereof are present in a single molecule of the exogenous polypeptide expressed in the recombinant *Spirulina.*

Embodiment 28. The non-parenterally delivered composition of embodiment 25 or 27, wherein 2, 3, 4, 5, 6, 8, 10, 15, 20, 25, 30, 40, or 50 copies of the at least one exogenous polypeptide or fragment thereof are present in a single molecule of the exogenous polypeptide expressed in the recombinant *Spirulina.*

Embodiment 29. The non-parenterally delivered composition of any of embodiments 25 or 27-28, wherein, within the molecule of the exogenous polypeptide, the copies of the exogenous polypeptide are linked in tandem.

Embodiment 30. The non-parenterally delivered composition of any of embodiments 25 or 27-28, wherein, within the molecule of exogenous polypeptide or fragment thereof, the copies of the exogenous polypeptide or fragment thereof are separated by a spacer sequence.

Embodiment 31. The non-parenterally delivered composition of any of embodiments 25-30, wherein, within the molecule of exogenous polypeptide or fragment thereof, some of the copies of the exogenous polypeptide or fragment thereof are linked in tandem and the remaining copies of the exogenous polypeptide or fragment thereof are separated by a spacer sequence.

Embodiment 32. The non-parenterally delivered composition of embodiment 30 or 31, wherein the spacer sequence is between about 1 and 50 amino acids long.

Embodiment 33. The non-parenterally delivered composition of any of embodiments 30-32, wherein more than one spacer sequence is present within the molecule of the exogenous polypeptide or fragment thereof.

Embodiment 34. The non-parenterally delivered composition of any one of embodiments 9-34, wherein the recombinant *Spirulina* comprises at least 2, at least 3, at least 4, or at least 5 different exogenous polypeptides or fragments thereof.

Embodiment 35. The non-parenterally delivered composition of any one of embodiments 23-34, wherein the fusion protein comprises a carrier protein.

Embodiment 36. The non-parenterally delivered composition of embodiment 35, wherein the carrier protein is selected from the group consisting of: maltose binding protein, hedgehog hepatitis virus-like particle, thioredoxin, and phycocyanin.

Embodiment 37. The non-parenterally delivered composition of any one of embodiments 23-36, wherein the fusion protein comprises a scaffold protein.

Embodiment 38. The non-parenterally delivered composition of embodiment 37, wherein the at least one exogenous polypeptide is linked to a scaffold protein at the N-terminus or the C-terminus, or in the body of the scaffold protein.

Embodiment 39. The non-parenterally delivered composition of embodiment 37 or 38, wherein the scaffold protein is selected from the oligomerization domain of C4b-binding protein (C4BP), cholera toxin b subunit, or oligomerization domains of extracellular matrix proteins.

Embodiment 40. The non-parenterally delivered composition of any of embodiments 37-39, wherein the at least one exogenous polypeptide and the scaffold protein are separated by about 1 to about 50 amino acids.

Embodiment 41. The non-parenterally delivered composition of any of embodiments 37-40, wherein the fusion protein comprises multiple copies of the at least one exogenous polypeptide or fragment thereof, wherein the at least one exogenous polypeptide or fragment thereof and the scaffold protein are arranged in any one of the following patterns: (E)n-(SP), (SP)-(E)n, (SP)-(E)n-(SP), (E)n1-(SP)-(E)n2, (SP)-(E)n1-(SP)-(E)n2, and (SP)-(E)n1-(SP)-(E)n2-(SP), wherein E is the at least one exogenous polypeptide or fragment thereof, SP is the scaffold protein, n, n1, and n2 represent the number of copies of the at least one exogenous polypeptide or fragment thereof.

Embodiment 42. The non-parenterally delivered composition of any of embodiments 9-42, wherein the recombinant *Spirulina* comprises an anti-*Campylobacter* VHH.

Embodiment 43. The non-parenterally delivered composition of embodiment 42, wherein the campylobacter is a *C. jejuni.*

Embodiment 44. The non-parenterally delivered composition of any of embodiments 42-43, wherein the VHH binds to a campylobacter component.

Embodiment 45. The non-parenterally delivered composition of embodiment 44, wherein the VHH binds flagellin.

Embodiment 46. The non-parenterally delivered composition of any of embodiments 42-45, wherein administration increases *Campylobacter* shedding.

Embodiment 47. The non-parenterally delivered composition of any of embodiments 42-46, wherein administration reduces the levels of biomarkers.

Embodiment 48. The non-parenterally delivered composition of embodiment 47, wherein the biomarker is an inflammation biomarker.

Embodiment 49. The non-parenterally delivered composition of any of embodiments 9-42 wherein the recombinant *Spirulina* comprises a VHH that binds to an anti-*Clostridium* toxin.

Embodiment 50. The non-parenterally delivered composition of embodiment 49, wherein *Clostridium* is *C. difficile.*

Embodiment 51. The non-parenterally delivered composition of any one of embodiments 48-49, wherein the VHH binds to a *Clostridium* component, toxin A, or toxin B.

Embodiment 52. The non-parenterally delivered composition of any of embodiments 49-51, wherein the VHH comprises the amino acid sequence of any of SEQ ID NO:s 5-10.

Embodiment 53. The non-parenterally delivered composition of any of embodiments 1-52, wherein the therapeutic or prophylactic molecule is monomeric.

Embodiment 54. The non-parenterally delivered composition of any of embodiments 1-52, wherein the therapeutic or prophylactic molecule is multimeric.

Embodiment 55. The non-parenterally delivered composition of embodiment 54, wherein the therapeutic or prophylactic molecule is trimeric.

Embodiment 56. The non-parenterally delivered composition of any of embodiments 54-55, wherein the multimer is heteromeric.

Embodiment 57. The non-parenterally delivered composition of any of embodiments 54-55, wherein the multimer is homomeric.

Embodiment 58. The non-parenterally delivered composition of any of embodiments 54-57, wherein the multimer is arranged in a nanoparticle.

Embodiment 59. The non-parenterally delivered composition of any of embodiments 54-57, wherein the multimer binds to a target or target molecule at a high affinity.

Embodiment 60. The non-parenterally delivered composition of embodiment 59, wherein the multimer binding affinity is greater than that of a monomer or a dimer.

Embodiment 61. The non-parenterally delivered composition of embodiment 60, wherein the multimer has an $EC_{50}$ of over 5 μg/mL.

Embodiment 62. The non-parenterally delivered composition of embodiment 61, wherein the multimer has an $EC_{50}$ of over 10 μg/mL.

Embodiment 63. The orally delivered composition of embodiment 61, wherein the multimer has an $EC_{50}$ of about 5 μg/mL to about 40 μg/mL.

Embodiment 64. The non-parenterally delivered composition of any of embodiments 59-63, wherein the multimer binding affinity is greater than that of a multimer comprising fewer copies of the exogenous therapeutic or fewer copies of combinations of exogenous therapeutics.

Embodiment 65. The non-parenterally delivered composition of any of embodiments 59-64, wherein administration of *Spirulina* comprising multimeric exogenous therapeutics results in a smaller dose of *Spirulina* for efficacy than administration of a *Spirulina* comprising a monomer of the same exogenous therapeutic.

Embodiment 66. The non-parenterally delivered composition of any of embodiments 1-65, wherein the recombinant *Spirulina* is selected from the group consisting of: *A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri Stizenberger, A. jenneri* f. *purpurea, A. joshii, A. khannae, A. laxa, A. laxissima, A. laxissima, A. leopoliensis, A. major, A. mar garitae, A. massartii, A. massartii* var. *indica, A. maxima, A. meneghiniana, A. miniata* var. *constricta, A. miniata, A. miniata* f. *acutissima, A. neapolitana, A. nordstedtii, A. oceanica, A. okensis, A. pellucida, A. platensis, A. platensis* var. non-constricta, *A. platensis* f. *granulate, A. platensis* f. *minor, A. platensis* var. *tenuis, A. santannae, A. setchellii, A. skujae, A. spirulinoides* f. *tenuis, A. spirulinoides, A. subsalsa, A. subtilissima, A. tenuis, A. tenuissima*, and *A. versicolor*

Embodiment 67. The non-parenterally delivered composition of any one of embodiments 1-66, wherein the recombinant *Spirulina* is non-living.

Embodiment 68. The non-parenterally delivered composition of any one of embodiments 1-67, wherein the recombinant *Spirulina* is dried, spray dried, freeze-dried, or lyophilized.

Embodiment 69. The non-parenterally delivered composition of any one of embodiments 1-68, wherein the oral composition comprises a pharmaceutically acceptable excipient.

Embodiment 70. The non-parenterally delivered composition of any of embodiments 1-69, wherein the composition survives in the gastrointestinal tract or a simulated stomach environment.

Embodiment 71. The non-parenterally delivered composition of embodiment 70, wherein the composition survives in the gastrointestinal tract or a simulated stomach environment for at least 5 minutes.

Embodiment 72. The non-parenterally delivered composition of embodiment 71, wherein the composition survives in the gastrointestinal tract or a simulated stomach environment overnight.

Embodiment 73. A method of treating or preventing a disease or disorder in a subject in need thereof, comprising administering to the subject the non-parenterally delivered composition of any one of embodiments 1-72 or 87-92.

Embodiment 74. The method of embodiment 73, wherein the disease or disorder is an infection.

Embodiment 75. The method of embodiment 74, wherein the infection is bacterial, viral, fungal, or parasitical.

Embodiment 76. The method of embodiment 75, wherein the bacteria causing the infection is selected from the group consisting of: *E. coli, Enterotoxigenic E. coli* (ETEC), *Shigella, Mycobacterium, Streptococcus, Staphylococcus, Shigella, Campylobacter, Salmonella, Clostridium, Corynebacterium, Pseudomonas, Neisseria, Listeria, Vibrio, Bordetella*, and *Legionella.*

Embodiment 77. The method of embodiment 75, wherein the virus causing the infection is selected from the group consisting of: bacteriophage, RNA bacteriophage (e.g. MS2, AP205, PP7 and Qβ), Infectious Haematopoietic Necrosis Virus, Parvovirus, Herpes Simplex Virus, Hepatitis A virus, Hepatitis B virus, Hepatitis C virus, Measles virus, Mumps virus, Rubella virus, HIV, Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, White Spot Syndrome Virus, a coronavirus, MERS, SARS, and SARS-CoV-2.

Embodiment 78. The method of embodiment 75, wherein the fungus causing the infection is selected from the group consisting of: *Aspergillus, Candida, Blastomyces, Coccidioides, Cryptococcus*, and *Histoplasma.*

Embodiment 79. The method of embodiment 75, wherein the parasite causing the infection is selected from the group consisting of: *Plasmodium, P. falciparum, P. malariae, P. ovale, P. vivax, Trypanosoma, Toxoplasma, Giardia, Leishmania Cryptosporidium*, helminthic parasites: *Trichuris* spp., *Enterobius* spp., *Ascaris* spp., *Ancylostoma* spp. and Necatro spp., *Strongyloides* spp., *Dracunculus* spp., *Onchocerca* spp. and *Wuchereria* spp., *Taenia* spp., *Echinococcus* spp., and *Diphyllobothrium* spp., *Fasciola* spp., and *Schistosoma* spp.

Embodiment 80. The method of embodiment 73, wherein the disease or disorder is selected from the list consisting of: Celiac disease, Type 1 diabetes, Type 2 diabetes, cancer, an inflammatory disorder, a gastrointestinal disease, an autoimmune disease or disorder, an endocrine disorder, gastroesophageal reflux disease (GERD), ulcers, high cholesterol, inflammatory bowel disorder, irritable bowel syndrome, crohn's disease, ulcerative colitis, constipation, and diarrhea Embodiment 81. A method of treating or preventing a *Campylobacter* infection comprising administering to a subject the non-parenterally delivered composition of any of embodiments 1-72.

Embodiment 82. The method of embodiment 81, wherein administration of the non-parenterally delivered composition decreases or prevents development of campylobacter symptoms.

Embodiment 83. The method of any of embodiments 81-82, wherein administration of the non-parenterally delivered composition decreases or prevents the development of inflammation in the subject.

Embodiment 83. A method of treating or preventing a *C. difficile* infection comprising administering to a subject the non-parenterally delivered composition of any of embodiments 1-72.

Embodiment 84. The method of embodiment 83, wherein administration of the non-parenterally delivered composition decreases or prevents development of *C. difficile* symptoms.

Embodiment 85. The method of any one of embodiments 81-84, wherein administration of the non-parenterally delivered composition decreases or prevents the development of diarrhea in the subject.

Embodiment 86. The non-parenterally delivered composition or method of any one of embodiments 1-85 wherein the therapeutic or prophylactic molecule is not an antigen or epitope.

Embodiment 88. The non-parenterally delivered composition or method of any of the preceding embodiments, wherein the administration of two or more different recombinant *Spirulina* comprising different exogenous polypeptides or antigens or fragments thereof exert a synergistic effect.

Embodiment 89. The non-parenterally delivered composition or method of embodiment 88, wherein the different recombinant *Spirulina* administered each comprise a different VHH.

Embodiment 90. The non-parenterally delivered composition or method of any of the preceding embodiments, wherein the administration of a recombinant *Spirulina* comprising different exogenous polypeptides or antigens or fragments thereof exerts a synergistic effect.

Embodiment 91. The non-parenterally delivered composition or method of embodiment 90, wherein the recombinant *Spirulina* comprises two or more different VHH sequences.

Embodiment 92. The non-parenterally delivered composition or method of any of embodiments 88-92, wherein the recombinant *Spirulina* comprises a lysin.

Embodiment 93. The non-parenterally delivered composition or method of any of embodiments 88-92, wherein the recombinant *Spirulina* comprises a lysin and a exogenous polypeptide.

Embodiment 94. The non-parenterally delivered composition or method of embodiment 94, wherein the recombinant *Spirulina* comprises a lysin and a VHH.

Embodiment 95. The non-parenterally delivered composition or method of any of the preceding embodiments, wherein the composition is administered orally.

Embodiment 96. The non-parenterally delivered composition or method of any of the preceding embodiments, wherein the composition is delivered to the respiratory tract.

Embodiment 97. The non-parenterally delivered composition or method of embodiment 88, wherein the composition is delivered via inhalation or intranasally.

Embodiment 98. The non-parenterally delivered composition or method of any of the preceding embodiments, wherein the composition is a *Spirulina* biomass.

Embodiment 99. The non-parenterally delivered composition or method of any of the preceding embodiments, wherein the composition is delivered as an extract of a *Spirulina* biomass.

Embodiment 100. The non-parenterally delivered composition or method of any of the preceding embodiments, wherein the composition is delivered as a purified composition obtained from a *Spirulina* biomass.

REFERENCES

Giallourou et al. A novel mouse model of *Campylobacter jejuni* enteropathy and diarrhea. PLoS Pathog. 2018 March; 14(3): e1007083.

Riazi et al. Pentavalent Single-Domain Antibodies Reduce *Campylobacter jejuni Motility and Colonization in Chickens. PLoS One.* 2013; 8(12): e83928.

INCORPORATION BY REFERENCE

This patent application incorporates by reference in their entireties for all purposes the following patent publications and applications: U.S. Pat. No. 10,131,870, U.S. 62/672,891 filed May 17, 2018, and PCT/US2019/032998 filed May 17, 2019.

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

TABLE 1

| Cell Rounding Assay results ("+" is no rounding, "−" is all round, "+/−" is mixed) | | | | | | | | | | | |
|---|---|---|---|---|---|---|---|---|---|---|---|
| SP968 | | SP981 (5D) | | SP989 (5D) | | SP1090 | | SP1096 | | SP745 | |
| Hi/.01 | + | Hi/.01 | + | Hi/.01 | + | Hi/.01 | + | Hi/.01 | + | Hi/.01 | + |
| Hi/.1 | + | Hi/.1 | + | Hi/.1 | + | Hi/.1 | + | Hi/.1 | + | Hi/.1 | + |
| Hi/1. | +/− | Hi/1. | + | Hi/1. | + | Hi/1. | +/− | Hi/1. | +/− | Hi/1. | +/− |
| Lo/.01 | + | Lo/.01 | + | Lo/.01 | + | Lo/.01 | + | Lo/.01 | + | Lo/.01 | + |
| Lo/.1 | + | Lo/.1 | + | Lo/.1 | + | Lo/.1 | + | Lo/.1 | + | Lo/.1 | +/− |
| Lo/1. | +/− | Lo/1. | +/− | Lo/1. | +/− | Lo/1. | − | Lo/1. | − | Lo/1. | − |
| SP974 | | SP982 | | SP990 | | SP1091 (5D) | | SP1097 | | SP746 | |
| Hi/.01 | + | Hi/.01 | + | Hi/.01 | + | Hi/.01 | + | Hi/.01 | + | Hi/.01 | + |
| Hi/.1 | + | Hi/.1 | + | Hi/.1 | + | Hi/.1 | + | Hi/.1 | + | Hi/.1 | + |
| Hi/1. | − | Hi/1. | − | Hi/1. | − | Hi/1. | + | Hi/1. | +/− | Hi/1. | + |
| Lo/.01 | + | Lo/.01 | + | Lo/.01 | + | Lo/.01 | + | Lo/.01 | + | Lo/.01 | + |
| Lo/.1 | + | Lo/.1 | + | Lo/.1 | +/− | Lo/.1 | + | Lo/.1 | + | Lo/.1 | + |
| Lo/1. | − | Lo/1. | − | Lo/1. | − | Lo/1. | +/− | Lo/1. | +/− | Lo/1. | +/− |
| SP977 (5D) | | SP985 (5D) | | SP1086 (E3) | | SP1094 | | SP1102 | | SP747 | |
| Hi/.01 | + | Hi/.01 | + | Hi/.01 | + | Hi/.01 | + | Hi/.01 | + | Hi/.01 | + |
| Hi/.1 | + | Hi/.1 | + | Hi/.1 | + | Hi/.1 | + | Hi/.1 | + | Hi/.1 | + |
| Hi/1. | + | Hi/1. | + | Hi/1. | + | Hi/1. | +/− | Hi/1. | − | Hi/1. | − |

TABLE 1-continued

Cell Rounding Assay results ("+" is no rounding, "−" is all round, "+/−" is mixed)

| | | | | | | | | | | | |
|---|---|---|---|---|---|---|---|---|---|---|---|
| Lo/.01 | + | Lo/.01 | + | Lo/.01 | + | Lo/.01 | + | Lo/.01 | + | Lo/.01 | + |
| Lo/.1 | + | Lo/.1 | + | Lo/.1 | + | Lo/.1 | +/− | Lo/.1 | + | Lo/.1 | + |
| Lo/1. | +/− | Lo/1. | +/− | Lo/1. | +/− | Lo/1. | − | Lo/1. | − | Lo/1. | − |
| SP978 | | SP986 | | SP1087 (5D) | | SP1095 (E3/5D) | | SP744 (5D) | | SP994 | |
| Hi/.01 | + | Hi/.01 | + | Hi/.01 | + | Hi/.01 | + | Hi/.01 | + | Hi/.01 | +/− |
| Hi/.1 | +/− | Hi/.1 | + | Hi/.1 | + | Hi/.1 | + | Hi/.1 | + | Hi/.1 | − |
| Hi/1. | − | Hi/1. | − | Hi/1. | + | Hi/1. | + | Hi/1. | + | Hi/1. | − |
| Lo/.01 | + | Lo/.01 | + | Lo/.01 | + | Lo/.01 | + | Lo/.01 | + | Lo/.01 | +/− |
| Lo/.1 | +/− | Lo/.1 | +/− | Lo/.1 | + | Lo/.1 | + | Lo/.1 | + | Lo/.1 | − |
| Lo/1. | − | Lo/1. | − | Lo/1. | + | Lo/1. | + | Lo/1. | + | Lo/1. | − |

The invention claimed is:

1. An oral composition comprising three recombinant *Spirulina*, wherein each of the three recombinant *Spirulina* encapsulates a different VHH molecule or binding fragment thereof that binds to a *C. difficile* toxin, and wherein the VHH molecules or binding fragments thereof comprise:

a) amino acid residues 26-32 (CDR1), 52-57 (CDR2), and 98-116 (CDR3) of SEQ ID NO: 5;

b) amino acid residues 26-32 (CDR1), 52-56 (CDR2), and 98-100 (CDR3) of SEQ ID NO: 6; and c) amino acid residues 26-32 (CDR1), 52-56 (CDR2), and 98-105 (CDR3) of SEQ ID NO: 13.

2. The oral composition of claim 1, wherein the VHH molecules or binding fragments thereof further comprise:

a) an amino acid sequence consisting of amino acid residues 2-126 of SEQ ID NO: 5;

b) an amino acid sequence consisting of amino acid residues 2-110 of SEQ ID NO: 6; or c) an amino acid sequence consisting of amino acid residues 2-115 of SEQ ID NO: 13.

3. The oral composition of claim 1, further comprising a lysin.

4. The oral composition of claim 1, wherein at least one of the VHH molecules or binding fragments thereof is fused to a maltose binding protein (MBP).

5. The oral composition of claim 1, further comprising a lysin, and wherein at least one of the VHH molecules or binding fragments thereof is fused to a maltose binding protein (MBP).

6. The oral composition of claim 3, wherein the lysin is PlyCD.

7. The oral composition of claim 1, wherein the composition comprises a pharmaceutically acceptable excipient.

8. The oral composition of claim 1, wherein the composition retains its efficacy in binding to a *C. difficile* toxin after passage through the stomach.

9. The oral composition of claim 1, wherein the recombinant *Spirulina* are dried, spray dried, freeze-dried, or lyophilized.

10. The oral composition of claim 9, wherein the recombinant *Spirulina* are spray dried.

11. The oral composition of claim 1, wherein the recombinant *Spirulina* are non-living.

12. An oral composition comprising:

i) three non-living recombinant *Spirulina*, wherein each of the three non-living recombinant *Spirulina* encapsulates a different VHH molecule or binding fragment thereof that binds to a *C. difficile* toxin, wherein the VHH molecules or binding fragments thereof comprise:

a) amino acid residues 26-32 (CDR1), 52-57 (CDR2), and 98-116 (CDR3) of SEQ ID NO: 5;

b) amino acid residues 26-32 (CDR1), 52-56 (CDR2), and 98-100 (CDR3) of SEQ ID NO: 6; and c) amino acid residues 26-32 (CDR1), 52-56 (CDR2), and 98-105 (CDR3) of SEQ ID NO: 13; and ii) a lysin.

13. The oral composition of claim 12, wherein the VHH molecules or binding fragments thereof further comprise:

a) an amino acid sequence consisting of amino acid residues 2-126 of SEQ ID NO: 5;

b) an amino acid sequence consisting of amino acid residues 2-110 of SEQ ID NO: 6; and c) an amino acid sequence consisting of amino acid residues 2-115 of SEQ ID NO: 13.

14. A method of treating an infection in a subject, comprising administering to the subject the oral composition of claim 1, orally.

15. The method of claim 14, wherein the infection is a *C. difficile* infection.

16. The method of claim 14, wherein administration of the oral composition decreases or prevents development of *C. difficile* symptoms.

17. A method of treating an infection in a subject, comprising administering to the subject the oral composition of claim 12.

18. The method of claim 17, wherein the infection is a *C. difficile* infection.

19. The method of claim 17, wherein administration of the oral composition decreases or prevents development of *C. difficile* symptoms.

20. The oral composition of claim 1, further comprising a $PlyCD_{1-174}$ lysin.

* * * * *

SEQUENCE LISTING

```
<160> NUMBER OF SEQ ID NOS: 79

<210> SEQ ID NO 1
<211> LENGTH: 65
<212> TYPE: PRT
<213> ORGANISM: Artificial Sequence
<220> FEATURE:
<223> OTHER INFORMATION: partial oligomerization domain of C4BP

<400> SEQUENCE: 1

Ser Ala Gly Ala His Ala Gly Trp Glu Thr Pro Glu Gly Cys Glu Gln
1               5                   10                  15

Val Leu Thr Gly Lys Arg Leu Met Gln Cys Leu Pro Asn Pro Glu Asp
            20                  25                  30

Val Lys Met Ala Leu Glu Val Tyr Lys Leu Ser Leu Glu Ile Glu Gln
        35                  40                  45

Leu Glu Leu Gln Arg Asp Ser Ala Arg Gln Ser Thr Leu Asp Lys Glu
    50                  55                  60

Leu
65


<210> SEQ ID NO 2
<211> LENGTH: 55
<212> TYPE: PRT
<213> ORGANISM: Artificial Sequence
<220> FEATURE:
<223> OTHER INFORMATION: partial oligomerization domain of C4BP

<400> SEQUENCE: 2

Trp Val Ile Pro Glu Gly Cys Gly His Val Leu Ala Gly Arg Lys Val
1               5                   10                  15

Met Gln Cys Leu Pro Asn Pro Glu Asp Val Lys Met Ala Leu Glu Val
            20                  25                  30

Tyr Lys Leu Ser Leu Glu Ile Glu Leu Leu Glu Ile Gln Arg Asp Lys
        35                  40                  45

Ala Arg Asp Pro Ala Met Asp
    50                  55


<210> SEQ ID NO 3
<211> LENGTH: 52
<212> TYPE: PRT
<213> ORGANISM: Artificial Sequence
<220> FEATURE:
<223> OTHER INFORMATION: partial oligomerization domain of C4BP

<400> SEQUENCE: 3
```

```
Trp Glu Tyr Ala Glu Gly Cys Glu Gln Val Val Lys Gly Lys Lys Leu
1               5                   10                  15

Met Gln Cys Leu Pro Thr Pro Glu Glu Val Arg Leu Ala Leu Glu Val
            20                  25                  30

Tyr Lys Leu Tyr Leu Glu Ile Gln Lys Leu Glu Leu Gln Lys Asp Glu
        35                  40                  45

Ala Lys Gln Ala
    50


<210> SEQ ID NO 4
<211> LENGTH: 58
<212> TYPE: PRT
<213> ORGANISM: Artificial Sequence
<220> FEATURE:
<223> OTHER INFORMATION: partial oligomerization domain of C4BP

<400> SEQUENCE: 4

Trp Val Val Pro Ala Gly Cys Glu Gln Val Ile Ala Gly Arg Glu Leu
1               5                   10                  15

Thr Gln Cys Leu Pro Ser Val Glu Asp Val Lys Met Ala Leu Glu Leu
            20                  25                  30

Tyr Lys Leu Ser Leu Glu Ile Glu Leu Leu Glu Leu Gln Lys Asp Lys
        35                  40                  45

Ala Lys Lys Ser Thr Leu Glu Ser Pro Leu
    50                  55


<210> SEQ ID NO 5
<211> LENGTH: 135
<212> TYPE: PRT
<213> ORGANISM: Artificial Sequence
<220> FEATURE:
<223> OTHER INFORMATION: Anti-tcdB VHH 5D

<400> SEQUENCE: 5

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Arg Gly Thr Gln Val Ala Val Ser Ser Glu
        115                 120                 125

Pro Lys Thr Pro Lys Pro Gln
    130                 135


<210> SEQ ID NO 6
<211> LENGTH: 119
<212> TYPE: PRT
<213> ORGANISM: Artificial Sequence
<220> FEATURE:
<223> OTHER INFORMATION: Anti-tcdB VHH E3
```

<400> SEQUENCE: 6

Gln Val Gln Leu Val Glu Ser Gly Gly Gly Leu Val Gln Thr Gly Gly
1 5 10 15

Ser Leu Arg Leu Ser Cys Ala Ser Ser Gly Ser Ile Ala Gly Phe Glu
20 25 30

Thr Val Thr Trp Ser Arg Gln Ala Pro Gly Lys Ser Leu Gln Trp Val
35 40 45

Ala Ser Met Thr Lys Thr Asn Asn Glu Ile Tyr Ser Asp Ser Val Lys
50 55 60

Gly Arg Phe Ile Ile Ser Arg Asp Asn Ala Lys Asn Thr Val Tyr Leu
65 70 75 80

Gln Met Asn Ser Leu Lys Pro Glu Asp Thr Gly Val Tyr Phe Cys Lys
85 90 95

Gly Pro Glu Leu Arg Gly Gln Gly Ile Gln Val Thr Val Ser Ser Glu
100 105 110

Pro Lys Thr Pro Lys Pro Gln
115

<210> SEQ ID NO 7
<211> LENGTH: 123
<212> TYPE: PRT
<213> ORGANISM: Artificial Sequence
<220> FEATURE:
<223> OTHER INFORMATION: Anti-tcdB VHH 5E

<400> SEQUENCE: 7

Val Gln Leu Val Glu Ser Gly Gly Gly Leu Val Gln Ala Gly Gly Ser
1 5 10 15

Leu Arg Leu Ser Cys Ala Ala Ser Gly Leu Met Phe Gly Ala Met Thr
20 25 30

Met Gly Trp Tyr Arg Gln Ala Pro Gly Lys Glu Arg Glu Met Val Ala
35 40 45

Tyr Ile Thr Ala Gly Gly Thr Glu Ser Tyr Ser Glu Ser Val Lys Gly
50 55 60

Arg Phe Thr Ile Ser Arg Ile Asn Ala Asn Asn Met Val Tyr Leu Gln
65 70 75 80

Met Thr Asn Leu Lys Val Glu Asp Thr Ala Val Tyr Tyr Cys Asn Ala
85 90 95

His Asn Phe Trp Arg Thr Ser Arg Asn Trp Gly Gln Gly Thr Gln Val
100 105 110

Thr Val Ser Ser Glu Pro Lys Thr Pro Lys Pro
115 120

<210> SEQ ID NO 8
<211> LENGTH: 131
<212> TYPE: PRT
<213> ORGANISM: Artificial Sequence
<220> FEATURE:
<223> OTHER INFORMATION: Anti-tcdB VHH B12

<400> SEQUENCE: 8

Val Gln Leu Val Glu Ser Gly Gly Gly Leu Val Gln Ala Gly Asp Ser
1 5 10 15

Leu Thr Leu Ser Cys Ala Ala Ser Glu Ser Thr Phe Asn Thr Phe Ser
20 25 30

Met Ala Trp Phe Arg Gln Ala Pro Gly Lys Glu Arg Glu Tyr Val Ala
35 40 45

Ala Phe Ser Arg Ser Gly Gly Thr Thr Asn Tyr Ala Asp Ser Val Lys
    50                  55                  60

Gly Arg Ala Thr Ile Ser Thr Asp Asn Ala Lys Asn Thr Val Tyr Leu
65                  70                  75                  80

His Met Asn Ser Leu Lys Pro Glu Asp Thr Ala Val Tyr Phe Cys Ala
                85                  90                  95

Ala Asp Arg Pro Ala Gly Arg Ala Tyr Phe Gln Ser Arg Ser Tyr Asn
            100                 105                 110

Tyr Trp Gly Gln Gly Thr Gln Val Thr Val Ser Ser Ala His His Ser
        115                 120                 125

Glu Asp Pro
    130

<210> SEQ ID NO 9
<211> LENGTH: 125
<212> TYPE: PRT
<213> ORGANISM: Artificial Sequence
<220> FEATURE:
<223> OTHER INFORMATION: Anti-tcdB VHH A11

<400> SEQUENCE: 9

Val Gln Leu Val Glu Ser Gly Gly Gly Ser Val Gln Ile Gly Gly Ser
1               5                   10                  15

Leu Arg Leu Ser Cys Val Ala Ser Gly Phe Thr Phe Ser Lys Asn Ile
            20                  25                  30

Met Ser Trp Ala Arg Gln Ala Pro Gly Lys Gly Leu Glu Trp Val Ser
        35                  40                  45

Thr Ile Ser Ile Gly Gly Ala Ala Thr Ser Tyr Ala Asp Ser Val Lys
    50                  55                  60

Gly Arg Phe Thr Ile Ser Arg Asp Asn Ala Asn Asp Thr Leu Tyr Leu
65                  70                  75                  80

Gln Met Asn Asn Leu Lys Pro Glu Asp Thr Ala Val Tyr Tyr Cys Ser
                85                  90                  95

Arg Gly Pro Arg Thr Tyr Ile Asn Thr Ala Ser Arg Gly Gln Gly Thr
            100                 105                 110

Gln Val Thr Val Ser Ser Glu Pro Lys Thr Pro Lys Pro
        115                 120                 125

<210> SEQ ID NO 10
<211> LENGTH: 129
<212> TYPE: PRT
<213> ORGANISM: Artificial Sequence
<220> FEATURE:
<223> OTHER INFORMATION: Anti-tcdB VHH A1

<400> SEQUENCE: 10

Val Gln Leu Val Glu Ser Gly Gly Gly Leu Val Gln Ala Gly Gly Ser
1               5                   10                  15

Leu Arg Leu Ser Cys Ala Ala Pro Gly Leu Thr Phe Thr Ser Tyr Arg
            20                  25                  30

Met Gly Trp Phe Arg Gln Ala Pro Gly Lys Glu Arg Glu Tyr Val Ala
        35                  40                  45

Ala Ile Thr Gly Ala Gly Ala Thr Asn Tyr Ala Asp Ser Ala Lys Gly
    50                  55                  60

Arg Phe Thr Ile Ser Lys Asn Asn Thr Ala Ser Thr Val His Leu Gln
65                  70                  75                  80

Met Asn Ser Leu Lys Pro Glu Asp Thr Ala Val Tyr Tyr Cys Ala Ala
                85                  90                  95

Ser Asn Arg Ala Gly Gly Tyr Trp Arg Ala Ser Gln Tyr Asp Tyr Trp
100 105 110

Gly Gln Gly Thr Gln Val Thr Val Ser Ser Ala His His Ser Glu Asp
115 120 125

Pro

<210> SEQ ID NO 11
<211> LENGTH: 135
<212> TYPE: PRT
<213> ORGANISM: Artificial Sequence
<220> FEATURE:
<223> OTHER INFORMATION: Anti-tcdB VHH 2D

<400> SEQUENCE: 11

Gln Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Asp Tyr Tyr
20 25 30

Gly Ile Gly Trp Phe Arg Gln Ala Pro Gly Lys Glu Arg Gln Glu Val
35 40 45

Ser Tyr Ile Ser Ala Ser Ala Lys Thr Lys Leu Tyr Ser Asp Ser Val
50 55 60

Lys Gly Arg Phe Thr Ile Ser Arg Asp Asn Ala Lys Asn Ala Val Tyr
65 70 75 80

Leu Glu Met Asn Ser Leu Lys Arg Glu Asp Thr Ala Val Tyr Tyr Cys
85 90 95

Ala Arg Arg Arg Phe Asp Ala Ser Ala Ser Asn Arg Trp Leu Ala Ala
100 105 110

Asp Tyr Asp Tyr Trp Gly Gln Gly Thr Gln Val Thr Val Ser Ser Glu
115 120 125

Pro Lys Thr Pro Lys Pro Gln
130 135

<210> SEQ ID NO 12
<211> LENGTH: 123
<212> TYPE: PRT
<213> ORGANISM: Artificial Sequence
<220> FEATURE:
<223> OTHER INFORMATION: Anti-tcdB VHH 2Ds

<400> SEQUENCE: 12

Gln Val Gln Leu Val Glu Ser Gly Gly Gly Leu Val Gln Ala Gly Gly
1 5 10 15

Ser Leu Arg Leu Ser Cys Val Ser Ser Glu Arg Asn Pro Gly Ile Asn
20 25 30

Ala Met Gly Trp Tyr Arg Gln Ala Pro Gly Ser Gln Arg Glu Leu Val
35 40 45

Ala Ile Trp Gln Thr Gly Gly Ser Leu Asn Tyr Ala Asp Ser Val Lys
50 55 60

Gly Arg Phe Thr Ile Ser Arg Asp Asn Leu Lys Asn Thr Val Tyr Leu
65 70 75 80

Gln Met Asn Ser Leu Lys Pro Glu Asp Thr Ala Val Tyr Tyr Cys Tyr
85 90 95

Leu Lys Lys Trp Arg Asp Gln Tyr Trp Gly Gln Gly Thr Gln Val Thr
100 105 110

Val Ser Ser Glu Pro Lys Thr Pro Lys Pro Gln
115 120

<210> SEQ ID NO 13
<211> LENGTH: 124
<212> TYPE: PRT
<213> ORGANISM: Artificial Sequence
<220> FEATURE:
<223> OTHER INFORMATION: Anti-tcdB VHH 7F

<400> SEQUENCE: 13

```
Gln Val Gln Leu Val Glu Ser Gly Gly Gly Leu Val Glu Ala Gly Gly
1               5                   10                  15

Ser Leu Arg Leu Ser Cys Val Val Thr Gly Ser Ser Phe Ser Thr Ser
            20                  25                  30

Thr Met Ala Trp Tyr Arg Gln Pro Pro Gly Lys Gln Arg Glu Trp Val
        35                  40                  45

Ala Ser Phe Thr Ser Gly Gly Ala Ile Lys Tyr Thr Asp Ser Val Lys
    50                  55                  60

Gly Arg Phe Thr Met Ser Arg Asp Asn Ala Lys Lys Met Thr Tyr Leu
65                  70                  75                  80

Gln Met Glu Asn Leu Lys Pro Glu Asp Thr Ala Val Tyr Tyr Cys Ala
                85                  90                  95

Leu His Asn Ala Val Ser Gly Ser Ser Trp Gly Arg Gly Thr Gln
            100                 105                 110

Val Thr Val Ser Ser Glu Pro Lys Thr Pro Lys Pro Gln
        115                 120
```

<210> SEQ ID NO 14
<211> LENGTH: 131
<212> TYPE: PRT
<213> ORGANISM: Artificial Sequence
<220> FEATURE:
<223> OTHER INFORMATION: Anti-tcdB VHH B12

<400> SEQUENCE: 14

```
Val Gln Leu Val Glu Ser Gly Gly Gly Leu Val Gln Ala Gly Asp Ser
1               5                   10                  15

Leu Thr Leu Ser Cys Ala Ala Ser Glu Ser Thr Phe Asn Thr Phe Ser
            20                  25                  30

Met Ala Trp Phe Arg Gln Ala Pro Gly Lys Glu Arg Glu Tyr Val Ala
        35                  40                  45

Ala Phe Ser Arg Ser Gly Gly Thr Thr Asn Tyr Ala Asp Ser Val Lys
    50                  55                  60

Gly Arg Ala Thr Ile Ser Thr Asp Asn Ala Lys Asn Thr Val Tyr Leu
65                  70                  75                  80

His Met Asn Ser Leu Lys Pro Glu Asp Thr Ala Val Tyr Phe Cys Ala
                85                  90                  95

Ala Asp Arg Pro Ala Gly Arg Ala Tyr Phe Gln Ser Arg Ser Tyr Asn
            100                 105                 110

Tyr Trp Gly Gln Gly Thr Gln Val Thr Val Ser Ser Ala His His Ser
        115                 120                 125

Glu Asp Pro
    130
```

<210> SEQ ID NO 15
<211> LENGTH: 121
<212> TYPE: PRT
<213> ORGANISM: Artificial Sequence
<220> FEATURE:
<223> OTHER INFORMATION: Anti-tcdB VHH AB8

<400> SEQUENCE: 15

Val Gln Leu Val Glu Ser Gly Gly Gly Leu Val Gln Ala Gly Gly Ser
1               5                   10                  15

Leu Arg Leu Ser Cys Val Gly Ser Gly Arg Asn Pro Gly Ile Asn Ala
            20                  25                  30

Met Gly Trp Tyr Arg Gln Ala Pro Gly Ser Gln Arg Glu Leu Val Ala
        35                  40                  45

Val Trp Gln Thr Gly Gly Ser Thr Asn Tyr Ala Asp Ser Val Lys Gly
    50                  55                  60

Arg Phe Thr Ile Ser Arg Asp Asn Leu Lys Asn Thr Val Tyr Leu Gln
65                  70                  75                  80

Met Asn Ser Leu Lys Pro Glu Asp Thr Ala Val Tyr Tyr Cys Tyr Leu
                85                  90                  95

Lys Lys Trp Arg Asp Glu Tyr Trp Gly Gln Gly Thr Gln Val Thr Val
            100                 105                 110

Ser Ser Ala His His Ser Glu Asp Pro
        115                 120

<210> SEQ ID NO 16
<211> LENGTH: 124
<212> TYPE: PRT
<213> ORGANISM: Artificial Sequence
<220> FEATURE:
<223> OTHER INFORMATION: Anti-tcdB VHH C6

<400> SEQUENCE: 16

Val Gln Leu Val Glu Ser Gly Gly Gly Leu Val Gln Ala Gly Glu Ser
1               5                   10                  15

Leu Arg Leu Ser Cys Val Val Ser Glu Ser Ile Phe Arg Ile Asn Thr
            20                  25                  30

Met Gly Trp Tyr Arg Gln Thr Pro Gly Lys Gln Arg Glu Val Val Ala
        35                  40                  45

Arg Ile Thr Leu Arg Asn Ser Thr Thr Tyr Ala Asp Ser Val Lys Gly
    50                  55                  60

Arg Phe Thr Ile Ser Arg Asp Asp Ala Lys Asn Thr Leu Tyr Leu Lys
65                  70                  75                  80

Met Asp Ser Leu Lys Pro Glu Asp Thr Ala Val Tyr Tyr Cys His Arg
                85                  90                  95

Tyr Pro Leu Ile Phe Arg Asn Ser Pro Tyr Trp Gly Gln Gly Thr Gln
            100                 105                 110

Val Thr Val Ser Ser Glu Pro Lys Thr Pro Lys Pro
        115                 120

<210> SEQ ID NO 17
<211> LENGTH: 122
<212> TYPE: PRT
<213> ORGANISM: Artificial Sequence
<220> FEATURE:
<223> OTHER INFORMATION: Anti-tcdB VHH C12

<400> SEQUENCE: 17

Val Gln Leu Val Glu Ser Gly Gly Gly Leu Val Gln Ala Gly Glu Ser
1               5                   10                  15

Leu Arg Leu Ser Cys Val Val Ser Glu Ser Ile Phe Arg Ile Asn Thr
            20                  25                  30

Met Gly Trp Tyr Arg Gln Thr Pro Gly Lys Gln Arg Glu Val Val Ala
        35                  40                  45

```
Arg Ile Thr Leu Arg Asn Ser Thr Thr Tyr Ala Asp Ser Val Lys Gly
    50                  55                  60

Arg Phe Thr Ile Ser Arg Asp Asp Ala Lys Asn Thr Leu Tyr Leu Lys
65                  70                  75                  80

Met Asp Ser Leu Lys Pro Glu Asp Thr Ala Val Tyr Tyr Cys His Arg
                85                  90                  95

Tyr Pro Leu Ile Phe Arg Asn Ser Pro Tyr Trp Gly Gln Gly Thr Gln
            100                 105                 110

Val Thr Val Ser Ser Glu Pro Lys Thr Pro
        115                 120


<210> SEQ ID NO 18
<211> LENGTH: 126
<212> TYPE: PRT
<213> ORGANISM: Artificial Sequence
<220> FEATURE:
<223> OTHER INFORMATION: K922 VHH

<400> SEQUENCE: 18

Gln Val Gln Leu Gln Glu Ser Gly Gly Gly Leu Val Gln Pro Gly Gly
1               5                   10                  15

Ser Leu Arg Leu Ser Cys Ala Leu Val Ser Gly Gly Thr Phe Ser Trp
            20                  25                  30

Tyr Ala Met Gly Trp Phe Arg Gln Ala Pro Gly Lys Glu Arg Glu Phe
        35                  40                  45

Val Ala Thr Val Ser Arg Gly Gly Gly Ser Ser Tyr Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Gly Arg Gly Ala Pro Ser Asp Thr Gly Arg Pro Asp Glu
            100                 105                 110

Tyr Asp Tyr Trp Gly Gln Gly Thr Gln Val Thr Val Ser Ser
        115                 120                 125


<210> SEQ ID NO 19
<211> LENGTH: 8
<212> TYPE: PRT
<213> ORGANISM: Artificial Sequence
<220> FEATURE:
<223> OTHER INFORMATION: VHH 5D helix 1

<400> SEQUENCE: 19

Ala Glu Ala Ala Ala Lys Ala Ser
1               5


<210> SEQ ID NO 20
<211> LENGTH: 13
<212> TYPE: PRT
<213> ORGANISM: Artificial Sequence
<220> FEATURE:
<223> OTHER INFORMATION: VHH 5D helix 2

<400> SEQUENCE: 20

Ala Glu Ala Ala Ala Lys Glu Ala Ala Ala Lys Ala Ser
1               5                   10


<210> SEQ ID NO 21
<211> LENGTH: 23
```

```
<212> TYPE: PRT
<213> ORGANISM: Artificial Sequence
<220> FEATURE:
<223> OTHER INFORMATION: VHH 5D helix 4

<400> SEQUENCE: 21

Ala Glu Ala Ala Ala Lys Glu Ala Ala Ala Lys Glu Ala Ala Ala Lys
1               5                   10                  15

Glu Ala Ala Ala Lys Ala Ser
            20


<210> SEQ ID NO 22
<211> LENGTH: 12
<212> TYPE: PRT
<213> ORGANISM: Artificial Sequence
<220> FEATURE:
<223> OTHER INFORMATION: VHH 5D PA5

<400> SEQUENCE: 22

Ala Pro Ala Pro Ser Pro Ala Pro Ser Pro Ala Ser
1               5                   10


<210> SEQ ID NO 23
<211> LENGTH: 22
<212> TYPE: PRT
<213> ORGANISM: Artificial Sequence
<220> FEATURE:
<223> OTHER INFORMATION: VHH 5D PA10

<400> SEQUENCE: 23

Ala Pro Ala Pro Ser Pro Ala Pro Ala Pro Ser Pro Ala Pro Ala Pro
1               5                   10                  15

Ser Pro Ala Pro Ala Ser
            20


<210> SEQ ID NO 24
<211> LENGTH: 34
<212> TYPE: PRT
<213> ORGANISM: Artificial Sequence
<220> FEATURE:
<223> OTHER INFORMATION: VHH 5D PA15

<400> SEQUENCE: 24

Ala Pro Ala Pro Ser Pro Ala Pro Ala Pro Ser Pro Ala Pro Ala Pro
1               5                   10                  15

Ser Pro Ala Pro Ala Pro Ser Pro Ala Pro Ala Pro Ser Pro Ala Pro
            20                  25                  30

Ala Ser


<210> SEQ ID NO 25
<211> LENGTH: 25
<212> TYPE: PRT
<213> ORGANISM: Artificial Sequence
<220> FEATURE:
<223> OTHER INFORMATION: VHH 5D IgA linker

<400> SEQUENCE: 25

Ala Pro Pro Pro Val Pro Ser Thr Pro Pro Thr Pro Ser Pro Ser Thr
1               5                   10                  15

Pro Pro Thr Pro Ser Pro Pro Pro Ser
            20                  25


<210> SEQ ID NO 26
<211> LENGTH: 729
```

```
<212> TYPE: DNA
<213> ORGANISM: Artificial Sequence
<220> FEATURE:
<223> OTHER INFORMATION: Malaria vaccine; P. yoelii CSP B cell epitope
      in monomer WHcAg

<400> SEQUENCE: 26

atggacatag atccctataa agaatttggt tcatcttatc agttgttgaa ttttcttcct      60

ttggacttct ttcctgacct taatgctttg gtggacactg ctactgcctt gtatgaagaa     120

gagctaacag gtagggaaca ttgctctccg caccatacag ctattagaca agctttagta     180

tgctgggatg aattaactaa attgatagct tggatgagct ctaacataac ttctcagggt     240

ccaggtgctc cacaaggacc tggagcacct cagggccctg gcgctcccca agggcctgga     300

gcccctcagg gacccggtgc accgcaaggt ccgggcgctc cccaagaacc acctcaacag     360

cctccacagc aacctcctca gcagccacca caacagcccc ctcagcaaga acaagtaaga     420

acaatcatag taaatcatgt caatgatacc tggggactta aggtgagaca aagtttatgg     480

tttcatttgt catgtctcac ttttggacaa catacagttc aagaattttt agtaagtttt     540

ggagtatgga tcagaactcc agctccatat agacctccta atgcacccat tctctcgact     600

cttccggaac atacagtcat taatgaagat agttatgttc cttctgctga acaaatttta     660

gaatttgagc aaaaattaat tagcgaggaa gacctagaac aaaaactgat ctctgaagag     720

gatctgtaa                                                             729


<210> SEQ ID NO 27
<211> LENGTH: 242
<212> TYPE: PRT
<213> ORGANISM: Artificial Sequence
<220> FEATURE:
<223> OTHER INFORMATION: Malaria vaccine; P. yoelii CSP B cell epitope
      in monomer WHcAg

<400> SEQUENCE: 27

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Gln Gly
65                  70                  75                  80

Pro Gly Ala Pro Gln Gly Pro Gly Ala Pro Gln Gly Pro Gly Ala Pro
                85                  90                  95

Gln Gly Pro Gly Ala Pro Gln Gly Pro Gly Ala Pro Gln Gly Pro Gly
            100                 105                 110

Ala Pro Gln Glu Pro Pro Gln Gln Pro Pro Gln Gln Pro Pro Gln Gln
        115                 120                 125

Pro Pro Gln Gln Pro Pro Gln Gln Glu Gln Val Arg Thr Ile Ile Val
    130                 135                 140

Asn His Val Asn Asp Thr Trp Gly Leu Lys Val Arg Gln Ser Leu Trp
145                 150                 155                 160

Phe His Leu Ser Cys Leu Thr Phe Gly Gln His Thr Val Gln Glu Phe
                165                 170                 175

Leu Val Ser Phe Gly Val Trp Ile Arg Thr Pro Ala Pro Tyr Arg Pro
```

```
            180                 185                 190

Pro Asn Ala Pro Ile Leu Ser Thr Leu Pro Glu His Thr Val Ile Asn
        195                 200                 205

Glu Asp Ser Tyr Val Pro Ser Ala Glu Gln Ile Leu Glu Phe Glu Gln
    210                 215                 220

Lys Leu Ile Ser Glu Glu Asp Leu Glu Gln Lys Leu Ile Ser Glu Glu
225                 230                 235                 240

Asp Leu


<210> SEQ ID NO 28
<211> LENGTH: 1155
<212> TYPE: DNA
<213> ORGANISM: Artificial Sequence
<220> FEATURE:
<223> OTHER INFORMATION: Malaria vaccine; P. falciparum CSP B cell
      epitope in tandem WHcAg dimer

<400> SEQUENCE: 28

atggacatag atccctataa agaatttggt tcatcttatc agttgttgaa ttttctacct      60

ttggacttct ttcctgacct aaatgctttg gtggacactg ctactgcctt gtatgaagaa     120

gagctaacag gtcgagaaca ttgctctccg caccatacag ctattagaca agctttagta     180

tgctgggatg aattaactaa attgatagct tggatgagct ctaacataac ttctgaacaa     240

gtaagaacaa tcatagtaaa tcatgtcaat gatacctggg gattaaaggt gagacaaagt     300

ttatggtttc atttgtcatg tttgactttt ggacaacata cagttcaaga atttttagta     360

agttttggag tatggatcag aactccagct ccatatagac ctcctaatgc acccattctc     420

tccactcttc ccgaacatac agtcattggt ggaagtggag ggtctggtgg gtccgggggt     480

agtggtgggt ctgatatcga tccctacaaa gaattcggca gttcttatca gttactaaat     540

ttcctgccgc tggatttttt tcccgatctg aacgccttgg tcgatactgc caccgccttg     600

tacgaggaag agctaaccgg gcgagagcat tgtagtccac atcatactgc tatccgccag     660

gctctggtct gctgggacga attgaccaag ttaattgcat ggatgagctc caatattact     720

agtgaagagg gtaatgcaaa ccctaatgcg aacccgaacg ctaaccctaa tgccaatcct     780

aacgctaatc ccaatgccaa cccgaatgca aacccaaatg cgaatccgaa tgctaacccg     840

aacgctaacc cgaatgcgaa tccaaacgcg aaccccaacg caaatccgaa tgcaaaccct     900

aatgcaaatc caggtgaaga ggagcaggtc cgcacgatca ttgttaacca cgtcaacgat     960

acctggggcc taaaggttcg ccaatctttg tggttccatc tgtcgtgcct gacctttggg    1020

caacacaccg tccaggagtt cctggtgagc ttcggcgttt ggatccgcac cccagcaccc    1080

taccgcccgc caaatgctcc cattttaagt accttgcccg aacacaccgt gattcaccac    1140

catcatcacc actaa                                                     1155


<210> SEQ ID NO 29
<211> LENGTH: 384
<212> TYPE: PRT
<213> ORGANISM: Artificial Sequence
<220> FEATURE:
<223> OTHER INFORMATION: Malaria vaccine; P. falciparum CSP B cell
      epitope in tandem WHcAg dimer

<400> SEQUENCE: 29

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
```

```
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Gly Gly Ser Gly Gly Ser Gly Gly Ser Gly Gly
145                 150                 155                 160

Ser Gly Gly Ser Asp Ile Asp Pro Tyr Lys Glu Phe Gly Ser Ser Tyr
                165                 170                 175

Gln Leu Leu Asn Phe Leu Pro Leu Asp Phe Phe Pro Asp Leu Asn Ala
            180                 185                 190

Leu Val Asp Thr Ala Thr Ala Leu Tyr Glu Glu Glu Leu Thr Gly Arg
        195                 200                 205

Glu His Cys Ser Pro His His Thr Ala Ile Arg Gln Ala Leu Val Cys
    210                 215                 220

Trp Asp Glu Leu Thr Lys Leu Ile Ala Trp Met Ser Ser Asn Ile Thr
225                 230                 235                 240

Ser Glu Glu Gly Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Ala Asn Pro Asn Ala Asn Pro Asn Ala Asn Pro Asn Ala Asn Pro
        275                 280                 285

Asn Ala Asn Pro Asn Ala Asn Pro Asn Ala Asn Pro Asn Ala Asn Pro
    290                 295                 300

Gly Glu Glu Glu Gln Val Arg Thr Ile Ile Val Asn His Val Asn Asp
305                 310                 315                 320

Thr Trp Gly Leu Lys Val Arg Gln Ser Leu Trp Phe His Leu Ser Cys
                325                 330                 335

Leu Thr Phe Gly Gln His Thr Val Gln Glu Phe Leu Val Ser Phe Gly
            340                 345                 350

Val Trp Ile Arg Thr Pro Ala Pro Tyr Arg Pro Pro Asn Ala Pro Ile
        355                 360                 365

Leu Ser Thr Leu Pro Glu His Thr Val Ile His His His His His His
    370                 375                 380
```

<210> SEQ ID NO 30
<211> LENGTH: 1971
<212> TYPE: DNA
<213> ORGANISM: Artificial Sequence
<220> FEATURE:
<223> OTHER INFORMATION: Malaria vaccine; P. falciparum CSP B cell
epitope + Salmonella fliC sequences in tandem WHcAg dimer

<400> SEQUENCE: 30

```
atggacatag atccctataa agaatttggt tcatcttatc agttgttgaa ttttctacct      60
ttggacttct ttcctgacct aaatgctttg gtggacactg ctactgcctt gtatgaagaa     120
gagctaacag gtcgagaaca ttgctctccg caccatacag ctattagaca agctttagta     180
tgctgggatg aattaactaa attgatagct tggatgagct ctaacataac ttctgaacaa     240
gtaagaacaa tcatagtaaa tcatgtcaat gatacctggg gattaaaggt gagacaaagt     300
ttatggtttc atttgtcatg tttgactttt ggacaacata cagttcaaga atttttagta     360
agttttggag tatggatcag aactccagct ccatatagac ctcctaatgc acccattctc     420
tccactcttc ccgaacatac agtcattggt ggaagtggag ggtctggtgg gtccgggggt     480
agtggtgggt ctgatatcga tccctacaaa gaattcggca gttcttatca gttactaaat     540
ttcctgccgc tggatttttt tcccgatctg aacgccttgg tcgatactgc caccgccttg     600
tacgaggaag agctaaccgg gcgagagcat tgtagtccac atcatactgc tatccgccag     660
gctctggtct gctgggacga attgaccaag ttaattgcat ggatgagctc caatattact     720
agtgaagagg gtgcgcaggt cattaacact aattcgctga gtttactaac acagaataat     780
ctaaacaaga gccaatccgc ccttggcacg gcgatcgagc ggctgagttc ggggctgcgt     840
atcaatagtg ccaaagatga cgcggccggc caggcgattg caaatcgttt tacggccaat     900
ataaaggggc ttacacaggc ttctcgtaat gccaacgacg gtatttccat tgcccaaaca     960
acggaaggcg cgctgaatga aatcaataat aatctgcagc gggtccggga gttagcggtg    1020
cagtctgcca actcaacaaa ttctcaatca gatctggatt ctatccaggc agaaataact    1080
cagaggctta atgaaatcga tcgtgtttct ggacaaaccc agtttaatgg tgtcaaggtc    1140
cttgctcagg acaacaccct gaccatccag gtaggcgcga acgatggaga aaccattgat    1200
attgatctga aacagattaa ttctcagact ctaggtcttg acaccttgaa tgtgcagggt    1260
tctaatgcaa accctaatgc gaacccgaac gctaacccta atgccaatcc taacgctaat    1320
cccaatgcca acccgaatgc aaacccaaat gcgaatccga atgctaaccc gaacgctaac    1380
ccgaatgcga atccaaacgc gaaccccaac gcaaatccga atgcaaaccc taatgcaaat    1440
ccaggttcta ccacaaccga gaatcctctg cagaaaatcg atgctgctct cgcgcaagtg    1500
gacactttgc gttcagattt gggagctgtg caaaatcgtt tcaacagcgc gattacaaac    1560
ctgggtaaca ccgtaaacaa tctgactagt gcccggagtc ggattgaaga tagcgattat    1620
gcgaccgaag tgtctaacat gagccgggcc caaatcttgc agcaagccgg cactagtgtt    1680
ctggcgcaag caaatcaggt cccccaaaac gttctcagcc ttctgcgggg tgaagaggag    1740
caggtccgca cgatcattgt taaccacgtc aacgatacct ggggcctaaa ggttcgccaa    1800
tctttgtggt tccatctgtc gtgcctgacc tttgggcaac acaccgtcca ggagttcctg    1860
gtgagcttcg gcgtttggat ccgcacccca gcaccctacc gcccgccaaa tgctcccatt    1920
ttaagtacct tgcccgaaca caccgtgatt caccaccatc atcaccacta a             1971
```

```
<210> SEQ ID NO 31
<211> LENGTH: 656
<212> TYPE: PRT
<213> ORGANISM: Artificial Sequence
<220> FEATURE:
<223> OTHER INFORMATION: Malaria vaccine; P. falciparum CSP B cell
      epitope + Salmonella fliC sequences in tandem WHcAg dimer

<400> SEQUENCE: 31

Met Asp Ile Asp Pro Tyr Lys Glu Phe Gly Ser Ser Tyr Gln Leu Leu
1               5                   10                  15
```

```
Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Gly Gly Ser Gly Gly Ser Gly Gly Ser Gly Gly
145                 150                 155                 160

Ser Gly Gly Ser Asp Ile Asp Pro Tyr Lys Glu Phe Gly Ser Ser Tyr
                165                 170                 175

Gln Leu Leu Asn Phe Leu Pro Leu Asp Phe Phe Pro Asp Leu Asn Ala
            180                 185                 190

Leu Val Asp Thr Ala Thr Ala Leu Tyr Glu Glu Glu Leu Thr Gly Arg
        195                 200                 205

Glu His Cys Ser Pro His His Thr Ala Ile Arg Gln Ala Leu Val Cys
    210                 215                 220

Trp Asp Glu Leu Thr Lys Leu Ile Ala Trp Met Ser Ser Asn Ile Thr
225                 230                 235                 240

Ser Glu Glu Gly Ala Gln Val Ile Asn Thr Asn Ser Leu Ser Leu Leu
                245                 250                 255

Thr Gln Asn Asn Leu Asn Lys Ser Gln Ser Ala Leu Gly Thr Ala Ile
            260                 265                 270

Glu Arg Leu Ser Ser Gly Leu Arg Ile Asn Ser Ala Lys Asp Asp Ala
        275                 280                 285

Ala Gly Gln Ala Ile Ala Asn Arg Phe Thr Ala Asn Ile Lys Gly Leu
    290                 295                 300

Thr Gln Ala Ser Arg Asn Ala Asn Asp Gly Ile Ser Ile Ala Gln Thr
305                 310                 315                 320

Thr Glu Gly Ala Leu Asn Glu Ile Asn Asn Asn Leu Gln Arg Val Arg
                325                 330                 335

Glu Leu Ala Val Gln Ser Ala Asn Ser Thr Asn Ser Gln Ser Asp Leu
            340                 345                 350

Asp Ser Ile Gln Ala Glu Ile Thr Gln Arg Leu Asn Glu Ile Asp Arg
        355                 360                 365

Val Ser Gly Gln Thr Gln Phe Asn Gly Val Lys Val Leu Ala Gln Asp
    370                 375                 380

Asn Thr Leu Thr Ile Gln Val Gly Ala Asn Asp Gly Glu Thr Ile Asp
385                 390                 395                 400

Ile Asp Leu Lys Gln Ile Asn Ser Gln Thr Leu Gly Leu Asp Thr Leu
                405                 410                 415

Asn Val Gln Gly Ser Asn Ala Asn Pro Asn Ala Asn Pro Asn Ala Asn
            420                 425                 430
```

Pro Asn Ala Asn Pro Asn Ala Asn Pro Asn Ala Asn Pro Asn Ala Asn
435 440 445

Pro Asn Ala Asn Pro Asn Ala Asn Pro Asn Ala Asn Pro Asn Ala Asn
450 455 460

Pro Asn Ala Asn Pro Asn Ala Asn Pro Asn Ala Asn Pro Asn Ala Asn
465 470 475 480

Pro Gly Ser Thr Thr Thr Glu Asn Pro Leu Gln Lys Ile Asp Ala Ala
485 490 495

Leu Ala Gln Val Asp Thr Leu Arg Ser Asp Leu Gly Ala Val Gln Asn
500 505 510

Arg Phe Asn Ser Ala Ile Thr Asn Leu Gly Asn Thr Val Asn Asn Leu
515 520 525

Thr Ser Ala Arg Ser Arg Ile Glu Asp Ser Asp Tyr Ala Thr Glu Val
530 535 540

Ser Asn Met Ser Arg Ala Gln Ile Leu Gln Gln Ala Gly Thr Ser Val
545 550 555 560

Leu Ala Gln Ala Asn Gln Val Pro Gln Asn Val Leu Ser Leu Leu Arg
565 570 575

Gly Glu Glu Glu Gln Val Arg Thr Ile Ile Val Asn His Val Asn Asp
580 585 590

Thr Trp Gly Leu Lys Val Arg Gln Ser Leu Trp Phe His Leu Ser Cys
595 600 605

Leu Thr Phe Gly Gln His Thr Val Gln Glu Phe Leu Val Ser Phe Gly
610 615 620

Val Trp Ile Arg Thr Pro Ala Pro Tyr Arg Pro Pro Asn Ala Pro Ile
625 630 635 640

Leu Ser Thr Leu Pro Glu His Thr Val Ile His His His His His His
645 650 655

<210> SEQ ID NO 32
<211> LENGTH: 621
<212> TYPE: DNA
<213> ORGANISM: Artificial Sequence
<220> FEATURE:
<223> OTHER INFORMATION: Canine parvovirus vaccine; 2L21 peptide epitope in 2x configuration; monomer WhcAg

<400> SEQUENCE: 32
atggacatag atccctataa agaatttggt tcatcttatc agttgttgaa ttttctacct 60
ttggacttct ttcctgacct aaatgctttg gtggacactg ctactgcctt gtatgaagaa 120
gagctaacag gtcgagaaca ttgctctccg caccatacag ctattagaca agctttagta 180
tgctgggatg aattaactaa attgatagct tggatgagct ctaacataac ttctgaagag 240
ggttctgacg gtgctgtgca gcccgatggc ggtcaacccg ctgttcgtaa tgaacgtgct 300
actggtggtg gctctagtga tggtgctgtt cagcctgacg gtggtcaacc tgctgtgcgc 360
aacgagcgtg caacaggagg tgaagaggaa caagtaagaa caatcatagt aaatcatgtc 420
aatgatacct ggggattaaa ggtgagacaa agtttatggt ttcatttgtc atgtttgact 480
tttggacaac atacagttca agaattttta gtaagttttg gagtatggat cagaactcca 540
gctccatata gacctcctaa tgcacccatt ctctccactc ttcccgaaca tacagtcatt 600
caccaccatc atcaccacta a 621

<210> SEQ ID NO 33
<211> LENGTH: 206
<212> TYPE: PRT

<213> ORGANISM: Artificial Sequence
<220> FEATURE:
<223> OTHER INFORMATION: Canine parvovirus vaccine; 2L21 peptide epitope
in 2x configuration; monomer WhcAg

<400> SEQUENCE: 33

Met Asp Ile Asp Pro Tyr Lys Glu Phe Gly Ser Ser Tyr Gln Leu Leu
1 5 10 15

Asn Phe Leu Pro Leu Asp Phe Phe Pro Asp Leu Asn Ala Leu Val Asp
20 25 30

Thr Ala Thr Ala Leu Tyr Glu Glu Glu Leu Thr Gly Arg Glu His Cys
35 40 45

Ser Pro His His Thr Ala Ile Arg Gln Ala Leu Val Cys Trp Asp Glu
50 55 60

Leu Thr Lys Leu Ile Ala Trp Met Ser Ser Asn Ile Thr Ser Glu Glu
65 70 75 80

Gly Ser Asp Gly Ala Val Gln Pro Asp Gly Gly Gln Pro Ala Val Arg
85 90 95

Asn Glu Arg Ala Thr Gly Gly Gly Ser Ser Asp Gly Ala Val Gln Pro
100 105 110

Asp Gly Gly Gln Pro Ala Val Arg Asn Glu Arg Ala Thr Gly Gly Glu
115 120 125

Glu Glu Gln Val Arg Thr Ile Ile Val Asn His Val Asn Asp Thr Trp
130 135 140

Gly Leu Lys Val Arg Gln Ser Leu Trp Phe His Leu Ser Cys Leu Thr
145 150 155 160

Phe Gly Gln His Thr Val Gln Glu Phe Leu Val Ser Phe Gly Val Trp
165 170 175

Ile Arg Thr Pro Ala Pro Tyr Arg Pro Pro Asn Ala Pro Ile Leu Ser
180 185 190

Thr Leu Pro Glu His Thr Val Ile His His His His His His
195 200 205

<210> SEQ ID NO 34
<211> LENGTH: 717
<212> TYPE: DNA
<213> ORGANISM: Artificial Sequence
<220> FEATURE:
<223> OTHER INFORMATION: Canine parvovirus vaccine; 3L17 peptide epitope
in 4x configuration; monomer WhcAg

<400> SEQUENCE: 34
atggacatag atccctataa agaatttggt tcatcttatc agttgttgaa ttttctacct 60
ttggacttct ttcctgacct aaatgctttg gtggacactg ctactgcctt gtatgaagaa 120
gagctaacag gtcgagaaca ttgctctccg caccatacag ctattagaca agctttagta 180
tgctgggatg aattaactaa attgatagct tggatgagct ctaacataac ttctgaagag 240
ggtgacggtg ctgtgcagcc cgatggcggt caacccgctg ttcgtaatga acgtggtggc 300
tctgatggtg ctgttcagcc tgacggtggt caacctgctg tgcgcaacga gcgtggtggt 360
tccgacggtg ccgttcaacc cgacggtggc caacccgccg tgcgtaatga gcgcggtggt 420
tctgacggcg ctgtgcaacc tgacggcggt cagcccgccg ttcgtaacga gcgtggtgaa 480
gaggaacaag taagaacaat catagtaaat catgtcaatg atacctgggg attaaaggtg 540
agacaaagtt tatggtttca tttgtcatgt ttgacttttg gacaacatac agttcaagaa 600
tttttagtaa gttttggagt atggatcaga actccagctc catatagacc tcctaatgca 660
cccattctct ccactcttcc cgaacataca gtcattcacc accatcatca ccactaa 717

<210> SEQ ID NO 35
<211> LENGTH: 238
<212> TYPE: PRT
<213> ORGANISM: Artificial Sequence
<220> FEATURE:
<223> OTHER INFORMATION: Canine parvovirus vaccine; 3L17 peptide epitope in 4x configuration; monomer WhcAg

<400> SEQUENCE: 35

Met Asp Ile Asp Pro Tyr Lys Glu Phe Gly Ser Ser Tyr Gln Leu Leu
1 5 10 15

Asn Phe Leu Pro Leu Asp Phe Phe Pro Asp Leu Asn Ala Leu Val Asp
20 25 30

Thr Ala Thr Ala Leu Tyr Glu Glu Glu Leu Thr Gly Arg Glu His Cys
35 40 45

Ser Pro His His Thr Ala Ile Arg Gln Ala Leu Val Cys Trp Asp Glu
50 55 60

Leu Thr Lys Leu Ile Ala Trp Met Ser Ser Asn Ile Thr Ser Glu Glu
65 70 75 80

Gly Asp Gly Ala Val Gln Pro Asp Gly Gly Gln Pro Ala Val Arg Asn
85 90 95

Glu Arg Gly Gly Ser Asp Gly Ala Val Gln Pro Asp Gly Gly Gln Pro
100 105 110

Ala Val Arg Asn Glu Arg Gly Gly Ser Asp Gly Ala Val Gln Pro Asp
115 120 125

Gly Gly Gln Pro Ala Val Arg Asn Glu Arg Gly Gly Ser Asp Gly Ala
130 135 140

Val Gln Pro Asp Gly Gly Gln Pro Ala Val Arg Asn Glu Arg Gly Glu
145 150 155 160

Glu Glu Gln Val Arg Thr Ile Ile Val Asn His Val Asn Asp Thr Trp
165 170 175

Gly Leu Lys Val Arg Gln Ser Leu Trp Phe His Leu Ser Cys Leu Thr
180 185 190

Phe Gly Gln His Thr Val Gln Glu Phe Leu Val Ser Phe Gly Val Trp
195 200 205

Ile Arg Thr Pro Ala Pro Tyr Arg Pro Pro Asn Ala Pro Ile Leu Ser
210 215 220

Thr Leu Pro Glu His Thr Val Ile His His His His His His
225 230 235

<210> SEQ ID NO 36
<211> LENGTH: 1152
<212> TYPE: DNA
<213> ORGANISM: Artificial Sequence
<220> FEATURE:
<223> OTHER INFORMATION: IHNV vaccine; E1+E2 epitopes in tandem WHcAg dimer

<400> SEQUENCE: 36
atggacatag atccctataa agaatttggt tcatcttatc agttgttgaa ttttctacct 60
ttggacttct ttcctgacct aaatgctttg gtggacactg ctactgcctt gtatgaagaa 120
gagctaacag gtcgagaaca ttgctctccg caccatacag ctattagaca agctttagta 180
tgctgggatg aattaactaa attgatagct tggatgagct ctaacataac ttctgaacaa 240
gtaagaacaa tcatagtaaa tcatgtcaat gatacctggg gattaaaggt gagacaaagt 300

```
ttatggtttc atttgtcatg tttgactttt ggacaacata cagttcaaga atttttagta    360

agttttggag tatggatcag aactccagct ccatatagac ctcctaatgc acccattctc    420

tccactcttc ccgaacatac agtcattggt ggaagtggag ggtctggtgg gtccgggggt    480

agtggtgggt ctgatatcga tccctacaaa gaattcggca gttcttatca gttactaaat    540

ttcctgccgc tggatttttt tcccgatctg aacgccttgg tcgatactgc caccgccttg    600

tacgaggaag agctaaccgg gcgagagcat tgtagtccac atcatactgc tatccgccag    660

gctctggtct gctgggacga attgaccaag ttaattgcat ggatgagctc caatattact    720

agtcctggtg gaagtggaga cgatgaaaat cgtggcttga tcgcttatcc taccagtatc    780

cgttccttga gtgtcggcgg aagtggaggg tctgatctga ttagcgtggt ttacaacagt    840

ggaagcgaga tcctgtcgtt tcctggtgga tcaggggagc aggtccgcac gatcattgtt    900

aaccacgtca acgatacctg gggcctaaag gttcgccaat ctttgtggtt ccatctgtcg    960

tgcctgacct ttgggcaaca caccgtccag gagttcctgg tgagcttcgg cgtttggatc   1020

cgcaccccag caccctaccg cccgccaaat gctcccattt taagtacctt gcccgaacac   1080

accgtgattg agcaaaaatt aattagcgag gaagacctag aacaaaaact gatctctgaa   1140

gaggatctgt aa                                                       1152
```

<210> SEQ ID NO 37
<211> LENGTH: 383
<212> TYPE: PRT
<213> ORGANISM: Artificial Sequence
<220> FEATURE:
<223> OTHER INFORMATION: IHNV vaccine; E1+E2 epitopes in tandem WHcAg dimer

<400> SEQUENCE: 37

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Gly Gly Ser Gly Gly Ser Gly Gly Ser Gly Gly
145                 150                 155                 160

Ser Gly Gly Ser Asp Ile Asp Pro Tyr Lys Glu Phe Gly Ser Ser Tyr
                165                 170                 175

Gln Leu Leu Asn Phe Leu Pro Leu Asp Phe Phe Pro Asp Leu Asn Ala
            180                 185                 190

Leu Val Asp Thr Ala Thr Ala Leu Tyr Glu Glu Glu Leu Thr Gly Arg
        195                 200                 205
```

```
Glu His Cys Ser Pro His His Thr Ala Ile Arg Gln Ala Leu Val Cys
    210                 215                 220

Trp Asp Glu Leu Thr Lys Leu Ile Ala Trp Met Ser Ser Asn Ile Thr
225                 230                 235                 240

Ser Pro Gly Gly Ser Gly Asp Asp Glu Asn Arg Gly Leu Ile Ala Tyr
                245                 250                 255

Pro Thr Ser Ile Arg Ser Leu Ser Val Gly Gly Ser Gly Gly Ser Asp
            260                 265                 270

Leu Ile Ser Val Val Tyr Asn Ser Gly Ser Glu Ile Leu Ser Phe Pro
        275                 280                 285

Gly Gly Ser Gly Glu Gln Val Arg Thr Ile Ile Val Asn His Val Asn
    290                 295                 300

Asp Thr Trp Gly Leu Lys Val Arg Gln Ser Leu Trp Phe His Leu Ser
305                 310                 315                 320

Cys Leu Thr Phe Gly Gln His Thr Val Gln Glu Phe Leu Val Ser Phe
                325                 330                 335

Gly Val Trp Ile Arg Thr Pro Ala Pro Tyr Arg Pro Pro Asn Ala Pro
            340                 345                 350

Ile Leu Ser Thr Leu Pro Glu His Thr Val Ile Glu Gln Lys Leu Ile
        355                 360                 365

Ser Glu Glu Asp Leu Glu Gln Lys Leu Ile Ser Glu Glu Asp Leu
    370                 375                 380
```

<210> SEQ ID NO 38
<211> LENGTH: 1356
<212> TYPE: DNA
<213> ORGANISM: Artificial Sequence
<220> FEATURE:
<223> OTHER INFORMATION: IHNV vaccine; DIII epitope in tandem WHcAg dimer

<400> SEQUENCE: 38

```
atggacatag atccctataa agaatttggt tcatcttatc agttgttgaa ttttctacct      60

ttggacttct ttcctgacct aaatgctttg gtggacactg ctactgcctt gtatgaagaa     120

gagctaacag gtcgagaaca ttgctctccg caccatacag ctattagaca agctttagta     180

tgctgggatg aattaactaa attgatagct tggatgagct ctaacataac ttctgaacaa     240

gtaagaacaa tcatagtaaa tcatgtcaat gatacctggg gattaaaggt gagacaaagt     300

ttatggtttc atttgtcatg tttgactttt ggacaacata cagttcaaga atttttagta     360

agttttggag tatggatcag aactccagct ccatatagac ctcctaatgc acccattctc     420

tccactcttc ccgaacatac agtcattggt ggaagtggag ggtctggtgg gtccgggggt     480

agtggtgggt ctgatatcga tccctacaaa gaattcggca gttcttatca gttactaaat     540

ttcctgccgc tggatttttt tcccgatctg aacgccttgg tcgatactgc caccgccttg     600

tacgaggaag agctaaccgg gcgagagcat tgtagtccac atcatactgc tatccgccag     660

gctctggtct gctgggacga attgaccaag ttaattgcat ggatgagctc caatattact     720

agtcctggtg gaagtggaga cgatgagaac agggggctaa ttgcctatcc cacatccatc     780

cggtccctgt cagtcggaaa cgacggtggc agtggagggt ctagccaaga gataaaagct     840

cacctctttg ttgataaaat ctccaatcga gtcgtgaagg caacgagcta cggacaccac     900

ccctggggac tgcatcaggc ctgtatgatt gaattctgtg ggcaacagtg gatacggaca     960

gatctcggtg acctaatatc tgtcgtatac aattctggat cagaaatcct ctcgttcccg    1020
```

```
aagtgtgaag acaagaccgt gggaccagca gagggtggcg gtccagcagg tggatcaggg   1080

gagcaggtcc gcacgatcat tgttaaccac gtcaacgata cctggggcct aaaggttcgc   1140

caatctttgt ggttccatct gtcgtgcctg acctttgggc aacacaccgt ccaggagttc   1200

ctggtgagct tcggcgtttg gatccgcacc ccagcaccct accgcccgcc aaatgctccc   1260

attttaagta ccttgcccga acacaccgtg attgagcaaa aattaattag cgaggaagac   1320

ctagaacaaa aactgatctc tgaagaggat ctgtaa                             1356
```

<210> SEQ ID NO 39
<211> LENGTH: 451
<212> TYPE: PRT
<213> ORGANISM: Artificial Sequence
<220> FEATURE:
<223> OTHER INFORMATION: IHNV vaccine; DIII epitope in tandem WHcAg dimer

<400> SEQUENCE: 39

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Gly Gly Ser Gly Gly Ser Gly Gly Ser Gly Gly
145                 150                 155                 160

Ser Gly Gly Ser Asp Ile Asp Pro Tyr Lys Glu Phe Gly Ser Ser Tyr
                165                 170                 175

Gln Leu Leu Asn Phe Leu Pro Leu Asp Phe Phe Pro Asp Leu Asn Ala
            180                 185                 190

Leu Val Asp Thr Ala Thr Ala Leu Tyr Glu Glu Glu Leu Thr Gly Arg
        195                 200                 205

Glu His Cys Ser Pro His His Thr Ala Ile Arg Gln Ala Leu Val Cys
    210                 215                 220

Trp Asp Glu Leu Thr Lys Leu Ile Ala Trp Met Ser Ser Asn Ile Thr
225                 230                 235                 240

Ser Pro Gly Gly Ser Gly Asp Asp Glu Asn Arg Gly Leu Ile Ala Tyr
                245                 250                 255

Pro Thr Ser Ile Arg Ser Leu Ser Val Gly Asn Asp Gly Gly Ser Gly
            260                 265                 270

Gly Ser Ser Gln Glu Ile Lys Ala His Leu Phe Val Asp Lys Ile Ser
        275                 280                 285

Asn Arg Val Val Lys Ala Thr Ser Tyr Gly His His Pro Trp Gly Leu
    290                 295                 300
```

His Gln Ala Cys Met Ile Glu Phe Cys Gly Gln Gln Trp Ile Arg Thr
305 310 315 320

Asp Leu Gly Asp Leu Ile Ser Val Val Tyr Asn Ser Gly Ser Glu Ile
325 330 335

Leu Ser Phe Pro Lys Cys Glu Asp Lys Thr Val Gly Pro Ala Glu Gly
340 345 350

Gly Gly Pro Ala Gly Gly Ser Gly Glu Gln Val Arg Thr Ile Ile Val
355 360 365

Asn His Val Asn Asp Thr Trp Gly Leu Lys Val Arg Gln Ser Leu Trp
370 375 380

Phe His Leu Ser Cys Leu Thr Phe Gly Gln His Thr Val Gln Glu Phe
385 390 395 400

Leu Val Ser Phe Gly Val Trp Ile Arg Thr Pro Ala Pro Tyr Arg Pro
405 410 415

Pro Asn Ala Pro Ile Leu Ser Thr Leu Pro Glu His Thr Val Ile Glu
420 425 430

Gln Lys Leu Ile Ser Glu Glu Asp Leu Glu Gln Lys Leu Ile Ser Glu
435 440 445

Glu Asp Leu
450

<210> SEQ ID NO 40
<211> LENGTH: 131
<212> TYPE: PRT
<213> ORGANISM: Lama glama

<400> SEQUENCE: 40

Gln Val Gln Leu Gln Glu Ser Gly Gly Gly Leu Val Gln Pro Gly Gly
1 5 10 15

Ser Leu Arg Leu Ser Cys Ala Ala Ser Glu Ser Thr Pro Ser Ile Asn
20 25 30

Thr Met Gly Trp Tyr Arg Gln Ala Pro Gly Lys Glu Arg Glu Leu Val
35 40 45

Ala Thr Ile Thr Ser Gly Gly Met Thr Asn Tyr Ala Asp Ser Val Lys
50 55 60

Gly Arg Phe Thr Ile Ser Arg Asp Asn Gly Lys Asn Thr Val Tyr Leu
65 70 75 80

Gln Met Asn Ser Leu Glu Pro Gly Asp Thr Ala Val Tyr Tyr Cys Asn
85 90 95

Leu Lys Arg Arg Asp Leu Gln Ala Arg Phe Gly Gly Tyr Trp Gly Gln
100 105 110

Gly Thr Gln Val Thr Val Ser Ser Glu Pro Lys Thr Gln Thr Thr Thr
115 120 125

Ser Gly Arg
130

<210> SEQ ID NO 41
<211> LENGTH: 132
<212> TYPE: PRT
<213> ORGANISM: Lama glama

<400> SEQUENCE: 41

Gln Val Lys Leu Gln Gln Ser Gly Gly Gly Leu Val Gln Pro Gly Gly
1 5 10 15

Ser Leu Arg Leu Ser Cys Ala Ala Ser Glu Ser Thr Ile Ser Ile Asn
20 25 30

```
Thr Leu Gly Trp Tyr Arg Gln Ala Pro Gly Asn Gln Arg Glu Leu Val
        35                  40                  45

Ala Thr Ile Thr Thr Gly Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Glu Pro Gly Asp Thr Ala Val Tyr Tyr Cys Asn
                85                  90                  95

Leu Lys Arg Arg Asp Leu Gln Ser Arg Phe Gly Gly Tyr Trp Gly Gln
            100                 105                 110

Gly Thr Gln Val Thr Val Ser Ser Glu Pro Gln Asp Thr Lys Thr Thr
        115                 120                 125

Thr Ser Gly Arg
    130


<210> SEQ ID NO 42
<211> LENGTH: 131
<212> TYPE: PRT
<213> ORGANISM: Lama glama

<400> SEQUENCE: 42

Gln Val Gln Leu Gln Gln Ser Gly Gly Gly Leu Val Gln Pro Gly Gly
1               5                   10                  15

Ser Leu Arg Leu Ser Cys Val Ala Ser Glu Ser Thr Val Ser Ile Asn
            20                  25                  30

Ile Met Gly Trp Tyr Arg Gln Ala Pro Gly Lys Gln Arg Glu Leu Val
        35                  40                  45

Ala Thr Ile Thr Thr Gly Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Glu Pro Glu Asp Thr Ala Val Tyr Tyr Cys Asn
                85                  90                  95

Leu Lys Arg Arg Asp Leu Gln Ala Arg Phe Gly Gly Tyr Trp Gly Gln
            100                 105                 110

Gly Thr Gln Val Thr Val Ser Ser Glu Pro Lys Thr Pro Lys Pro Thr
        115                 120                 125

Ser Gly Arg
    130


<210> SEQ ID NO 43
<211> LENGTH: 131
<212> TYPE: PRT
<213> ORGANISM: Lama glama

<400> SEQUENCE: 43

Gln Val Lys Leu Gln Gln Ser Gly Gly Gly Leu Val Gln Pro Gly Gly
1               5                   10                  15

Ser Leu Arg Leu Ser Cys Ala Ala Ser Glu Ser Thr Pro Ser Ile Asn
            20                  25                  30

Thr Met Gly Trp Tyr Arg Gln Ala Pro Gly Lys Glu Arg Glu Leu Val
        35                  40                  45

Ala Thr Ile Thr Ser Gly Gly Met Thr Asn Tyr Ala Asp Ser Val Lys
    50                  55                  60

Gly Arg Phe Thr Ile Ser Arg Asp Asn Gly Lys Asn Thr Val Tyr Leu
65                  70                  75                  80
```

```
Gln Met Asn Ser Leu Glu Pro Gly Asp Thr Ala Val Tyr Tyr Cys Asn
                85                  90                  95

Leu Lys Arg Arg Asp Leu Gln Ala Arg Phe Gly Gly Tyr Trp Gly Gln
            100                 105                 110

Gly Thr Gln Val Thr Val Ser Ser Glu Pro Lys Thr Pro Lys Pro Gln
        115                 120                 125

Ser Gly Arg
    130


<210> SEQ ID NO 44
<211> LENGTH: 132
<212> TYPE: PRT
<213> ORGANISM: Lama glama

<400> SEQUENCE: 44

Gln Val Lys Leu Gln Gln Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ala Ile Ala Ala Gly Gly Ala Val Thr Lys Tyr Ala Asp Ser Val
    50                  55                  60

Lys Gly Arg Phe Thr Ile Ser Arg Asp Asn Ala Arg Asp Thr Leu Tyr
65                  70                  75                  80

Leu Gln Met Asn Ser Leu Lys Pro Glu Asp Thr Ala Val Tyr Tyr Cys
                85                  90                  95

Ala Lys Pro Arg Asp Phe Trp Tyr Ser Pro Glu Phe Asp Phe Arg Gly
            100                 105                 110

Gln Gly Thr Gln Val Thr Val Ser Ser Glu Pro Lys Asn Gln Asn Gln
        115                 120                 125

Thr Ser Gly Arg
    130


<210> SEQ ID NO 45
<211> LENGTH: 133
<212> TYPE: PRT
<213> ORGANISM: Lama glama

<400> SEQUENCE: 45

Gln Val Gln Leu Gln Gln Ser Gly Gly Gly Leu Val Gln Ala Gly Asp
1               5                   10                  15

Ser Leu Thr Ile Ser Cys Ala Ser Ser Leu Phe Thr Phe Ser Thr Ser
            20                  25                  30

Thr Met Gly Trp Phe Arg Gln Ala Pro Gly Lys Glu Arg Glu Phe Val
        35                  40                  45

Ala Ala Ile Lys Ser Ser Gly Ser Ser Met Tyr Tyr Ala Asp Ser Val
    50                  55                  60

Gln Gly Arg Phe Thr Ile Ser Arg Asp Asn Ala Lys Lys Thr Val Thr
65                  70                  75                  80

Leu Gln Met Asn Ser Leu Lys Pro Glu Asp Thr Ala Val Tyr Tyr Cys
                85                  90                  95

Ala Lys Gly Val Tyr Gly Ser Arg Arg Ser Ala Asp Phe Gly Ser Trp
            100                 105                 110

Gly Gln Gly Thr Gln Val Thr Val Ser Ser Glu Pro Lys Thr Pro Lys
        115                 120                 125
```

Pro Gln Ser Gly Arg
    130

<210> SEQ ID NO 46
<211> LENGTH: 133
<212> TYPE: PRT
<213> ORGANISM: Lama glama

<400> SEQUENCE: 46

Gln Val Gln Leu Gln Gln Ser Gly Gly Gly Leu Val Gln Ala Gly Asp
1               5                   10                  15

Ser Leu Arg Ile Ser Cys Ala Ala Ser Leu Phe Thr Phe Ser Thr Ser
            20                  25                  30

Thr Met Gly Trp Phe Arg Gln Ala Pro Gly Lys Glu Arg Glu Phe Val
        35                  40                  45

Ala Ala Ile Arg Ser Thr Gly Asp Ser Met Tyr Tyr Ala Asp Ser Val
    50                  55                  60

Gln Gly Arg Phe Thr Ile Ser Arg Asp Asn Ala Lys Lys Met Val Tyr
65                  70                  75                  80

Leu Gln Met Asn Asn Leu Lys Pro Glu Asp Thr Ala Val Tyr Tyr Cys
                85                  90                  95

Ala Lys Gly Val Tyr Gly Ser Arg Arg Ser Ala Asp Phe Gly Ser Trp
            100                 105                 110

Gly Gln Gly Thr Gln Val Thr Val Ser Ser Glu Pro Lys Thr Pro Lys
        115                 120                 125

Pro Gln Ser Gly Arg
    130

<210> SEQ ID NO 47
<211> LENGTH: 133
<212> TYPE: PRT
<213> ORGANISM: Lama glama

<400> SEQUENCE: 47

Asp Val Gln Leu Gln Ala Ser Gly Gly Gly Leu Val Gln Ala Gly Gly
1               5                   10                  15

Ser Leu Arg Ile Ser Cys Thr Ala Asp Gly Tyr Thr Phe Ser Thr Ser
            20                  25                  30

Thr Met Gly Trp Phe Arg Gln Ala Pro Gly Lys Glu Arg Glu Phe Val
        35                  40                  45

Ala Ala Ile Lys Ser Asp Gly Ser Ile Met Tyr Tyr Ala Asp Ser Val
    50                  55                  60

Ala Gly Arg Phe Ile Ile Ser Arg Asp Asn Ala Lys Lys Met Val Phe
65                  70                  75                  80

Leu Gln Met Asp Arg Leu Lys Pro Glu Asp Thr Ala Val Tyr Tyr Cys
                85                  90                  95

Ala Lys Gly Val Tyr Gly Ser Arg Arg Ser Ala Asp Phe Gly Trp Trp
            100                 105                 110

Gly Gln Gly Thr Gln Val Thr Val Ser Ser Glu Pro Lys Thr Pro Lys
        115                 120                 125

Pro Gln Ser Gly Arg
    130

<210> SEQ ID NO 48
<211> LENGTH: 134
<212> TYPE: PRT
<213> ORGANISM: Lama glama

<400> SEQUENCE: 48

```
Gln Val Lys Leu Gln Glu Ser Gly Gly Gly Leu Val Gln Ala Gly Glu
1               5                   10                  15

Ser Leu Arg Leu Ser Cys Ala Ala Ser Gly Ser Asn Phe Ser Ile Asn
            20                  25                  30

Gly Val Gly Trp Tyr Arg Gln Ala Pro Gly Lys Gln Arg Glu Leu Val
        35                  40                  45

Ala Gly Ile Thr Asn Gly Gly Tyr Thr Ser Tyr Ala Asp Ser Val Lys
    50                  55                  60

Gly Arg Phe Thr Ile Ser Thr Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Asn Phe Gln Ile His Arg Ser Gly Ala Asp Tyr Val Arg Asn Tyr
            100                 105                 110

Trp Gly Gln Gly Thr Gln Val Thr Val Ser Ala Glu Pro Arg Thr Lys
        115                 120                 125

Thr Thr Thr Ser Gly Arg
    130
```

<210> SEQ ID NO 49
<211> LENGTH: 134
<212> TYPE: PRT
<213> ORGANISM: Lama glama

<400> SEQUENCE: 49

```
Gln Val Lys Leu Gln Gln Ser Gly Gly Gly Leu Val Gln Ala Gly Gly
1               5                   10                  15

Ser Leu Arg Leu Ser Cys Ala Ala Ser Gly Asn Phe Phe Thr Leu Asn
            20                  25                  30

Gly Val Ala Trp Tyr Arg Gln Ala Pro Gly Lys Gln Arg Glu Leu Val
        35                  40                  45

Ala Gly Ile Thr Ser Gly Gly Trp Thr Asn Tyr Ala Asp Ser Val Lys
    50                  55                  60

Gly Arg Phe Thr Ile Ser Ala Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Asn Leu Gln Ile His Arg Asp Ser Ser Gly Asp Val Arg Asn Val
            100                 105                 110

Trp Gly Gln Gly Thr Gln Val Thr Val Ser Ser Glu Pro Lys Thr Pro
        115                 120                 125

Lys Pro Gln Ser Gly Arg
    130
```

<210> SEQ ID NO 50
<211> LENGTH: 136
<212> TYPE: PRT
<213> ORGANISM: Lama glama

<400> SEQUENCE: 50

```
Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Phe Phe Ser Ile Asn
            20                  25                  30
```

Gly Val Gly Trp Tyr Arg Gln Ala Pro Gly Lys Gln Arg Glu Leu Val
35 40 45

Ala Gly Ile Thr Asn Gly Gly Phe Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Asn
85 90 95

Ala Asn Leu Gln Ile Ser Arg Ser Glu Asp Gly Ala Tyr Val Val Arg
100 105 110

Asn Tyr Trp Gly Gln Gly Thr Gln Ile Thr Val Ser Ser Glu Pro Lys
115 120 125

Thr Pro Lys Pro Gln Ser Gly Arg
130 135

<210> SEQ ID NO 51
<211> LENGTH: 134
<212> TYPE: PRT
<213> ORGANISM: Lama glama

<400> SEQUENCE: 51

Asp Val Gln Leu Gln Ala Ser Gly Gly Gly Leu Val Gln Ala Gly Gly
1 5 10 15

Ser Leu Arg Leu Ser Cys Ala Ala Ser Gly Ser Gly Phe Ser Ile Asn
20 25 30

Gly Val Gly Trp Tyr Arg Gln Thr Pro Gly Arg Gln Arg Glu Leu Val
35 40 45

Ala Gly Ile Thr Ile Gly Gly Tyr Thr Asn Tyr Ala Asp Ser Val Lys
50 55 60

Gly Arg Phe Thr Ile Ser Ser Asp Asn Ala Lys Asn Thr Val Tyr Leu
65 70 75 80

Gln Met Asn Ser Leu Lys Pro Glu Asp Thr Ala Val Tyr Tyr Cys Asn
85 90 95

Ala Asn Leu Gln Phe Tyr Arg Gly Gly Gly Ser Asp Val Lys Asn Tyr
100 105 110

Trp Gly Gln Gly Thr Gln Val Thr Val Ser Ser Glu Pro Lys Thr Pro
115 120 125

Lys Pro Gln Ser Gly Arg
130

<210> SEQ ID NO 52
<211> LENGTH: 135
<212> TYPE: PRT
<213> ORGANISM: Lama glama

<400> SEQUENCE: 52

Gln Val Gln Leu Gln Glu Ser Gly Gly Gly Leu Val Gln Ala Gly Gly
1 5 10 15

Ser Leu Arg Leu Ser Cys Ala Ala Ser Gly Leu Thr Phe Ser Ser Tyr
20 25 30

Ala Met Gly Trp Phe His Gln Ala Pro Gly Lys Glu Arg Glu Phe Val
35 40 45

Ala Ala Ile Asn Trp Ser Gly Arg Asp Thr Tyr Tyr Ala Asp Ser Val
50 55 60

Lys Gly Arg Phe Thr Ile Ser Arg Asp Asn Arg Lys Asn Thr Val Tyr
65 70 75 80

```
Leu Gln Met Asn Ser Leu Lys Pro Glu Asp Thr Ala Val Tyr Tyr Cys
                85                  90                  95

Ala Ala Ala Glu Phe Phe Ser Ser Gly Asp Pro Leu Pro Gly Met Asp
            100                 105                 110

Tyr Trp Gly Lys Gly Thr Leu Val Thr Val Ser Ser Glu Pro Lys Thr
        115                 120                 125

Gln Asn His Asn Ser Gly Arg
    130                 135


<210> SEQ ID NO 53
<211> LENGTH: 135
<212> TYPE: PRT
<213> ORGANISM: Lama glama

<400> SEQUENCE: 53

Gln Val Lys Leu Gln Gln Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Asn Trp Ser Gly Arg Asp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Thr Asn Ser Leu Lys Pro Glu Asp Thr Ala Val Tyr Tyr Cys
                85                  90                  95

Ala Ala Ala Glu Phe Leu Pro Thr Gln Arg Ser Pro Arg Glu Tyr Asp
            100                 105                 110

Tyr Trp Gly Leu Gly Thr Gln Val Thr Val Ser Ser Glu Pro Lys Thr
        115                 120                 125

Pro Lys Pro Gln Ser Gly Arg
    130                 135


<210> SEQ ID NO 54
<211> LENGTH: 136
<212> TYPE: PRT
<213> ORGANISM: Lama glama

<400> SEQUENCE: 54

Gln Val Lys Leu Gln Gln Ser Gly Gly Gly Leu Val Gln Ala Gly Gly
1               5                   10                  15

Ser Leu Arg Leu Ser Cys Ala Ala Ser Gly Tyr Ala Phe Asn Thr Tyr
            20                  25                  30

Thr Met Ala Trp Phe Arg Gln Ala Pro Gly Lys Glu Arg Glu Phe Val
        35                  40                  45

Ala Leu Val Gly Met Lys Val Asp Gly Lys Ile Tyr Ala Asp Ser Val
    50                  55                  60

Lys Gly Arg Phe Thr Ile Ser Arg Asp Asn Glu Gln Lys Thr Val Leu
65                  70                  75                  80

Leu Glu Met Asn His Leu Glu Pro Glu Asp Thr Ala Ile Tyr Tyr Cys
                85                  90                  95

Ala Ala Ser Arg Arg Phe Trp Thr Ala Ala Leu Asn Gly Ala Asp Tyr
            100                 105                 110

Pro Tyr Trp Gly Gln Gly Thr Gln Val Thr Val Ser Ser Glu Pro Lys
        115                 120                 125
```

Thr Pro Lys Pro Gln Ser Gly Arg
130 135

<210> SEQ ID NO 55
<211> LENGTH: 129
<212> TYPE: PRT
<213> ORGANISM: Lama glama

<400> SEQUENCE: 55

Gln Val Lys Leu Gln Gln Ser Gly Gly Gly Leu Val Gln Ala Gly Gly
1 5 10 15

Ser Leu Arg Leu Ser Cys Ala Ala Ser Gly Ile Val Phe Ser Phe Asn
20 25 30

Ala Met Gly Trp Tyr Arg Val Pro Pro Gly Lys Gln Arg Glu Leu Val
35 40 45

Ala Asp Ile Leu Lys Ser Gly Gly Thr Asn Val Val Asp Ser Val Lys
50 55 60

Gly Arg Phe Ala Ile Ser Arg Asp Ser Ala Gln Asn Thr Leu Tyr Leu
65 70 75 80

Gln Met Asn Arg Leu Lys Pro Glu Asp Thr Ala Val Tyr Tyr Cys Asn
85 90 95

Ala Arg Asp Trp Ser Asp Gly Phe Asp Glu Tyr Trp Gly Gln Gly Thr
100 105 110

Gln Val Thr Val Ser Ser Glu Pro Lys Thr Pro Lys Pro Gln Ser Gly
115 120 125

Arg

<210> SEQ ID NO 56
<211> LENGTH: 135
<212> TYPE: PRT
<213> ORGANISM: Lama glama

<400> SEQUENCE: 56

Gln Val Gln Leu Gln Gln Ser Gly Gly Gly Leu Val Gln Ala Gly Gly
1 5 10 15

Ser Leu Arg Leu Ser Cys Ser Ala Ser Gly Arg Thr Phe Ser Asn Tyr
20 25 30

Val Met Gly Trp Phe Arg Gln Ala Pro Gly Lys Glu Arg Glu Phe Val
35 40 45

Ala Thr Ile Ser Ala Ser Gly Gly Ser Thr Tyr Cys Ala Asp Ser Val
50 55 60

Glu Gly Arg Phe Thr Ile Ser Arg Asp Asn Ala Lys Asn Thr Ala Tyr
65 70 75 80

Leu Gln Met Asn Asn Leu Glu Pro Glu Asp Thr Ala Val Tyr Tyr Cys
85 90 95

Ala Ser Gly Pro Arg Ala Asn Ala Ser Ile Arg Arg Ser Gly Tyr Asn
100 105 110

Tyr Trp Gly Gln Gly Thr Gln Val Thr Val Ser Ser Glu Pro Lys Thr
115 120 125

Pro Lys Pro Gln Ser Gly Arg
130 135

<210> SEQ ID NO 57
<211> LENGTH: 136
<212> TYPE: PRT
<213> ORGANISM: Lama glama

<400> SEQUENCE: 57

```
Gln Val Gln Leu Gln Gln Ser Gly Gly Gly Leu Val Gln Ala Gly Gly
1               5                   10                  15

Ser Leu Arg Leu Ser Cys Ala Ala Ser Gly Leu Ala Phe Ser Ser Tyr
            20                  25                  30

Ala Ile Thr Trp Leu Arg Gln Ala Pro Gly Thr Glu Arg Glu Phe Val
        35                  40                  45

Ala Leu Ile Ser Gly Ser Gly Ser Ser Thr Tyr Tyr Ala Asp Ser Val
    50                  55                  60

Lys Gly Arg Phe Thr Ile Ser Arg Asn Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Thr Ala Ser Glu Phe Leu Leu His Pro Pro Pro Pro Asn Gln Lys Tyr
            100                 105                 110

Asp Tyr Trp Gly Gln Gly Thr Gln Val Thr Val Ser Ser Glu Pro Lys
        115                 120                 125

Thr Pro Lys His Thr Ser Gly Arg
    130                 135
```

<210> SEQ ID NO 58
<211> LENGTH: 135
<212> TYPE: PRT
<213> ORGANISM: Lama glama

<400> SEQUENCE: 58

```
Gln Val Gln Leu Gln Gln Ser Gly Gly Gly Leu Val Arg Ala Gly Gly
1               5                   10                  15

Ser Leu Arg Leu Ser Cys Ser Ala Ser Gly Arg Thr Phe Gly Asn Glu
            20                  25                  30

Val Met Gly Trp Phe Arg Gln Ala Pro Gly Lys Glu Arg Glu Phe Val
        35                  40                  45

Ala Ala Ile Asn Trp Ser Ser Gly Asn Thr Tyr Tyr Arg Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Glu Pro Glu Asp Thr Ala Val Tyr Tyr Cys
                85                  90                  95

Ala Ala Arg Ser Arg Pro Ala Ile Ser Thr Arg Arg Pro Asp Tyr Phe
            100                 105                 110

Ala Trp Gly Gln Gly Thr Gln Val Thr Val Ser Ser Glu Pro Lys Thr
        115                 120                 125

Pro Lys Pro Gln Ser Gly Arg
    130                 135
```

<210> SEQ ID NO 59
<211> LENGTH: 133
<212> TYPE: PRT
<213> ORGANISM: Lama glama

<400> SEQUENCE: 59

```
Gln Val Gln Leu Gln Gln Ser Gly Gly Gly Leu Val Gln Ala Gly Gly
1               5                   10                  15

Ser Leu Arg Leu Ser Cys Thr Ala Ser Gly Arg Ile Asp Arg Thr Tyr
            20                  25                  30

Thr Val Ser Trp Phe Arg Gln Gly Pro Gly Lys Glu Arg Glu Phe Val
        35                  40                  45
```

```
Ala Thr Ile Ser Trp Asp Gly Ser Ile Tyr Tyr Asp Asn Ala Val Glu
    50                  55                  60

Gly Arg Phe Ser Ile Ser Gly Asp Asn Ala Lys Thr Thr Val Ala Leu
65                  70                  75                  80

Gln Met Asn Ser Leu Lys Pro Glu Asp Thr Ala Val Tyr Tyr Cys Ala
                85                  90                  95

Ala Arg Arg Arg Val Phe Ser Arg Ala Ala Ala Ala Tyr Asn Tyr Trp
            100                 105                 110

Gly Gln Gly Thr Gln Val Thr Val Ser Ser Glu Pro Lys Thr Pro Lys
        115                 120                 125

Pro Gln Ser Gly Arg
    130


<210> SEQ ID NO 60
<211> LENGTH: 124
<212> TYPE: PRT
<213> ORGANISM: Lama glama

<400> SEQUENCE: 60

Gln Val Lys Leu Gln Gln Ser Gly Gly Gly Leu Val Gln Pro Gly Gly
1               5                   10                  15

Ser Leu Arg Leu Thr Cys Ala Ala Ser Gly Phe Pro Phe Ser Thr Tyr
            20                  25                  30

Ala Ile Arg Trp Val Arg Arg Pro Pro Gly Lys Gly Leu Glu Trp Val
        35                  40                  45

Ser Thr Ile His Pro Asp Phe Thr Thr Asn Tyr Ala Asp Ser Val Ser
    50                  55                  60

Arg Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Arg Gly Val Ser Gly Glu Arg Gly Gln Gly Thr Gln Val Thr Val Ser
            100                 105                 110

Ser Glu Pro Lys Thr Pro Lys Pro His Ser Gly Arg
        115                 120


<210> SEQ ID NO 61
<211> LENGTH: 132
<212> TYPE: PRT
<213> ORGANISM: Lama glama

<400> SEQUENCE: 61

Gln Val Gln Leu Gln Gln Ser Gly Gly Gly Leu Val Gln Pro Gly Gly
1               5                   10                  15

Ser Leu Arg Leu Ser Cys Ala Ala Ser Gly Ser Ile Phe Ser Ile His
            20                  25                  30

Thr Met Gly Trp Tyr Arg Gln Ala Pro Gly Lys Gln Arg Glu Leu Val
        35                  40                  45

Thr Thr Ile Thr Thr Gly Gly Thr Thr Asn Tyr Ala Asp Ser Val Lys
    50                  55                  60

Gly Arg Phe Thr Ile Ser Arg Asp Asp Ala Lys Asn Thr Val Tyr Leu
65                  70                  75                  80

Gln Met Asn Asn Leu Lys Pro Glu Asp Thr Ala Val Tyr Tyr Cys Tyr
                85                  90                  95

Ala Leu Ile Gln Thr Ala Ser Thr Thr Trp Tyr Arg Gln Tyr Trp Gly
            100                 105                 110
```

Gln Gly Thr Gln Val Thr Val Ser Ser Glu Pro Lys Thr Gln Asn His
        115                 120                 125

Asn Ser Gly Arg
    130

<210> SEQ ID NO 62
<211> LENGTH: 126
<212> TYPE: PRT
<213> ORGANISM: Lama glama

<400> SEQUENCE: 62

Gln Val Lys Leu Gln Glu Ser Gly Gly Gly Leu Val Gln Pro Gly Gly
1               5                   10                  15

Ser Leu Arg Leu Ser Cys Thr Ala Ser Arg Ser Ile Phe Thr Arg Ala
            20                  25                  30

Met Ala Trp Tyr Arg Gln Ala Pro Gly Lys Gln Arg Glu Leu Val Ala
        35                  40                  45

Ala Ile Asp Ser Gly Asp Arg Thr His Tyr Ala Asp Ser Val Lys Gly
    50                  55                  60

Arg Phe Thr Ile Ser Arg Asn Asn Ala Lys Asp Thr Leu Tyr Leu Gln
65                  70                  75                  80

Met Asn Ser Leu Lys Ser Glu Asp Thr Ala Val Tyr Tyr Cys Asn Ala
                85                  90                  95

Asn Leu Gly Ala Leu Leu Asp Tyr Trp Gly Gln Gly Thr Gln Val Thr
            100                 105                 110

Val Ser Ser Glu Pro Lys Thr Gln Thr Thr Thr Ser Gly Arg
        115                 120                 125

<210> SEQ ID NO 63
<211> LENGTH: 129
<212> TYPE: PRT
<213> ORGANISM: Lama glama

<400> SEQUENCE: 63

Gln Val Lys Leu Gln Glu Ser Gly Gly Gly Leu Val Gln Ala Gly Gly
1               5                   10                  15

Ser Leu Arg Leu Ser Cys Ala Ala Ser Gly Phe Thr Phe Ala Thr Tyr
            20                  25                  30

Ala Met Ala Trp Tyr Arg Gln Ala Pro Gly Lys Gln Arg Glu Leu Val
        35                  40                  45

Ala Ser Ile Ser Asn Phe Gly Ser Thr Ala Tyr Gly Asp Ser Val Lys
    50                  55                  60

Gly Arg Phe Thr Ile Ser Arg Asp Asn Ala Lys Asn Thr Val Tyr Leu
65                  70                  75                  80

Glu Met Asn Ser Leu Lys Ser Glu Asp Thr Ala Val Tyr Tyr Cys Lys
                85                  90                  95

Arg Val Arg Asp Val Ile Gly Arg Pro Glu Leu Trp Gly Gln Gly Thr
            100                 105                 110

Gln Val Thr Val Ser Ser Glu Pro Lys Thr Pro Lys Pro His Ser Gly
        115                 120                 125

Arg

<210> SEQ ID NO 64
<211> LENGTH: 132
<212> TYPE: PRT
<213> ORGANISM: Lama glama

<400> SEQUENCE: 64

```
Gln Val Lys Leu Gln Glu Ser Gly Gly Gly Leu Val Gln Pro Gly Gly
1               5                   10                  15

Ser Leu Arg Leu Ser Cys Leu Pro Ser Ile Asn Ile Phe Ser Leu Ala
            20                  25                  30

Ala Met Gly Trp Tyr Arg Gln Ala Pro Gly Lys Gln Arg Glu Leu Val
        35                  40                  45

Ala Ser Ile Ser Ser Gly Gly Thr Ala Asn Tyr Ala Asp Ser Tyr Ala
    50                  55                  60

Asp Ser Val Lys Gly Arg Phe Thr Ile Ser Arg Asp Ile Ala Lys Asn
65                  70                  75                  80

Thr Val Asp Leu Gln Met Asn Ser Leu Lys Pro Glu Asp Thr Ala Val
                85                  90                  95

Tyr Tyr Cys Lys Val Asp Ser Tyr Thr Tyr Gly Thr Asp Ile Trp Gly
            100                 105                 110

Lys Gly Val Leu Val Thr Val Ser Ser Glu Pro Gln Asp Thr Lys Thr
        115                 120                 125

Thr Ser Gly Arg
    130
```

<210> SEQ ID NO 65
<211> LENGTH: 140
<212> TYPE: PRT
<213> ORGANISM: Lama glama

<400> SEQUENCE: 65

```
Gln Val Lys Leu Gln Gln Ser Gly Gly Gly Leu Val Gln Ala Gly Gly
1               5                   10                  15

Ser Leu Arg Leu Ser Cys Ala Ala Ser Gly Thr Phe Ser Arg Tyr Ala
            20                  25                  30

Met Gly Trp Phe Arg Gln Ala Pro Gly Lys Glu Arg Glu Phe Val Ala
        35                  40                  45

Ala Ile Asn Trp Thr Gly Gly Ser Thr Tyr Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Ser Leu Lys Pro Gly Asp Thr Ala Val Tyr Tyr Cys Ala
                85                  90                  95

Ala Glu Val His Pro Gly Asp Tyr Gly Leu Thr Tyr Met Gln Ser Gln
            100                 105                 110

Tyr Glu Tyr Asp Tyr Trp Gly Gln Gly Thr Gln Val Thr Val Ser Ser
        115                 120                 125

Glu Pro Lys Thr Pro Lys Pro Thr Thr Ser Gly Arg
    130                 135                 140
```

<210> SEQ ID NO 66
<211> LENGTH: 131
<212> TYPE: PRT
<213> ORGANISM: Lama glama

<400> SEQUENCE: 66

```
Asp Val Gln Leu Gln Ala Ser Gly Gly Gly Leu Val Gln Ala Gly Gly
1               5                   10                  15

Ser Leu Arg Leu Ser Cys Ala Ala Ser Thr Ser Arg Phe Ser Ser Tyr
            20                  25                  30

Ala Met Gly Trp Ser Arg Gln Ala Pro Gly Lys Gln Arg Glu Leu Val
```

```
        35                  40                  45

Ala Ser Ile Ser Ser Ser Gly Leu Thr Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Lys Ala Asp Gly Arg Arg Tyr Ser Leu Asn Glu Tyr Trp Gly Gln Gly
            100                 105                 110

Thr Gln Val Thr Val Ser Ser Glu Pro Lys Thr Pro Lys Pro Gln Pro
        115                 120                 125

Ser Gly Arg
    130


<210> SEQ ID NO 67
<211> LENGTH: 133
<212> TYPE: PRT
<213> ORGANISM: Lama glama

<400> SEQUENCE: 67

Asp Val Gln Leu Gln Ala Ser Gly Gly Gly Leu Val Gln Ala Gly Gly
1               5                   10                  15

Ser Leu Arg Leu Ser Cys Ala Ala Ser Gly Ser Thr Ile Ser Ser Tyr
            20                  25                  30

Ala Met Ala Trp Tyr Arg Gln Ala Pro Gly Lys Arg Arg Glu Leu Val
        35                  40                  45

Ala His Ile Ser Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ile Tyr Tyr Gly Gly Asp Tyr Tyr Tyr Thr Gly Val Lys Pro Asn Pro
            100                 105                 110

Trp Gly Gln Gly Thr Gln Val Thr Val Ser Ser Ala His His Ser Glu
        115                 120                 125

Asp Pro Arg Gly Arg
    130


<210> SEQ ID NO 68
<211> LENGTH: 137
<212> TYPE: PRT
<213> ORGANISM: Lama glama

<400> SEQUENCE: 68

Gln Val Lys Leu Gln Glu Ser Gly Gly Gly Trp Val Gln Ala Gly Gly
1               5                   10                  15

Ser Leu Arg Leu Ser Cys Ala Ala Ser Ala Leu Thr Ala Ser Ile Thr
            20                  25                  30

Thr Met Gly Trp Phe Arg Gln Thr Pro Glu Lys Glu Arg Glu Phe Leu
        35                  40                  45

Ala Ala Ile Asn Trp Thr Gly Asp Tyr Lys Tyr Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Gln Leu Lys Pro Glu Asp Thr Ala Val Tyr Tyr Cys
```

```
                85                  90                  95

Ala Ala Ser Lys Ile Arg Asn Asp Ile Tyr Leu Asn Asp Tyr Thr Trp
            100                 105                 110

Tyr Gln Tyr Trp Gly Gln Gly Thr Gln Val Thr Val Ser Ser Glu Pro
        115                 120                 125

Lys Thr Pro Lys Pro Gln Ser Gly Arg
    130                 135


<210> SEQ ID NO 69
<211> LENGTH: 143
<212> TYPE: PRT
<213> ORGANISM: Lama glama

<400> SEQUENCE: 69

Asp Val Gln Leu Gln Ala Ser Gly Gly Gly Leu Val Gln Ala Gly Gly
1               5                   10                  15

Ser Leu Arg Leu Ser Cys Val Ala Ser Ala Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ala Ser Thr Asp Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Thr Leu Lys Pro Glu Asp Thr Ala Val Tyr Tyr Cys
                85                  90                  95

Ala Ala His His Ile Thr Pro Thr Gly Ser Tyr Tyr Tyr Ser Glu Pro
            100                 105                 110

Leu Pro Val Asp Met Val Tyr Asp Tyr Trp Gly Gln Gly Thr Gln Val
        115                 120                 125

Thr Val Ser Ser Glu Pro Lys Thr Lys Thr Thr Thr Ser Gly Arg
    130                 135                 140


<210> SEQ ID NO 70
<211> LENGTH: 360
<212> TYPE: DNA
<213> ORGANISM: Artificial Sequence
<220> FEATURE:
<223> OTHER INFORMATION: Nano85 (Targets capsids of Norovirus strains
      with GII genotypes)

<400> SEQUENCE: 70

caggtccagc ttcaggaaag cggcgggggt ttagttcagc caggcggatc tcttcgtctt      60

tcctgtgcgg cgagtggctc aattttttcg atttatgcta tgggatggta tcgtcaggcc     120

ccaggcaagc agcgtgagtt ggtcgcaagt atcagcagtg gggggaggtac gaactatgcg    180

gacagtgtga aggggcgctt cactattagc ggagataacg cgaaaaatac cgtatatttg     240

caaatgaata gtttgaaacc agaagacacc gccgtatatt attgtaaacg cgaagattac     300

tcggcttacg caccgcctag tggtagtcgt ggtcgcggta ctcaggtaac tgtttcctca     360


<210> SEQ ID NO 71
<211> LENGTH: 120
<212> TYPE: PRT
<213> ORGANISM: Artificial Sequence
<220> FEATURE:
<223> OTHER INFORMATION: Nano85 (Targets capsids of Norovirus strains
      with GII genotypes)

<400> SEQUENCE: 71
```

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Tyr
            20                  25                  30

Ala Met Gly Trp Tyr Arg Gln Ala Pro Gly Lys Gln Arg Glu Leu Val
        35                  40                  45

Ala Ser Ile Ser Ser Gly Gly Gly Thr Asn Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Glu Asp Tyr Ser Ala Tyr Ala Pro Pro Ser Gly Ser Arg Gly Arg
            100                 105                 110

Gly Thr Gln Val Thr Val Ser Ser
        115                 120
```

<210> SEQ ID NO 72
<211> LENGTH: 345
<212> TYPE: DNA
<213> ORGANISM: Artificial Sequence
<220> FEATURE:
<223> OTHER INFORMATION: Nano26 (Targets capsids of Norovirus strains with GII genotypes)

<400> SEQUENCE: 72

```
caagtgcaat tgcaagagag tgggggcggt ttagtgcaac ctggtgggag cctgcgcctg      60

tcttgcaccg ccccacgtat tatctttttt atgtatgatg taggatggta ccgtcaggct     120

cctgaaaagc agcgtgaact tgtagctcag atcaatagcg atgtatctac caaatatgct     180

gacagtgtca aagggcgctt cactatcagc cgtgataacg ccaagcgcac ggtctattta     240

caaatgaacg acctgaaacc ggaagatgct gcggtctact attgcaatgt acgtcgtgct     300

tcagcggatt actgggggca ggggactcaa gtgacggtgt cctcg                     345
```

<210> SEQ ID NO 73
<211> LENGTH: 115
<212> TYPE: PRT
<213> ORGANISM: Artificial Sequence
<220> FEATURE:
<223> OTHER INFORMATION: Nano26 (Targets capsids of Norovirus strains with GII genotypes)

<400> SEQUENCE: 73

```
Gln Val Gln Leu Gln Glu Ser Gly Gly Gly Leu Val Gln Pro Gly Gly
1               5                   10                  15

Ser Leu Arg Leu Ser Cys Thr Ala Pro Arg Ile Ile Phe Phe Met Tyr
            20                  25                  30

Asp Val Gly Trp Tyr Arg Gln Ala Pro Glu Lys Gln Arg Glu Leu Val
        35                  40                  45

Ala Gln Ile Asn Ser Asp Val Ser Thr Lys Tyr Ala Asp Ser Val Lys
    50                  55                  60

Gly Arg Phe Thr Ile Ser Arg Asp Asn Ala Lys Arg Thr Val Tyr Leu
65                  70                  75                  80

Gln Met Asn Asp Leu Lys Pro Glu Asp Ala Ala Val Tyr Tyr Cys Asn
                85                  90                  95

Val Arg Arg Ala Ser Ala Asp Tyr Trp Gly Gln Gly Thr Gln Val Thr
            100                 105                 110
```

```
Val Ser Ser
        115


<210> SEQ ID NO 74
<211> LENGTH: 363
<212> TYPE: DNA
<213> ORGANISM: Artificial Sequence
<220> FEATURE:
<223> OTHER INFORMATION: Nano94 (Targets capsids of Norovirus strains
      with GI genotypes)

<400> SEQUENCE: 74

caagtacagt tacaggaaag tggcggagga ttggtacagg cgggagggtc attacgtctt     60

tcgtgcgcgg cctccggtcg tatgttcagc atcaattcga tggggtggta ccgtcaagcc    120

ccagggaagg agcgtgagtt agtagcgaca atttctgaag cgggaacaac tacctatgcg    180

gattcggtgc gtgggcgttt cacgattgct cgtgacaacg ccaaaaacac ggtttactta    240

caaatgaaca gcttgaatcc cgaagacacc gcggtatatt actgcaatgc ttatatccaa    300

cttgactcca ccatctggtt tcgtgcttat tggggtcagg ggacgcaggt aacagtaagc    360

tct                                                                  363


<210> SEQ ID NO 75
<211> LENGTH: 121
<212> TYPE: PRT
<213> ORGANISM: Artificial Sequence
<220> FEATURE:
<223> OTHER INFORMATION: Nano94 (Targets capsids of Norovirus strains
      with GI genotypes)

<400> SEQUENCE: 75

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Met Phe Ser Ile Asn
            20                  25                  30

Ser Met Gly Trp Tyr Arg Gln Ala Pro Gly Lys Glu Arg Glu Leu Val
        35                  40                  45

Ala Thr Ile Ser Glu Ala Gly Thr Thr Thr Tyr Ala Asp Ser Val Arg
    50                  55                  60

Gly Arg Phe Thr Ile Ala Arg Asp Asn Ala Lys Asn Thr Val Tyr Leu
65                  70                  75                  80

Gln Met Asn Ser Leu Asn Pro Glu Asp Thr Ala Val Tyr Tyr Cys Asn
                85                  90                  95

Ala Tyr Ile Gln Leu Asp Ser Thr Ile Trp Phe Arg Ala Tyr Trp Gly
            100                 105                 110

Gln Gly Thr Gln Val Thr Val Ser Ser
        115                 120


<210> SEQ ID NO 76
<211> LENGTH: 357
<212> TYPE: DNA
<213> ORGANISM: Artificial Sequence
<220> FEATURE:
<223> OTHER INFORMATION: Nano14 (Targets capsids of Norovirus strains
      with GII.10 genotypes, not cross-reactive)

<400> SEQUENCE: 76

caggtccagt tacaagaaag tgggggaggt ttggttcaat ctggaggttc attgcgtttg     60

tcctgtgcgg catcacgcaa cattaactcc atgcatgtgg taggatggta tcgtcaggca    120
```

ccaggaaacc agcgcgagtt ggttgcctcc attactgacg atggctctac tgactatgta 180
gattcagtca aggggcgttt tactatctcg cgcgacattg ccgaaaacac ggtctatctt 240
caaatgaatt cattaaatcc ggaggacacc gcagtttact actgtaaagg gactatcgta 300
gtgttcacga ccccaatgca ttactggggg aaagggactc aggtgacggt ttcctcg 357

<210> SEQ ID NO 77
<211> LENGTH: 119
<212> TYPE: PRT
<213> ORGANISM: Artificial Sequence
<220> FEATURE:
<223> OTHER INFORMATION: Nano14 (Targets capsids of Norovirus strains with GII.10 genotypes, not cross-reactive)

<400> SEQUENCE: 77

Gln Val Gln Leu Gln Glu Ser Gly Gly Gly Leu Val Gln Ser Gly Gly
1 5 10 15

Ser Leu Arg Leu Ser Cys Ala Ala Ser Arg Asn Ile Asn Ser Met His
20 25 30

Val Val Gly Trp Tyr Arg Gln Ala Pro Gly Asn Gln Arg Glu Leu Val
35 40 45

Ala Ser Ile Thr Asp Asp Gly Ser Thr Asp Tyr Val Asp Ser Val Lys
50 55 60

Gly Arg Phe Thr Ile Ser Arg Asp Ile Ala Glu Asn Thr Val Tyr Leu
65 70 75 80

Gln Met Asn Ser Leu Asn Pro Glu Asp Thr Ala Val Tyr Tyr Cys Lys
85 90 95

Gly Thr Ile Val Val Phe Thr Thr Pro Met His Tyr Trp Gly Lys Gly
100 105 110

Thr Gln Val Thr Val Ser Ser
115

<210> SEQ ID NO 78
<211> LENGTH: 363
<212> TYPE: DNA
<213> ORGANISM: Artificial Sequence
<220> FEATURE:
<223> OTHER INFORMATION: Nano32 (Targets capsids of Norovirus strains with GII genotypes, not cross-reactive)

<400> SEQUENCE: 78
caagtacagt tacaggaaag tggcggagga ttggtacagg cgggagggtc attacgtctt 60
tcgtgcgcgg cctccggtcg tatgttcagc atcaattcga tggggtggta ccgtcaagcc 120
ccagggaagg agcgtgagtt agtagcgaca atttctgaag cgggaacaac tacctatgcg 180
gattcggtgc gtgggcgttt cacgattgct cgtgacaacg ccaaaaacac ggtttactta 240
caaatgaaca gcttgaatcc cgaagacacc gcggtatatt actgcaatgc ttatatccaa 300
cttgactcca ccatctggtt tcgtgcttat tggggtcagg ggacgcaggt aacagtaagc 360
tct 363

<210> SEQ ID NO 79
<211> LENGTH: 135
<212> TYPE: PRT
<213> ORGANISM: Artificial Sequence
<220> FEATURE:
<223> OTHER INFORMATION: Nano32 (Targets capsids of Norovirus strains with GII genotypes, not cross-reactive)

<400> SEQUENCE: 79

-continued

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Gly Tyr Tyr
            20                  25                  30

Pro Ile Gly Trp Phe Arg Gln Ala Pro Gly Lys Gly Leu Glu Gly Val
        35                  40                  45

Ser Cys Ile Ser Gly Ser Gly Gly Ser Ala Asn Tyr Ala Ala Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Asp Leu Ser Ser Leu Thr Thr Val Gln Ala Met Cys Val Ile
            100                 105                 110

Pro Arg Pro Gly Phe Ser Ala Lys Ala Tyr Asp Tyr Trp Gly Leu Gly
        115                 120                 125

Thr Gln Val Thr Val Ser Ser
    130                 135
```